US012458689B2

(12) United States Patent
Donald et al.

(10) Patent No.: US 12,458,689 B2
(45) Date of Patent: Nov. 4, 2025

(54) ***ESCHERICHIA COLI* COMPOSITIONS AND METHODS THEREOF**

(71) Applicant: Pfizer Inc., New York, NY (US)

(72) Inventors: Robert G. K. Donald, South Orange, NJ (US); Rosalind Pan, Morris Plains, NJ (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 18/596,916

(22) Filed: Mar. 6, 2024

(65) Prior Publication Data

US 2024/0325513 A1 Oct. 3, 2024

Related U.S. Application Data

(62) Division of application No. 17/180,959, filed on Feb. 22, 2021, now abandoned.

(60) Provisional application No. 63/144,058, filed on Feb. 1, 2021, provisional application No. 62/980,433, filed on Feb. 23, 2020.

(51) Int. Cl.

| | |
|---|---|
| ***A61K 39/02*** | (2006.01) |
| ***A61K 39/108*** | (2006.01) |
| ***A61K 39/385*** | (2006.01) |
| ***A61P 31/04*** | (2006.01) |
| ***A61P 37/04*** | (2006.01) |
| *A61K 39/00* | (2006.01) |

(52) U.S. Cl.
CPC ...... *A61K 39/0258* (2013.01); *A61K 39/0266* (2013.01); *A61K 39/385* (2013.01); *A61P 31/04* (2018.01); *A61P 37/04* (2018.01); *A61K 2039/6031* (2013.01)

(58) Field of Classification Search
CPC . A61K 39/0258; A61K 39/0266; A61P 37/04; A61P 31/04
See application file for complete search history.

(56) References Cited

U.S. PATENT DOCUMENTS

| | | | |
|---|---|---|---|
| 2003/0199071 A1 | 10/2003 | Langermann et al. | |
| 2016/0136285 A1 | 5/2016 | Gozdziewicz et al. | |
| 2021/0221856 A1 | 7/2021 | Grijpstra et al. | |
| 2021/0268095 A1 | 9/2021 | Donald et al. | |

FOREIGN PATENT DOCUMENTS

| | | | |
|---|---|---|---|
| WO | 95/20657 A1 | 8/1995 | |
| WO | WO 2006/113528 A2 | 10/2006 | |
| WO | WO-2015052344 A1 * | 4/2015 | ......... A61K 39/0258 |

OTHER PUBLICATIONS

Franco et al. 1998 (The Wzz (C1d) Protein in *Escherichia coli*: Amino Acid sequence variation determines O-antigen chain length specificity; Journal of Bacteriology, 180(10): 2670-2675) (Year: 1998).*

Murray et al. 2003 (Regulation of *Salmonella typhimurium* lipopolysaccharide O antigen chain length is required for virulence; identification of FepE as a second Wzz; Molecular Microbiology 47(5)1395-1406). (Year: 2003).*

Stenutz et al. 2006 (The structures of *Escherichia coli* O-polysaccharide antigen; FEMS Microbiol Rev 30:382-403). (Year: 2006).*

Aucken & Pitt, "Serological relationships of the O antigens of Klebsiella pneumoniae 05, *Escherichia coli* 08 and a new O serotype of Serratia marcescens", FEMS Microbiology Letters 80:93-98 (1991).

Costantino et al, "The design of semi-synthetic and synthetic glycoconjugate vaccines", Expert Opinion Drug Discovery 6(10):1045-1066 (2011).

Greenspan et al, "Defining epitopes: It's not as easy as it seems", Nature Biotechnology 17:936-938 (1999).

Rojas-Macias et al, "Development of the ECODAB into a relational database for *Escherichia coli* O-antigens and other bacterial polysaccharides", Glycobiology 25(3):341-347 (2015).

Sarshar et al, "FimH and Anti-Adhesive Therapeutics: A Disarming Strategy Against Uropathogens", Antibiotics 9(7):397 (2020).

Yakovenko et al, "Inactive conformation enhances binding function in physiological conditions", PNAS 112(32):9884-9889 (2015).

Kido, N., et al., "Inhibition by Succinyl Concanavalin A of Strong Adjuvant Activity of Lipopolysaccharides Which Possess Mannans as the O-Specific Polysaccharide Chains", Cellular Immunology, 1985, 92(2):328-337.

Kido, N., et al., "Potent Adjuvant Action of Lipopolysaccharides Possessing the O-Specific Polysaccharide Moieties Consisting of Mannans in Antibody Response against Protein Antigen", Cellular Immunology, 1985, 91:52-59.

Micoli, F., et al., "Potential targets for next generation antimicrobial glycoconjugate vaccines", FEMS Microbiology Reviews, 2018, 42(3):388-423.

(Continued)

*Primary Examiner* — Mary Maille Lyons
(74) *Attorney, Agent, or Firm* — Rebecca Wright

(57) ABSTRACT

This invention provides a polypeptide derived from *E. coli* or a fragment thereof, including compositions and methods thereof. In one embodiment, the compositions comprise a polypeptide derived from *E. coli* or a fragment thereof, and modified O-polysaccharide molecules derived from *E. coli* lipopolysaccharides or conjugates thereof. In a further aspect, the compositions further comprise modified O-polysaccharide molecules derived from *Klebsiella pneumoniae* or conjugates thereof.

14 Claims, 54 Drawing Sheets

Specification includes a Sequence Listing.

(56) References Cited

OTHER PUBLICATIONS

Sugiyama, T., et al., "Generation of *Escherichia coli* O9a Serotype, a Subtype of *E. coli* 09, by Transfer of the wb Gene Cluster of Klebsiella O3 into *E. coli* via Recombination", Journal of Bacteriology, 1998, 180(10):2775-2778.
Vinogradov, E., et al., "The structure of the core region of the lipopolysaccharide from Klebsiella pneumoniae 03: 3-Deoxy-alpha-D-manno-octulosonic acid (alpha-Kdo) residue in the outer part of the core, a common structural element of Klebsiella pneumoniae 01, 02, 03, 04, 05, 08 and 012 lipopolysaccharides", Eur. J. Biochem., 2001, 268:1722-1729.

* cited by examiner

FIG. 1A type 1 fimbriae D-mannose specific adhesin [Escherichia coli FimH J96 ELL41155.1 [E.coli J96]; 300 aa

1 MKRVITLFAV LLMGWSVNAW SFACKTANGT AIPIGGGSAN VYVNLAPVVN
51 VGQNLVVDLS TQIFCHNDYP ETITDYVTLQ RGSAYGGVLS NFSGTVKYSG
101 SSYPFPTTSE TPRVVYNSRT DKPWPVALYL TPVSSAGGVA IKAGSLIAVL
151 ILRQTNNYNS DDFQFVWNIY ANNDVVVPTG GCDVSARDVT VTLPDYPGSV
201 PIPLTVYCAK SQNLGYYLSG TTADAGNSIF TNTASFSPAQ GVGVQLTRNG
251 TIIPANNTVS LGAVGTSAVS LGLTANYART GGQVTAGNVQ SIIGVTFVYQ
(SEQ ID NO: 1)

FimH J96 sequence

1 MKRVITLFAV LLMGWSVNAW SFACKTANGT AIPIGGGSAN VYVNLAPVVN
51 VGQNLVVDLS TQIFCHNDYP ETITDYVTLQ RGSAYGGVLS NFSGTVKYSG
101 SSYPFPTTSE TPRVVYNSRT DKPWPVALYL TPVSSAGGVA IKAGSLIAVL
151 ILRQTNNYNS DDFQFVWNIY ANNDVVVPTG GCDVSARDVT VTLPDYPGSV
201 PIPLTVYCAK SQNLGYYLSG TTADAGNSIF TNTASFSPAQ GVGVQLTRNG
251 TIIPANNTVS LGAVGTSAVS LGLTANYART GGQVTAGNVQ SIIGVTFVYQ (SEQ ID NO: 1)

Fragment of FimH, corresponding to aa residues 22-300 of SEQ ID NO: 1 [mature FimH protein]

1 facktangt aipigggsan vyvnlapvvn vgqnlvvdls tqifchndyp etitdyvtlq
rgsayggvls nfsgtvkysg ssypfpttse tprvvynsrt dkpwpvalyl tpvssaggva
ikagsliavl ilrqtnnyns ddfqfvwniy anndvvvptg gcdvsardvt vtlpdypgsv
pipltvycak sqnlgyylsg ttadagnsif tntasfspaq gvgvqltrng tiipanntvs
lgavgtsavs lgltanyart ggqvtagnvq siigvtfvyq 279 (SEQ ID NO: 2)

FimH lectin domain (SEQ ID NO: 3, which corresponds to aa residues 1–158 of SEQ ID NO: 2)

1 facktangt aipigggsan vyvnlapvvn vgqnlvvdls tqifchndyp etitdyvtlq
rgsayggvls nfsgtvkysg ssypfpttse tprvvynsrt dkpwpvalyl tpvssaggva
ikagsliavl ilrqtnnyns ddfqfvwniy anndvvv 158 (SEQ ID NO: 3)

FIG. 1A continued

FIG. 1A continued

FimH pilin domain (SEQ ID NO: 4, which corresponds to aa residues 160–279 of SEQ ID NO: 2)

160 gcdvsardvt vtlpdypgsv pipltvycak sqnlgyylsg ttadagnsif tntasfspaq gvgvqltrng tiipanntvs lgavgtsavs lgltanyart ggqvtagnvq siigvtfvyq 279 (SEQ ID NO: 4)

pSB02198 - FimH mIgK signal pept / F22..Q300 J96 FimH N28S V48C L55C N91S N249Q / 7 AA linker / FimG A1..K14 / GGHis8 in pcDNA3.1(+)
VETDTLLLWVLLLWVPGSTGFACKTASGTAIPIGGGSANVYVNLAPCVNVGQNCVVDLSTQIFCHNDYPETITDYVTLQRGSAYGGVLSSFSGTVKYSGSSYPFPTTSETPRVVYNSRTDKPWPVALYLTPVSSAGGVAIKAGSLIAVLILRQTNNYNSDDFQFVWNIYANNDVVVPTGGCDVSARDVTVTLPDYPGSVPIPLTVYCAKSQNLGYYLSGTTADAGNSIFTNTASFSPAQGVGVQLTRQGTIIPANNTVSLGAVGTSAVSLGLTANYARTGGQVTAGNVQSIIGVTFVYQGGSSGGGADVTITVNGKVVAKGGHHHHHHHH (SEQ ID NO: 5)

pSB02307 - FimH mIgK signal pept / F22..Q300 J96 FimH N28S N91S N249Q / His8 in pcDNA3.1(+)
METDT LLLWV LLLWV PGSTG FACKT ASGTA IPIGG GSANV YVNLA PVVNV GQNLV VDLST QIFCH NDYPE TITDY VTLQR GSAYG GVLSS FSGTV KYSGS SYPFP TTSET PRVVY NSRTD KPWPV ALYLT PVSSA GGVAI KAGSL IAVLI LRQTN NYNSD DFQFV WNIYA NNDVV VPTGG CDVSA RDVTV TLPDY PGSVP IPLTV YCAKS QNLGY YLSGT TADAG NSIFT NTASF SPAQG VGVQL TRQGT IIPAN NTVSL GAVGT SAVSL GLTAN YARTG GQVTA GNVQS IIGVT FVYQG GSSGG GADVT ITVNG KVVAK GGHHH HHHHH (SEQ ID NO: 6)

Number of amino acids: 310 Molecular weight: 32095.80 Theoretical pI: 7.25 pSB02083 FimH Lectin Domain Wild Type construct
METDT LLLWV LLLWV PGSTG FACKT ASGTA IPIGG GSANV YVNLA PVVNV GQNLV VDLST QIFCH NDYPE TITDY VTLQR GSAYG GVLSS FSGTV KYSGS SYPFP TTSET PRVVY NSRTD KPWPV ALYLT PVSSA GGVAI KAGSL IAVLI LRQTN NYNSD DFQFV WNIYA NNDVV VPTGG HHHHHHHH (SEQ ID NO: 7)

pSB02158 FimH Lectin Domain Lock Mutant
METDTLLLWVLLLWVPGSTG FACKT ASGTA IPIGG GSANV YVNLA PCVNV GQNCV VDLST QIFCH NDYPE TITDY VTLQR GSAYG GVLSS FSGTV KYSGS SYPFP TTSET

FIG. 1A continued

FIG. 1A continued

PRVVY NSRTD KPWPV ALYLT PVSSA GGVAI KAGSL IAVLI LRQTN NYNSD DFQFV
WNIYA NNDVV VPTGG HHHHHHHH (SEQ ID NO: 8)

FIG. 1B

FimG A1..K14 sequence
ADVTI TVNGK VVAK (SEQ ID NO: 9)

ADVT ITVNG KVVAK GGHHH HHHHH (SEQ ID NO: 21)

FIG. 1C

FimC sequence

1 MSNKNVNVRK SQEITFCLLA GILMFMAMMV AGRAEAGVAL GATRVIYPAG
51 QKQVQLAVTN NDENSTYLIQ SWVENADGVK DGRFIVTPPL FAMKGKKENT
101 LRILDATNNQ LPQDRESLFW MNVKAIPSMD KSKLTENTLQ LAIISRIKLY
151 YRPAKLALPP DQAAEKLRFR RSANSLTLIN PTPYYLTVTE LNAGTRVLEN
201 ALVPPMGEST VKLPSDAGSN ITYRTINDYG ALTPKMTGVM E (SEQ ID NO: 10)

FIG. 1D

| | | |
|---|---|---|
| DNKQ | 4 aa | (SEQ ID NO: 11) |
| GGSGG | 5 aa | (SEQ ID NO: 12) |
| GGSSG G | 6 aa | (SEQ ID NO: 13) |
| GGSSG GG | 7 aa | (SEQ ID NO: 14) |
| GGGSS GGG | 8 aa | (SEQ ID NO: 15) |
| GGGSG SGGG | 9 aa | (SEQ ID NO: 16) |
| GGGSG GSGGG | 10 aa | (SEQ ID NO: 17) |

FIG. 1E

FimH J96 signal sequence
MKRVI TLFAV LLMGW SVNAW S (SEQ ID NO: 18)

pSB02198 - FimH mIgK signal pept / F22..Q300 J96 FimH N28S V48C L55C N91S N249Q / 7 AA linker / FimG A1..K14 / GGHis8 in pcDNA3.1(+) [Number of amino acids: 310 Molecular weight: 32089.79 Theoretical pI: 7.23]

VETDT LLLWV LLLWV PGSTG (SEQ ID NO: 19) FACKT ASGTA IPIGG GSANV YVNLA PCVNV GQNCV VDLST QIFCH NDYPE TITDY VTLQR GSAYG GVLSS FSGTV KYSGS SYPFP TTSET PRVVY NSRTD KPWPV ALYLT PVSSA GGVAI KAGSL IAVLI LRQTN NYNSD DFQFV WNIYA NNDVV VPTGG CDVSA RDVTV TLPDY PGSVP IPLTV YCAKS QNLGY YLSGT TADAG NSIFT NTASF SPAQG VGVQL TRQGT IIPAN NTVSL GAVGT SAVSL GLTAN YARTG GQVTA GNVQS IIGVT FVYQ (SEQ ID NO: 20) GGSSG GG (SEQ ID NO: 14) ADVTI TVNGK VVAK GGHHH HHHHH (SEQ ID NO: 21)

pSB02307 - FimH mIgK signal pept / F22..Q300 J96 FimH N28S N91S N249Q / His8 in pcDNA3.1(+)

METDT LLLWV LLLWV PGSTG (SEQ ID NO: 22)
FACKT ASGTA IPIGG GSANV YVNLA PVVNV GQNLV VDLST QIFCH NDYPE TITDY VTLQR GSAYG GVLSS FSGTV KYSGS SYPFP TTSET PRVVY NSRTD KPWPV ALYLT PVSSA GGVAI KAGSL IAVLI LRQTN NYNSD DFQFV WNIYA NNDVV VPTGG CDVSA RDVTV TLPDY PGSVP IPLTV YCAKS QNLGY YLSGT TADAG NSIFT NTASF SPAQG VGVQL TRQGT IIPAN NTVSL GAVGT SAVSL GLTAN YARTG GQVTA GNVQS IIGVT FVYQ (SEQ ID NO: 23) GGSSG GG (SEQ ID NO: 14)
ADVT ITVNG KVVAK GGHHH HHHHH (SEQ ID NO: 21)

FIG. 1E continued

FIG. 1E continued pSB02083 FimH Lectin Domain Wild Type construct

METDT LLLWV LLLWV PGSTG (SEQ ID NO: 22)
FACKT ASGTA IPIGG GSANV YVNLA PVVNV GQNLV VDLST QIFCH
NDYPE TITDY VTLQR GSAYG GVLSS FSGTV KYSGS SYPFP TTSET
PRVVY NSRTD KPWPV ALYLT PVSSA GGVAI KAGSL IAVLI LRQTN
NYNSD DFQFV WNIYA NNDVV VPTGG (SEQ ID NO: 24) HHHHH HHH
(SEQ ID NO: 25)

pSB02158 FimH Lectin Domain Lock Mutant

METDT LLLWV LLLWV PGSTG (SEQ ID NO: 22)
FACKT ASGTA IPIGG GSANV YVNLA PCVNV GQNCV VDLST QIFCH
NDYPE TITDY VTLQR GSAYG GVLSS FSGTV KYSGS SYPFP TTSET
PRVVY NSRTD KPWPV ALYLT PVSSA GGVAI KAGSL IAVLI LRQTN
NYNSD DFQFV WNIYA NNDVV VPTGG (SEQ ID NO: 26) HHHHHHHH
(SEQ ID NO: 25)

FIG. 1F pSB01878 processed sequence:

FACKTANGTAIPIGGGSANVYVNLAPVVNVGQNLVVDLSTQIFCHNDYP
ETITDYVTLQRGSAYGGVLSNFSGTVKYSGSSYPFPTTSETPRVVYNSRTD
KPWPVALYLTPVSSAGGVAIKAGSLIAVLILRQTNNYNSDDFQFVWNIYA
NNDVVVPTGGHHHHHHHH (SEQ ID NO: 27)

NXS/T sites are indicated in bold text as these are potentially glycosylated.

pSB02083 FimH Lectin Domain Wild Type with murine IgK signal peptide

METDTLLLWVLLLWVPGSTGFACKTASGTAIPIGGGSANVYVNLAPVVNVGQNLVVDLSTQIFCHNDYP
ETITDYVTLQRGSAYGGVLSSFSGTVKYSGSSYPFPTTSETPRVVYNSRTDKPWPVALYLTPVSSAGGVAIK
AGSLIAVLILRQTNNYNSDDFQFVWNIYANNDVVVPTGGHHHHHHHH (SEQ ID NO: 7)

FIG. 1F continued

FIG. 1F continued pSB02158 FimH Lectin Domain Lock Mutant with murine IgK signal peptide

METDTLLLWVLLLWVPGSTGFACKTASGTAIPIGGGSANVYVNLAPCVNVGQNCVVDLSTQIFCHNDYPE

TITDYVTLQRGSAYGGVLSSFSGTVKYSGSSYPFPTTSETPRVVYNSRTDKPWPVALYLTPVSSAGGVAIKAG

SLIAVLILRQTNNYNSDDFQFVWNIYANNDVVVPTGGHHHHHHHH (SEQ ID NO: 8)

FIG. 1G

Amino acid sequence of FimH of K12

FACKTANGTAIPIGGGSANV YVNLAPVVNVGQNLVVDLST QIFCHNDYPETITDYVTLQR

GSAYGGVLSNFSGTVKYSGS SYPFPTTSETPRVVYNSRTD KPWPVALYLTPVSSAGGVAI

KAGSLIAVLILRQTNNYNSD DFQFVWNIYANNDVVVPTGG CDVSARDVTVTLPDYPGSVP

IPLTVYCAKSQNLGYYLSGT TADAGNSIFTNTASFSPAQG VGVQLTRNGTIIPANNTVSL

GAVGTSAVSLGLTANYARTG GQVTAGNVQSIIGVTFVYQ* (SEQ ID NO: 28)

Amino acid sequence of FimH of UTI89, which differs from the FimH of K12

FACKTANGTAIPIGGGSANV YVNLAPAVNVGQNLVVDLST QIFCHNDYPETITDYVTLQR

GAAYGGVLSSFSGTVKYNGS SYPFPTTSETPRVVYNSRTD KPWPVALYLTPVSSAGGVAI

KAGSLIAVLILRQTNNYNSD DFQFVWNIYANNDVVVPTGG CDVSARDVTVTLPDYPGSVP

IPLTVYCAKSQNLGYYLSGT TADAGNSIFTNTASFSPAQG VGVQLTRNGTIIPANNTVSL

GAVGTSAVSLGLTANYARTG GQVTAGNVQSIIGVTFVYQ* (SEQ ID NO: 29)

FIG. 1H

Exemplary wzzB sequences include:

>O25b 2401 WzzB

MRVENNNVSGQNHDPEQIDLIDLLVQLWRGKMTIIISVIVAIALAIGYLAVAKEKWTSTAIITQP

DVGQIAGYNNAMNVIYGQAAPKVSDLQETLIGRFSSAFSALAETLDNQEEPEKLTIEPSVKN

QQLPLTVSYVGQTAEGAQMKLAQYIQQVDDKVNQELEKDLKDNIALGRKNLQDSLRTQEVV

AQEQKDLRIRQIQEALQYANQEQVTKPQVQQTEDVTQDTLFLLGSEALESMIKHEATRPLVF

SSNYYQTRQNLLDIESLKVDDLDIHAYRYVMKPTLPIRRDSPKKAITLILAVLLGGMVGAGIVL

GRNALRNYNAK (SEQ ID NO: 30)

>O25a:K5:H1 WzzB

MRVENNNVSGQNNDPEQIDLIDLLVQLWRGKMTIIISVIVAIALAIGYLAVAKEKWTSTAIITQP

DVGQIAGYNNAMNVIYGQAAPKVSDLQETLIGRFSSAFSALAETLDNQDEPEKLTIEPSVKN

QQLPLTVSYVGQTAEGAQMKLAQYIQQVDDKVNQELEKDLKDNIALGRKNLQDSLRTQEVV

FIG. 1H continued

FIG. 1H continued

AQEQKDLRIRQIQEALQYANQAQVTKPQIQQTGEDITQDTLFLLGSEALESMIKHEATRPLVF
SPNYYQTRQNLLDIESLKVDDLDIHAYRYVMKPTLPIRRDSPKKAITLILAVLLGGMVGAGIVL
GRNALRNYNAK (SEQ ID NO: 31)

>O25a ETEC ATCC WzzB
MRVENNNVSGQNHDPEQIDLIDLLVQLWRGKMTIIISVVVAIALAIGYLAVAKEKWTSTAIITQ
PDVGQIAGYNNAMNVIYGQAAPKVSDLQETLIGRFSFAFSALAETLDNQKEPEKLTIEPSVK
NQQLPLTVSYVGQTAEDAQMKLAQYIQQVDDKVNQELEKDLKDNLALGRKNLQDSLRTQE
VVAQEQKDLRIRQIQEALQYANQAQVTKPQIQQTGEDITQDTLFLLGSEALESMIKHEATRPL
VFSPNYYQTRQNLLDIENLKVDDLDIHAYRYVMKPTLPIRRDSPKKAITLILAVLLGGMVGAGI
VLGRNALRNYNSK (SEQ ID NO: 32)

>K12 W3110 WzzB
MRVENNNVSGQNHDPEQIDLIDLLVQLWRGKMTIIISVIVAIALAIGYLAVAKEKWTSTAIITQP
DVGQIAGYNNAMNVIYGQAAPKVSDLQETLIGRFSSAFSALAETLDNQEEREKLTIEPSVKN
QQLPLTVSYVGQTAEGAQMKLAQYIQQVDDKVNQELEKDLKDNIALGRKNLQDSLRTQEVV
AQEQKDLRIRQIQEALQYANQAQVTKPQIQQTGEDITQDTLFLLGSEALESMIKHEATRPLVF
SPNYYQTRQNLLDIESLKVDDLDIHAYRYVMKPMLPIRRDSPKKAITLILAVLLGGMVGAGIVL
GRNALRNYNAK (SEQ ID NO: 33)

>Salmonella LT2 WzzB
MTVDSNTSSGRGNDPEQIDLIELLLQLWRGKMTIIVAVIIAILLAVGYLMIAKEKWTSTAIITQP
DAAQVATYTNALNVLYGGNAPKISEVQANFISRFSSAFSALSEVLDNQKEREKLTIEQSVKG
QALPLSVSYVSTTAEGAQRRLAEYIQQVDEEVAKELEVDLKDNITLQTKTLQESLETQEVVA
QEQKDLRIKQIEEALRYADEAKITQPQIQQTQDVTQDTMFLLGSDALKSMIQNEATRPLVFS
PAYYQTKQTLLDIKNLKVTADTVHVYRYVMKPTLPVRRDSPKTAITLVLAVLLGGMIGAGIVL
GRNALRSYKPKAL (SEQ ID NO: 34)

Exemplary FepE sequences include:

>O25b GAR2401 FepE
MSSLNIKQGSDAHFPDYPLASPSNNEIDLLNLISVLWRAKKTVMAVVFAFACAGLLISFILPQ
KWTSAAVVTPPEPVQWQELEKSFTKLRVLDLDIKIDRTEAFNLFIKKFQSVSLLEEYLRSSPY
VMDQLKEAKIDELDLHRAIVALSEKMKAVDDNASKKKDEPSLYTSWTLSFTAPTSEEAQTVL
SGYIDYISTLVVKESLENVRNKLEIKTQFEKEKLAQDRIKTKNQLDANIQRLNYSLDIANAAGIK
KPVYSNGQAVKDDPDFSISLGADGIERKLEIEKAVTDVAELNGELRNRQYLVEQLTKAHVND
VNFTPFKYQLSPSLPVKKDGPGKAIIVILSALIGGMVACGGVLLRYAMASRKQDAMMADHLV
(SEQ ID NO: 35)

FIG. 1H continued

FIG. 1H continued

>O25a:K5:H1 FepE
MSSLNIKQGSEAHFPEYPLASPSNNEIDLLNLIEVLWRAKKTVMAVVFAFACAGLLISFILPQK
WTSAAVVTPPEPVQWQELEKTFTKLRVLDLDIKIDRTEAFNLFIKKFQSVSLLEEYLRSSPYV
MDQLKEAKIDPLDLHRAIVALSEKMKAVDDNASKKKDESALYTSWTLSFTAPTSEEAQKVLA
GYIDYISALVVKESIENVRNKLEIKTQFEKEKLAQDRIKTKNQLDANIQRLNYSLDIANAAGIKK
PVYSNGQAVKDDPDFSISLGADGIERKLEIEKAVTDVAELNGELRNRQYLVEQLTKTNINDV
NFTPFKYQLRPSLPVKKDGQGKAIIVILSALVGGMVACGGVLLRHAMASRKQDAMMADHLV
(SEQ ID NO: 36)

> O25a ETEC ATCC FepE
MSSLNIKQGSDAHFPDYPLASPSNNEIDLLNLISVLWRAKKTVMAVVFAFACAGLLISFILPQ
KWTSAAVVTPPEPVQWQELEKSFTKLRVLDLDIKIDRTEAFNLFIKKFQSVSLLEEYLRSSPY
VMDQLKEAKIDELDLHRAIVALSEKMKAVDDNASKKKDEPSLYTSWTLSFTAPTSEEAQTVL
SGYIDYISTLVVKESLENVRNKLEIKTQFEKEKLAQDRIKTKNQLDANIQRLNYSLDIANAAGIK
KPVYSNGQAVKDDPDFSISLGADGIERKLEIEKAVTDVAELNGELRNRQYLVEQLTKAHVND
VNFTPFKYQLSPSLPVKKDGPGKAIIVILSALIGGMVACGGVLLRYAMASRKQDAMMADHLV
(SEQ ID NO: 37)
> O157 FepE
MSSLNIKQGSDAHFPDYPLASPSNNEIDLLNLISVLWRAKKTVMAVVFAFACAGLLISFILPQ
KWTSAAVVTPPEPVQWQELEKTFTKLRVLDLDIKIDRTEAFNLFIKKFQSVSLLEEYLRSSPY
VMDQLKEAKIDELDLHRAIVALSEKMKAVDDNASKKKDEPSLYTSWTLSFTAPTSEEAQTVL
SGYIDYISALVVKESIENVRNKLEIKTQFEKEKLAQDRIKMKNQLDANIQRLNYSLDIANAAGIK
KPVYSNGQAVKDDPDFSISLGADGIERKLEIEKAVTDVAELNGELRNRQYLVEQLTKANIND
VNFTPFKYQLSPSLPVKKDGPGKAIIVILSALIGGMVACGSVLLRYAMASRKQDAMMADHLV
(SEQ ID NO: 38)
>Salmonella LT2 FepE
MPSLNVKQEKNQSFAGYSLPPANSHEIDLFSLIEVLWQAKRRILATVFAFACVGLLLSFLLPQ
KWTSQAIVTPAESVQWQGLERTLTALRVLDMEVSVDRGSVFNLFIKKFSSPSLLEEYLRSSP
YVMDQLKGAQIDEQDLHRAIVLLSEKMKAVDSNVGKKNETSLFTSWTLSFTAPTREEAQKV
LAGYIQYISDIVVKETLENIRNQLEIKTRYEQEKLAMDRVRLKNQLDANIQRLHYSLEIANAAGI
KRPVYSNGQAVKDDPDFSISLGADGISRKLEIEKGVTDVAEIDGDLRNRQYHVEQLAAMNV
SDVKFTPFKYQLSPSLPVKKDGPGKAIIIILAALIGGMMACGGVLLRHAMVSRKMENALAIDE
RLV (SEQ ID NO: 39)

Results from Expression and Purification

Results from Expression and Purification pSB02083

17 mg total yield pSB02158

10.8 mg total yield

Expression of pSB2307 FimH dscG wild type

FIG. 9A

<table>
<tr><th>Serogroup</th><th>Structure</th></tr>
<tr><td>O1A, O1A1</td><td>→3)-α-L-Rha-(1→3)-α-L-Rha-(1→3)-β-L-Rha-(1→4)-β-D-GlcNAc-(1→ | β-D-ManNAc-(1→2)</td></tr>
<tr><td>O1B</td><td>→3)-α-L-Rha-(1→2)-α-L-Rha-(1→2)-α-D-Gal-(1→3)-β-D-GlcNAc-(1→|β-D-ManNAc-(1→2)</td></tr>
<tr><td>O1C</td><td>→3)-α-L-Rha-(1→2)-α-L-Rha-(1→3)-α-D-Gal-(1→3)-β-D-GlcNAc-(1→|β-D-ManNAc-(1→2)</td></tr>
<tr><td>O2</td><td>→3)-α-L-Rha-(1→2)-α-L-Rha-(1→3)-β-L-Rha-(1→4)-β-D-GlcNAc-(1→ | α-D-Fuc3NAc-(1→2)</td></tr>
<tr><td>O3</td><td>β-L-RhaNAc(1→4)α-D-Glc-(1→4)| | →3)-β-D-GlcNAc-(1→3)-α-D-Gal-(1→3)-β-D-GlcNAc-(1→</td></tr>
<tr><td>O4:K52</td><td>→2)-α-L-Rha-(1→6)-α-D-Glc-(1→3)-α-L-FucNAc-(1→3)-β-D-GlcNAc(1→</td></tr>
<tr><td>O4:K6</td><td>α-D-Glc-(1→3) | →2)-α-L-Rha-(1→6)-α-D-Glc-(1→3)-α-L-FucNAc-(1→3)-β-D-GlcNAc(1→</td></tr>
<tr><td>O5ab</td><td>→4)-β-D-Qui3NAc-(1→3)-β-D-Ribf-(1→4)-β-D-Gal-(1→3)-α-D-GalNAc(1→</td></tr>
<tr><td>O5ac(strain 180/C3)</td><td>→2)-β-D-Qui3NAc-(1→3)-β-D-Ribf-(1→4)-β-D-Gal-(1→3)-α-D-GalNAc(1→</td></tr>
<tr><td>O6:K2; K13; K15</td><td>→4)-α-D-GalNAc-(1→3)-β-D-Man-(1→4)-β-D-Man-(1→3)-α-D-GlcNAc-(1→ | β-D-Glc-(1→2)</td></tr>
<tr><td>O6:K54</td><td>→4)-α-D-GalNAc-(1→3)-β-D-Man-(1→4)-β-D-Man-(1→3)-α-D-GlcNAc-(1→|β-D-GlcNAc-(1→2)</td></tr>
<tr><td>O7</td><td>α-L-Rha-(1→3) | →3)-β-D-Qui4NAc-(1→2)-α-D-Man-(1→4)-β-D-Gal-(1→3)-α-D-GlcNAc-(1→</td></tr>
<tr><td>O10</td><td>→3)-α-L-Rha-(1→3)-α-L-Rha-(1→3)-α-D-Gal-(1→3)-β-D-GlcNAc-(1→ | α-D-Fuc4NAcyl-(1→2)<br>Acyl=acetyl (60%) or (R)-3-hydroxybutyryl (40%)</td></tr>
<tr><td>O16</td><td>→2)-β-D-Galf-(1→6)-α-D-Glc-(1→3)-α-L-Rha2Ac-(1→3)-α-D-GlcNAc-(1→</td></tr>
<tr><td>O17</td><td>α-D-Glc-(1→6) | →6)-α-D-Man-(1→2)-α-D-Man-(1→2)-β-D-Man-(1→3)-α-D-GlcNAc(1→</td></tr>
<tr><td>O18A, O18ac</td><td>→2)-α-L-Rha-(1→6)-α-D-Glc-(1→4)-α-D-Gal-(1→3)-α-D-GlcNAc-(1→ | β-D-GlcNAc-(1→3)</td></tr>
<tr><td>O18A1</td><td>α-D-Glc-(1→6) | →2)-α-L-Rha-(1→6)-α-D-Glc-(1→4)-α-D-Gal-(1→3)-α-D-GlcNAc-(1→ | β-D-GlcNAc-(1→3)</td></tr>
<tr><td>O18B</td><td>→3)-α-L-Rha-(1→6)-α-D-Glc-(1→4)-α-D-Gal-(1→3)-α-D-GlcNAc-(1→ | β-D-Glc-(1→3)</td></tr>
<tr><td>O18B1</td><td>α-D-Glc-(1→4) | →3)-α-L-Rha-(1→6)-α-D-Glc-(1→4)-α-D-Gal-(1→3)-α-D-GlcNAc-(1→ | β-D-Glc-(1→3)</td></tr>
<tr><td>O21</td><td>β-D-Gal-(1→4) | →3)-β-D-Gal-(1→4)-β-D-Glc-(1→3)-β-D-GalNAc-(1→ | β-D-GlcNAc-(1→2)</td></tr>
<tr><td>O23A</td><td>α-D-Glc-(1→6) | →6)-α-D-Glc-(1→4)-β-D-Gal-(1→3)-α-D-GalNAc-(1→3)-β-D-GlcNAc-(1→ | β-D-GlcNAc(1→3)</td></tr>
<tr><td>O24</td><td>→7)-α-Neu5Ac-(2→3)-β-D-Glc-(1→3)-β-D-GalNAc-(1→ | α-D-Glc-(1→2)</td></tr>
</table>

FIG. 9B

β-Glc*p*-
1
↓
6

| | |
|---|---|
| O25b | α-Rha*p*-(1⟶3)-α-Glc*p*-(1⟶3)-Rha*p*20Ac-(1⟶3)-β-Glc*p*NAc- |
| O25 | β-D-Glc-(1⟶6) \| ⟶4)-α-D-Glc-(1⟶3)-α-L-FucNAc-(1⟶3)-β-D-GlcNAc-(1⟶ \| α-L-Rha-(1⟶3) |
| O26 | ⟶3)-α-L-Rha-(1⟶4)-α-L-FucNAc-(1⟶3)-β-D-GlcNAc-(1⟶ |
| O28 | ⟶2)-(R)-Gro-1-P⟶4)-β-D-GlcNAc-(1⟶3)-β-D-Galf2Ac-(1⟶3)-α-D-GlcNAc-(1⟶ |
| O44 | a-D-Glc-(1 ⟶ 4)\|⟶ 6)-a-D-Man-(1 ⟶ 2)-a-D-Man-(1 ⟶ 2)-b-D-Man-(1 ⟶ 3)-a-D-GlcNAc(1 ⟶ |
| O45 | ⟶ 2)-b-D-Glc-(1 ⟶ 3)-a-L-6dTal2Ac-(1 ⟶ 3)-a-D-FucNAc-(1 ⟶ |
| O45rel | ⟶ 2)-b-D-Glc-(1 ⟶ 3)-a-L-6dTal2Ac-(1 ⟶ 3)-b-D-GlcNAc-(1 ⟶ |
| O55 | ⟶ 6)-b-D-GlcNAc-(1 ⟶ 3)-a-D-Gal-(1 ⟶ 3)-b-D-GalNAc-(1 ⟶\|a-Col-(1 ⟶ 2)-b-D-Gal-(1 ⟶ 3) |
| O56 | ⟶ 7)-a-Neu5Ac-(2 ⟶ 3)-b-D-Glc-(1 ⟶ 3)-b-D-GlcNAc-(1 ⟶\|a-D-Gal-(1 ⟶ 2) |
| O58 | 3-O-[(R)-1-carboxyethyl]-a-L-Rha -(1 ⟶ 3)\|⟶ 4)-a-D-Man-(1 ⟶ 4)-a-D-Man2Ac-(1 ⟶ 3)-b-D-GlcNAc-(1 ⟶ |
| O64 | b-D-Gal-(1 ⟶ 6)\|⟶ 3)-a-D-ManNAc-(1 ⟶ 3)-b-D-GlcA-(1 ⟶ 3)-b-D-Gal-(1 ⟶ 3)-b-D-GlcNAc(1 ⟶ |
| O69 | ⟶ 2)-a-L-Rha-(1 ⟶ 2)-a-L-Rha-(1 ⟶ 2)-a-D-Gal-(1 ⟶ 3)-b-D-GlcNAc-(1 ⟶ Erbing et al. (1977) |
| O73 (Strain 73-1) | a-D-Glc-(1 ⟶ 3)\|⟶ 4)-a-D-Man-(1 ⟶ 2)-a-D-Man-(1 ⟶ 2)-b-D-Man-(1 ⟶ 3)-a-D-GalNAc(1 ⟶ |
| O75 | b-D-Man-(1 ⟶ 4)\|⟶ 3)-a-D-Gal-(1 ⟶ 4)-a-L-Rha-(1 ⟶ 3)-b-D-GlcNAc-(1 ⟶ |
| O77 | ⟶ 6)-a-D-Man-(1 ⟶ 2)-a-D-Man-(1 ⟶ 2)-b-D-Man-(1 ⟶ 3)-a-D-GlcNAc(1 ⟶ |
| O78 | ⟶ 4)-b-D-GlcNAc-(1 ⟶ 4)-b-D-Man-(1 ⟶ 4)-a-D-Man-(1 ⟶ 3)-b-D-GlcNAc-(1 ⟶ |
| O86 | a-D-Gal-(1 ⟶ 3)\|⟶ 4)-a-L-Fuc-(1 ⟶ 2)-b-D-Gal-(1 ⟶ 3)-a-D-GalNAc-(1 ⟶ 3)-b-D-GalNAc-(1 ⟶ |
| O88 | a-L-6dTal-(1 ⟶ 3)\|⟶ 4)-a-D-Man-(1 ⟶ 3)-a-D-Man-(1 ⟶ 3)-b-D-GlcNAc-(1 ⟶ |
| O90 | ⟶ 4)-a-L-Fuc2/3Ac-(1 ⟶ 2)-b-D-Gal-(1 ⟶ 3)-a-D-GalNAc-(1 ⟶ 3)-b-D-GalNAc-(1 ⟶ |
| O98 | ⟶ 3)-a-L-QuiNAc-(1 ⟶ 4)-a-D-GalNAcA-(1 ⟶ 3)-a-L-QuiNAc-(1 ⟶ 3)-b-D-GlcNAc-(1 ⟶ |
| O104 | ⟶ 4)-a-D-Gal-(1 ⟶ 4)-a-Neu5,7,9Ac3-(2 ⟶ 3)-b-D-Gal-(1 ⟶ 3)-b-D-GalNAc-(1 ⟶ |
| O111 | a-Col-(1 ⟶ 6)\|⟶ 4)-a-D-Glc-(1 ⟶ 4)-a-D-Gal-(1 ⟶ 3)-b-D-GlcNAc-(1 ⟶\|a-Col-(1 ⟶ 3) |
| O113 | ⟶ 4)-a-D-GalNAc-(1 ⟶ 4)-a-D-GalA-(1 ⟶ 3)-a-D-Gal-(1 ⟶ 3)-b-D-GlcNAc-(1 ⟶\|b-D-Gal-(1 ⟶ 3) |
| O114 | ⟶ 4)-b-D-Qui3N(N-acetyl-L-seryl)-(1 ⟶ 3)-b-D-Ribf-(1 ⟶ 4)-b-D-Gal-(1 ⟶ 3)-a-D-GlcNAc(1 ⟶ |

FIG. 9C

O119 β-D-RhaNAc3NFo-(1→3) | →2)-β-D-Man-(1→3)-α-D-Gal-(1→4)-α-L-Rha-(1→3)-α-D-GlcNAc-(1→

O121 →3)-β-D-Qui4N(N-acetyl-glycyl)-(1→4)-α-D-GalNAc3AcA6N-(1→4)-α-D-GalNAcA-(1→3)-α-D-GlcNAc-(1→

O124 4-O-[(R)-1-carboxyethyl]-β-D-Glc-(1→6)-α-D-Glc(1→4) |→3)-α-D-Gal-(1→6)-β-D-Galf-(1→3)-β-D-GalNAc-(1→

O125 α-D-Glc-(1→3) | →4)-β-D-GalNAc-(1→2)-α-D-Man-(1→3)-α-L-Fuc-(1→3)-α-D-GalNAc-(1→ | β-D-Gal-(1→3)

O126 →2)-β-D-Man-(1→3)-β-D-Gal-(1→3)-α-D-GlcNAc-(1→3)-β-D-GlcNAc-(1→ | α-L-Fuc-(1→2)

O127 →2)-α-L-Fuc-(1→2)-β-D-Gal-(1→3)-α-D-GalNAc-(1→3)-α-D-GalNAc-(1→

O128 α-L-Fuc-(1→2) | →6)-β-D-Gal-(1→3)-β-D-GalNAc-(1→4)-α-D-Gal-(1→3)-β-D-GalNAc-(1→

O136 →4)-β-Pse5Ac7Ac-(2→4)-β-D-Gal-(1→4)
-β-D-GlcNAc-(1→β-Pse5Ac7Ac=5,7-diacetamido-3,5,7,9-tetradeoxy-L-glycero-β-L-manno-nonulosonic acid O138 →2)-α-L-Rha-(1→3)-α-L-Rha-(1→4)-α-D-GalNAcA-(1→3)-β-D-GlcNAc-(1→

O141 α-L-Rha-(1→3) |→4)-α-D-Man-(1→3)-α-D-Man6Ac-(1→3)-β-D-GlcNAc-(1→ | β-D-GlcA-(1→2)

O142 →2)-α-L-Rha-(1→6)-α-D-GalNAc-(1→4)-α-D-GalNAc-(1→3)-α-D-GalNAc-(1→ | β-D-GlcNAc-(1→3)

O143 →2)-β-D-GalA6R3,4Ac-(1→3)-α-D-GalNAc-(1→4)-β-D-GlcA-(1→3)-β-D-GlcNAc-(1→ R=1,3-dihydroxy-2-propylamino O147 →2)-α-L-Rha-(1→2)-α-L-Rha-(1→4)-β-D-GalA-(1→3)-β-D-GalNAc-(1→

O149 →3)-β-D-GlcNAc-(S)-4,6Py-(1→3)-β-L-Rha-(1→4)-β-D-GlcNAc-(1→ (S)-4,6Py=4,6-O-[(S)-1-carboxyethylidene]-

O152 β-L-Rha-(1→4) | →3)-α-D-GlcNAc-(1-P→6)-α-D-Glc-(1→2)-β-D-Glc-(1→3)-β-D-GlcNAc-(1→

O157 →2)-α-D-Rha4NAc-(1→3)-α-L-Fuc-(1→4)-β-D-Glc-(1→3)-α-D-GalNAc-(1→

O158 α-D-Glc-(1→6) | →4)-α-D-Glc-(1→3)-α-D-GalNAc-(1→3)-β-D-GalNAc-(1→ | α-L-Rha-(1→3)

O159 α-L-Fuc-(1→4) | →3)-β-D-GlcNAc-(1→4)-α-D-GalA-(1→3)-α-L-Fuc-(1→3)-β-D-GlcNAc-(1→

O164 β-D-Glc-(1→6)-α-D-Glc(1→4) | →3)-β-D-Gal-(1→6)-β-D-Galf-(1→3)-β-D-GalNAc-(1→

O173 α-L-Fuc-(1→4) | →3)-α-D-Glc-(1-P→6)-α-D-Glc-(1→2)-β-D-Glc-(1→3)-β-D-GlcNAc-(1→

62D1 α-D-Gal(1→6) | →2)-β-D-Qui3NAc-(1→3)-α-L-Rha-(1→3)-β-D-Gal-(1→3)-α-D-FucNAc-(1→ Suggested as Erwinia herbicola

FIG. 10A

| | |
|---|---|
| O22 | →6)-α-D-Glc-(1→4)-β-D-GlcA-(1→4)-β-D-GalNAc3Ac-(1→3)-α-D-Gal-(1→3)-β-D-GalNAc-(1→ |
| O35 | →3)-α-L-Rha-(1→2)-α-L-Rha-(1→3)-α-L-Rha-(1→2)-α-L-Rha-(1→3)-β-D-GlcNAc-(1→ \| α-D-GalNAcA6N-(1→2) |
| O65 | →2)-β-D-Qui3NAc-(1→4)-α-D-GalA6N-(1→4)-α-D-GalNAc-(1→4)-β-D-GalA-(1→3)-α-D-GlcNAc-(1→ |
| O66 | →2)-β-D-Man-(1→3)-α-D-GlcNAc-(1→2)-β-D-Glc3Ac-(1→3)-α-L-6dTal-(1→3)-α-D-GlcNAc(1→ |
| O83 | →6)-α-D-Glc-(1→4)-β-D-GlcA-(1→6)-β-D-Gal-(1→4)-β-D-Gal-(1→4)-β-D-GlcNAc-(1→ |
| O91 | →4)-α-D-Qui3NAcyl-(1→4)-β-D-Gal-(1→4)-β-D-GlcNAc-(1→4)-β-D-GlcA6NGly-(1→3)-β-D-GlcNAc-(1→ Acyl=(R)-3-hydroxybutyryl |
| O105 | β-D-Ribf-(1→3) \|→4)-α-D-GlcA2Ac3Ac-(1→2)-α-L-Rha4Ac-(1→3)-β-L-Rha-(1→4)-β-L-Rha-(1→3)-β-D-GlcNAc6Ac-(1→ |
| O116 | →2)-β-D-Qui4NAc-(1→6)-α-D-GlcNAc-(1→4)-α-D-GalNAc-(1→4)-α-D-GalA-(1→3)-β-D-GlcNAc-(1→ |
| O117 | →4)-β-D-GalNAc-(1→3)-α-L-Rha-(1→4)-α-D-Glc-(1→4)-β-D-Gal-(1→3)-α-D-GalNAc-(1→ |
| O139 | β-D-Glc-(1→3) \| →3)-α-L-Rha-(1→4)-α-D-GalA-(1→2)-α-L-Rha-(1→3)-α-L-Rha-(1→2)-α-L-Rha-(1→3)-α-D-GlcNAc-(1→ |
| O153 | →2)-β-D-Ribf-(1→4)-β-D-Gal-(1→4)-α-D-GlcNAc-(1→4)-β-D-Gal-(1→3)-α-D-GlcNAc-(1→ Ratnayake (1994a) |
| O167 | α-D-Galf-(1→4) \| →2)-β-D-GalA6N(L)Ala-(1→3)-α-D-GlcNAc-(1→2)-β-D-Galf-(1→5)-β-D-Galf-(1→3)-β-D-GlcNAc-(1→ |
| O172 | →3)-α-L-FucNAc-(1→4)-α-D-Glc6Ac-(1-P→4)-α-D-Glc-(1→3)-α-L-FucNAc-(1→3)-α-D-GlcNAc-(1→ |

FIG. 10B

| | |
|---|---|
| O8 | →2)-α-D-Man-(1→2)-α-D-Man-(1→3)-β-D-Man-(1→ |
| O9a | →2)-α-D-Man-(1→2)-α-D-Man-(1→3)-α-D-Man-(1→3)-α-D-Man-(1→ |
| O9 | →2)-[α-D-Man-(1→2)]2-α-D-Man-(1→3)-α-D-Man-(1→3)-α-D-Man-(1→ |
| O20ab | →2)-β-D-Ribf-(1→4)-α-D-Gal-(1→ Vasil'ev & Zakharova (1976) |
| O20ac | α-D-Gal-(1→3) \| →2)-β-D-Ribf-(1→4)-α-D-Gal-(1→ |
| O52 | →3)-β-D-Fucf-(1→3)-β-D-6dmanHep2Ac-(1→ |
| O97 | →3)-α-L-Rha-(1→3)-β-L-Rha-(1→ \|\| β-D-Xulf-(2→2)β-D-Xulf-(2→2) |
| O101 | →6)-α-D-GlcNAc-(1→4)-α-D-GalNAc-(1→ |

FIG. 11
Predicted Phe1 destabilizing mutations
Predicted Phe1 destabilizing mutations
50
40
30
20
10
0
-10
-20
ALA
ARG
ASN
ASP
CYS
GLN
GLU
GLY
HIS
ILE
LEU
LYS
MET
SER
THR
TRP
TYR
VAL

FIG. 33

C B A

*E. coli* O8: -3)-β-D-Man*p*-(1--2)-α-D-Man*p*-(1--2)-α-Man*p*-(1- =*K.pneumoniae* O5 (3RU)

C B A

-3)-α-D-Man*p*-(1--2)-α-D-Man*p*-(1--2)-α-Man*p*-(1- =*K.pneumoniae* O3b (3RU)

D C B A

*E. coli* O9A: -3)-α-D-Man*p*-(1--2)-α-D-Man*p*-(1--3)-α-Man*p*-(1--3)-α-Man*p*-(1- =*K.pneumoniae* O3a (4RU)

E D C B A

*E. coli* O9: -2)-α-D-Man*p*-(1--2)-[α-D-Man*p*-(1--2)-α-Man*p*-(1--3)-α-Man*p*-(1--3)-α-Man*p*-(1- =*K.pneumoniae* O3 (5RU)

*ESCHERICHIA COLI* COMPOSITIONS AND METHODS THEREOF

REFERENCE TO SEQUENCE LISTING

This application is being filed electronically via EFS-Web and includes an electronically submitted sequence listing in .xml format. The .xml file contains a sequence listing entitled "PC072591B v2 Sequence Listing .xml" created on Mar. 4, 2024 and having a size of 163 KB. The sequence listing contained in this .xml file is part of the specification and is incorporated herein by reference in its entirety.

FIELD OF THE INVENTION

The present invention relates to *Escherichia coli* compositions and methods thereof.

BACKGROUND OF THE INVENTION

The threat to public health posed by increasing antimicrobial drug resistance is described in recent reports published by the WHO and the CDC (Thelwall S N, et al. Annual Epidemiological Commentary Mandatory MRSA, MSSA and *E. coli* bacteraemia and *C. difficile* infection data 2015/16. 2016; Russo T A, et al. Microbes and infection 2003; 5:449-56). Priority pathogens described by both agencies include Enterobacteriacea resistant to third-generation cephalosporins, conferred through the production extended-spectrum beta-lactamases (ESBLs), and to carbapenems due to the production of carbapenemase enzymes. According to the CDC, ESBL-expressing Enterobacteriacea are a serious threat while Enterobacteriacea resistance to last-line carbapenem antibiotics is considered an urgent threat. *E. coli* ESBL strains are becoming more widespread and untreatable infections caused by *Klebsiella pneumoniae* producing both ESBLs and carbapenemases are becoming increasingly common, especially in developing countries.

*Escherichia coli* is one of the most common human bacterial pathogens with clinical presentations that include blood stream infections (70/100,000 in the US) (Marder E P, et al. Foodborne pathogens and disease 2014; 11:593-5), urinary tract infections (catheter associated (250,00-525,000 annual US cases) (Al-Hasan M N, et al. The Journal of antimicrobial chemotherapy 2009; 64:169-7)); non-catheter associated (6-8 million annual US cases) (id.)); surgical site infections (127,500 annual US cases), pneumonia (14,100-23,400 annual US cases) (id.) and serious food poisoning related diarrhea (63,000 annual US cases) (Zowawi H M, et al. Nature reviews Urology 2015; 12:570-84). They are classified serologically by differences in the structure of the lipopolysaccharide-associated O-antigen (>180 known serotypes), the capsule polysaccharide K-antigen (>80 serotypes), and the flagellar H-antigen (>50 serotypes).

Urinary tract infections (UTIs) most often present as a cystitis that in some individuals can recur repeatedly following resolution. Left untreated, they can progress to pylonephritis and blood stream infections. *E. coli* infections are associated with high levels of antibiotic resistance (Rogers B A, et al. The Journal of antimicrobial chemotherapy 2011; 66:1-14) with many strains being resistant to multiple antibiotics including antibiotics of last resort such as carbapenems and polymyxins (Nicolas-Chanoine M-H, et al. Clinical Microbiology Reviews 2014; 27:543-74). In particular, O25b serotype multilocus sequence type (MLST) 131 has emerged as a worldwide pandemic clone, causing predominantly community-onset infections with high rates of resistance to extended-spectrum cephalosporins (ESBLs) and fluoroquinolones (Poolman J T, et al. The Journal of infectious diseases 2016; 213:6-13; Podschun R, et al. Clin Microbiol Rev 1998; 11:589-603). *E. coli* BSI and UTI infecting strains are also known as invasive Extra-intestinal Pathogenic *E. coli* (ExPEC) or uropathogenic *E. coli* (UPEC). Of the >180 identified *E. coli* O-antigen serotypes, among ExPEC strains it is reported that a subset of between 10 and 12 O serotypes account for >60% of bacteremia cases (Yinnon A M, et al. QJM: monthly journal of the Association of Physicians 1996; 89:933-41). Second to *E. coli, Klebsiella* spp. (including *K. pneumoniae* and *K. oxytoca*) are the next most common Gram-negative pathogens associated with invasive infections including UTIs, pneumonia, intra-abdominal infection, and bloodstream infection (BSI) (Podschun R, et al. Clin Microbiol Rev 1998; 11:589-603; Anderson D J, et al. PLOS One 2014; 9: e91713; Chen L, et al. Trends Microbiol 2014; 22:686-96; Iredell J, et al. Bmj 2016; 352: h6420). *Klebsiella* maintain a profound ability to acquire antibiotic resistance through horizontally transmissible ESBL and carbapenem resistance conferring genes (Follador R, et al. Microbial Genomics 2016; 2: e000073; Schrag S J, Farley M M, Petit S, et al. Epidemiology of Invasive Early-Onset Neonatal Sepsis, 2005 to 2014. 2016; 138: e20162013). Accordingly, during the last decade the prevalence of ESBL-resistant *Klebsiella* producing extended-spectrum β-lactamases (ESBL) has increased dramatically globally. *Klebsiella* spp. can express up to 8 different O-types and >80 K-types. While there are a multitude of K-antigens associated with virulent *Klebsiella* strains, only four O-antigen serotypes account for >80% of *Klebsiella* clinical isolates irrespective of sample site (blood, urine, sputum), infection status (invasive versus non-invasive) or the nature of acquisition (community vs nosocomial) (Stoll B J, et al. Pediatrics 2011; 127:817-26).

The increased rate of invasive multidrug-resistant (MDR) *E. coli* and *Klebsiella* infections in the vulnerable newborn population and the elderly underscores the need for vaccine-based approaches as an alternative to standard-of-care antibiotics which are becoming less effective.

SUMMARY OF THE INVENTION

To meet these and other needs, the present invention relates to compositions and methods of use thereof for eliciting immune responses against *E. coli* and *K. pneumoniae* serotypes.

In one embodiment, the invention provides a composition comprising a polypeptide derived from FimH or a fragment thereof; and a saccharide comprising a structure selected from any one of Formula O1, Formula O1A, Formula O1B, Formula O1C, Formula O2, Formula O3, Formula O4, Formula O4: K52, Formula 04: K6, Formula O5, Formula O5ab, Formula O5ac, Formula O6, Formula O6: K2; K13; K15, Formula O6: K54, Formula O7, Formula O8, Formula O9, Formula O10, Formula O11, Formula O12, Formula O13, Formula O14, Formula O15, Formula O16, Formula O17, Formula O18, Formula O18A, Formula O18ac, Formula O18A1, Formula O18B, Formula O18B1, Formula O19, Formula O20, Formula O21, Formula O22, Formula O23, Formula O23A, Formula O24, Formula O25, Formula O25a, Formula O25b, Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45, Formula O45, Formula O45rel, Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula 62D1, Formula O63, Formula O64, Formula O65, Formula O66, Formula O68, Formula O69, Formula O70, Formula O71, Formula O73, Formula O73, Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144, Formula O145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, Formula O187.

In one aspect, the composition further comprises at least one saccharide derived from any one *K. pneumoniae* type selected from the group consisting of O1, O2, O3, and O5.

In another aspect, wherein the composition further comprises the saccharide derived from *K. pneumoniae* which is conjugated to a carrier protein; and the saccharide derived from *E. coli* is conjugated to a carrier protein.

In another embodiment, the invention provides a composition comprising a polypeptide derived from FimH or a fragment thereof; and at least one saccharide derived from any one *K. pneumoniae* type selected from the group consisting of O1, O2, O3, and O5. In one aspect, the composition further comprising at least one saccharide comprising a structure selected from any one of Formula O1, Formula O1A, Formula O1B, Formula O1C, Formula O2, Formula O3, Formula O4, Formula 04: K52, Formula O4: K6, Formula O5, Formula O5ab, Formula O5ac, Formula O6, Formula O6: K2; K13; K15, Formula O6: K54, Formula O7, Formula O8, Formula O9, Formula O10, Formula O11, Formula O12, Formula O13, Formula O14, Formula O15, Formula O16, Formula O17, Formula O18, Formula O18A, Formula O18ac, Formula O18A1, Formula O18B, Formula O18B1, Formula O19, Formula O20, Formula O21, Formula O22, Formula O23, Formula O23A, Formula O24, Formula O25, Formula O25a, Formula O25b, Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45, Formula O45, Formula O45rel, Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula $62D_1$, Formula O63, Formula O64, Formula O65, Formula O66, Formula O68, Formula O69, Formula O70, Formula O71, Formula O73, Formula O73, Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144, Formula O145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, Formula O187.

In another aspect, wherein the saccharide derived from *K. pneumoniae* is conjugated to a carrier protein; and the saccharide derived from *E. coli* is conjugated to a carrier protein.

In a further embodiment, the invention provides a composition comprising at least one saccharide derived from any one *K. pneumoniae* type selected from the group consisting of O1, O2, O3, and O5; and at least one saccharide comprising a structure selected from any one of Formula O1, Formula O1A, Formula O1B, Formula O1C, Formula O2, Formula O3, Formula O4, Formula O4: K52, Formula O4: K6, Formula O5, Formula O5ab, Formula O5ac, Formula O6, Formula O6: K2; K13; K15, Formula O6: K54, Formula O7, Formula O8, Formula O9, Formula O10, Formula O11, Formula O12, Formula O13, Formula O14, Formula O15, Formula O16, Formula O17, Formula O18, Formula O18A, Formula O18ac, Formula O18A1, Formula O18B, Formula O18B1, Formula O19, Formula O20, Formula O21, Formula O22, Formula O23, Formula O23A, Formula O24, Formula O25, Formula O25a, Formula O25b, Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45, Formula O45, Formula O45rel, Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula $62D_1$, Formula O63, Formula O64, Formula O65, Formula O66, Formula O68, Formula O69, Formula O70, Formula O71, Formula O73, Formula O73, Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144, Formula O145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, Formula O187.

In one aspect, the composition further comprises a polypeptide derived from FimH or a fragment thereof. In another aspect, wherein the *E. coli* saccharide comprises Formula O8. In another aspect, wherein the *E. coli* saccharide comprises Formula O9.

In another embodiment, the invention provides a method of eliciting an immune response against *Escherichia coli* in a mammal, comprising administering to the mammal an effective amount of the composition according to any one of the above embodiments and aspects thereof.

In a further embodiment, the invention provides a method of eliciting an immune response against *Klebsiella pneumoniae* in a mammal, comprising administering to the mammal an effective amount of the composition according to any one of the above embodiments and aspects thereof.

In one aspect, the invention relates to a recombinant mammalian cell, including a polynucleotide encoding a polypeptide derived from *E. coli* or a fragment thereof. In some embodiments, the polynucleotide encodes a polypeptide derived from *E. coli* fimbrial H (fimH) polypeptide or a fragment thereof. In some embodiments, the polypeptide derived from *E. coli* FimH or fragment thereof includes a phenylalanine residue at the N-terminus of the polypeptide.

In one aspect, the invention relates to a method for producing a polypeptide derived from *E. coli* or a fragment thereof in a recombinant mammalian cell. The method includes culturing a recombinant mammalian cell under a suitable condition, thereby expressing the polypeptide or fragment thereof; and harvesting the polypeptide or fragment thereof. In some embodiments, the method further includes purifying the polypeptide or fragment thereof. In some embodiments, the yield of the polypeptide is at least 0.05 g/L. In some embodiments, the yield of the polypeptide is at least 0.10 g/L.

In one aspect, the invention relates to a composition that includes a polypeptide having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identity to SEQ ID NO: 1, SEQ ID NO: 2, SEQ ID NO: 3, SEQ ID NO: 4, SEQ ID NO: 20, SEQ ID NO: 23, SEQ ID NO: 24, SEQ ID NO: 26, SEQ ID NO: 28, and SEQ ID NO: 29, or any combination thereof.

In another aspect, the invention relates to a composition that includes a polypeptide having at least n consecutive amino acids from any one of SEQ ID NO: 1, SEQ ID NO: 2, SEQ ID NO: 3, SEQ ID NO: 4, SEQ ID NO: 20, SEQ ID NO: 23, SEQ ID NO: 24, SEQ ID NO: 26, SEQ ID NO: 28, and SEQ ID NO: 29, wherein n is 7 or more (eg. 8, 10, 12, 14, 16, 18, 20 or more). In some embodiments, the composition further includes a saccharide selected from any one Formula in Table 1, preferably Formula O1A, Formula O1B, Formula O2, Formula 06, and Formula O25B, wherein n is an integer from 1 to 100, preferably 31 to 100.

BRIEF DESCRIPTION OF THE DRAWINGS

FIG. 1A-1H—depict amino acid sequences, including amino acid sequences for exemplary polypeptides derived from *E. coli* or fragments thereof; and amino acid sequences for exemplary wzzB sequences.

FIG. 9A-9C—depict structures of O-antigens synthesized by the polymerase-dependent pathway with four or less residues in the backbone.

FIG. 10A-10B—FIG. 10A depicts structures of O-antigens synthesized by the polymerase-dependent pathway with five or six residues in the backbone; FIG. 10B depicts O-antigens believed to be synthesized by the ABC-transporter-dependent pathway.

(FIG. 20A) Information regarding vaccination schedule for rabbit study 1 VAC-2017-PRL-EC-0723; (FIG. 20B) vaccination schedule for rabbit study 2 VAC-2018-PRL-EC-077.

FIG. 21A depicts results from Rabbit 1-3 (Medium Activation); FIG. 21B depicts results from Rabbit 2-3 (Low Activation); FIG. 21C depicts results from Rabbit 3-1 (High Activation).

FIG. 22A depicts results from Rabbit A-1 (Unconjugated Poly); FIG. 22B depicts results from Rabbit A-3 (Unconjugated Poly); FIG. 22C depicts results from Rabbit A-4 (Unconjugated Poly); FIG. 22D depicts results from Rabbit 2-1 (low activation); FIG. 22E depicts results from Rabbit 2-2 (low activation); and FIG. 22F depicts results from Rabbit 2-3 (low activation).

FIG. 23A depicts results wherein —●— represents results from 025b 2831 vs PD3 antisera; —■— represents results from O25b 2831 wt vs prebleed; —▲— represents results from O25b 2831/fepE vs PD3 antisera; —▼— represents results from 025b 2831/fepE vs prebleed.

FIG. 23B depicts results wherein —●— represents results from O25b 2401 vs PD3 antisera; —■— represents results from O25b 2401 vs prebleed; —▲— represents results from 025b 2401/fepE vs PD3 antisera; —▼— represents results from 025b 2401/fepE vs prebleed. FIG. 23C depicts results wherein —●— represents results from *E. coli* K12 vs PD3 antisera; and —■— represents results from *E. coli* K12 vs prebleed.

FIG. 26A shows OPA titers of Rabbit 2-3 pre-immune serum (—●—) and post-immune serum wk 13 (—■—). FIG. 26B shows OPA titers of Rabbit 1-2 pre-immune serum (—●—) and post-immune serum wk 19 (—■—). FIG. 26C shows Rabbit 1-2 wk 19 OPA Titer Specificity, in which OPA activity of Rabbit 1-2 immune serum is blocked by pre-incubation with 100 μg/mL of purified unconjugated O25b long O-antigen polysaccharide, wherein —■— represents results from Rabbit 1-2 immune serum wk 19; and —▼— represents results from Rabbit 1-2 wk 19 w/R1 Long-OAg.

FIG. 27B and FIG. 27C show graphs depicting O-antigen O25b IgG levels elicited by unconjugated O25b long O-antigen polysaccharide (FIG. 27B, **025*b* Free Poly (2 μg)) and derived O25b RAC/DMSO long O-antigen glycoconjugate (FIG. 27**C, O25b-$CRM_{197}$ RAC Long (2 μg)), wherein — . . . — (dotted line) represents Naïve CD1 O25b IgG level.

FIG. 33—depicts structures of the repeat unit (RU) of *E. coli* and *K. pneumoniae* polymannan O-antigens. Legend: Trimeric *E. coli* O8 and *K. pneumoniae* O5 are identical, as are the terameric *E. coli* O9A/*K. pneumoniae* O3a and pentameric *E. coli* O9/*K. pneumoniae* O3. Differentiation of the *K. pneumoniae* 03 subtypes at the level of biosynthetic enzyme sequences is described in Guachalla L M et al. (Scientific Reports 2017; 7:6635).

SEQUENCE IDENTIFIERS

Figure 2A:
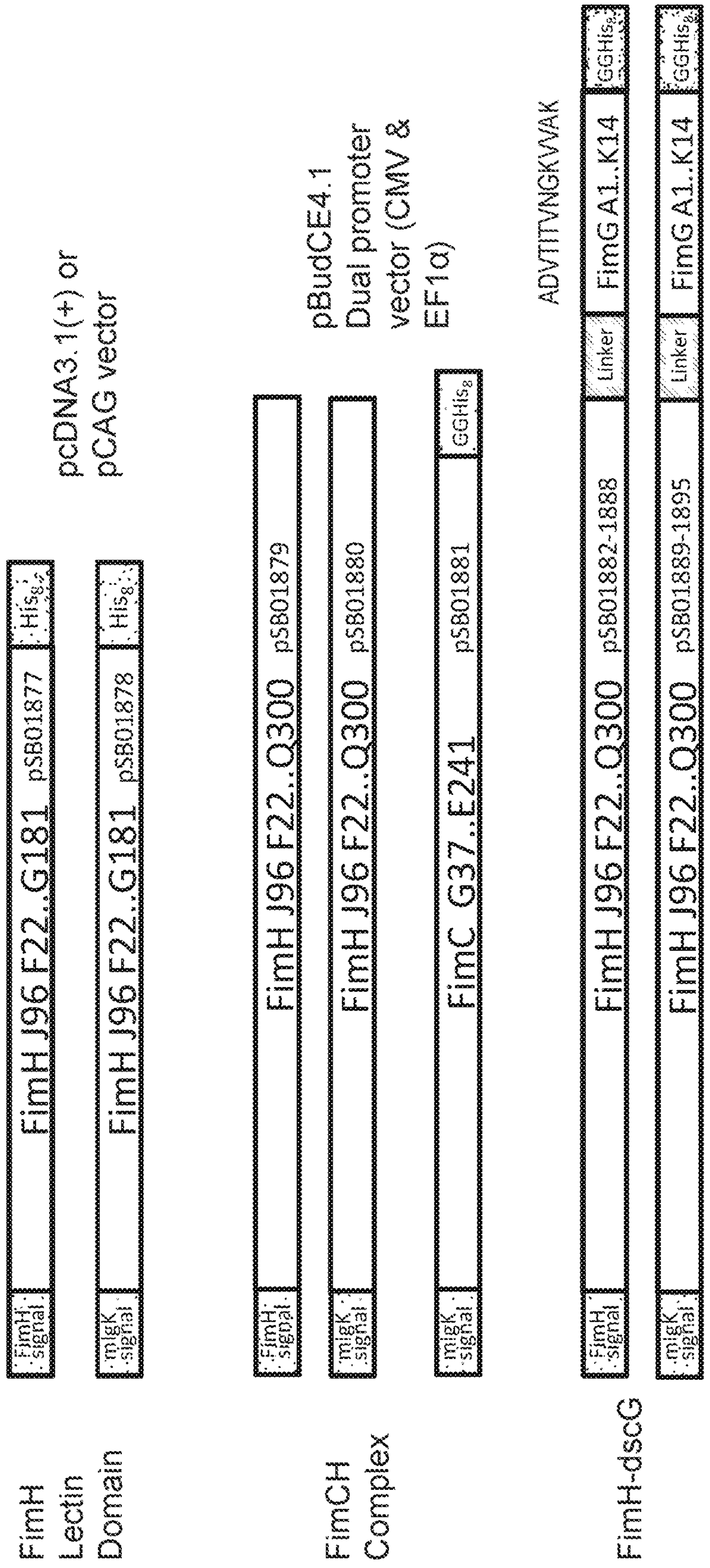
FIG. 2A-2T—depict maps of exemplary expression vectors.
Figure 2B:
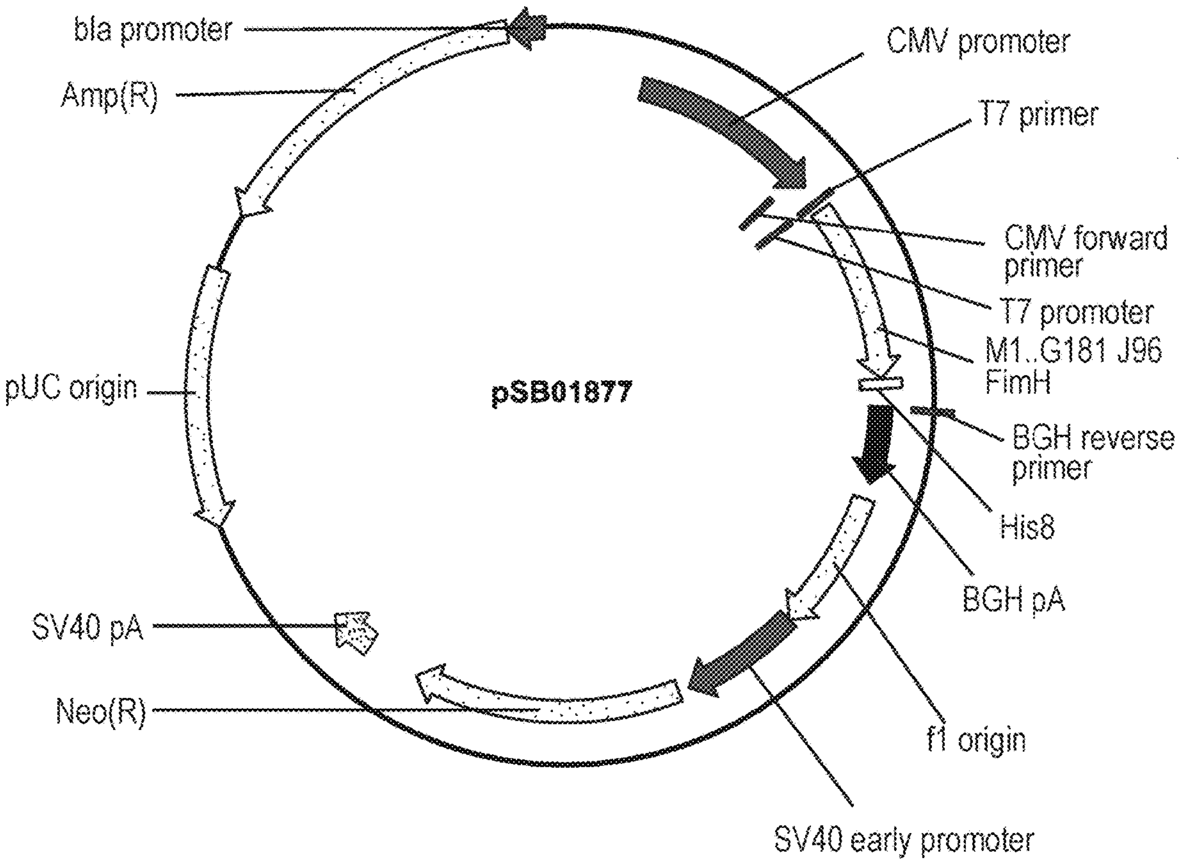
Figure 2C:
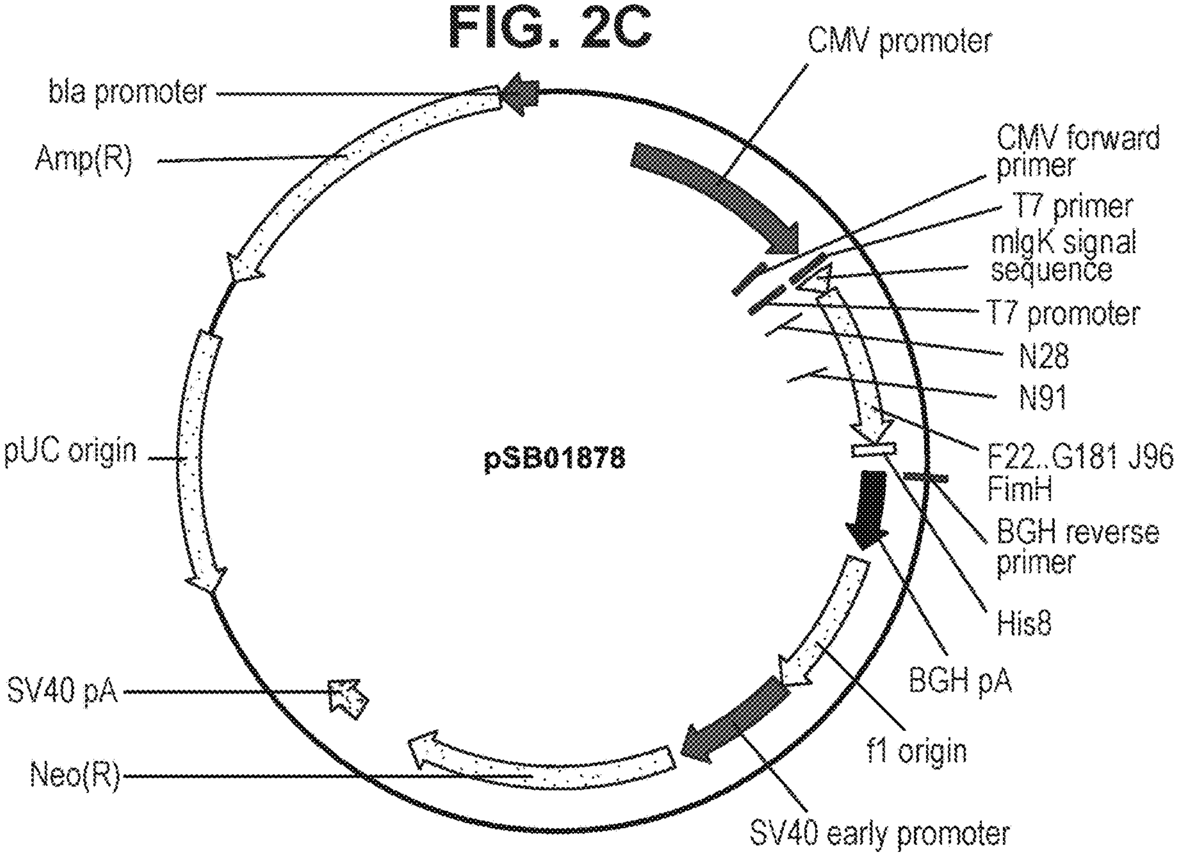
Figure 2D:
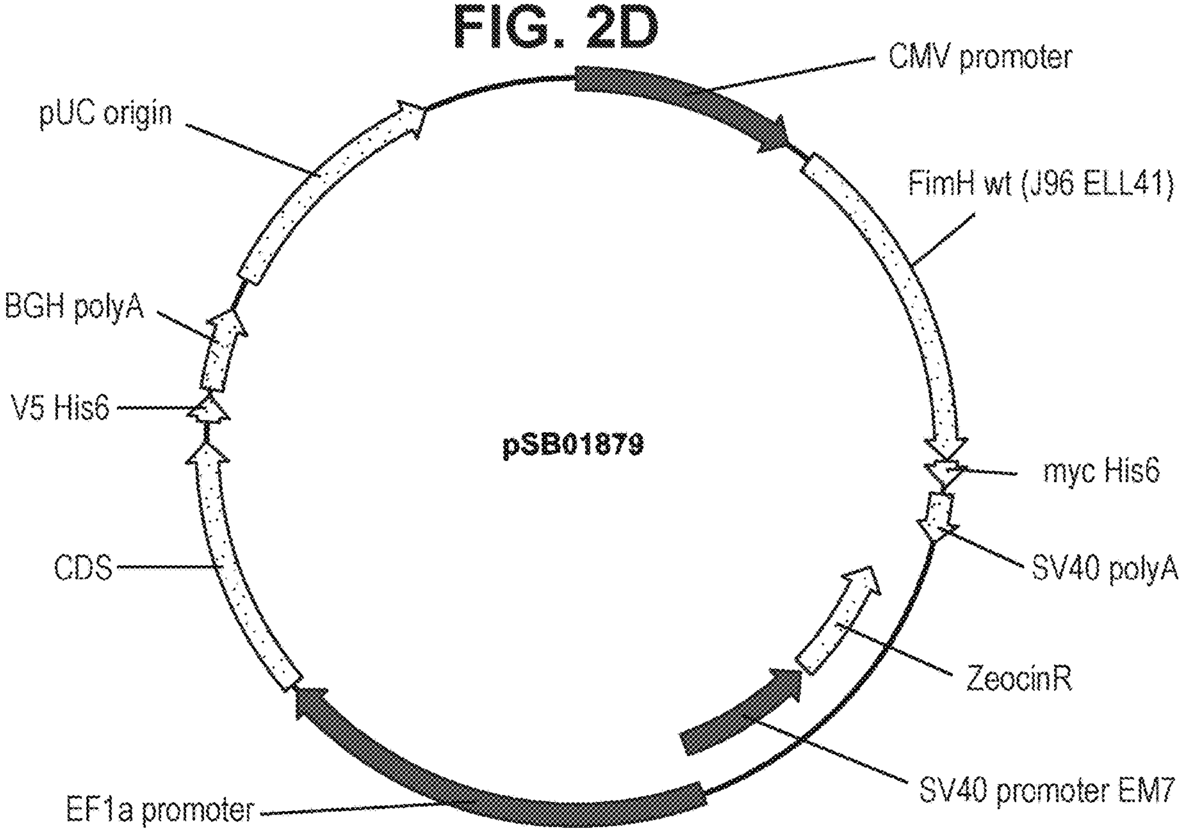
Figure 2E:
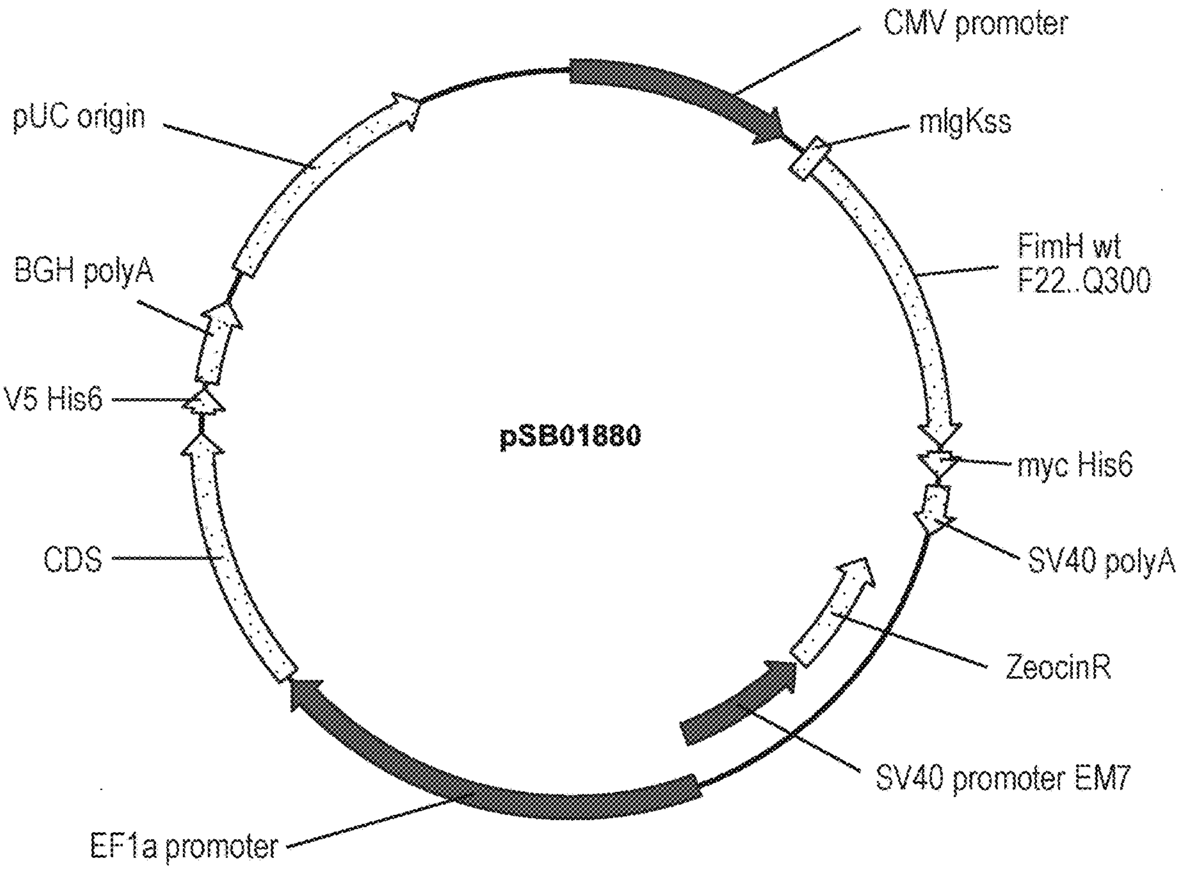
Figure 2F:
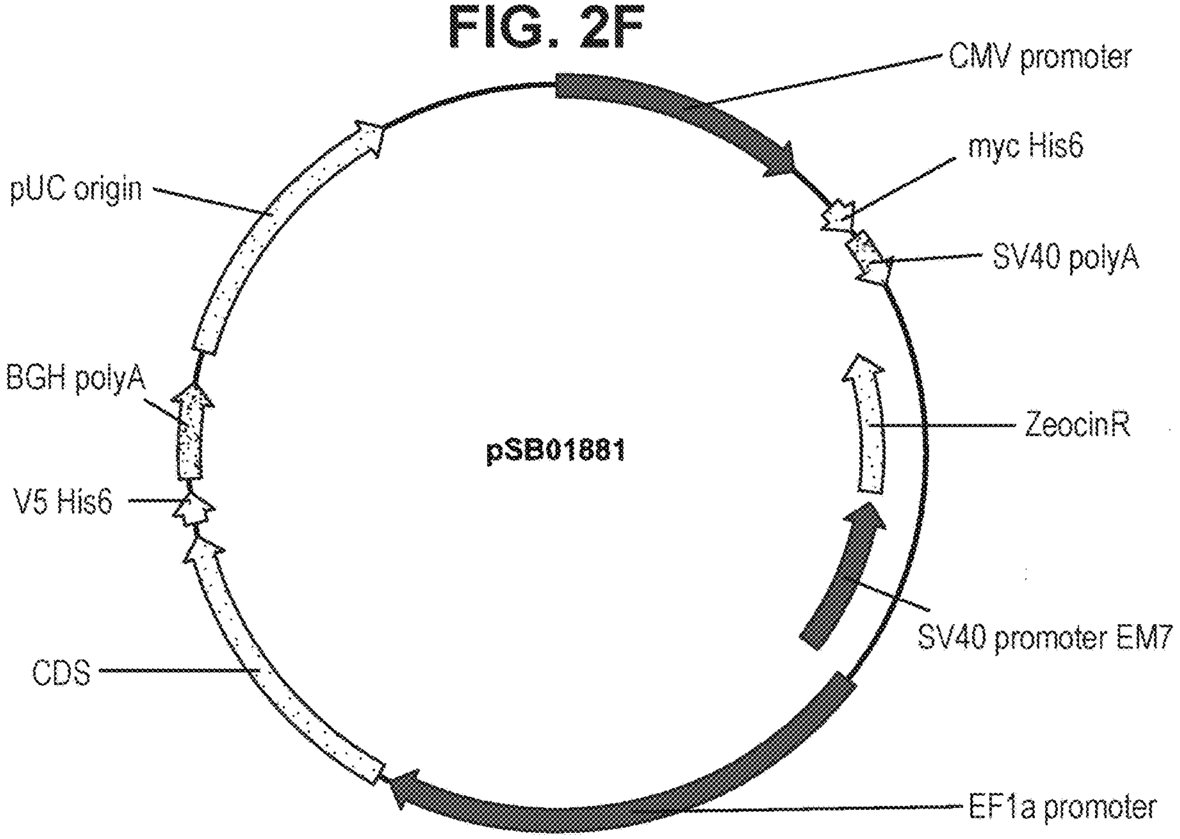
Figure 2G:
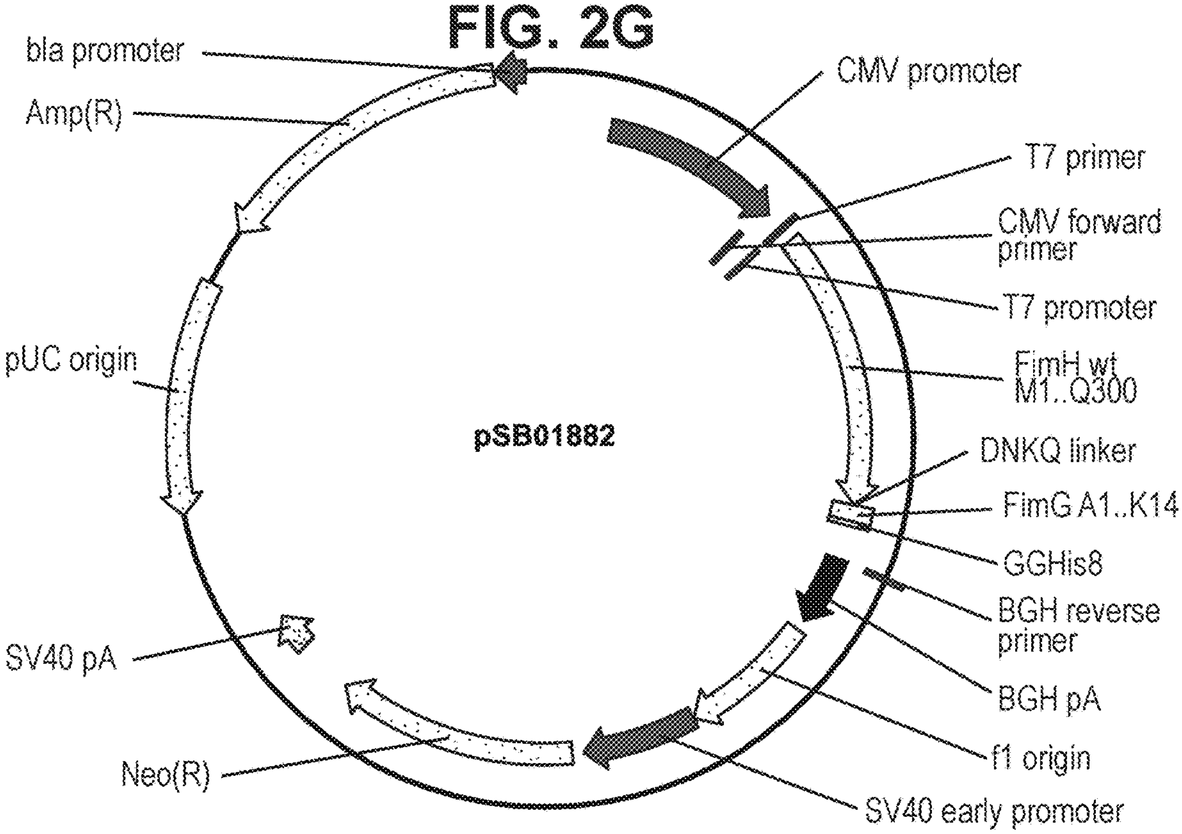
Figure 2H:
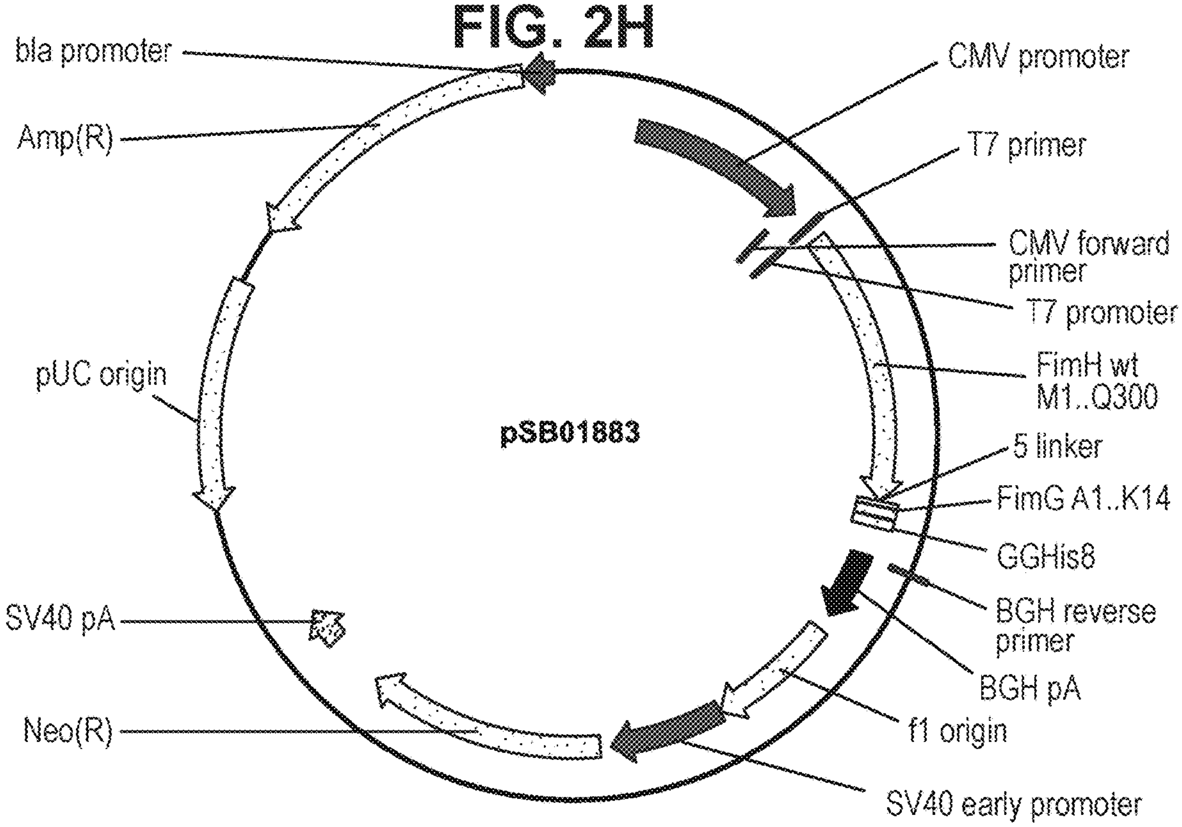
Figure 2I:
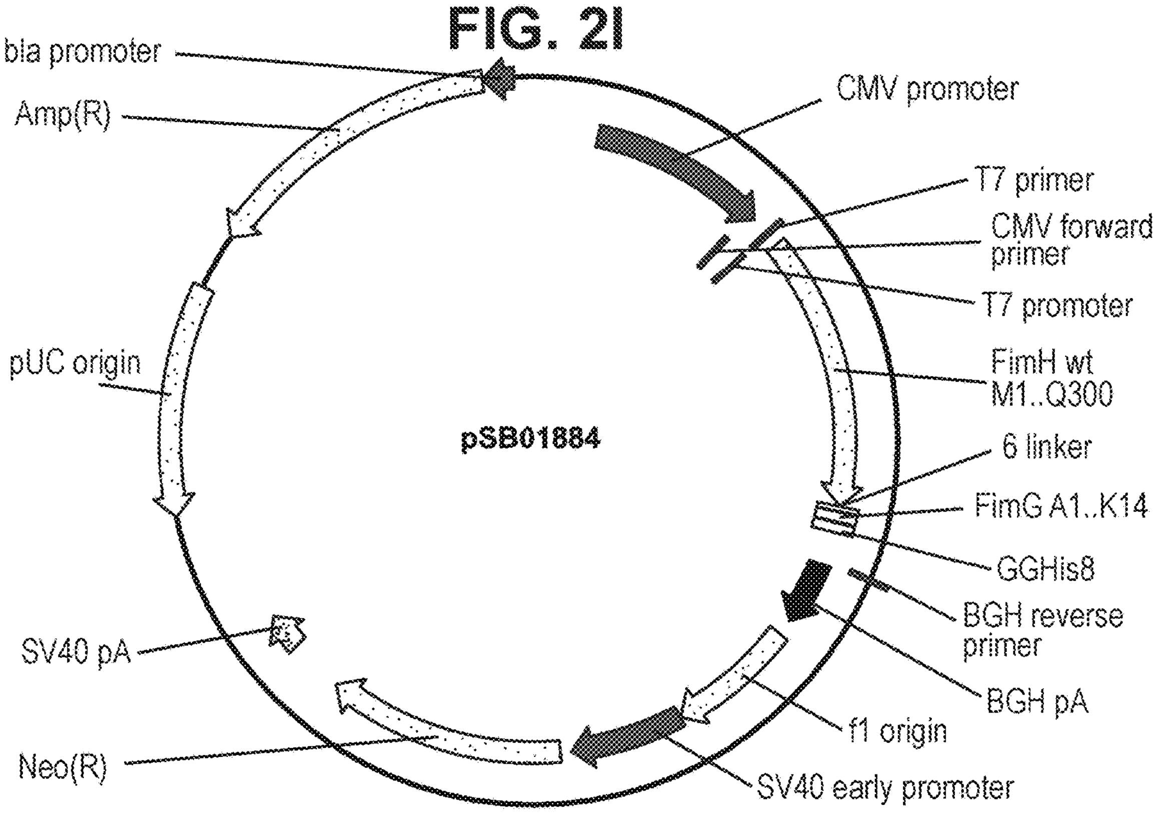
Figure 2J:
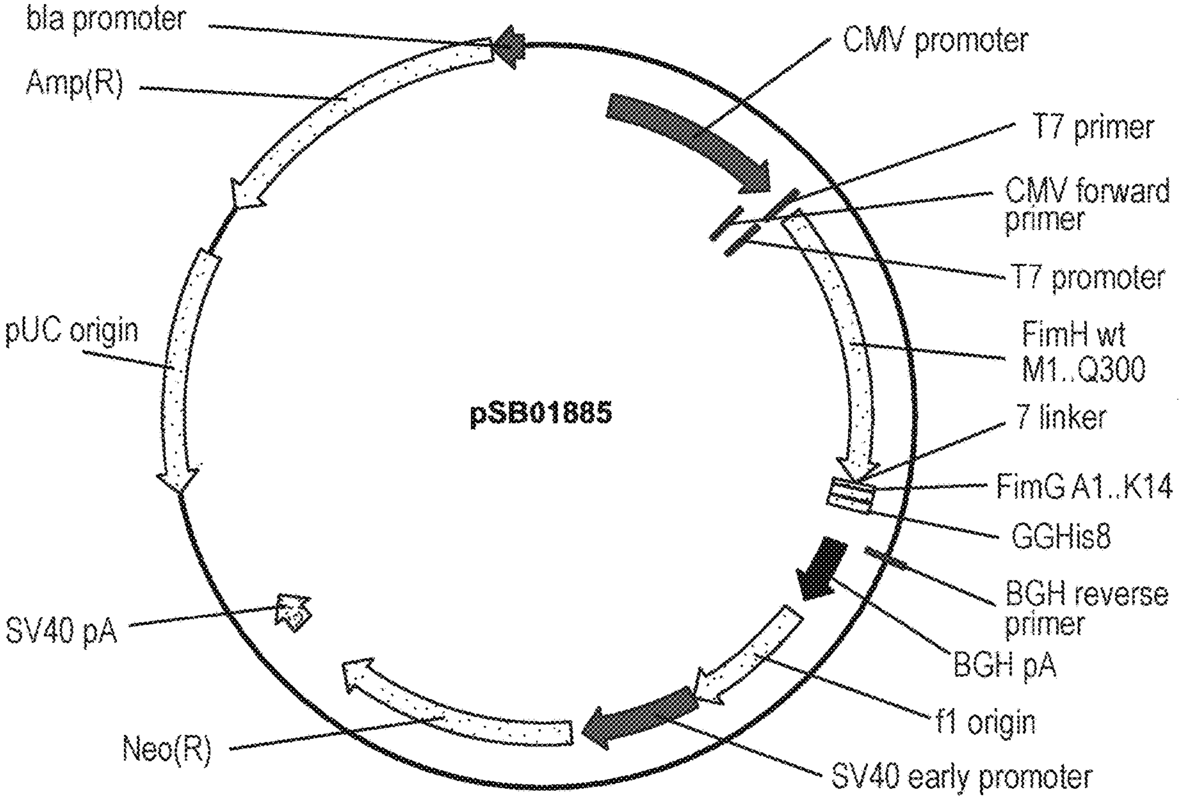
Figure 2K:
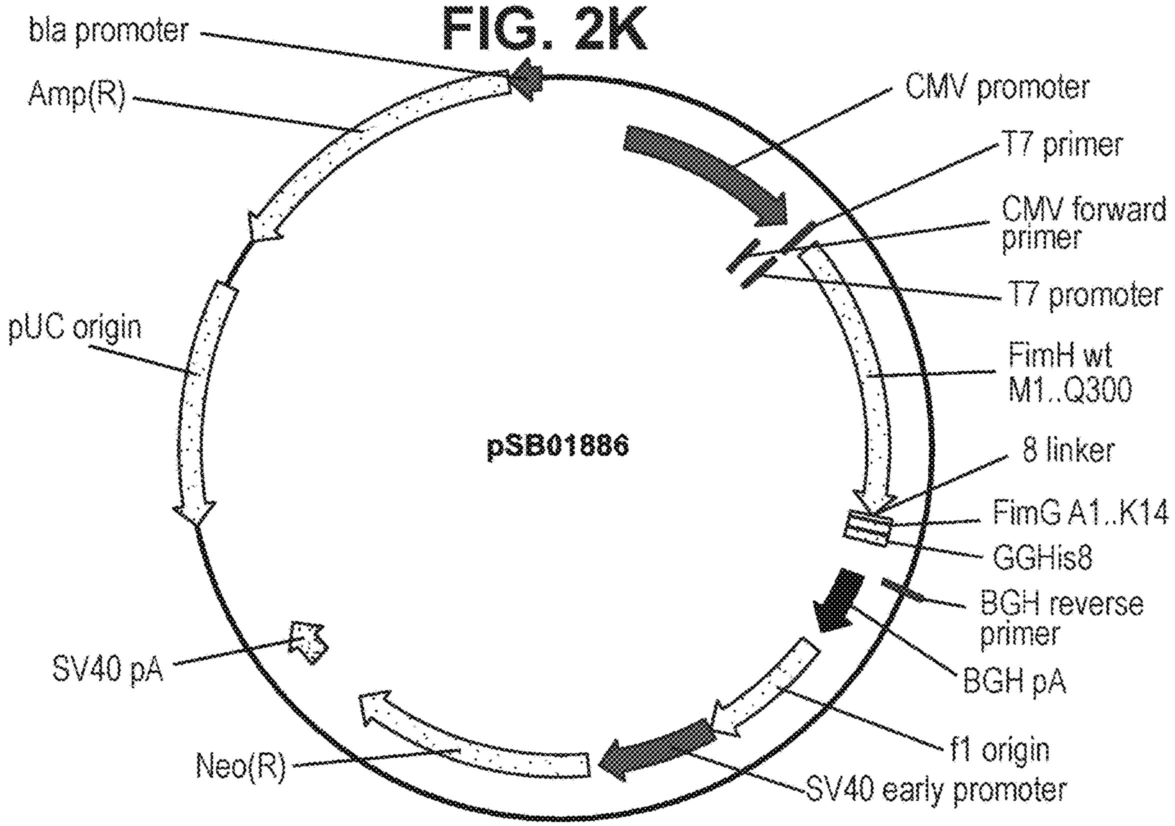
Figure 2L:
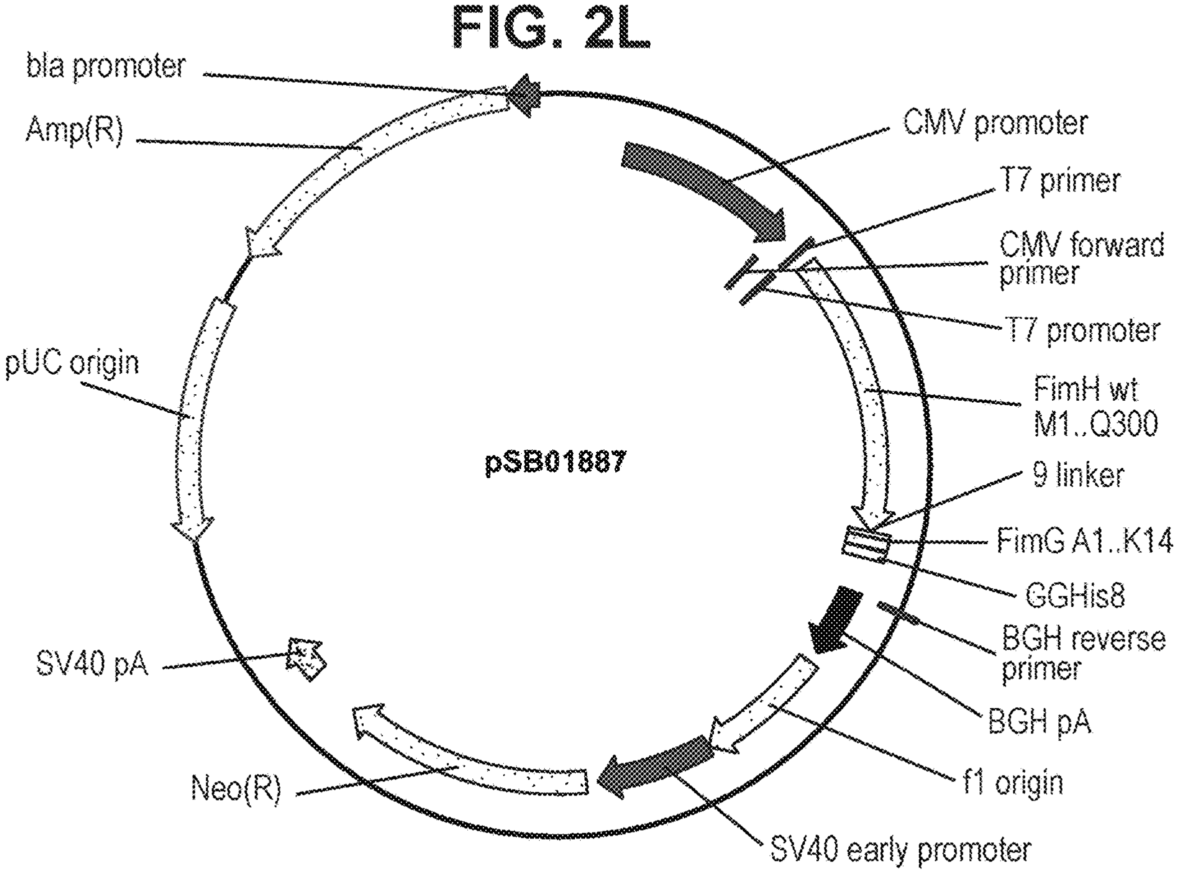
Figure 2M:
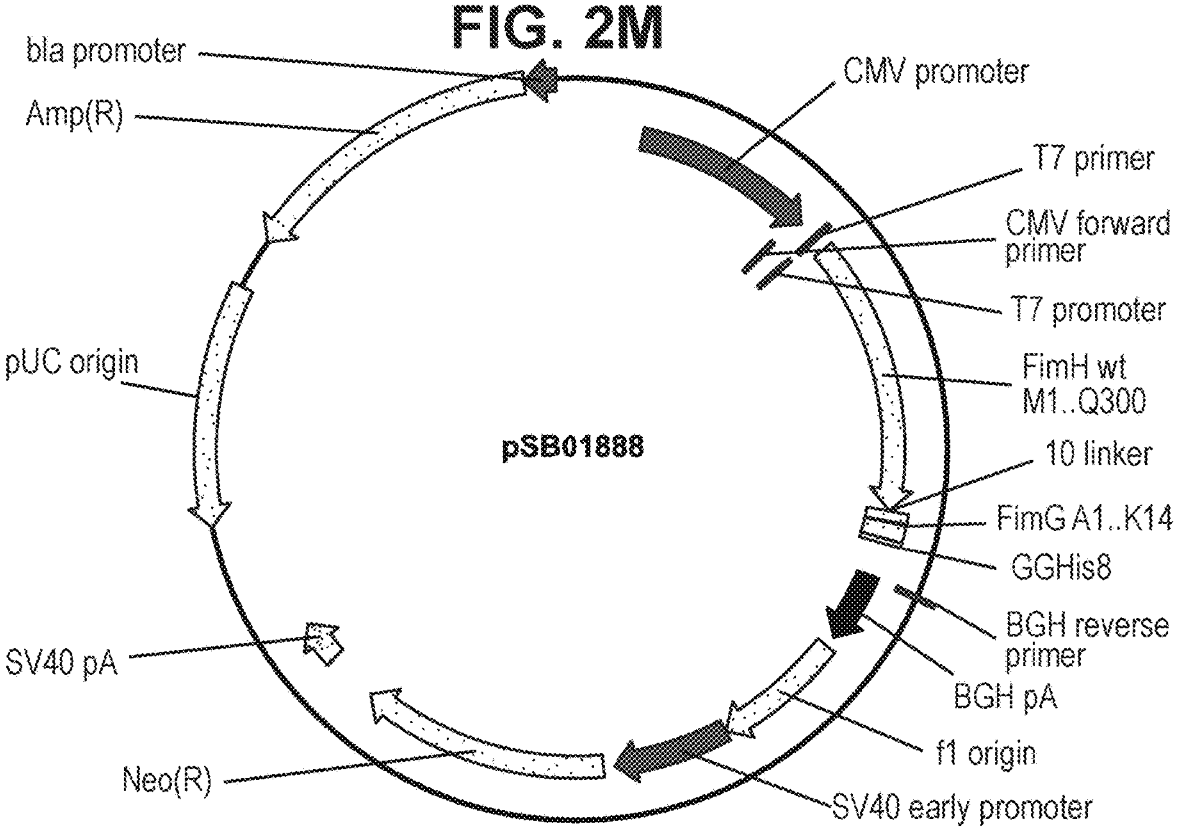
Figure 2N:
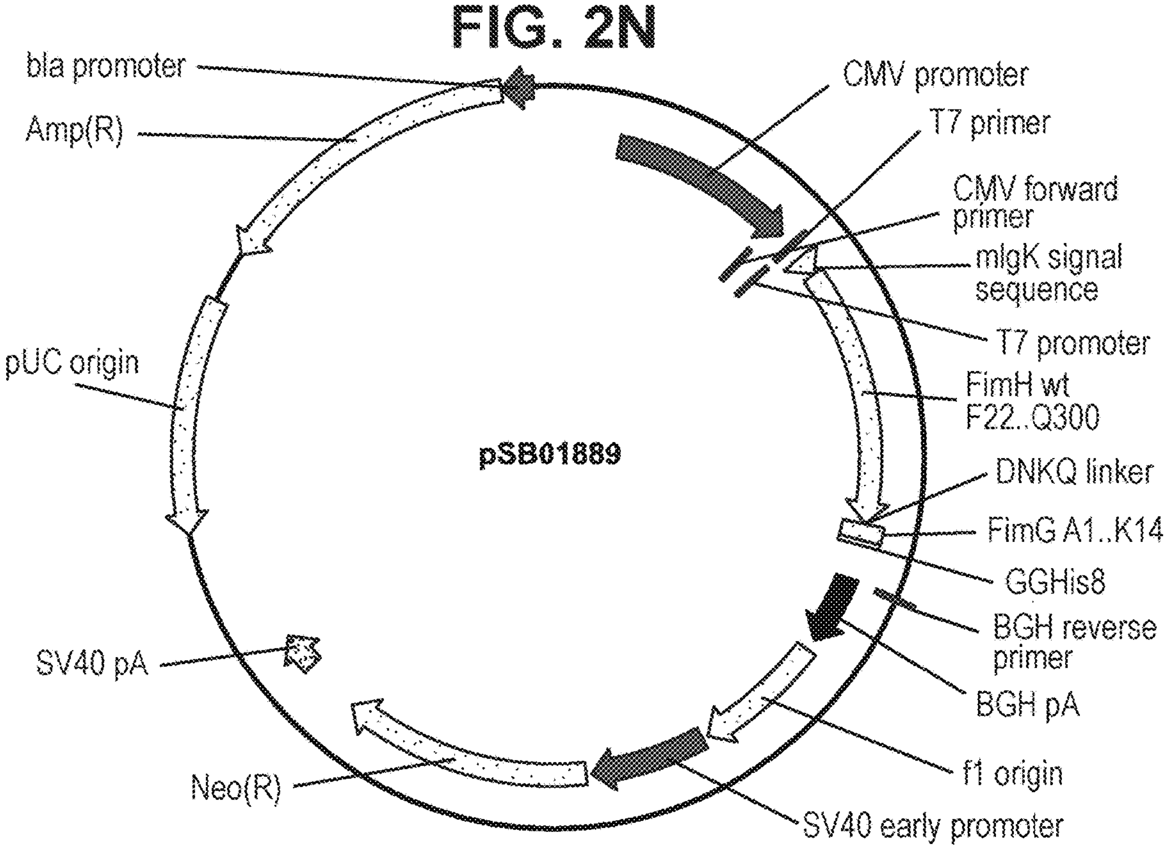
Figure 2O:
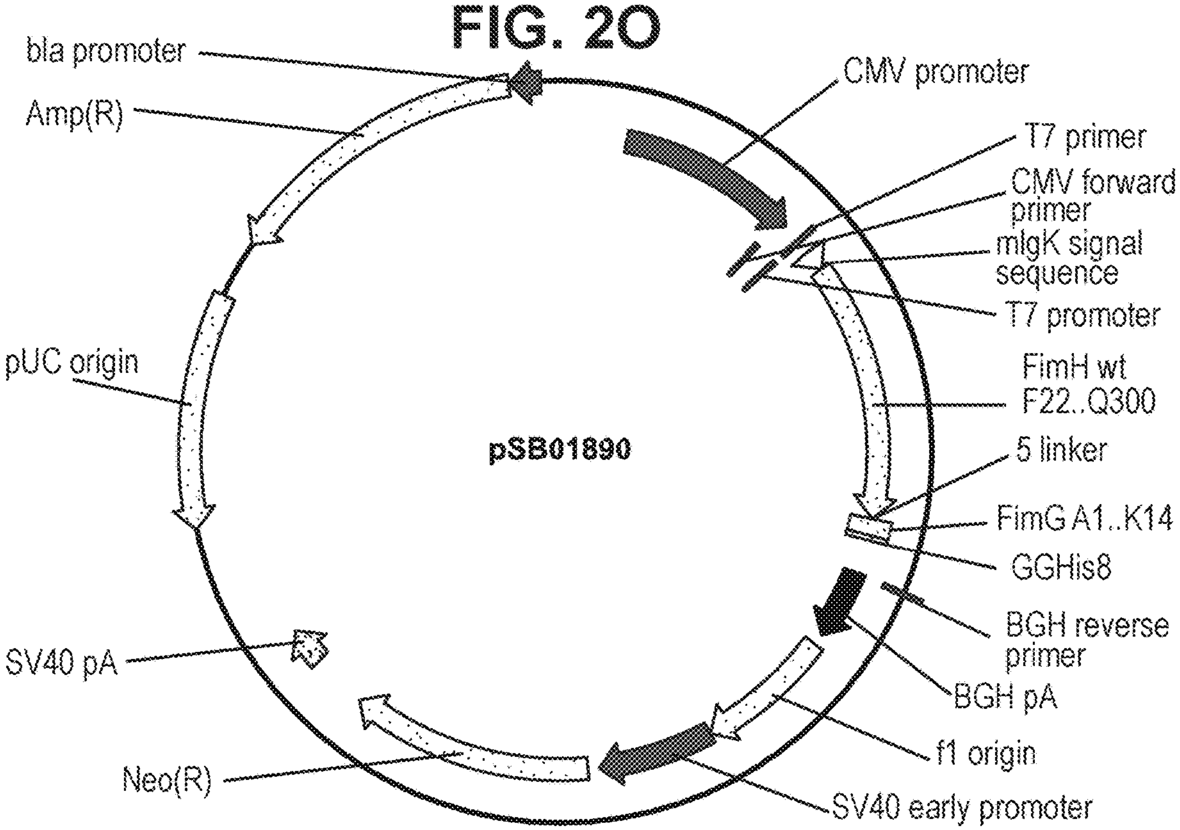
Figure 2P:
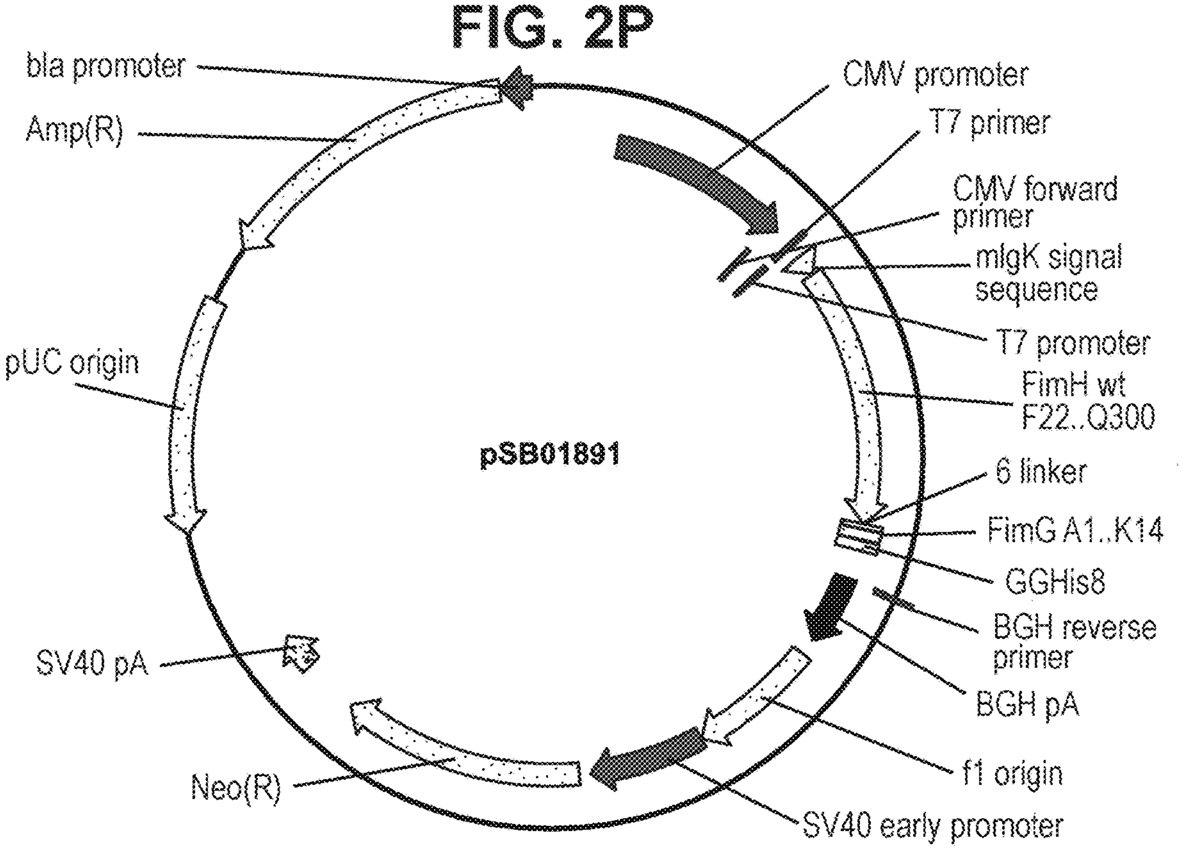
Figure 2Q:
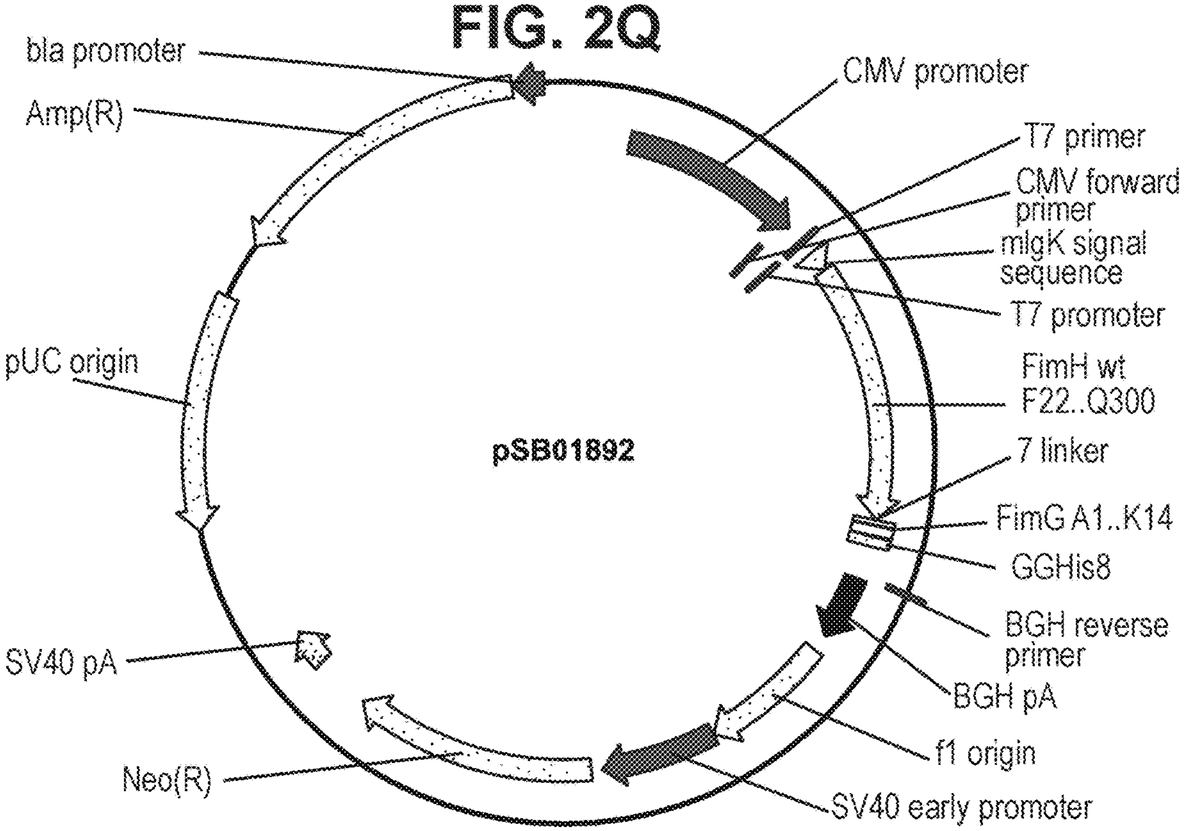
Figure 2R:
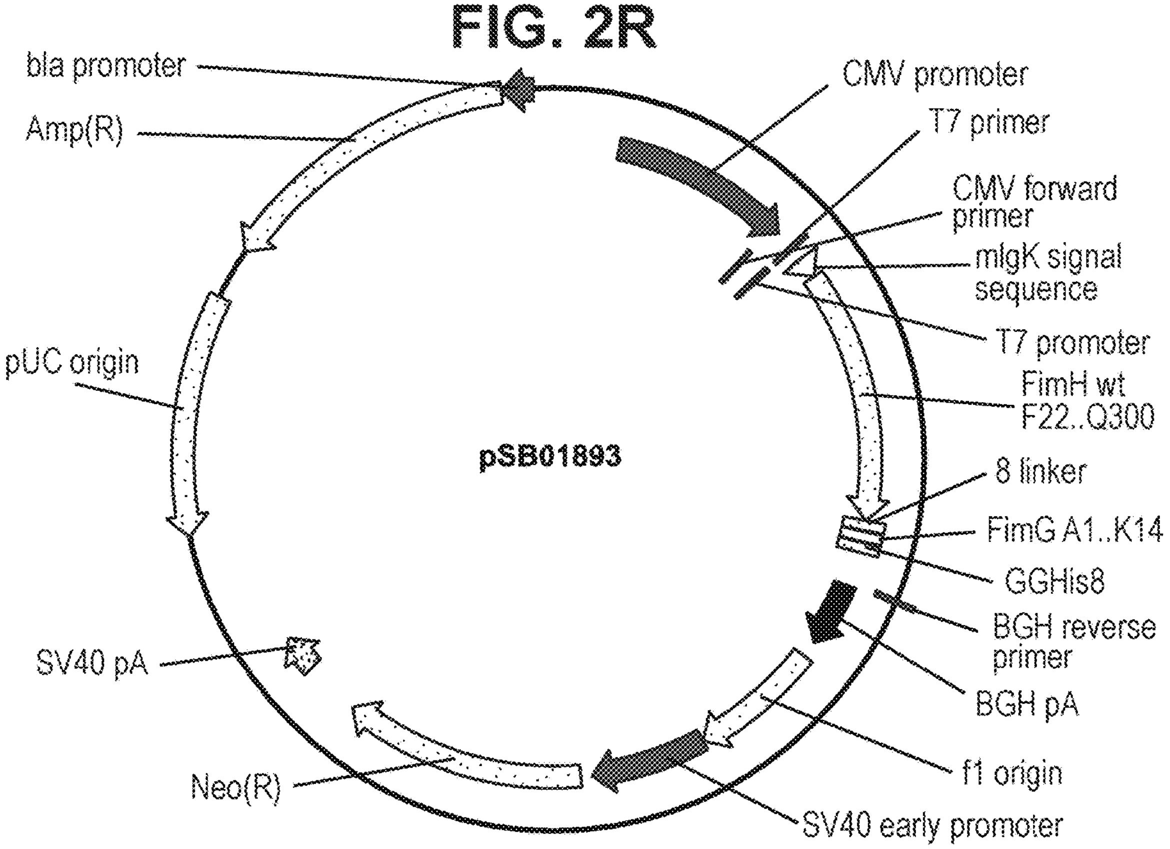
Figure 2S:
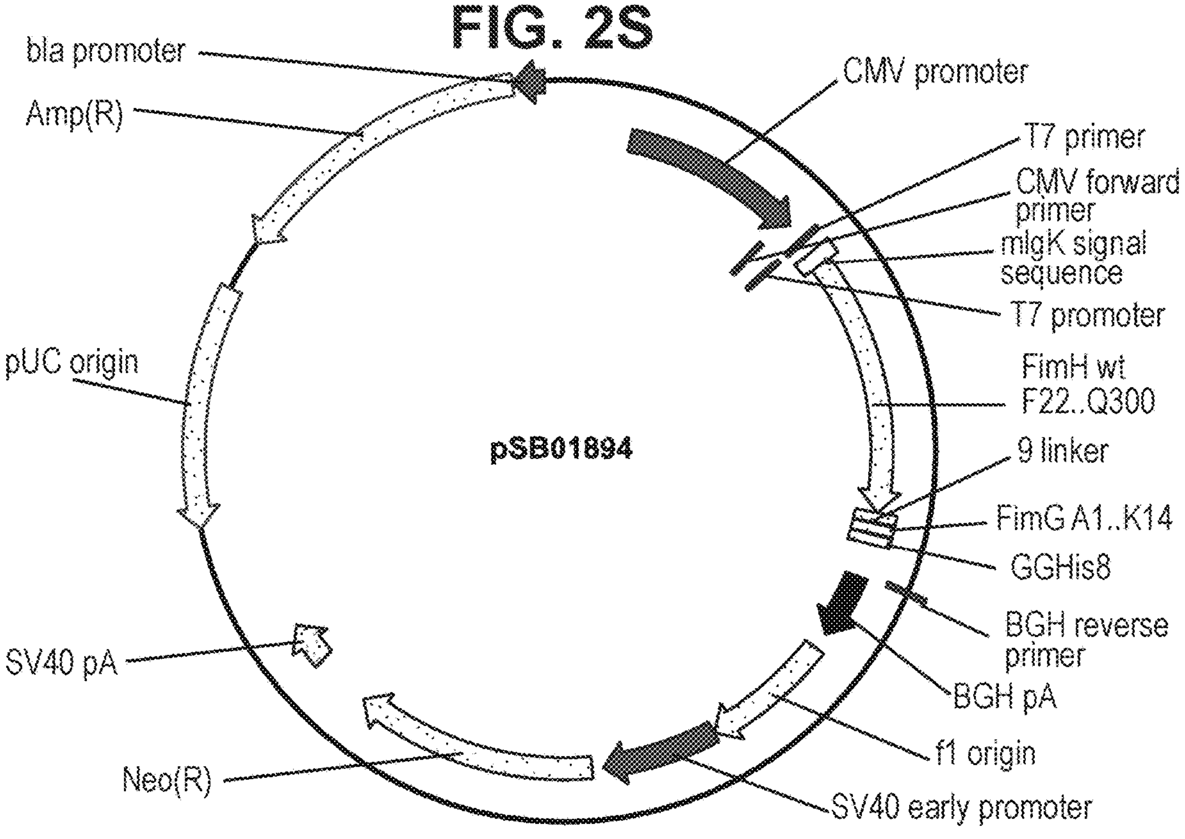

SEQ ID NO: 1 sets forth an amino acid sequence for a wild type type 1 fimbriae D-mannose specific adhesin [*Escherichia coli* FimH J96].

SEQ ID NO: 2 sets forth an amino acid sequence for a fragment of FimH, corresponding to aa residues 22-300 of SEQ ID NO: 1 (mature FimH protein).

SEQ ID NO: 3 sets forth an amino acid sequence for a FimH lectin domain.

SEQ ID NO: 4 sets forth an amino acid sequence for a FimH pilin domain.

SEQ ID NO: 5 sets forth an amino acid sequence for a polypeptide derived from *E. coli* FimH (pSB02198-FimH mlgK signal pept/F22 . . . Q300 J96 FimH N28S V48C L55C N91S N249Q/7 AA linker/FimG A1 . . . K14/GGHis8 in pcDNA3.1 (+))

SEQ ID NO: 6 sets forth an amino acid sequence for a polypeptide derived from *E. coli* FimH (pSB02307-FimH mlgK signal pept/F22 . . . Q300 J96 FimH N28S N91S N249Q/His8 in pcDNA3.1 (+))

SEQ ID NO: 7 sets forth an amino acid sequence for a fragment of a polypeptide derived from *E. coli* FimH (pSB02083 FimH Lectin Domain Wild Type construct)

SEQ ID NO: 8 sets forth an amino acid sequence for a fragment of a polypeptide derived from *E. coli* FimH (pSB02158 FimH Lectin Domain Lock Mutant)

SEQ ID NO: 9 sets forth an amino acid sequence for a fragment of a polypeptide derived from *E. coli* FimG (FimG A1 . . . K14)

SEQ ID NO: 10 sets forth an amino acid sequence for a fragment of a polypeptide derived from *E. coli* FimC.

SEQ ID NO: 11 sets forth an amino acid sequence for a 4 aa linker.

SEQ ID NO: 12 sets forth an amino acid sequence for a 5 aa linker.

SEQ ID NO: 13 sets forth an amino acid sequence for a 6 aa linker.

SEQ ID NO: 14 sets forth an amino acid sequence for a 7 aa linker.

SEQ ID NO: 15 sets forth an amino acid sequence for a 8 aa linker.

SEQ ID NO: 16 sets forth an amino acid sequence for a 9 aa linker.

SEQ ID NO: 17 sets forth an amino acid sequence for a 10 aa linker.

SEQ ID NO: 18 sets forth an amino acid sequence for a FimH J96 signal sequence.

SEQ ID NO: 19 sets forth an amino acid sequence for the signal peptide of SEQ ID NO: 5 (pSB02198-FimH mlgK signal pept/F22 . . . Q300 J96 FimH N28S V48C L55C N91S N249Q/7 AA linker/FimG A1 . . . K14/GGHis8 in pcDNA3.1 (+)).

SEQ ID NO: 20 sets forth an amino acid sequence for a polypeptide derived from *E. coli* FimH according to SEQ ID NO: 5 (mature protein of pSB02198-FimH mlgK signal pept/F22 . . . Q300 J96 FimH N28S V48C L55C N91S N249Q/7 AA linker/FimG A1 . . . K14/GGHis8 in pcDNA3.1 (+)).

SEQ ID NO: 21 sets forth an amino acid sequence for a polypeptide derived from *E. coli* FimG.

SEQ ID NO: 22 sets forth an amino acid sequence for the signal peptide of SEQ ID NO: 6 (pSB02307-FimH mlgK signal pept/F22 . . . Q300 J96 FimH N28S N91S N249Q/His8 in pcDNA3.1 (+)).

SEQ ID NO: 23 sets forth an amino acid sequence for a polypeptide derived from *E. coli* FimH according to SEQ ID NO: 6 (mature protein of FimH mlgK signal pept/F22 . . . Q300 J96 FimH N28S N91S N249Q/His8 in pcDNA3.1 (+)).

SEQ ID NO: 24 sets forth an amino acid sequence for a polypeptide derived from *E. coli* FimH according to SEQ ID NO: 7 (mature protein of pSB02083 FimH Lectin Domain Wild Type construct).

SEQ ID NO: 25 sets forth an amino acid sequence for a His-tag.

SEQ ID NO: 26 sets forth an amino acid sequence for a polypeptide derived from *E. coli* FimH according to SEQ ID NO: 8 (mature protein of pSB02158 FimH Lectin Domain Lock Mutant) SEQ ID NO: 27 sets forth an amino acid sequence for a polypeptide derived from *E. coli* FimH (pSB01878).

SEQ ID NO: 28 sets forth an amino acid sequence for a polypeptide derived from *E. coli* FimH (K12).

SEQ ID NO: 29 sets forth an amino acid sequence for a polypeptide derived from *E. coli* FimH (UTI89).

SEQ ID NO: 30 sets forth a O25b 2401 WzzB amino acid sequence.

SEQ ID NO: 31 sets forth a O25a: K5: H1 WzzB amino acid sequence.

SEQ ID NO: 32 sets forth a O25a ETEC ATCC WzzB amino acid sequence.

SEQ ID NO: 33 sets forth a K12 W3110 WzzB amino acid sequence.

SEQ ID NO: 34 sets forth a *Salmonella* LT2 WzzB amino acid sequence.

SEQ ID NO: 35 sets forth a O25b 2401 FepE amino acid sequence.

SEQ ID NO: 36 sets forth a O25a: K5: H1 FepE amino acid sequence.

SEQ ID NO: 37 sets forth a 025a ETEC ATCC FepE amino acid sequence.

SEQ ID NO: 38 sets forth a O157 FepE amino acid sequence.

SEQ ID NO: 39 sets forth a *Salmonella* LT2 FepE amino acid sequence.

SEQ ID NO: 40 sets forth a primer sequence for LT2wzzB_S.

SEQ ID NO: 41 sets forth a primer sequence for LT2wzzB_AS.

SEQ ID NO: 42 sets forth a primer sequence for O25bFepE_S.

SEQ ID NO: 43 sets forth a primer sequence for O25bFepE_A.

SEQ ID NO: 44 sets forth a primer sequence for wzzB P1_S.

SEQ ID NO: 45 sets forth a primer sequence for wzzB P2_AS.

SEQ ID NO: 46 sets forth a primer sequence for wzzB P3_S.

SEQ ID NO: 47 sets forth a primer sequence for wzzB P4_AS.

SEQ ID NO: 48 sets forth a primer sequence for O157 FepE_S.

SEQ ID NO: 49 sets forth a primer sequence for O157 FepE_AS.

SEQ ID NO: 50 sets forth a primer sequence for pBAD33_adaptor_S.

SEQ ID NO: 51 sets forth a primer sequence for pBAD33_adaptor_AS.

SEQ ID NO: 52 sets forth a primer sequence for JUMP-START_r.

SEQ ID NO: 53 sets forth a primer sequence for gnd_f.

SEQ ID NO: 54 sets forth an amino acid sequence for a mouse IgK signal sequence.

SEQ ID NO: 55 sets forth an amino acid sequence for a human IgG receptor FcRn large subunit p51 signal peptide.

SEQ ID NO: 56 sets forth an amino acid sequence for a human IL10 protein signal peptide.

SEQ ID NO: 57 sets forth an amino acid sequence for a human respiratory syncytial virus A (strain A2) fusion glycoprotein F0 signal peptide.

SEQ ID NO: 58 sets forth an amino acid sequence for an influenza A hemagglutinin signal peptide.

SEQ ID NOs: 59-101 set forth amino acid and nucleic acid sequences for a nanostructure-related polypeptide or fragment thereof.

SEQ ID NOs: 102-109 set forth SignalP 4.1 (DTU Bioinformatics) sequences from various species used for signal peptide predictions.

DETAILED DESCRIPTION OF THE INVENTION

In one embodiment, the invention provides a composition comprising a polypeptide derived from FimH or a fragment thereof; and a saccharide comprising a structure selected from any one of Formula O1, Formula O1A, Formula O1B, Formula O1C, Formula O2, Formula O3, Formula O4, Formula O4: K52, Formula O4: K6, Formula O5, Formula O5ab, Formula O5ac, Formula O6, Formula O6: K2; K13; K15, Formula O6: K54, Formula O7, Formula O8, Formula O9, Formula O10, Formula O11, Formula O12, Formula O13, Formula O14, Formula O15, Formula O16, Formula O17, Formula O18, Formula O18A, Formula O18ac, Formula O18A1, Formula O18B, Formula O18B1, Formula O19, Formula O20, Formula O21, Formula O22, Formula O23, Formula O23A, Formula O24, Formula O25, Formula O25a, Formula O25b, Formula O26, Formula O27, Formula 028, Formula 029, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45, Formula O45, Formula O45rel, Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula $62D_1$, Formula O63, Formula O64, Formula O65, Formula O66, Formula O68, Formula O69, Formula O70, Formula O71, Formula O73, Formula O73, Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144, Formula O145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, Formula O187.

In one aspect, the composition further comprises at least one saccharide derived from any one *K. pneumoniae* type selected from the group consisting of O1, O2, O3, and O5. In another aspect, the composition further comprises a saccharide derived from *Klebsiella pneumoniae* type 01. In another aspect, the composition further comprises a saccharide derived from *K. pneumoniae* type 02. In another aspect, the composition further comprises a saccharide derived from *K. pneumoniae* type 03. In another aspect, the composition further comprises a saccharide derived from *K. pneumoniae* type O5. In another aspect, the composition further comprises a saccharide derived from *K. pneumoniae* type O1 and a saccharide derived from *K. pneumoniae* type O2.

In another aspect, wherein the composition further comprises the saccharide derived from *K. pneumoniae* which is conjugated to a carrier protein; and the saccharide derived from *E. coli* is conjugated to a carrier protein.

In another aspect, the composition further comprises a polypeptide derived from *K. pneumoniae.*

In another embodiment, the invention provides a composition comprising a polypeptide derived from FimH or a fragment thereof; and at least one saccharide derived from any one *K. pneumoniae* type selected from the group consisting of O1, O2, O3, and O5. In one aspect, the composition further comprising at least one saccharide comprising a structure selected from any one of Formula O1, Formula O1A, Formula O1B, Formula O1C, Formula O2, Formula O3, Formula O4, Formula O4: K52, Formula O4: K6, Formula O5, Formula O5ab, Formula O5ac, Formula O6, Formula O6: K2; K13; K15, Formula O6: K54, Formula O7, Formula O8, Formula O9, Formula O10, Formula O11, Formula O12, Formula O13, Formula O14, Formula O15, Formula O16, Formula O17, Formula O18, Formula O18A, Formula O18ac, Formula O18A1, Formula O18B, Formula O18B1, Formula O19, Formula O20, Formula O21, Formula O22, Formula O23, Formula O23A, Formula O24, Formula O25, Formula O25a, Formula O25b, Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45, Formula O45, Formula O45rel, Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula $62D_1$, Formula O63, Formula O64, Formula O65, Formula O66, Formula O68, Formula O69, Formula O70, Formula O71, Formula O73, Formula O73, Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144, Formula O145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, Formula O187.

In another aspect, wherein the saccharide derived from *K. pneumoniae* is conjugated to a carrier protein; and the saccharide derived from *E. coli* is conjugated to a carrier protein.

In a further aspect, wherein the composition further comprises a polypeptide derived from *K. pneumoniae.*

In a further embodiment, the invention provides a composition comprising at least one saccharide derived from any one *K. pneumoniae* type selected from the group consisting of O1, O2, O3, and O5; and at least one saccharide comprising a structure selected from any one of Formula O1, Formula O1A, Formula O1B, Formula O1C, Formula O2, Formula O3, Formula O4, Formula O4: K52, Formula O4: K6, Formula O5, Formula O5ab, Formula O5ac, Formula O6, Formula O6: K2; K13; K15, Formula O6: K54, Formula O7, Formula O8, Formula O9, Formula O10, Formula O11, Formula O12, Formula O13, Formula O14, Formula O15, Formula O16, Formula O17, Formula O18, Formula O18A, Formula O18ac, Formula O18A1, Formula O18B, Formula O18B1, Formula O19, Formula O20, Formula O21, Formula O22, Formula O23, Formula O23A, Formula O24, Formula O25, Formula O25a, Formula O25b, Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45, Formula O45, Formula O45rel, Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula $62D_1$, Formula O63, Formula O64, Formula O65, Formula O66, Formula O68, Formula O69, Formula O70, Formula O71, Formula O73, Formula O73, Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144, Formula O145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, Formula O187.

In one aspect, the composition further comprises a polypeptide derived from FimH or a fragment thereof. In another aspect, wherein the *E. coli* saccharide comprises Formula O8. In another aspect, wherein the *E. coli* saccharide comprises Formula O9.

In a further aspect, wherein the composition further comprises a polypeptide derived from *K. pneumoniae*.

In one aspect of the above embodiments, wherein the saccharide is covalently bound to a carrier protein. In one aspect, wherein the saccharide further comprises a 3-deoxy-d-manno-oct-2-ulosonic acid (KDO) moiety. In another aspect, wherein the carrier protein is selected from any one of CRM197, diphtheria toxin fragment B (DTFB), DTFB C8, Diphtheria toxoid (DT), tetanus toxoid (TT), fragment C of TT, pertussis toxoid, cholera toxoid, or exotoxin A from *Pseudomonas aeruginosa*; detoxified Exotoxin A of *P. aeruginosa* (EPA), maltose binding protein (MBP), detoxified hemolysin A of *S. aureus*, clumping factor A, clumping factor B, Cholera toxin B subunit (CTB), *Streptococcus pneumoniae Pneumolysin and detoxified variants thereof, C. jejuni* AcrA, *C. jejuni* natural glycoproteins and Streptococcal C5a peptidase (SCP).

In another embodiment, the invention provides a method of eliciting an immune response against *Escherichia coli* in a mammal, comprising administering to the mammal an effective amount of the composition according to any one of the above embodiments and aspects thereof. In one aspect, wherein the immune response comprises opsonophagocytic antibodies against *E. coli*. In another aspect, wherein the immune response protects the mammal from an *E. coli* infection.

In a further embodiment, the invention provides a method of eliciting an immune response against *Klebsiella pneumoniae* in a mammal, comprising administering to the mammal an effective amount of the composition according to any one of the above embodiments and aspects thereof. In one aspect, wherein the immune response comprises opsonophagocytic antibodies against *Klebsiella pneumoniae*. In another aspect, wherein the immune response protects the mammal from a *Klebsiella pneumoniae* infection.

The inventors overcame challenges of production of polypeptides derived from *E. coli* adhesin proteins by using mammalian cells for expression. As exemplified in the present disclosure throughout and in the Examples section, it was discovered that mammalian cell expression of the recombinant polypeptides consistently achieved high yields as compared to expression of the polypeptides in *E. coli*. In addition, the inventors surprisingly identified mutations and expression constructs to stabilize the recombinant polypeptides and fragments thereof in a desirable conformation.

Blocking the primary stages of infection, namely bacterial attachment to host cell receptors and colonization of the mucosal surface, is important to prevent, treat, and/or reduce the likelihood of bacterial infections. Bacterial attachment may involve an interaction between a bacterial surface protein called an adhesin and the host cell receptor. Previous preclinical studies with the FimH adhesin (derived from uropathogenic *E. coli*) have confirmed that antibodies are elicited against an adhesin. Advances in the identification, characterization, and isolation of adhesins are needed in an effort to prevent infections, from otitis media and dental caries to pneumonia and sepsis.

To produce adhesin proteins such as FimH and fragments thereof at a commercial scale, there is a need to identify suitable constructs and suitable hosts, such that the polypeptide and fragments thereof may be expressed in sufficient amounts for a sustained period of time and in the preferred conformation. For example, in some embodiments, the preferred conformation of the recombinant polypeptide exhibits a low affinity (for example, $K_d$~300 μM) for monomannose. In some embodiments, the preferred conformation exhibits a high affinity (for example, $K_d$<1.2 μM) for monomannose.

Adhesin proteins derived from *E. coli* have been recombinantly expressed in *E. coli* cells. However, the yields have been less than 10 mg/L. Purifying large amounts of pilus-associated adhesin may be challenging when produced in *E. coli*. Without being bound by theory or mechanism, it has been suggested that the product as expressed in *E. coli* may exhibit a conformation that is not optimal for eliciting an effective immune response in mammals.

In one aspect, the invention includes a recombinant mammalian cell that includes a polynucleotide sequence encoding a polypeptide derived from a bacterial adhesin protein or fragment thereof.

In another aspect, the invention includes a process for producing the polypeptide or fragment thereof in a mammalian cell, including: (i) culturing the mammalian cell under a suitable condition, thereby expressing said polypeptide or fragment thereof; and (ii) harvesting said polypeptide or fragment thereof from the culture. The process may further include purifying the polypeptide or fragment thereof. Also disclosed herein is a polypeptide or fragment thereof produced by this process.

In another aspect, the invention includes a composition including the polypeptide or fragment thereof described herein. The composition may include a polypeptide or fragment thereof that is suitable for in vivo administration. For example, the polypeptide or fragment thereof in such a composition may have a purity of at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, by mass. The composition may further comprise an adjuvant.

In a further aspect, the invention includes a composition for use in inducing an immune response against *E. coli*. Use of the composition described herein for inducing an immune response against *E. coli* and use of the composition described herein in the manufacture of a medicament for inducing an immune response against *E. coli*, are also disclosed.

I. Polypeptides Derived from *E. coli* and Fragments Thereof

In one aspect, disclosed herein is a mammalian cell that includes a polynucleotide that encodes a polypeptide derived from *E. coli* or a fragment thereof. The term "derived from" as used herein refers to a polypeptide that comprises an amino acid sequence of a FimH polypeptide or FimCH polypeptide complex or a fragment thereof as described herein that has been altered by the introduction of an amino acid residue substitution, deletion or addition. Preferably, the polypeptide derived from *E. coli* or a fragment thereof includes a sequence having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identity to the sequence of the corresponding wild-type *E. coli* FimH polypeptide or fragment. In some embodiments, the polypeptide derived from *E. coli* or a fragment thereof has the identical total length of amino acids as the corresponding wild-type FimH polypeptide or FimCH polypeptide complex or a fragment thereof.

The fragments should include at least n consecutive amino acids from the sequences and, depending on the particular sequence, n is 7 or more (eg. 8, 10, 12, 14, 16, 18, 20 or more). Preferably the fragments include an epitope from the sequence. In some embodiments, the fragment includes an amino acid sequence of at least 50 consecutive amino acid residues, at least 100 consecutive amino acid residues, at least 125 consecutive amino acid residues, at least 150 consecutive amino acid residues, at least 175 consecutive amino acid residues, at least 200 consecutive amino acid residues, or at least 250 consecutive amino acid residues of the amino acid sequence of a polypeptide derived from *E. coli.*

In some embodiments, the polypeptide derived from *E. coli* or a fragment thereof includes one or more non-classical amino acids, as compared to a corresponding wild-type *E. coli* FimH polypeptide or fragment.

In some embodiments, the polypeptide derived from *E. coli* or a fragment thereof possess a similar or identical function as a corresponding wild-type FimH polypeptide or a fragment thereof.

In a preferred embodiment, polypeptides or polypeptide complexes or fragments thereof of the invention are isolated or purified.

In some embodiments, the polynucleotide encoding the polypeptide derived from *E. coli* or a fragment thereof is integrated into the genomic DNA of the mammalian cell, and, when cultured in a suitable condition, said polypeptide derived from *E. coli* or a fragment thereof is expressed by the mammalian cell.

In a preferred embodiment, the polypeptide derived from *E. coli* or a fragment thereof is soluble.

In some embodiments, the polypeptide derived from *E. coli* or a fragment thereof is secreted from the mammalian host cell.

In some embodiments, the polypeptide derived from *E. coli* or a fragment thereof may include additional amino acid residues, such as N-terminal or C-terminal extensions.

Such extensions may include one or more tags, which may facilitate detection (e.g. an epitope tag for detection by monoclonal antibodies) and/or purification (e.g. a polyhistidine-tag to allow purification on a nickel-chelating resin) of the polypeptide or fragment thereof. In some embodiments, the tag includes the amino acid sequence selected from any one of SEQ ID NO: 21 and SEQ ID NO: 25. Such affinity-purification tags are known in the art. Examples of affinity-purification tags include, e.g., His tag (hexahistidine, which may, for example, bind to metal ion), maltose-binding protein (MBP), which may, for example, bind to amylose), glutathione-S-transferase (GST), which may, for example, bind to glutathione, FLAG tag, which may, for example, bind to an anti-flag antibody), Strep tag, which may, for example, bind to streptavidin or a derivative thereof). In preferred embodiments, the polypeptide derived from *E. coli* or a fragment thereof does not include additional amino acid residues, such as N-terminal or C-terminal extensions. In some embodiments, the polypeptide derived from *E. coli* or a fragment thereof described herein does not include an exogenous tag sequence.

While specific strains of *E. coli* may be referenced herein, it should be understood that the polypeptide derived from *E. coli* or a fragment thereof are not limited to specific strains unless specified.

In some embodiments, the polypeptide derived from *E. coli* FimH or a fragment thereof includes a phenylalanine residue at the N-terminus of the polypeptide. In some embodiments, the polypeptide derived from FimH or fragment thereof includes a phenylalanine residue within the first 20 residue positions of the N-terminus. Preferably, the phenylalanine residue is located at position 1 of the polypeptide. For example, in some embodiments, the polypeptide derived from *E. coli* FimH or a fragment thereof does not include an additional glycine residue at the N-terminus of the polypeptide derived from *E. coli* FimH or a fragment thereof.

In some embodiments, the phenylalanine residue at position 1 of the wild-type mature *E. coli* FimH is replaced by an aliphatic hydrophobic amino acid, such as, for example, any one of kke, Leu and Val residues.

In some embodiments, a signal peptide may be used for expressing the polypeptide derived from *E. coli* or a fragment thereof. Signal sequences and expression cassettes for producing proteins are known in the art. In general, leader peptides are 5-30 amino acids long, and are typically present at the N-terminus of a newly synthesized polypeptide. The signal peptide generally contains a long stretch of hydrophobic amino acids that has a tendency to form a single alpha-helix. In addition, many signal peptides begin with a short positively charged stretch of amino acids, which may help to enforce proper topology of the polypeptide during translocation. At the end of the signal peptide there is typically a stretch of amino acids that is recognized and cleaved by signal peptidase. Signal peptidase may cleave either during or after completion of translocation to generate a free signal peptide and a mature protein. In some embodiments, the signal peptide includes the amino acid sequence having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.9%, or 100% identity to any one of SEQ ID NO: 9, SEQ ID NO: 18, SEQ ID NO: 19, and SEQ ID NO: 22.

In some embodiments, the polypeptide derived from *E. coli* or a fragment thereof described herein may include a cleavable linker. Such linkers allow for the tag to be separated from the purified complex, for example by the addition of an agent capable of cleaving the linker. Cleavable linkers are known in the art. Such linkers may be cleaved for example, by irradiation of a photolabile bond or acid-catalyzed hydrolysis. Another example of a cleavable linker includes a polypeptide linker, which incorporates a protease recognition site and may be cleaved by the addition of a suitable protease enzyme.

In some embodiments, the polypeptide derived from *E. coli* or a fragment thereof includes a modification as compared to the corresponding wild-type *E. coli* FimH polypeptide or fragment. The modification may include a covalent attachment of a molecule to the polypeptide. For example, such modifications may include glycosylation, acetylation, pegylation, phosphorylation, amidation, derivatization by known protecting/blocking groups, proteolytic cleavage, linkage to a cellular ligand or other protein, etc. In some embodiments, the polypeptide derived from *E. coli* or a fragment thereof may include a modification, such as by chemical modifications using techniques known to those of skill in the art, including, but not limited to specific chemical cleavage, acetylation, formylation, metabolic synthesis of tunicamycin, etc., as compared to a corresponding wild-type *E. coli* FimH polypeptide or fragment. In another embodiment, the modification may include a covalent attachment of a lipid molecule to the polypeptide. In some embodiments, the polypeptide does not include a covalent attachment of a molecule to the polypeptide as compared to the corresponding wild-type *E. coli* FimH polypeptide or fragment thereof.

For example, proteins and polypeptides produced in cell culture may be glycoproteins that contain covalently linked carbohydrate structures including oligosaccharide chains.

These oligosaccharide chains are linked to the protein via either N-linkages or O-linkages. The oligosaccharide chains may comprise a significant portion of the mass of the glycoprotein. Generally, N-linked oligosaccharide is added to the amino group on the side chain of an asparagine residue within the target consensus sequence of Asn-X-Ser/Thr, where X may be any amino acid except proline. In some embodiments, the glycosylation site includes an amino acid sequence selected from any one of the following: asparagine-glycine-threonine (NGT), asparagine-isoleucine-threonine (NIT), asparagine-glycine-serine (NGS), asparagine-serine-threonine (NST), and asparagine-threonine-serine (NTS). The polypeptide derived from *E. coli* or a fragment thereof produced in mammalian cells may by glycosylated. The glycosylation may occur at the N-linked glycosylation signal Asn-Xaa-Ser/Thr in the sequence of the polypeptide derived from *E. coli* or a fragment thereof. "N-linked glycosylation" refers to the attachment of the carbohydrate moiety via GIcNAc to an asparagine residue in a polypeptide chain. The N-linked carbohydrate contains a common Man 1-6 (Man1-3) Manβ1-4GlcNAcβ1-4GIcNAcβ-R core structure, where R represents an asparagine residue of the produced polypeptide derived from *E. coli* or a fragment thereof.

In some embodiments, a glycosylation site in the polypeptide derived from *E. coli* or a fragment thereof is removed by a mutation within the sequence of the polypeptide derived from *E. coli* or a fragment thereof. For example, in some embodiments, the Asn residue of a glycosylation motif (Asn-Xaa-Ser/Thr) may be mutated, preferably by a substitution. In some embodiments, the residue substitution is selected from any one of Ser, Asp, Thr, and Gln.

In some embodiments, the Ser residue of a glycosylation motif may be mutated, preferably by a substitution. In some embodiments, the residue substitution is selected from any one of Asp, Thr, and Gin.

In some embodiments, the Thr residue of a glycosylation motif may be mutated, preferably by a substitution. In some embodiments, the residue substitution is selected from any one of Ser, Asp, and Gin.

In some embodiments, a glycosylation site (such as Asn-Xaa-Ser/Thr) in the polypeptide derived from *E. coli* or a fragment thereof is not removed or modified. In some embodiments, a compound to decrease or inhibit glycosylation may be added to the cell culture medium. In such embodiments, the polypeptide or protein includes at least one more unglycosylated (i.e., aglycosylated) site, that is, a completely unoccupied glycan site with no carbohydrate moiety attached thereto, or comprises at least one carbohydrate moiety less at the same potential glycosylation site than an otherwise identical polypeptide or protein which is produced by a cell under otherwise identical conditions but in the absence of a glycosylation inhibiting compound. Such compounds are known in the art and may include, but are not limited to, tunicamycin, tunicaymycin homologs, streptovirudin, mycospocidin, amphomycin, tsushimycin, antibiotic 24010, antibiotic MM 19290, bacitracin, corynetoxin, showdomycin, duimycin, 1-deoxymannonojirimycin, deoxynojirimycin, N-methyl-1-dexoymannojirimycin, brefeldin A, glucose and mannose analogs, 2-deoxy-D-glucose, 2-deoxyglucose, D-(+)-mannose, D-(+) galactose, 2-deoxy-2-fluoro-D-glucose, 1,4-dideoxy-1,4-imino-D-mannitol (DIM), fluoroglucose, fluoromannose, UDP-2-deoxyglucose, GDP-2-deoxyglucose, hydroxymethylglutaryl-CoA reductase inhibitors, 25-hydroxycholesterol, hydroxycholesterol, swainsonine, cycloheximide, puromycin, actinomycin D, monensin, m-Chlorocarbonyl-cyanide phenylhydrazone (CCCP), compactin, dolichyl-phosphoryl/\-deoxyglucose, N-Acetyl-D-Glucosamine, hygoxanthine, thymidine, cholesterol, glucosamine, mannosamine, castanospermine, glutamine, bromoconduritol, conduritol epoxide and conduritol derivatives, glycosylmethyl-p-nitrophenyltriazenes, β-Hydroxynorvaline, threo-β-fluoroasparagine, D-(+)-Gluconic acid δ-lactone, di(2-ethyl hexyl)phosphate, tributyl phosphate, dodecyl phosphate, 2-dimethylamino ethyl ester of (diphenyl methyl)-phosphoric acid, [2-(diphenyl phosphinyloxy)ethyl]trimethyl ammonium iodide, iodoacetate, and/or fluoroacetate One of ordinary skill in the art will readily recognize or will be able to determine glycosylation-inhibiting substances that may be used in accordance with methods and compositions of the present invention without undue experimentation. In such embodiments, glycosylation of the polypeptide or fragment thereof may be controlled without the introduction of an amino acid mutation into the polypeptide or fragment thereof.

In some embodiments, the level of glycosylation (e.g., number of glycan sites that are occupied on the polypeptide or fragment thereof, the size and/or complexity of glycoform at the site, and the like) of the polypeptide or fragment thereof produced by the mammalian cell are lower than levels of glycosylation of the polypeptide or fragment thereof produced under otherwise identical conditions in an otherwise identical medium that lacks such a glycolysis-inhibiting compound and/or mutation.

In some embodiments, the sequence of a polypeptide derived from *E. coli* or a fragment thereof does not include a site of N-linked protein glycosylation. In some embodiments, the sequence of a polypeptide derived from *E. coli* or a fragment thereof does not include at least one site of N-linked protein glycosylation. In some embodiments, the sequence of a polypeptide derived from *E. coli* or a fragment thereof does not include any sites of N-linked protein glycosylation. In some embodiments, the sequence of a polypeptide derived from *E. coli* or a fragment thereof includes a site for N-linked protein glycosylation. In some embodiments, the sequence of a polypeptide derived from *E. coli* or a fragment thereof includes at most 1 site of N-linked protein glycosylation. In some embodiments, the sequence of a polypeptide derived from *E. coli* or a fragment thereof includes at most 2 sites of N-linked protein glycosylation.

A polypeptide derived from *E. coli* or a fragment thereof expressed by different cell lines or in transgenic animals may have different glycan site occupancies, glycoforms and/or glycosylation patterns compared with each other. In some embodiments, the invention encompasses a polypeptide derived from *E. coli* or a fragment thereof regardless of the glycosylation, glycan occupancy or glycoform pattern of the polypeptide derived from *E. coli* or a fragment thereof produced in a mammalian cell.

In some embodiments, the polypeptide derived from *E. coli* or a fragment thereof may be derived from an *E. coli* FimH polypeptide, wherein the amino acid residue at position 1 of the polypeptide is phenylalanine, not methionine, for example, a polypeptide having the amino acid sequence SEQ ID NO: 2. Preferably, the polypeptide derived from *E. coli* FimH comprises a phenylalanine at position 1 of the amino acid sequence of the polypeptide derived from *E. coli*. In another preferred embodiment, the polypeptide derived from *E. coli* FimH comprises the amino acid sequence SEQ ID NO: 3, preferably wherein the residue at position 1 of the amino acid sequence of the polypeptide derived from *E. coli* is phenylalanine. In some embodiments, the polypeptide derived from *E. coli* or a fragment thereof may include the amino acid sequence SEQ ID NO: 4, which may be derived from an *E. coli* FimH polypeptide.

In some embodiments, the polypeptide derived from *E. coli* or a fragment thereof includes the amino acid sequence having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.9%, or 100% identity to any one of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 20, SEQ ID NO: 23, SEQ ID NO: 24, SEQ ID NO: 26, SEQ ID NO: 27, SEQ ID NO: 28, and SEQ ID NO: 29. In some embodiments, the polypeptide derived from *E. coli* or a fragment thereof may be derived from an *E. coli* FimG polypeptide, for example, having the amino acid sequence SEQ ID NO: 9. In some embodiments, the polypeptide derived from *E. coli* or a fragment thereof may be derived from an *E. coli* FimC polypeptide, for example, having the amino acid sequence SEQ ID NO: 10.

A. Polypeptides Derived from *E. coli* FimH and Fragments Thereof

Bacterial fimbrial adhesins FimH and FmIH allow *Escherichia coli* to exploit distinct urinary tract microenvironments through recognition of specific host cell glycoproteins. FimH binds to manosylated uroplakin receptors in the uroepithelium whereas FmIH binds to galactose or N-acetylgalactosamine O-glycans on epithelial surface proteins in the kidney and inflamed bladder. FimH fimbriae also play a role in colonization of enterotoxigenic *E. coli* (ETEC) and multidrug-resistant invasive *E. coli* in the gut through binding to highly mannosylated proteins on the intestinal epithelia.

Full length FimH is composed of two domains: the N-terminal lectin domain and the C-terminal pilin domain, which are connected by a short linker. The lectin domain of FimH contains the carbohydrate recognition domain, which is responsible for binding to the mannosylated uroplakin 1a on the urothelial cell surface. The pilin domain is anchored to the core of the pilus via a donor strand of the subsequent FimG subunit, which is a process termed donor strand complementation.

Conformation and ligand-binding properties of the lectin domain of FimH are under the allosteric control of the pilin domain of FimH. Under static conditions, the interaction of the two domains of full length FimH stabilizes the lectin domain in the low-affinity to monomannose (for example, $K_d$~300 UM) state, which is characterized by a shallow binding pocket. Binding to a mannoside ligand induces a conformational change leading to a medium affinity state, where the lectin and pilin domains remain in close contact. However, upon shear stress, the lectin and pilin domains separate, thereby inducing the high-affinity state (for example, $K_d$<1.2 μM).

Because of the absence of negative allosteric regulation exerted by the pilin domain, the isolated lectin domain of FimH is locked in the high-affinity state. The isolated, recombinant lectin domain, which is locked in the high-affinity state, exhibits high stability. Locking the adhesin in a low-binding conformation, however, induces the production of adhesion-inhibiting antibodies. Accordingly, there is an interest in stabilizing the lectin domain in the low-affinity state.

There is an additional interest in methods to express FimH in high yields sufficient for product development. An impediment for development of compositions that include FimH is the low yield achieved with FimH expressed in its native state in the *E. coli* periplasm. Typical yields reported at lab-bench scale are 3-5 mg/L for the purified FimCH complex and 4-10 mg/L for FimH (LD), which are below levels considered scalable for the manufacturing of clinical trial material. The in vivo conformation of FimH is different from the conformation attained by a purified recombinant form of the protein. In general, FimH has a native conformation that is at least partly determined by the in vivo interaction of FimH with its periplasmic chaperone protein, called FimC.

Recombinant production of FimH remains challenging. Protein expression and purification is not a routine process.

In a preferred embodiment, the polypeptide or fragment thereof is derived from an *E. coli* FimH. In some embodiments, the polypeptide or fragment thereof includes full length *E. coli* FimH. Full length FimH includes two domains: an N-terminal lectin domain and a C-terminal pilin domain, which are connected by a short linker. In some embodiments, the full length of *E. coli* FimH includes 279 amino acids, which includes the full length of the mature protein of *E. coli* FimH. In some embodiments, the full length of *E. coli* FimH includes 300 amino acids, which includes the full length of the mature protein of *E. coli* FimH and a signal peptide sequence having 21 amino acids in length. The primary structure of the 300 amino acid-long wild type FimH is highly conserved across *E. coli* strains.

An exemplary sequence for a full-length *E. coli* FimH is SEQ ID NO: 1. The full length FimH sequence includes a sequence for a lectin domain and a sequence for a pilin domain. The lectin domain of FimH contains the carbohydrate recognition domain, which is responsible for binding to the mannosylated uroplakin 1a on the urothelial cell surface. The pilin domain is anchored to the core of the pilus via a donor strand of the subsequent FimG subunit, which is a process termed donor strand complementation.

Starting from the N-terminus, the names and in parenthesis the exemplary amino acid sequences of each domain of a full length FimH are as follows: FimH lectin (SEQ ID NO: 2) and FimH pilin (SEQ ID NO: 3).

Other suitable polypeptides and fragments thereof derived from *E. coli* FimH include variants that have various degrees of identity to any one of SEQ ID NO: 1, SEQ ID NO: 2, SEQ ID NO: 3, SEQ ID NO: 4, SEQ ID NO: 20, SEQ ID NO: 23, SEQ ID NO: 24, SEQ ID NO: 26, SEQ ID NO: 28, and SEQ ID NO: 29, such as at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identity to any one of SEQ ID NO: 1, SEQ ID NO: 2, SEQ ID NO: 3, SEQ ID NO: 4, SEQ ID NO: 20, SEQ ID NO: 23, SEQ ID NO: 24, SEQ ID NO: 26, SEQ ID NO: 28, and SEQ ID NO: 29. In certain embodiments, the FimH variant proteins: (i) form part of the FimH-FimC; (ii) comprise at least one epitope from SEQ ID NO: 1, SEQ ID NO: 2, SEQ ID NO: 3, SEQ ID NO: 4, SEQ ID NO: 20, SEQ ID NO: 23, SEQ ID NO: 24, SEQ ID NO: 26, SEQ ID NO: 28, and SEQ ID NO: 29; and/or (iii) may elicit antibodies in vivo which immunologically cross react with an *E. coli* FimH.

In some embodiments, the composition includes a polypeptide having at least n consecutive amino acids from any one of SEQ ID NO: 1, SEQ ID NO: 2, SEQ ID NO: 3, SEQ ID NO: 4, SEQ ID NO: 20, SEQ ID NO: 23, SEQ ID NO: 24, SEQ ID NO: 26, SEQ ID NO: 28, and SEQ ID NO: 29, wherein n is 7 or more (eg. 8, 10, 12, 14, 16, 18, 20 or more). Preferably the fragments include an epitope from the sequence. In some embodiments, composition includes a polypeptide having at least 50 consecutive amino acid residues, at least 100 consecutive amino acid residues, at least 125 consecutive amino acid residues, at least 150 consecutive amino acid residues, at least 175 consecutive amino acid residues, at least 200 consecutive amino acid residues, or at least 250 consecutive amino acid residues of the amino acid sequence of any one of SEQ ID NO: 1, SEQ ID NO: 2, SEQ ID NO: 3, SEQ ID NO: 4, SEQ ID NO: 20, SEQ ID NO: 23, SEQ ID NO: 24, SEQ ID NO: 26, SEQ ID NO: 28, and SEQ ID NO: 29.

In some embodiments, the composition includes a polypeptide having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identity to SEQ ID NO: 1. In some embodiments, the composition includes a polypeptide having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identity to SEQ ID NO: 2. In some embodiments, the composition includes a polypeptide having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identity to SEQ ID NO: 3. In some embodiments, the composition includes a polypeptide having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identity to SEQ ID NO: 4. In some embodiments, the composition includes a polypeptide having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identity to SEQ ID NO: 20. In some embodiments, the composition includes a polypeptide having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identity to SEQ ID NO: 23. In some embodiments, the composition includes a polypeptide having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identity to SEQ ID NO: 24. In some embodiments, the composition includes a polypeptide having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identity to SEQ ID NO: 26. In some embodiments, the composition includes a polypeptide having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identity to SEQ ID NO: 28. In some embodiments, the composition includes a polypeptide having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identity to SEQ ID NO: 30.

Another example of a suitable polypeptide and fragments thereof derived from *E. coli* FimH described herein is shown as SEQ ID NO: 2, which lacks the wild-type N-terminal signal sequence, and corresponds to amino acid residues 22-300 of SEQ ID NO: 1. Another example of a FimH fragment includes the entire N-terminal signal sequence and the mature protein, such as set forth in SEQ ID NO: 1.

In some embodiments, a glycosylation site in the polypeptide derived from *E. coli* or a fragment thereof is removed by a mutation within the sequence of the polypeptide derived from *E. coli* or a fragment thereof. For example, in some embodiments, the Asn residue at position 7 of a mature *E. coli* FimH polypeptide (e.g., according to the numbering of SEQ ID NO: 2) may be mutated, preferably by a substitution. In some embodiments, the Asn residue at position 7 of a lectin domain of an *E. coli* FimH polypeptide (e.g., according to the numbering of SEQ ID NO: 3) may be mutated, preferably by a substitution. In some embodiments, the residue substitution is selected from any one of Ser, Asp, Thr, and Gin.

In some embodiments, the Thr residue at position 10 of a mature *E. coli* FimH polypeptide (e.g., according to the numbering of SEQ ID NO: 2) may be mutated, preferably by a substitution. In some embodiments, the Thr residue at position 7 of a lectin domain of an *E. coli* FimH polypeptide (e.g., according to the numbering of SEQ ID NO: 3) may be mutated, preferably by a substitution. In some embodiments, the residue substitution is selected from any one of Ser, Asp, and Gln.

In some embodiments, the Asn residue at position N235 of a mature *E. coli* FimH polypeptide (e.g., according to the numbering of SEQ ID NO: 2) may be mutated, preferably by a substitution. In some embodiments, the Asn residue at position N228 of a mature *E. coli* FimH polypeptide (e.g., according to the numbering of SEQ ID NO: 2) may be mutated, preferably by a substitution. In some embodiments, the residue substitution is selected from any one of Ser, Asp, Thr, and Gln.

In some embodiments, the Asn residue at position 70 of a mature *E. coli* FimH polypeptide (e.g., according to the numbering of SEQ ID NO: 2) may be mutated, preferably by a substitution. In some embodiments, the Asn residue at position 70 of a lectin domain of an *E. coli* FimH polypeptide (e.g., according to the numbering of SEQ ID NO: 3) may be mutated, preferably by a substitution. In some embodiments, the residue substitution is selected from any one of Ser, Asp, Thr, and Gln.

In some embodiments, the Ser residue at position 72 of a mature *E. coli* FimH polypeptide (e.g., according to the numbering of SEQ ID NO: 2) may be mutated, preferably by a substitution. In some embodiments, the Ser residue at position 72 of a lectin domain of an *E. coli* FimH polypeptide (e.g., according to the numbering of SEQ ID NO: 3) may be mutated, preferably by a substitution. In some embodiments, the residue substitution is selected from any one of Asp, Thr, and Gln.

By the term "fragment" as used herein refers to a polypeptide and is defined as any discrete portion of a given polypeptide that is unique to or characteristic of that polypeptide. The term as used herein also refers to any discrete portion of a given polypeptide that retains at least a fraction of the activity of the full-length polypeptide. In certain embodiments, the fraction of activity retained is at least 10% of the activity of the full-length polypeptide. In certain embodiments, the fraction of activity retained is at least 20%, 30%, 40%, 50%, 60%, 70%, 80% or 90% of the activity of the full-length polypeptide. In certain embodiments, the fraction of activity retained is at least 95%, 96%, 97%, 98% or 99% of the activity of the full-length polypeptide. In certain embodiments, the fraction of activity retained is 100% or more of the activity of the full-length polypeptide. In some embodiments, a fragment includes at least 5, 10, 15, 20, 25, 30, 35, 40, 45, 50, 55, 60, 65, 70, 75, 80, 85, 90, 95, 100 or more consecutive amino acids of the full-length polypeptide.

B. Complex of FimH, FimC, and Fragments Thereof

In some embodiments, the polypeptide derived from *E. coli* FimH or fragment thereof is present in a complex with polypeptide derived from *E. coli* FimC or fragment thereof. In a preferred embodiment, the polypeptide derived from *E. coli* FimH or fragment thereof and the polypeptide derived from *E. coli* FimC or fragment thereof are present in a complex, preferably in a 1:1 ratio in the complex. Without being bound by theory or mechanism, the full length FimH may be stabilized in an active conformation by the periplasmic chaperone FimC, thereby making it possible to purify full-length FimH protein. Accordingly, in some embodiments, the polypeptide or fragment thereof includes full length FimH and full length FimC.

In some embodiments, the polypeptide or fragment thereof includes a fragment of FimH and a fragment of FimC. In some embodiments, the polypeptide or fragment thereof includes full length FimH and a fragment of FimC. An exemplary sequence for *E. coli* FimC is set forth in SEQ ID NO: 10. In some embodiments, the polypeptide derived from *E. coli* or a fragment thereof includes complex-forming fragments of FimH.

A complex-forming fragment of FimH may be any part or portion of the FimH protein that retain the ability to form a complex with FimC or a fragment thereof. A suitable complex-forming fragment of FimH may also be obtained or determined by standard assays known in the art, such as co-immunoprecipitation assay, cross-linking, or co-localization by fluorescent staining, etc. SDS-PAGE or western blot may also be used (e.g., by showing that the FimH fragment and FimC or fragment thereof are in a complex as evidenced by gel electrophoresis). In certain embodiments, the complex-forming fragment of FimH (i) forms part of the FimH-FimC complex; (ii) comprises at least one epitope from SEQ ID NO: 1, SEQ ID NO: 2, SEQ ID NO: 3, SEQ ID NO: 4, SEQ ID NO: 10, SEQ ID NO: 20, SEQ ID NO: 23, SEQ ID NO: 24, SEQ ID NO: 26, SEQ ID NO: 28, and SEQ ID NO: 29; and/or (iii) may elicit antibodies in vivo which immunologically cross react with an *E. coli* FimH.

In some embodiments, the polypeptide derived from *E. coli* or a fragment thereof includes full length FimH, wherein the FimH is not complexed with FimC. In further embodiments, the polypeptide or fragment thereof includes a fragment of FimH, wherein the fragment is not complexed with FimC. In some embodiments, the polypeptide derived from *E. coli* or a fragment thereof FimC includes SEQ ID NO: 10. In some embodiments, the complex may be expressed from the same plasmid, preferably under the control of separate promoters for each polypeptide or fragment thereof.

In some embodiments, the polypeptide derived from *E. coli* FimH or a fragment thereof binds to a polypeptide derived from *E. coli* FimC or a fragment thereof, which may be engineered into the structure of the polypeptide derived from *E. coli* FimH or fragment thereof. The portion of the FimC molecule that binds to the FimH in the complex is called a “donor strand” and the mechanism of formation of the native FimH structure using the strand from FimC thatbinds to FimH in the FimCH complex is known as “donor strand complementation.”

In some embodiments, the polypeptide derived from *E. coli* FimH or a fragment thereof may be expressed by the appropriate donor strand complemented version of FimH, wherein the amino acid sequence of FimC that interacts with FimH in the FimCH complex is itself engineered at the C-terminal end of FimH to provide the native conformation without the need for the remainder of the FimC molecule to be present. In some embodiments, the polypeptide derived from *E. coli* FimH or a fragment thereof may be expressed in the form of a complex that includes isolated domains thereof, such as the lectin binding domain and the piling domain, and such domains may be linked together covalently or non-covalently. For example, in some embodiments, the linking segment may include amino acid sequences or other oligomeric structures, including simple polymer structures.

The methods and compositions of the invention may include complexes described herein, in which said polypeptides or fragments thereof derived from *E. coli* are co-expressed or formed in a combined state.

C. Lectin Domain, Pilin Domain, and Variants Thereof

Conformation and ligand-binding properties of the lectin domain of FimH may be under the allosteric control of the pilin domain of FimH. Under static conditions, the interaction of the two domains of full length FimH stabilizes the lectin domain in a low-affinity to monomannose state (for example, $K_d$~300 UM), which is characterized by a shallow binding pocket. Binding to a mannoside ligand may induce a conformational change leading to a medium affinity state, in which the lectin and pilin domains remain in close contact. However, upon shear stress, the lectin and pilin domains may separate and induce the high-affinity state (for example, $K_d$<1.2 μM).

Because of the absence of negative allosteric regulation exerted by the pilin domain, isolated lectin domain of FimH is locked in the high-affinity state (for example, $K_d$<1.2 μM). The isolated, recombinant lectin domain, which is locked in the high-affinity state. Locking the adhesin in a low-affinity conformation (for example, $K_d$~300 μM), however, induces the production of adhesion-inhibiting antibodies. Accordingly, there is an interest in stabilizing the lectin domain in the low-affinity state.

In some embodiments, the polypeptide derived from *E. coli* or a fragment thereof includes the lectin domain of an *E. coli* FimH. Exemplary sequences for a lectin domain include any one of SEQ ID NO: 3, SEQ ID NO: 7, SEQ ID NO: 8, SEQ ID NO: 24, and SEQ ID NO: 26. In some embodiments, the lectin domain of an *E. coli* FimH includes cysteine substitutions. In a preferred embodiment, the lectin domain of an *E. coli* FimH includes cysteine substitutions within the first 50 amino acid residues of the lectin domain. In some embodiments, the lectin domain may include 1, 2, 3, 4, 5, 6, 7, 8, 9, or 10 cysteine substitutions. Preferably, the lectin domain includes 2 cysteine substitutions. See, for example, pSB02158 and pSB02198.

Other suitable polypeptides and fragments thereof derived from *E. coli* FimH include FimH lectin domain variants that have various degrees of identity to SEQ ID NO: 3, such as at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identity to the sequence recited in SEQ ID NO: 3. In some embodiments, the composition includes a polypeptide having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identity to SEQ ID NO: 3. In some embodiments, the polypeptide derived from *E. coli* or a fragment thereof includes the pilin domain of an *E. coli* FimH. Other suitable polypeptides and fragments thereof derived from *E. coli* FimH include FimH pilin domain variants that have various degrees of identity to SEQ ID NO: 7, such as at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identity to the sequence recited in SEQ ID NO: 7. In some embodiments, the composition includes a polypeptide having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identity to SEQ ID NO: 4. Other suitable polypeptides and fragments thereof derived from *E. coli* FimH include FimH lectin domain variants that have various degrees of identity to SEQ ID NO: 8, such as at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identity to the sequence recited in SEQ ID NO: 8. In some embodiments, the composition includes a polypeptide having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identity to SEQ ID NO: 8. In some embodiments, the polypeptide derived from *E. coli* or a fragment thereof includes the pilin domain of an *E. coli* FimH. Other suitable polypeptides and fragments thereof derived from *E. coli* FimH include FimH pilin domain variants that have various degrees of identity to SEQ ID NO: 24, such as at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identity to the sequence recited in SEQ ID NO: 24. In some embodiments, the composition includes a polypeptide having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identity to SEQ ID NO: 24. Other suitable polypeptides and fragments thereof derived from *E. coli* FimH include FimH lectin domain variants that have various degrees of identity to SEQ ID NO: 26, such as at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identity to the sequence recited in SEQ ID NO: 26. In some embodiments, the composition includes a polypeptide having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identity to SEQ ID NO: 26.

In some embodiments, the composition includes a polypeptide having at least n consecutive amino acids from any one of SEQ ID NO: 3, SEQ ID NO: 7, SEQ ID NO: 8, SEQ ID NO: 24, and SEQ ID NO: 26, wherein n is 7 or more (eg. 8, 10, 12, 14, 16, 18, 20 or more). Preferably the fragments include an epitope from the sequence. In some embodiments, the composition includes a polypeptide having at least 50 consecutive amino acid residues, at least 100 consecutive amino acid residues, at least 125 consecutive amino acid residues, at least 150 consecutive amino acid residues, at least 175 consecutive amino acid residues, at least 200 consecutive amino acid residues, or at least 250 consecutive amino acid residues of the amino acid sequence of any one of SEQ ID NO: 3, SEQ ID NO: 7, SEQ ID NO: 8, SEQ ID NO: 24, and SEQ ID NO: 26.

The location and length of a lectin domain of *E. coli* FimH or a homologue or a variant thereof may be predicted based on pairwise alignment of its sequence to any one of SEQ ID NO: 3, SEQ ID NO: 7, SEQ ID NO: 8, SEQ ID NO: 24, and SEQ ID NO: 26, for example by aligning the amino acid sequence of a FimH to SEQ ID NO: 1, and identifying the sequence that aligns to residues 22-179 of SEQ ID NO: 1.

D. Wild-Type N-Terminal Signal Sequence

In some embodiments, the N-terminal wild type signal sequence of full-length FimH is cleaved in a host cell to produce a mature FimH polypeptide. As such, the FimH expressed by the host cell may lack the N-terminal signal sequence. In preferred embodiments, the polypeptide derived from *E. coli* or a fragment thereof may be encoded by a nucleotide sequence that lacks the coding sequence for the wild type N-terminal signal sequence.

In some embodiments, the polypeptide derived from *E. coli* or a fragment thereof includes the FimH-FimC complex forming fragments of FimH, the N-terminal signal sequence (such as, residues 1-21 of SEQ ID NO: 1), or a combination thereof. A complex-forming fragment of FimH may be any part or portion of the FimH protein that retains the ability to form a complex with FimC.

In some embodiments, the polypeptide derived from *E. coli* or a fragment thereof may lack between 1 and 21 amino acid residues (e.g. 1, 2, 3, 4, 5, 6, 7, 8, 9, 10, 11, 12, 13, 14, 15, 16, 17, 18, 19, 20, or 21 amino acid residues, or lack 1-21 residues, 1-20 residues, 1-15 residues, 1-10 residues, 2-20 residues, 2-15 residues, 2-10 residues, 5-20 residues, 5-15 residues, or 5-10 residues) at the N-terminus and/or C-terminus of the full-length FimH polypeptide, which may include the signal sequence, lectin domain, and pilin domain.

II. Nucleic Acids

In one aspect, nucleic acids encoding the polypeptide derived from *E. coli* or a fragment thereof are disclosed. One or more nucleic acid constructs encoding the polypeptide derived from *E. coli* or a fragment thereof may be used for genomic integration and subsequent expression of the polypeptide derived from *E. coli* or a fragment thereof. For example, a single nucleic acid construct encoding the polypeptide derived from *E. coli* or fragment thereof may be introduced to a host cell. Alternatively, the coding sequences for the polypeptide derived from *E. coli* or a fragment thereof may be carried by two or more nucleic acid constructs, which are then introduced into host cell simultaneously or sequentially.

For example, in one exemplary embodiment, a single nucleic acid construct encodes the lectin domain and pilin domain of an *E. coli* FimH. In another exemplary embodiment, one nucleic acid construct encodes the lectin domain and a second nucleic acid construct encodes the pilin domain of an *E. coli* FimH. In some embodiments, genomic integration is achieved.

The nucleic acid construct may comprise genomic DNA that comprises one or more introns, or cDNA. Some genes are expressed more efficiently when introns are present. In some embodiments, the nucleic acid sequence is suitable for the expression of exogenous polypeptides in said mammalian cell.

In some embodiments, the nucleic acid encoding the polypeptide or fragment thereof is codon optimized to increase the level of expression in any particular cell.

In some embodiments, the nucleic acid construct includes a signal sequence that encodes a peptide that directs secretion of the polypeptide derived from *E. coli* or a fragment thereof. In some embodiments, the nucleic acid includes the native signal sequence of the polypeptide derived from *E. coli* FimH. In some embodiments where the polypeptide derived from *E. coli* or a fragment thereof includes an endogenous signal sequence, the nucleic acid sequence encoding the signal sequence may be codon optimized to increase the level of expression of the protein in a host cell.

In some embodiments, the signal sequence is any one of the following lengths: 15, 16, 17, 18, 19, 20, 21, 22, 23, 24, 25, 26, 27, 28, 29, and 30 amino acids long. In some embodiments, the signal sequence is 20 amino acids long. In some embodiments, the signal sequence is 21 amino acids long.

In some embodiments, where the polypeptide or fragment thereof includes a signal sequence, the endogenous signal sequence naturally associated with the polypeptide may be replaced with a signal sequence not associated with the wild type polypeptide to improve the level of expression of the polypeptide or fragment thereof in cultured cells. Accordingly, in some embodiments, the nucleic acid does not include the native signal sequence of the polypeptide derived from *E. coli* or a fragment thereof. In some embodiments, the nucleic acid does not include the native signal sequence of the polypeptide derived from *E. coli* FimH. In some embodiments, the polypeptide derived from *E. coli* or a fragment thereof may be expressed with a heterologous peptide, which is preferably a signal sequence or other peptide having a specific cleavage site at the N-terminus of the mature protein or polypeptide derived from *E. coli* or a fragment thereof. For example, the polypeptide derived from *E. coli* FimH or a fragment thereof may be expressed with a heterologous peptide (e.g., IgK signal sequence), which is preferably a signal sequence or other peptide having a specific cleavage site at the N-terminus of the mature *E. coli* FimH protein. In preferred embodiments, the specific cleavage site at the N-terminus of the mature protein *E. coli* FimH occurs immediately before the initial phenylalanine residue of the mature *E. coli* FimH protein. The heterologous sequence selected is preferably one that is recognized and processed (i.e., cleaved by signal peptidase) by the host cell.

In preferred embodiments, the signal sequence is an IgK signal sequence. In some embodiments, the nucleic acid encodes the amino acid sequence SEQ ID NO: 18. In some embodiments, the nucleic acid encodes the amino acid sequence SEQ ID NO: 19. In some embodiments, the nucleic acid encodes the amino acid sequence SEQ ID NO: 22. In preferred embodiments, the signal sequence is a mouse IgK signal sequence.

Suitable mammalian expression vectors for producing the polypeptide derived from E. *coli* or fragments thereof are known in the art and may be commercially available, such as pSecTag2 expression vector from Invitrogen™. An exemplary mouse Ig Kappa signal peptide sequence includes the sequence ETDTLLLWVLLLWVPGSTG (SEQ ID NO: 54). In some embodiments, the vector includes pBudCE4.1 mammalian expression vector from Thermo Fisher. Additional exemplary and suitable vectors include the pcDNA™3.1 mammalian expression vector (Thermo Fisher).

In some embodiments, the signal sequence does not include a hemagglutinin signal sequence.

In some embodiments, the nucleic acid includes the native signal sequence of the polypeptide derived from *E. coli* or a fragment thereof. In some embodiments, the signal sequence is not an IgK signal sequence. In some embodiments, the signal sequence includes a hemagglutinin signal sequence.

In one aspect, disclosed herein are vectors that include the coding sequences for the polypeptide derived from *E. coli* or a fragment thereof. Exemplary vectors include plasmids that are able to replicate autonomously or to be replicated in a mammalian cell. Typical expression vectors contain suitable promoters, enhancers, and terminators that are useful for regulation of the expression of the coding sequence(s) in the expression construct. The vectors may also include selection markers to provide a phenotypic trait for selection of transformed host cells (such as conferring resistance to antibiotics such as ampicilin or neomycin).

Suitable promoters are known in the art. Exemplary promoters include, e.g., CMV promoter, adenovirus, EF1 a, GAPDH metallothionine promoter, SV-40 early promoter, SV-40 later promoter, murine mammary tumor virus promoter, Rous sarcoma virus promoter, polyhedrin promoter, etc. Promoters may be constitutive or inducible. One or more vectors may be used (e.g., one vector encoding all subunits or domains or fragments thereof, or multiple vectors together encoding the subunits or domains or fragments thereof).

Internal ribosome entry site (IRES) and 2A peptide sequences may also be used. IRES and 2A peptide provides alternative approaches for co-expression of multiple sequences. IRES is a nucleotide sequence that allows for translation initiation in the middle of a messenger RNA (mRNA) sequence as part of the greater process of protein synthesis. Usually, in eukaryotes, translation may be initiated only at the 5' end of the mRNA molecule. IRES elements allow expression of multiple genes in one transcript. IRES-based polycistronic vectors, which express multiple proteins from one transcript, may reduce the escape of non-expressing clones from selection. The 2A peptide allows translation of multiple proteins in a single open reading frame into a polyprotein that is subsequently cleaved into individual proteins through a ribosome-skipping mechanism. 2A peptide may provide more balanced expression of multiple protein products. Exemplary IRES sequences include, e.g., EV71 IRES, EMCV IRES, HCV IRES. For genomic integration, the integration may be site-specific or random. Site-specific recombination may be achieved by introducing homologous sequence(s) into the nucleic acid constructs described herein. Such homologous sequence substantially matches the endogenous sequence at a specific target site in the host genome. Alternatively, random integration may be used. Sometimes, the expression level of a protein may vary depending upon the integration site. Therefore, it may be desirable to select a number of clones according to recombinant protein expression level to identify a clone that achieves the desired level of expression.

Figure 2T:
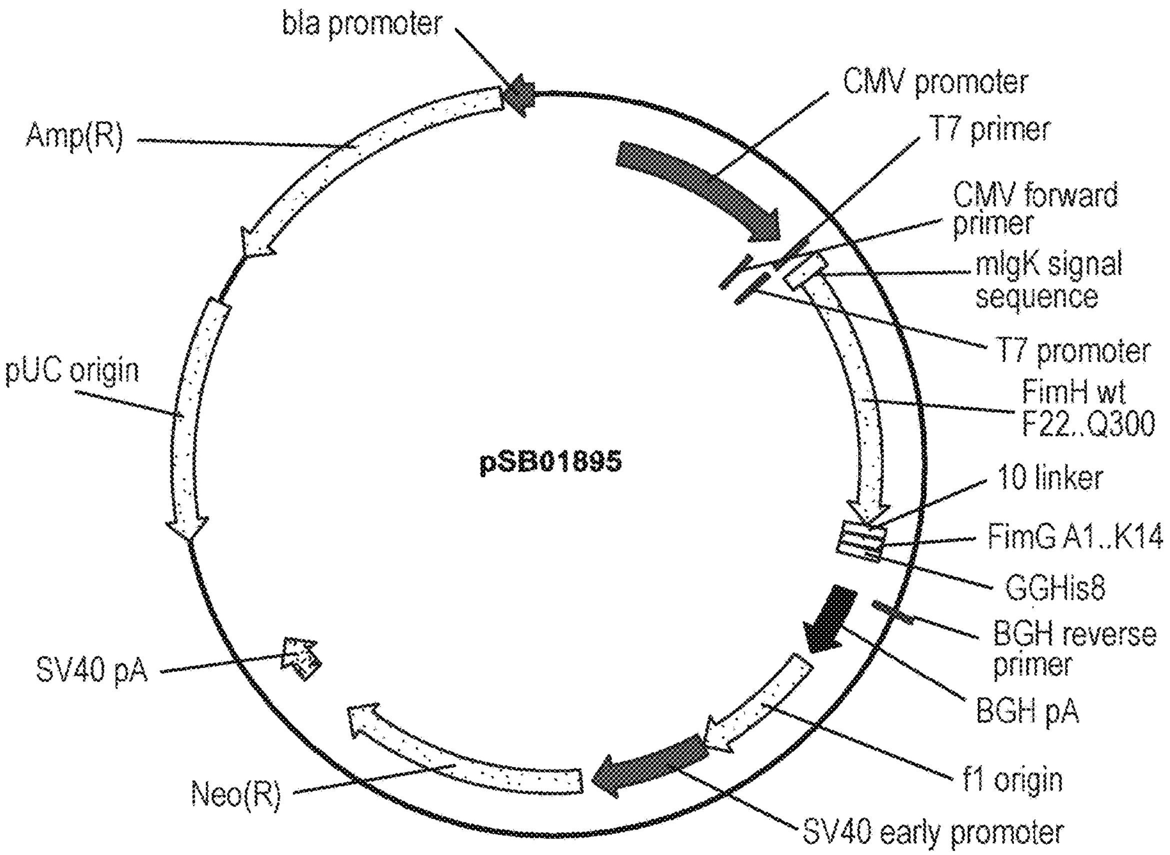

Exemplary nucleic acid constructs are further described in the figures, such as any one of FIG. 2A-2T.

In one aspect, the nucleic acid sequence encodes the amino acid sequence having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.9% or 100% identity to any one of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 20, SEQ ID NO: 23, SEQ ID NO: 24, SEQ ID NO: 26, SEQ ID NO: 27, SEQ ID NO: 28, and SEQ ID NO: 29.

III. Host Cells

In one aspect, the invention relates to cells in which the sequences encoding the polypeptide derived from *E. coli* or a fragment thereof are expressed in a mammalian host cell. In one embodiment, the polypeptide derived from *E. coli* or a fragment thereof is transiently expressed in the host cell. In another embodiment, the polypeptide derived from *E. coli* or a fragment thereof is stably integrated into the genome of the host cells, and, when cultured under a suitable condition, express the polypeptide derived from *E. coli* or a fragment thereof. In a preferred embodiment, the polynucleotide sequence is expressed with high efficiency and genomic stability.

Suitable mammalian host cells are known in the art. Preferably, the host cell is suitable for producing protein at industrial manufacturing scale. Exemplary mammalian host cells include any one of the following and derivatives thereof: Chinese Hamster Ovary (CHO) cells, COS cells (a cell line derived from monkey kidney (African green monkey), Vero cells, Hela cells, baby hamster kidney (BHK) cells, Human Embryonic Kidney (HEK) cells, NSO cells (Murine myeloma cell line), and C127 cells (nontumorigenic mouse cell line). Further exemplary mammalian host cells include mouse Sertoli (TM4), buffalo rat liver (BRL 3A), mouse mammary tumor (MMT), rat hepatoma (HTC), mouse myeloma (NSO), murine hybridoma (Sp2/0), mouse thymoma (EL4), Chinese Hamster Ovary (CHO) and CHO cell derivatives, murine embryonic (NIH/3T3, 3T3 Li), rat myocardial (H9c2), mouse myoblast (C2C12), and mouse kidney (miMCD-3). Further examples of mammalian cell lines include NS0/1, Sp2/0, Hep G2, PER.C6, COS-7, TM4, CV1, VERO-76, MDCK, BRL 3A, W138, MMT 060562, TR1, MRC5, and FS4.

Any cell susceptible to cell culture may be utilized in accordance with the present invention. In some embodiments, the cell is a mammalian cell. Non-limiting examples of mammalian cells that may be used in accordance with the present invention include BALB/c mouse myeloma line (NSO/I, ECACC No: 85110503); human retinoblasts (PER.C6, CruCell, Leiden, The Netherlands); monkey kidney CV1 line transformed by SV40 (COS-7, ATCC CRL 1651); human embryonic kidney line (293 or 293 cells subcloned for growth in suspension culture, Graham et al., J. Gen Virol., 36:59,1977); baby hamster kidney cells (BHK, ATCC CCL 10); Chinese hamster ovary cells +/−DHFR (CHO, Urlaub and Chasin, Proc. Natl. Acad. Sci. USA, 77:4216, 1980); mouse sertoli cells (TM4, Mather, Biol. Reprod., 23:243-251, 1980); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68, 1982); MRC 5 cells; FS4 cells; and a human hepatoma line (Hep G2). In some preferred embodiment, the cells are CHO cells. In some preferred embodiments, the cells are GS-cells.

Additionally, any number of commercially and non-commercially available hybridoma cell lines may be utilized in accordance with the present invention. The term "hybridoma" as used herein refers to a cell or progeny of a cell resulting from fusion of an immortalized cell and an antibody-producing cell. Such a resulting hybridoma is an immortalized cell that produces antibodies. Individual cells used to create the hybridoma can be from any mammalian source, including, but not limited to, rat, pig, rabbit, sheep, pig, goat, and human. In some embodiments, a hybridoma is a trioma cell line, which results when progeny of heterohybrid myeloma fusions, which are the product of a fusion between human cells and a murine myeloma cell line, are subsequently fused with a plasma cell. In some embodiments, a hybridoma is any immortalized hybrid cell line that produces antibodies such as, for example, quadromas (See, e.g., Milstein et al., Nature, 537:3053, 1983). One skilled in the art will appreciate that hybridoma cell lines might have different nutrition requirements and/or might require different culture conditions for optimal growth, and will be able to modify conditions as needed.

In some embodiments, the cell comprises a first gene of interest, wherein the first gene of interest is chromosomally-integrated. In some embodiments, the first gene of interest comprises a reporter gene, a selection gene, a gene of interest (e.g., encoding a polypeptide derived from *E. coli* or a fragment thereof), an ancillary gene, or a combination thereof. In some embodiments, the gene of therapeutic interest comprises a gene encoding a difficult to express (DIE) protein.

In some embodiments, the first gene of interest is located between two of the distinct recombination target sites (RTS) in a site-specific integration (SSI) mammalian cell, wherein two RTS are chromosomally-integrated within the NL1 locus or the NL2 locus. See, for example, United States Patent Application Publication No. 20200002727, for a description of the NL1 locus, the NL2 locus, the NL3 locus, the NL4 locus, the NL5 locus, and the NL6 locus. In some embodiments, the first gene of interest is located within the NL1 locus. In some embodiments, the cell comprises a second gene of interest, wherein the second gene of interest is chromosomally-integrated. In some embodiments, the second gene of interest comprises a reporter gene, a selection gene, a gene of therapeutic interest (such as a polypeptide derived from *E. coli* or a fragment thereof), an ancillary gene, or a combination thereof. In some embodiments, the gene of therapeutic interest comprises a gene encoding a DtE protein. In some embodiments, the second gene of interest is located between two of the RTS. In some embodiments, the second gene of interest is located within the NL1 locus or the NL2 locus. In some embodiments, the first gene of interest is located within the NL1 locus, and the second gene of interest is located within the NL2 locus. In some embodiments, the cell comprises a third gene of interest, wherein the third gene of interest is chromosomally-integrated. In some embodiments, the third gene of interest comprises a reporter gene, a selection gene, a gene of therapeutic interest (such as a polypeptide derived from *E. coli* or a fragment thereof), an ancillary gene, or a combination thereof. In some embodiments, the gene of therapeutic interest comprises a gene encoding a DtE protein. In some embodiments, the third gene of interest is located between two of the RTS. In some embodiments, the third gene of interest is located within the NL1 locus or the NL2 locus. In some embodiments, the third gene of interest is located within a locus distinct from the NL1 locus and the NL2 locus. In some embodiments, the first gene of interest, the second gene of interest, and the third gene of interest are within three separate loci. In some embodiments, at least one of the first genes of interest, the second gene of interest, and the third gene of interest is within the NL1 locus, and at least one of the first gene of interest, the second gene of interest, and the third gene of interest is within the NL2 locus. In some embodiments, the cell comprises a site-specific recombinase gene. In some embodiments, the site-specific recombinase gene is chromosomally-integrated.

In some embodiments, the present disclosure provides a mammalian cell comprising at least four distinct RTS, wherein the cell comprises (a) at least two distinct RTS are chromosomally-integrated within the NL1 locus or NL2 locus; (b) a first gene of interest is integrated between the at least two RTS of (a), wherein the first gene of interest comprises a reporter gene, a gene encoding a DtE protein, an ancillary gene or a combination thereof; (c) and a second gene of interest is integrated within a second chromosomal locus distinct from the locus of (a), wherein the second gene of interest comprises a reporter gene, a gene encoding a DtE protein (such as a polypeptide derived from *E. coli* or a fragment thereof), an ancillary gene or a combination thereof. In some embodiments, the present disclosure provides a mammalian cell comprising at least four distinct RTS, wherein the cell comprises (a) at least two distinct RTS are chromosomally-integrated within the Fer1L4 locus; (b) at least two distinct RTS are chromosomally-integrated within the NL1 locus or the NL2 locus; (c) a first gene of interest is chromosomally-integrated within the Fer1L4 locus, wherein the first gene of interest comprises a reporter gene, a gene encoding a DtE protein, an ancillary gene or a combination thereof; and (d) a second gene of interest is chromosomally-integrated within the within the NL1 locus or NL2 locus of (b), wherein the second gene of interest comprises a reporter gene, a gene encoding a DtE protein (such as a polypeptide derived from *E. coli* or a fragment thereof), an ancillary gene or a combination thereof.

In some embodiments, the present disclosure provides a mammalian cell comprising at least six distinct RTS, wherein the cell comprises (a) at least two distinct RTS and a first gene of interest are chromosomally-integrated within the Fer1L4 locus; (b) at least two distinct RTS and a second gene of interest are chromosomally-integrated within the NL1 locus; and (c) at least two distinct RTS and a third gene of interest are chromosomally-integrated within the NL2 locus.

As referred to herein, the terms "in operable combination," "in operable order," and "operably linked" refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced. In some embodiments, a gene of interest is operably linked to a promoter, wherein the gene of interest is chromosomally-integrated into the host cell. In some embodiments, the gene of interest is operably linked to a heterologous promoter; where in the gene of interest is chromosomally-integrated into the host cell. In some embodiments, an ancillary gene is operably linked to a promoter, wherein the ancillary gene is chromosomally-integrated into the host cell genome. In some embodiments, the ancillary gene is operably linked to a heterologous promoter; where in the ancillary gene is chromosomally-integrated into the host cell genome. In some embodiments, a gene encoding a DtE protein is operably linked to a promoter, wherein the gene encoding a DtE protein is chromosomally-integrated into the host cell genome. In some embodiments, the gene encoding a DE protein is operably linked to a heterologous promoter, where in the gene encoding a DIE protein is chromosomally-integrated into the host cell genome. In some embodiments, a recombinase gene is operably linked to a promoter, wherein the recombinase gene is chromosomally-integrated into the host cell. In some embodiments, the recombinase gene is operably linked to a promoter, where in the recombinase gene is not integrated into the host cell genome. In some embodiments, a recombinase gene is operably linked to a heterologous promoter, wherein the recombinase gene is not chromosomally-integrated into the host cell genome. In some embodiments, the recombinase gene is operably linked to a heterologous promoter, wherein the recombinase gene is not chromosomally-integrated into the host cell genome.

s referred to herein, the term "chromosomally-integrated" or "chromosomal integration" refers to the stable incorporation of a nucleic acid sequence into the chromosome of a host cell, e.g. a mammalian cell. i.e., a nucleic acid sequence that is chromosomally-integrated into the genomic DNA (gDNA) of a host cell, e.g. a mammalian cell. In some embodiments, a nucleic acid sequence that is chromosomally-integrated is stable. In some embodiments, a nucleic acid sequence that is chromosomally-integrated is not located on a plasmid or a vector. In some embodiments, a nucleic acid sequence that is chromosomally-integrated is not excised. In some embodiments, chromosomal integration is mediated by the clustered regularly interspaced short palindromic repeats (CRISPR) and CRISPR associated protein (Cas) gene editing system (CRISPR/CAS).

In some embodiments, the host cells are suitable for growth in suspension cultures. Suspension competent host cells are generally monodisperse or grow in loose aggregates without substantial aggregation. Suspension competent host cells include cells that are suitable for suspension culture without adaptation or manipulation (e.g., hematopoietic cells, lymphoid cells) and cells that have been made suspension competent by modification or adaptation of attachment-dependent cells (e.g., epithelial cells, fibroblasts).

In some embodiments, the expression level or activity of the polypeptide derived from *E. coli* or fragment thereof is increased by at least 2-fold, at least 3 fold, at least 5 fold, at least 10 fold, at least 20 fold, at least 30 fold, at least 40 fold, at least 50 fold, at least 60 fold, at least 70 fold, at least 75 fold, at least 80 fold, at least 90 fold, at least 100 fold, as compared to expression of the polypeptide derived from *E. coli* or a fragment thereof in a bacterial cell, such as, for example, an *E. coli* host cell.

The host cells described herein are suitable for large scale culture. For example, the cell cultures may be 10 L, 30 L, 50 L, 100 L, 150 L, 200 L, 300 L, 500 L, 1000 L, 2000 L, 3000 L, 4000 L, 5000 L, 10,000 L or larger. In some embodiments, the cell culture size may range from 10 L to 5000 L, from 10 L to 10,000 L, from 10 L, to 20,000 L, from 10 I, to 50,000 L, from 40 I, to 50,000 L, from 100 L to 50,000 L, from 500 L to 50,000 L, from 1000 L to 50,000 L, from 2000 L to 50,000 L, from 3000 I, to 50,000 L, from 4000 L to 50,000 L, from 4500 L to 50,000 L, from 1000 L to 10,000 L, from 1000 L to 20,000 L, from 1000 L to 25,000 L, from 1000 L to 30,000 L, from 15 L to 2000 L, from 40 L to 1000 L, from 100 L to 500 L, from 200 L to 400 L, or any integer there between. Media components for cell culture are known in the art, and may include, e.g., buffer, amino acid content, vitamin content, salt content, mineral content, serum content, carbon source content, lipid content, nucleic acid content, hormone content, trace element content, ammonia content, co-factor content, indicator content, small molecule content, hydrolysate content and enzyme modulator content.

The terms "medium", "cell culture medium" and "culture medium" as used herein refer to a solution containing nutrients which nourish growing mammalian cells. Typically, such solutions provide essential and non-essential amino acids, vitamins, energy sources, lipids, and trace elements required by the cell for minimal growth and/or survival. Such a solution may also contain supplementary components that enhance growth and/or survival above the minimal rate, including, but not limited to, hormones and/or other growth factors, particular ions (such as sodium, chloride, calcium, magnesium, and phosphate), buffers, vitamins, nucleosides or nucleotides, trace elements (inorganic compounds usually present at very low final concentrations), inorganic compounds present at high final concentrations (e.g., iron), amino acids, lipids, and/or glucose or other energy source. In some embodiments, a medium is advantageously formulated to a pH and salt concentration optimal for cell survival and proliferation. In some embodiments, a medium is a feed medium that is added after the beginning of the cell culture.

In some embodiments, cells may be grown in one of a variety of chemically defined media, wherein the components of the media are both known and controlled. In some embodiments, cells may be grown in a complex medium, in which not all components of the medium are known and/or controlled. Chemically defined growth media for mammalian cell culture have been extensively developed and published over the last several decades. All components of defined media are well characterized, and so defined media do not contain complex additives such as serum or hydrolysates. Early media formulations were developed to permit cell growth and maintenance of viability with little or no concern for protein production. More recently, media formulations have been developed with the express purpose of supporting highly productive recombinant protein producing cell cultures. Such media are preferred for use in the method of the invention. Such media generally comprises high amounts of nutrients and in particular of amino acids to support the growth and/or the maintenance of cells at high density. If necessary, these media can be modified by the skilled person for use in the method of the invention. For example, the skilled person may decrease the amount of phenylalanine, tyrosine, tryptophan and/or methionine in these media for their use as base media or feed media in a method as disclosed herein.

Not all components of complex media are well characterized, and so complex media may contain additives such as simple and/or complex carbon sources, simple and/or complex nitrogen sources, and serum, among other things. In some embodiments, complex media suitable for the present invention contains additives such as hydrolysates in addition to other components of defined medium as described herein. In some embodiments, defined media typically includes roughly fifty chemical entities at known concentrations in water. Most of them also contain one or more well-characterized proteins such as insulin, IGF-1, transferrin or BSA, but others require no protein components and so are referred to as protein-free defined media. Typical chemical components of the media fall into five broad categories: amino acids, vitamins, inorganic salts, trace elements, and a miscellaneous category that defies neat categorization.

Cell culture medium may be optionally supplemented with supplementary components. The term "supplementary components" as used herein refers to components that enhance growth and/or survival above the minimal rate, including, but not limited to, hormones and/or other growth factors, particular ions (such as sodium, chloride, calcium, magnesium, and phosphate), buffers, vitamins, nucleosides or nucleotides, trace elements (inorganic compounds usually present at very low final concentrations), amino acids, lipids, and/or glucose or other energy source. In some embodiments, supplementary components may be added to the initial cell culture. In some embodiments, supplementary components may be added after the beginning of the cell culture. Typically, trace elements refer to a variety of inorganic salts included at micromolar or lower levels. For example, commonly included trace elements are zinc, selenium, copper, and others. In some embodiments, iron (ferrous or ferric salts) can be included as a trace element in the initial cell culture medium at micromolar concentrations. Manganese is also frequently included among the trace elements as a divalent cation ($MnCl_2$ or $MnSO_4$) in a range of nanomolar to micromolar concentrations. Numerous less common trace elements are usually added at nanomolar concentrations.

In some embodiments, the medium used in the method of the invention is a medium suitable for supporting high cell density, such as for example $1\times10^6$ cells/mL, $5\times10^6$ cells/mL, $1\times10^7$ cells/mL, $5\times10^7$ cells/mL, $1\times10^8$ cells/mL or $5\times10^8$ cells/mL, in a cell culture. In some embodiments, the cell culture is a mammalian cell fed-batch culture, preferably a CHO cells fed-batch culture.

In some embodiments, the cell culture medium comprises phenylalanine at a concentration below 2 mM, below 1 mM, between 0.1 and 2 mM, between 0.1 to 1 mM, between 0.5 and 1.5 mM or between 0.5 to 1 mM. In some embodiments, the cell culture medium comprises tyrosine at a concentration below 2 mM, below 1 mM, between 0.1 and 2 mM, between 0.1 to 1 mM, between 0.5 and 1.5 mM or between 0.5 to 1 mM. In some embodiments, the cell culture medium comprises tryptophan at a concentration below 2 mM, below 1 mM, between 0.1 and 2 mM, between 0.1 to 1 mM, between 0.5 and 1.5 mM or between 0.5 to 1 mM. In some embodiments, the cell culture medium comprises methionine at a concentration below 2 mM, below 1 mM, between 0.1 and 2 mM, between 0.1 to 1 mM, between 0.5 and 1.5 mM or between 0.5 to 1 mM. In some embodiments, the cell culture medium comprises leucine at a concentration below 2 mM, below 1 mM, between 0.1 and 2 mM, between 0.1 to 1 mM, between 0.5 and 1.5 mM or between 0.5 to 1 mM. In some embodiments, the cell culture medium comprises serine at a concentration below 2 mM, below 1 mM, between 0.1 and 2 mM, between 0.1 to 1 mM, between 0.5 and 1.5 mM or between 0.5 to 1 mM. In some embodiments, the cell culture medium comprises threonine at a concentration below 2 mM, below 1 mM, between 0.1 and 2 mM, between 0.1 to 1 mM, between 0.5 and 1.5 mM or between 0.5 to 1 mM. In some embodiments, the cell culture medium comprises glycine at a concentration below 2 mM, below 1 mM, between 0.1 and 2 mM, between 0.1 to 1 mM, between 0.5 and 1.5 mM or between 0.5 to 1 mM. In some embodiments, the cell culture medium comprises two of phenylalanine, tyrosine, tryptophan, methionine, leucine, serine, threonine and glycine at a concentration below 2 mM, below 1 mM, between 0.1 and 2 mM, between 0.1 to 1 mM, between 0.5 and 1.5 mM or between 0.5 to 1 mM. In some embodiments, the cell culture medium comprises phenylalanine and tyrosine at a concentration below 2 mM, below 1 mM, between 0.1 and 2 mM, between 0.1 to 1 mM, between 0.5 and 1.5 mM or between 0.5 to 1 mM. In some embodiments, the cell culture medium comprises phenylalanine and tryptophan at a concentration below 2 mM, below 1 mM, between 0.1 and 2 mM, between 0.1 to 1 mM, between 0.5 and 1.5 mM or between 0.5 to 1 mM. In some embodiments, the cell culture medium comprises phenylalanine and methionine at a concentration below 2 mM, below 1 mM, between 0.1 and 2 mM, between 0.1 to 1 mM, between 0.5 and 1.5 mM or between 0.5 to 1 mM. In some embodiments, the cell culture medium comprises tyrosine and tryptophan at a concentration below 2 mM, below 1 mM, between 0.1 and 2 mM, between 0.1 to 1 mM, between 0.5 and 1.5 mM or between 0.5 to 1 mM. In some embodiments, the cell culture medium comprises tyrosine and methionine at a concentration below 2 mM, below 1 mM, between 0.1 and 2 mM, between 0.1 to 1 mM, between 0.5 and 1.5 mM or between 0.5 to 1 mM. In some embodiments, the cell culture medium comprises tryptophan and methionine at a concentration below 2 mM, below 1 mM, between 0.1 and 2 mM, between 0.1 to 1 mM, between 0.5 and 1.5 mM or between 0.5 to 1 mM. In some embodiments, the cell culture medium comprises three of phenylalanine, tyrosine, tryptophan, methionine, leucine, serine, threonine and glycine at a concentration below 2 mM, below 1 mM, between 0.1 and 2 mM, between 0.1 to 1 mM, between 0.5 and 1.5 mM or between 0.5 to 1 mM. In some embodiments, the cell culture medium comprises phenylalanine, tyrosine and tryptophan at a concentration below 2 mM, below 1 mM, between 0.1 and 2 mM, between 0.1 to 1 mM, between 0.5 and 1.5 mM or between 0.5 to 1 mM. In some embodiments, the cell culture medium comprises phenylalanine, tyrosine and methionine at a concentration below 2 mM, below 1 mM, between 0.1 and 2 mM, between 0.1 to 1 mM, between 0.5 and 1.5 mM or between 0.5 to 1 mM. In some embodiments, the cell culture medium comprises phenylalanine, tryptophan and methionine at a concentration below 2 mM, below 1 mM, between 0.1 and 2 mM, between 0.1 to 1 mM, between 0.5 and 1.5 mM or between 0.5 to 1 mM. In some embodiments, the cell culture medium comprises tyrosine, tryptophan and methionine at a concentration below 2 mM, below 1 mM, between 0.1 and 2 mM, between 0.1 to 1 mM, between 0.5 and 1.5 mM or between 0.5 to 1 mM. In some embodiments, the cell culture medium comprises four of phenylalanine, tyrosine, tryptophan, methionine, leucine, serine, threonine and glycine at a concentration below 2 mM, below 1 mM, between 0.1 and 2 mM, between 0.1 to 1 mM, between 0.5 and 1.5 mM or between 0.5 to 1 mM. In some embodiments, the cell culture medium comprises phenylalanine, tyrosine, tryptophan and methionine at a concentration below 2 mM, below 1 mM, between 0.1 and 2 mM, between 0.1 to 1 mM, between 0.5 and 1.5 mM or between 0.5 to 1 mM. In some embodiments, the cell culture medium comprises five of phenylalanine, tyrosine, tryptophan, methionine, leucine, serine, threonine and glycine at a concentration below 2 mM, below 1 mM, between 0.1 and 2 mM, between 0.1 to 1 mM, between 0.5 and 1.5 mM or between 0.5 to 1 mM. In some embodiments, the cell culture medium comprises six of phenylalanine, tyrosine, tryptophan, methionine, leucine, serine, threonine and glycine at a concentration below 2 mM, below 1 mM, between 0.1 and 2 mM, between 0.1 to 1 mM, between 0.5 and 1.5 mM or between 0.5 to 1 mM. In some embodiments, the cell culture medium comprises seven of phenylalanine, tyrosine, tryptophan, methionine, leucine, serine, threonine and glycine at a concentration below 2 mM, below 1 mM, between 0.1 and 2 mM, between 0.1 to 1 mM, between 0.5 and 1.5 mM or between 0.5 to 1 mM. In some embodiments, the cell culture medium comprises phenylalanine, tyrosine, tryptophan, methionine, leucine, serine, threonine and glycine at a concentration below 2 mM, below 1 mM, between 0.1 and 2 mM, between 0.1 to 1 mM, between 0.5 and 1.5 mM or between 0.5 to 1 mM. In some embodiments, the cell culture medium further comprises at least 1, 2, 3, 4, 5, 6, 7, 8, 9, 10, 11, 12 or 13 of glycine, valine, leucine, isoleucine, proline, serine, threonine, lysine, arginine, histidine, aspartate, glutamate and asparagine at a concentration above 2 mM, 3 mM, 4 mM, 5 mM, 10 mM, 15 mM, preferably 2 mM. In some embodiments, the cell culture medium further comprises at least 5 of glycine, valine, leucine, isoleucine, proline, serine, threonine, lysine, arginine, histidine, aspartate, glutamate and asparagine at a concentration above 2 mM, 3 mM, 4 mM, 5 mM, 10 mM, 15 mM, preferably 2 mM. In some embodiments, the cell culture medium further comprises glycine, valine, leucine, isoleucine, proline, serine, threonine, lysine, arginine, histidine, aspartate, glutamate and asparagine at a concentration above 2 mM, 3 mM, 4 mM, 5 mM, 10 mM, 15 mM, preferably 2 mM. In some embodiments, the cell culture medium further comprises at least 1, 2, 3, 4, 5, 6, 7, 8, or 9 of valine, isoleucine, proline, lysine, arginine, histidine, aspartate, glutamate and asparagine at a concentration above 2 mM, 3 mM, 4 mM, 5 mM, 10 mM, 15 mM, preferably 2 mM. In some embodiments, the cell culture medium further comprises at least 5 of valine, isoleucine, proline, lysine, arginine, histidine, aspartate, glutamate and asparagine at a concentration above 2 mM, 3 mM, 4 mM, 5 mM, 10 mM, 15 mM, preferably 2 mM. In some embodiments, the cell culture medium further comprises valine, isoleucine, proline, lysine, arginine, histidine, aspartate, glutamate and asparagine at a concentration above 2 mM, 3 mM, 4 mM, 5 mM, 10 mM, 15 mM, preferably 2 mM. In some embodiments, the cell culture medium comprises serine at a concentration above 3 mM, 5 mM, 7 mM, 10 mM, 15 mM or 20 mM, preferably 10 mM. In some embodiments, the cell culture medium comprises valine at a concentration above 3 mM, 5 mM, 7 mM, 10 mM, 15 mM or 20 mM, preferably 10 mM. In some embodiments, the cell culture medium comprises cysteine at a concentration above 3 mM, 5 mM, 7 mM, 10 mM, 15 mM or 20 mM, preferably 10 mM. In some embodiments, the cell culture medium comprises isoleucine at a concentration above 3 mM, 5 mM, 7 mM, 10 mM, 15 mM or 20 mM, preferably 10 mM. In some embodiments, the cell culture medium comprises leucine at a concentration above 3 mM, 5 mM, 7 mM, 10 mM, 15 mM or 20 mM, preferably 10 mM. In some embodiments, the above cell culture medium is for use in a method as disclosed herein. In some embodiments, the above cell culture medium is used in a method as disclosed herein as a base media. In some embodiments, the above cell culture medium is used a method as disclosed herein as a feed media.

IV. Method of Producing

In one aspect, the invention includes a method of producing a polypeptide derived from *E. coli* or a fragment thereof. The method includes culturing a mammalian cell under a suitable condition, thereby expressing the polypeptide derived from *E. coli* or a fragment thereof. The method may further include harvesting the polypeptide derived from *E. coli* or a fragment thereof from the culture. The process may further include purifying the polypeptide derived from *E. coli* or a fragment thereof.

In some embodiments, the method produces the polypeptide or fragment thereof at a yield as 0.1 g/L to 0.5 g/L.

In some embodiments, the cells may be grown in batch or fed-batch cultures, where the culture is terminated after sufficient expression of the polypeptide, after which the expressed polypeptide is harvested and optionally purified. In some embodiments, the cells may be grown in perfusion cultures, where the culture is not terminated and new nutrients and other components are periodically or continuously added to the culture, during which the expressed polypeptide is periodically or continuously harvested.

In some embodiments, the cells may be grown in small scale reaction vessels ranging in volume from a few milliliters to several liters. In some embodiments, the cells may be grown in large scale commercial bioreactors ranging in volume from approximately least 1 liter to 10, 100, 250, 500, 1,000, 2,500, 5,000, 8,000, 10,000, 12,000 liters or more, or any volume in between.

The temperature of the cell culture will be selected based primarily on the range of temperatures at which the cell culture remains viable, at which a high level of polypeptide is produced, the temperature at which production or accumulation of metabolic waste products is minimized, and/or any combination of these or other factors deemed important by the practitioner. As one non-limiting example, CHO cells grow well and produce high levels or protein or polypeptide at approximately 37° C. In general, most mammalian cells grow well and/or can produce high levels or protein or polypeptide within a range of about 25° C. to 42° C., although methods taught by the present disclosure are not limited to these temperatures. Certain mammalian cells grow well and/or can produce high levels or protein or polypeptide within the range of about 35° C. to 40° C. In certain embodiments, the cell culture is grown at a temperature of 20° C., 21° C., 22° C., 23° C., 24° C., 25° C., 26° C., 27 C, 28° C., 29 C, 30° C., 31° C., 32° C., 33° C., 34° C., 35 C, 36° C., 37 C, 38° C., 39° C., 40 C, 41° C., 42° C., 43° C., 44° C., or 45 C at one or more times during the cell culture process.

The terms "culture" and "cell culture" as used herein refer to a cell population that is suspended in a medium under conditions suitable to survival and/or growth of the cell population. As will be clear to those of ordinary skill in the art, in some embodiments, these terms as used herein refer to the combination comprising the cell population and the medium in which the population is suspended. In some embodiments, the cells of the cell culture comprise mammalian cells.

The present invention may be used with any cell culture method that is amenable to the desired process (e.g., production of a recombinant protein (e.g., antibody)). As a non-limiting example, cells may be grown in batch or fed-batch cultures, where the culture is terminated after sufficient expression of the recombinant protein (e.g., antibody), after which the expressed protein (e.g., antibody) is harvested. Alternatively, as another non-limiting example, cells may be grown in batch-refeed, where the culture is not terminated and new nutrients and other components are periodically or continuously added to the culture, during which the expressed recombinant protein (e.g., antibody) is harvested periodically or continuously. Other suitable methods (e.g., spin-tube cultures) are known in the art and can be used to practice the present invention.

In some embodiments, a cell culture suitable for the present invention is a fed-batch culture. The term "fed-batch culture" as used herein refers to a method of culturing cells in which additional components are provided to the culture at a time or times subsequent to the beginning of the culture process. Such provided components typically comprise nutritional components for the cells which have been depleted during the culturing process. A fed-batch culture is typically stopped at some point and the cells and/or components in the medium are harvested and optionally purified. In some embodiments, the fed-batch culture comprises a base medium supplemented with feed media.

Cells may be grown in any convenient volume chosen by the practitioner. For example, cells may be grown in small scale reaction vessels ranging in volume from a few milliliters to several liters. Alternatively, cells may be grown in large scale commercial Bioreactors ranging in volume from approximately at least 1 liter to 10, 50, 100, 250, 500, 1000, 2500, 5000, 8000, 10,000, 12,000, 15000, 20000 or 25000 liters or more, or any volume in between.

The temperature of a cell culture will be selected based primarily on the range of temperatures at which the cell culture remains viable and the range in which a high level of desired product (e.g., a recombinant protein) is produced. In general, most mammalian cells grow well and can produce desired products (e.g., recombinant proteins) within a range of about 25° C. to 42° C., although methods taught by the present disclosure are not limited to these temperatures. Certain mammalian cells grow well and can produce desired products (e.g., recombinant proteins or antibodies) within the range of about 35° C. to 40° C. In certain embodiments, a cell culture is grown at a temperature of 20° C., 21° C., 22 C, 23° C., 24° C., 25° C., 26° C., 27 C, 28 C, 29° C., 30° C., 31° C., 32° C., 33 C, 34° C., 35 C, 36° C., 37° C., 38° C., 39° C., 40° C., 41° C., 42° C., 43° C., 44° C., or 45° ° C. at one or more times during the cell culture process. Those of ordinary skill in the art will be able to select appropriate temperature or temperatures in which to grow cells, depending on the particular needs of the cells and the particular production requirements of the practitioner. The cells may be grown for any amount of time, depending on the needs of the practitioner and the requirement of the cells themselves. In some embodiment, the cells are grown at 37° C. In some embodiments, the cells are grown at 36.5° C.

In some embodiments, the cells may be grown during the initial growth phase (or growth phase) for a greater or lesser amount of time, depending on the needs of the practitioner and the requirement of the cells themselves. In some embodiments, the cells are grown for a period of time sufficient to achieve a predefined cell density. In some embodiments, the cells are grown for a period of time sufficient to achieve a cell density that is a given percentage of the maximal cell density that the cells would eventually reach if allowed to grow undisturbed. For example, the cells may be grown for a period of time sufficient to achieve a desired viable cell density of 1, 5, 10, 15, 20, 25, 30, 35, 40, 45, 50, 55, 60, 65, 70, 75, 80, 85, 90, 95 or 99 percent of maximal cell density. In some embodiments, the cells are grown until the cell density does not increase by more than 15%, 14%, 13%, 12%, 11%, 10%, 9%, 8%, 7%, 6%, 5%, 4%, 3%, 2% or 1% per day of culture. In some embodiments, the cells are grown until the cell density does not increase by more than 5% per day of culture.

In some embodiment the cells are allowed to grow for a defined period of time. For example, depending on the starting concentration of the cell culture, the temperature at which the cells are grown, and the intrinsic growth rate of the cells, the cells may be grown for 0, 1, 2, 3, 4, 5, 6, 7, 8, 9, 10, 11, 12, 13, 14, 15, 16, 17, 18, 19, 20 or more days, preferably for 4 to 10 days. In some cases, the cells may be allowed to grow for a month or more. The practitioner of the present invention will be able to choose the duration of the initial growth phase depending on protein production requirements and the needs of the cells themselves.

The cell culture may be agitated or shaken during the initial culture phase in order to increase oxygenation and dispersion of nutrients to the cells. In accordance with the present invention, one of ordinary skill in the art will understand that it can be beneficial to control or regulate certain internal conditions of the bioreactor during the initial growth phase, including but not limited to pH, temperature, oxygenation, etc.

At the end of the initial growth phase, at least one of the culture conditions may be shifted so that a second set of culture conditions is applied and a metabolic shift occurs in the culture. A metabolic shift can be accomplished by, e.g., a change in the temperature, pH, osmolality or chemical inductant level of the cell culture. In one non-limiting embodiment, the culture conditions are shifted by shifting the temperature of the culture. However, as is known in the art, shifting temperature is not the only mechanism through which an appropriate metabolic shift can be achieved. For example, such a metabolic shift can also be achieved by shifting other culture conditions including, but not limited to, pH, osmolality, and sodium butyrate levels. The timing of the culture shift will be determined by the practitioner of the present invention, based on protein production requirements or the needs of the cells themselves.

When shifting the temperature of the culture, the temperature shift may be relatively gradual. For example, it may take several hours or days to complete the temperature change. Alternatively, the temperature shift may be relatively abrupt. For example, the temperature change may be complete in less than several hours. Given the appropriate production and control equipment, such as is standard in the commercial large-scale production of polypeptides or proteins, the temperature change may even be complete within less than an hour.

In some embodiments, once the conditions of the cell culture have been shifted as discussed above, the cell culture is maintained for a subsequent production phase under a second set of culture conditions conducive to the survival and viability of the cell culture and appropriate for expression of the desired polypeptide or protein at commercially adequate levels.

As discussed above, the culture may be shifted by shifting one or more of a number of culture conditions including, but not limited to, temperature, pH, osmolality, and sodium butyrate levels. In some embodiments, the temperature of the culture is shifted. According to this embodiment, during the subsequent production phase, the culture is maintained at a temperature or temperature range that is lower than the temperature or temperature range of the initial growth phase. As discussed above, multiple discrete temperature shifts may be employed to increase cell density or viability or to increase expression of the recombinant protein.

In some embodiments, the cells may be maintained in the subsequent production phase until a desired cell density or production titer is reached. In another embodiment of the present invention, the cells are allowed to grow for a defined period of time during the subsequent production phase. For example, depending on the concentration of the cell culture at the start of the subsequent growth phase, the temperature at which the cells are grown, and the intrinsic growth rate of the cells, the cells may be grown for 1, 2, 3, 4, 5, 6, 7, 8, 9, 10, 11, 12, 13, 14, 15, 16, 17, 18, 19, 20 or more days. In some cases, the cells may be allowed to grow for a month or more. The practitioner of the present invention will be able to choose the duration of the subsequent production phase depending on polypeptide or protein production requirements and the needs of the cells themselves.

The cell culture may be agitated or shaken during the subsequent production phase in order to increase oxygenation and dispersion of nutrients to the cells. In accordance with the present invention, one of ordinary skill in the art will understand that it can be beneficial to control or regulate certain internal conditions of the bioreactor during the subsequent growth phase, including but not limited to pH, temperature, oxygenation, etc.

In some embodiments, the cells express a recombinant protein and the cell culture method of the invention comprises a growth phase and a production phase.

In some embodiments, step (ii) of any of the methods disclosed herein is applied during the totality of the cell culture method. In some embodiments, step (ii) of any of the methods disclosed herein is applied during a part of the cell culture method. In some embodiments, step (ii) is applied until a predetermined viable cell density is obtained.

In some embodiments, the cell culture method of the invention comprises a growth phase and a production phase and step (ii) is applied during the growth phase. In some embodiments, the cell culture method of the invention comprises a growth phase and a production phase and step (ii) is applied during a part of the growth phase. In some embodiments, the cell culture method of the invention comprises a growth phase and a production phase and step (ii) is applied during the growth phase and the production phase.

In step (ii) of any of the methods disclosed herein, the term "maintaining" can refer to maintaining the concentration of amino acid or metabolite below C1 or C2 for the entire culture process (until harvesting) or for a part of the culture process such as for example the growth phase, a part of the growth phase or until a predetermined cell density is obtained.

In some embodiments of any of the above mentioned methods, cell growth and/or productivity are increased as compared to a control culture, said control culture being identical except that it does not comprise step (ii).

In some embodiments of any of the above mentioned methods, the method of the invention is a method for improving cell growth. In some embodiment, the method of the invention is a method for improving cell growth in high density cell culture at high cell density.

High cell density as used herein refers to cell density above $1\times10^6$ cells/mL, $5\times10^6$ cells/mL, $1\times10^7$ cells/mL, $5\times10^7$ cells/mL, $1\times10^8$ cells/mL or $5\times10^8$ cells/mL, preferably above $1\times10^7$ cells/mL, more preferably above $5\times10^7$ cells/mL.

In some embodiments, the method of the invention is a method for improving cell growth in a cell culture where cell density is above $1\times10^6$ cells/mL, $5\times10^6$ cells/mL, $1\times10^7$ cells/mL, $5\times10^7$ cells/mL, $1\times10^8$ cells/mL or $5\times10^8$ cells/mL. In some embodiments, the method of the invention is a method for improving cell growth in a cell culture where maximum cell density is above $1\times10^6$ cells/mL, $5\times10^6$ cells/mL, $1\times10^7$ cells/mL, $5\times10^7$ cells/mL, $1\times10^8$ cells/mL or $5\times10^8$ cells/mL.

In some embodiments, cell growth is determined by viable cell density (VCD), maximum viable cell density, or Integrated viable cell count (IVCC). In some embodiments, cell growth is determined by maximum viable cell density.

The term "viable cell density" as used herein refers to the number of cells present in a given volume of medium. Viable cell density can be measured by any method known to the skilled person. Preferably, Viable cell density is measured using an automated cell counter such as Bioprofile Flex®. The term maximum cell density as used herein refers to the maximum cell density achieved during the cell culture. The term "cell viability" as used herein refers to the ability of cells in culture to survive under a given set of culture conditions or experimental variations. Those of ordinary skill in the art will appreciate that one of many methods for determining cell viability are encompassed in this invention. For example, one may use a dye (e.g., trypan blue) that does not pass through the membrane of a living cell, but can pass through the disrupted membrane of a dead or dying cell in order to determine cell viability.

The term "Integrated viable cell count (IVCC)" as used herein refers to as the area under the viable cell density (VCD) curve. IVCC can be calculated using the following formula: $IVCC_{t+1}=IVCC_t+(VCD_t+VCD_{t+1})*(\Delta t)/2$, where $\Delta t$ is the time difference between t and t+1 time points. $IVCC_{t=0}$ can be assumed negligible. $VCD_t$ and $VCD_{t+1}$ are viable cell densities at t and t+1 time points.

The term "titer" as used herein refers, for example, to the total amount of recombinantly expressed protein produced by a cell culture in a given amount of medium volume. Titer is typically expressed in units of grams of protein per liter of medium.

In some embodiments, cell growth is increased by at least 5%, 10%, 15%, 20% or 25% as compared to the control culture. In some embodiments, cell growth is increased by at least 10% as compared to the control culture. In some embodiments, cell growth is increased by at least 20% as compared to the control culture.

In some embodiments, the productivity is determined by titer and/or volumetric productivity.

The term "titer" as used herein refers, for example, to the total amount of recombinantly expressed protein produced by a cell culture in a given amount of medium volume. Titer is typically expressed in units of grams of protein per liter of medium.

In some embodiments, the productivity is determined by titer. In some embodiments, the productivity is increased by at least 5%, 10%, 15%, 20% or 25% as compared to the control culture. In some embodiments, the productivity is increased by at least 10% as compared to a control culture. In some embodiments, the productivity is increased by at least 20% as compared to a control culture.

In some embodiments, the maximum cell density of the cell culture is greater than $1\times10^6$ cells/mL, $5\times10^6$ cells/mL, $1\times10^7$ cells/mL, $5\times10^7$ cells/mL, $1\times10^8$ cells/mL or $5\times10^8$ cells/mL. In some embodiments, the maximum cell density of the cell culture is greater than $5\times10^6$ cells/mL. In some embodiments, the maximum cell density of the cell culture is greater than $1\times10^8$ cells/mL.

V. Purification

In some embodiments, the method for producing a polypeptide derived from *E. coli* or a fragment thereof includes isolating and/or purifying the polypeptide derived from *E. coli* or a fragment thereof. In some embodiments, the expressed polypeptide derived from *E. coli* or a fragment thereof is secreted into the medium and thus cells and other solids may be removed by centrifugation and/or filtration.

The polypeptide derived from *E. coli* or a fragment thereof produced in accordance with the methods described herein may be harvested from host cells and purified using any suitable method. Suitable methods for purifying the polypeptide or fragment thereof include precipitation and various types of chromatography, such as hydrophobic interaction, ion exchange, affinity, chelation, and size exclusion, all of which are known in the art. Suitable purification schemes may include two or more of these or other suitable methods. In some embodiments, one or more of the polypeptide or fragments thereof derived from *E. coli* may include a "tag" that facilitates purification, such as an epitope tag or a HIS tag, Strep tag. Such tagged polypeptides may conveniently be purified, for example from conditioned media, by chelating chromatography or affinity chromatography. Optionally, the tag sequence may be cleaved post-purification.

In some embodiments, the polypeptide derived from *E. coli* or a fragment thereof may include a tag for affinity purification. Affinity purification tags are known in the art. Examples include, e.g., His tag (binds to metal ion), an antibody, maltose-binding protein (MBP) (binds to amylose), glutathione-S-transferase (GST) (binds to glutathione), FLAG tag, Strep tag (binds to streptavidin or a derivative thereof).

In a preferred embodiment, the polypeptide derived from *E. coli* or a fragment thereof does not include a purification tag.

In some embodiments, the yield of the polypeptide derived from *E. coli* or a fragment thereof is at least about 1 mg/L, at least about 2 mg/L, at least about 3 mg/L, at least about 4 mg/L, at least about 5 mg/L, at least about 6 mg/L, at least about 7 mg/L, at least about 8 mg/L, at least about 9 mg/L, at least about 10 mg/L, at least about 11 mg/L, at least about 12 mg/L, at least about 13 mg/L, at least about 14 mg/L, at least about 15 mg/L, at least about 16 mg/L, at least about 17 mg/L, at least about 18 mg/L, at least about 19 mg/L, at least about 20 mg/L, at least about 25 mg/L, at least about 30 mg/L, at least about 35 mg/L, at least about 40 mg/L, at least about 45 mg/L, at least about 50 mg/L, at least about 55 mg/L, at least about 60 mg/L, at least about 65 mg/L, at least about 70 mg/L, at least about 75 mg/L, at least about 80 mg/L, at least about 85 mg/L, at least about 90 mg/L, at least about 95 mg/L, or at least about 100 mg/L.

In some embodiments, the culture is at least about 10 liters in size, e.g., a volume of at least about 10L, at least about 20L, at least about 30L, at least about 40L, at least about 50L, at least about 60 L, at least about 70L, at least about 80L, at least about 90L, at least about 100L, at least about 150L, at least about 200L, at least about 250L, at least about 300L, at least about 400L, at least about 500L, at least about 600L, at least about 700L, at least about 800L, at least about 900L, at least about 1000 L, at least about 2000 L, at least about 3000 L, at least about 4000 L, at least about 5000 L, at least about 6000 L, at least about 10,000 L, at least about 15,000 L, at least about 20,000 L, at least about 25,000 L, at least about 30,000 L, at least about 35,000 L, at least about 40,000 L, at least about 45,000 L, at least about 50,000 L, at least about 55,000 L, at least about 60,000 L, at least about 65,000 L, at least about 70,000 L, at least about 75,000 L, at least about 80,000 L, at least about 85,000 L, at least about 90,000 L, at least about 95,000 L, at least about 100,000 L, etc.

VI. Compositions and Formulations

In one aspect, the invention includes a composition that includes a polypeptide derived from *E. coli* or a fragment thereof. In some embodiments, the composition elicits an immune response, including antibodies, that may confer immunity to pathogenic species of *E. coli.*

In some embodiments, the composition includes the polypeptide derived from *E. coli* or fragment thereof as the only antigen. In some embodiments, the composition does not include a conjugate.

In some embodiments, the composition includes the polypeptide derived from *E. coli* or fragment thereof and an additional antigen. In some embodiments, the composition includes the polypeptide derived from *E. coli* or fragment thereof and an additional *E. coli* antigen. In some embodiments, the composition includes the polypeptide derived from *E. coli* or fragment thereof and a glycoconjugate from *E. coli.*

In some embodiments, the polypeptide or a fragment thereof is derived from *E. coli* FimH.

In some embodiments, the composition includes a polypeptide derived from *E. coli* FimC or a fragment thereof.

In some embodiments, the composition includes a polypeptide derived from *E. coli* FimH or a fragment thereof; and a polypeptide derived from *E. coli* FimC or a fragment thereof.

In one aspect, the invention includes a composition including a polypeptide derived from *E. coli* FimH or a fragment thereof; and a saccharide comprising a structure selected from any one of Formula O1 (e.g., Formula O1A, Formula O1B, and Formula O1C), Formula O2, Formula O3, Formula O4 (e.g., Formula O4: K52 and Formula O4:

K6), Formula O5 (e.g., Formula O5ab and Formula O5ac (strain 180/C3)), Formula 06 (e.g., Formula O6: K2; K13; K15 and Formula O6: K54), Formula O7, Formula O8, Formula O9, Formula O10, Formula O11, Formula O12, Formula O13, Formula O14, Formula O15, Formula O16, Formula O17, Formula O18 (e.g., Formula O18A, Formula O18ac, Formula O18A1, Formula O18B, and Formula O18B1), Formula O19, Formula O20, Formula O21, Formula O22, Formula O23 (e.g., Formula O23A), Formula O24, Formula O25 (e.g., Formula O25a and Formula O25b), Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45 (e.g., Formula O45 and Formula O45rel), Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula $62D_1$, Formula O63, Formula O64, Formula O65, Formula O66, Formula O68, Formula O69, Formula O70, Formula O71, Formula O73 (e.g., Formula O73 (strain 73-1)), Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144, Formula O145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, and Formula O187, wherein n is an integer from 1 to 100.

In some embodiments, the composition includes one or more saccharides that are, or derived from, one or more *K. pneumoniae* serotypes selected from 01 (and d-Gal-Ill variants), 02 (and d-Gal-III variants), O2ac, O3, O4, O5, O7, O8, and 012. In some embodiments, the composition includes a saccharide from or derived from one or more of serotypes O1, O2, O3, and O5, or a combination thereof. In some embodiments, the composition includes a saccharide from or derived from each of *K. pneumoniae* serotypes O1, O2, O3, and O5.

In some embodiments, the composition further includes at least one saccharide derived from any one *K. pneumoniae* type selected from the group consisting of O1, O2, O3, and O5. In some embodiments, the composition further includes at least one saccharide derived from *K. pneumoniae* type 01. In some embodiments, the composition further includes at least one saccharide derived from *K. pneumoniae* type 02. In some embodiments, the composition includes a combination of saccharides wherein the saccharide is derived from any one of *K. pneumoniae* types selected from the group consisting of O1, O2, O3, and O5. For example, in some embodiments, the composition includes at least one saccharide derived from *K. pneumoniae* type O1 and at least one saccharide derived from *K. pneumoniae* type 02. In a preferred embodiment, the saccharide derived from *K. pneumoniae* is conjugated to a carrier protein; and the saccharide derived from *E. coli* is conjugated to a carrier protein.

In some embodiments, the composition includes any one of the saccharides disclosed herein. In preferred embodiments, the composition includes any one of the conjugates disclosed herein.

In some embodiments, the composition includes at least one glycoconjugate from *E. coli* serotype O25, preferably serotype O25b. In one embodiment, the composition includes at least one glycoconjugate from *E. coli* serotype O1, preferably serotype O1a. In one embodiment, the composition includes at least one glycoconjugate from *E. coli* serotype O2. In one embodiment, the composition includes at least one glycoconjugate from *E. coli* serotype O6.

In one embodiment, the composition includes at least one glycoconjugate selected from any one of the following *E. coli* serotypes O25, O1, O2, and O6, preferably O25b, O1a, O2, and O6. In one embodiment, the composition includes at least two glycoconjugates selected from any one of the following *E. coli* serotypes O25, O1, O2, and O6, preferably O25b, O1a, O2, and O6. In one embodiment, the composition includes at least three glycoconjugates selected from any one of the following *E. coli* serotypes O25, O1, O2, and O6, preferably O25b, O1a, O2, and O6. In one embodiment, the composition includes a glycoconjugate from each of the following *E. coli* serotypes O25, O1, O2, and O6, preferably O25b, O1a, O2, and O6.

In a preferred embodiment, the glycoconjugate of any of the above compositions is individually conjugated to $CRM_{197}$.

Accordingly, in some embodiments, the composition includes a polypeptide derived from *E. coli* or a fragment thereof, and an O-antigen from at least one *E. coli* serotype. In a preferred embodiment, the composition includes a polypeptide derived from *E. coli* or a fragment thereof; and an O-antigen from more than 1 *E. coli* serotype. For example, the composition may include an O-antigen from two different *E. coli* serotypes (or "v", valences) to 12 different serotypes (12v). In one embodiment, the composition includes a polypeptide derived from *E. coli* or a fragment thereof; and an O-antigen from 3 different serotypes. In one embodiment, the composition includes a polypeptide derived from *E. coli* or a fragment thereof; and an O-antigen from 4 different *E. coli* serotypes. In one embodiment, the composition includes an O-antigen from 5 different *E. coli* serotypes. In one embodiment, the composition includes a polypeptide derived from *E. coli* or a fragment thereof; and an O-antigen from 6 different *E. coli* serotypes. In one embodiment, the composition includes a polypeptide derived from *E. coli* or a fragment thereof; and an O-antigen from 7 different *E. coli* serotypes. In one embodiment, the composition includes a polypeptide derived from *E. coli* or a fragment thereof; and an O-antigen from 8 different *E. coli* serotypes. In one embodiment, the composition includes a polypeptide derived from *E. coli* or a fragment thereof; and an O-antigen from 9 different *E. coli* serotypes. In one embodiment, the composition includes a polypeptide derived from *E. coli* or a fragment thereof; and an O-antigen from 10 different *E. coli* serotypes. In one embodiment, the composition includes a polypeptide derived from *E. coli* or a fragment thereof; and an O-antigen from 11 different *E. coli* serotypes. In one embodiment, the composition includes a polypeptide derived from *E. coli* or a fragment thereof; and an O-antigen from 12 different serotypes. In one embodiment, the composition includes a polypeptide derived from *E. coli* or a fragment thereof; and an O-antigen from 13 different serotypes. In one embodiment, the composition includes a polypeptide derived from *E. coli* or a fragment thereof; and an O-antigen from 14 different serotypes. In one embodiment, the composition includes a polypeptide derived from *E. coli* or a fragment thereof; and an O-antigen from 15 different serotypes. In one embodiment, the composition includes a polypeptide derived from *E. coli* or a fragment thereof; and an O-antigen from 16 different serotypes. In one embodiment, the composition includes a polypeptide derived from *E. coli* or a fragment thereof; and an O-antigen from 17 different serotypes. In one embodiment, the composition includes a polypeptide derived from *E. coli* or a fragment thereof; and an O-antigen from 18 different serotypes. In one embodiment, the composition includes a polypeptide derived from *E. coli* or a fragment thereof; and an O-antigen from 19 different serotypes. In one embodiment, the composition includes a polypeptide derived from *E. coli* or a fragment thereof; and an O-antigen from 20 different serotypes.

Preferably, the number of *E. coli* saccharides can range from 1 serotype (or “v”, valences) to 26 different serotypes (26v). In one embodiment there is one serotype. In one embodiment there are 2 different serotypes. In one embodiment there are 3 different serotypes. In one embodiment there are 4 different serotypes. In one embodiment there are 5 different serotypes. In one embodiment there are 6 different serotypes. In one embodiment there are 7 different serotypes. In one embodiment there are 8 different serotypes. In one embodiment there are 9 different serotypes. In one embodiment there are 10 different serotypes. In one embodiment there are 11 different serotypes. In one embodiment there are 12 different serotypes. In one embodiment there are 13 different serotypes. In one embodiment there are 14 different serotypes. In one embodiment there are 15 different serotypes. In one embodiment there are 16 different serotypes. In one embodiment there are 17 different serotypes. In one embodiment there are 18 different serotypes. In one embodiment there are 19 different serotypes. In one embodiment there are 20 different serotypes. In one embodiment there are 21 different serotypes. In one embodiment there are 22 different serotypes. In one embodiment there are 23 different serotypes. In one embodiment there are 24 different serotypes. In an embodiment there are 25 different serotypes. In one embodiment there are 26 different serotypes. The saccharides are conjugated to a carrier protein to form glycoconjugates as described herein.

In one aspect, the composition includes a polypeptide derived from *E. coli* or a fragment thereof; and a glycoconjugate that includes an O-antigen from at least one *E. coli* serogroup, wherein the O-antigen is conjugated to a carrier protein. In one embodiment, the composition includes a polypeptide derived from *E. coli* or a fragment thereof; and an O-antigen from more than 1 *E. coli* serotype, wherein each O-antigen is conjugated to a carrier protein. In one embodiment, the composition includes a polypeptide derived from *E. coli* or a fragment thereof; and an O-antigen from 2 different *E. coli* serotypes, wherein each O-antigen is conjugated to a carrier protein. In one embodiment, the composition includes a polypeptide derived from *E. coli* or a fragment thereof; and an O-antigen from 3 different *E. coli* serotypes, wherein each O-antigen is conjugated to a carrier protein. In one embodiment, the composition includes a polypeptide derived from *E. coli* or a fragment thereof; and an O-antigen from 4 different *E. coli* serotypes, wherein each O-antigen is conjugated to a carrier protein. In one embodiment, the composition includes a polypeptide derived from *E. coli* or a fragment thereof; and an O-antigen from 5 different *E. coli* serotypes, wherein each O-antigen is conjugated to a carrier protein. In one embodiment, the composition includes a polypeptide derived from *E. coli* or a fragment thereof; and an O-antigen from 6 different *E. coli* serotypes, wherein each O-antigen is conjugated to a carrier protein. In one embodiment, the composition includes a polypeptide derived from *E. coli* or a fragment thereof; and an O-antigen from 7 different *E. coli* serotypes, wherein each O-antigen is conjugated to a carrier protein. In one embodiment, the composition includes a polypeptide derived from *E. coli* or a fragment thereof; and an O-antigen from 8 different *E. coli* serotypes, wherein each O-antigen is conjugated to a carrier protein. In one embodiment, the composition includes a polypeptide derived from *E. coli* or a fragment thereof; and an O-antigen from 9 different *E. coli* serotypes, wherein each O-antigen is conjugated to a carrier protein. In one embodiment, the composition includes an O-antigen from a polypeptide derived from *E. coli* or a fragment thereof; and 10 different *E. coli* serotypes, wherein each O-antigen is conjugated to a carrier protein. In one embodiment, the composition includes an O-antigen from a polypeptide derived from *E. coli* or a fragment thereof; and 11 different *E. coli* serotypes, wherein each O-antigen is conjugated to a carrier protein. In one embodiment, the composition includes a polypeptide derived from *E. coli* or a fragment thereof; and an O-antigen from 12 different serotypes, wherein each O-antigen is conjugated to a carrier protein. In one embodiment, the composition includes a polypeptide derived from *E. coli* or a fragment thereof; and an O-antigen from 13 different serotypes, wherein each O-antigen is conjugated to a carrier protein. In one embodiment, the composition includes a polypeptide derived from *E. coli* or a fragment thereof; and an O-antigen from 14 different serotypes, wherein each O-antigen is conjugated to a carrier protein. In one embodiment, the composition includes a polypeptide derived from *E. coli* or a fragment thereof; and an O-antigen from 15 different serotypes, wherein each O-antigen is conjugated to a carrier protein. In one embodiment, the composition includes a polypeptide derived from *E. coli* or a fragment thereof; and an O-antigen from 16 different serotypes, wherein each O-antigen is conjugated to a carrier protein. In one embodiment, the composition includes a polypeptide derived from *E. coli* or a fragment thereof; and an O-antigen from 17 different serotypes, wherein each O-antigen is conjugated to a carrier protein. In one embodiment, the composition includes a polypeptide derived from *E. coli* or a fragment thereof; and an O-antigen from 18 different serotypes, wherein each O-antigen is conjugated to a carrier protein. In one embodiment, the composition includes a polypeptide derived from *E. coli* or a fragment thereof; and an O-antigen from 19 different serotypes, wherein each O-antigen is conjugated to a carrier protein. In one embodiment, the composition includes a polypeptide derived from *E. coli* or a fragment thereof; and an O-antigen from 20 different serotypes, wherein each O-antigen is conjugated to a carrier protein.

In another aspect, the composition includes an O-polysaccharide from at least one *E. coli* serotype. In a preferred embodiment, the composition includes an O-polysaccharide from more than 1 *E. coli* serotype. For example, the composition may include an O-polysaccharide from two different *E. coli* serotypes to 12 different *E. coli* serotypes. In one embodiment, the composition includes an O-polysaccharide from 3 different *E. coli* serotypes. In one embodiment, the composition includes an O-polysaccharide from 4 different *E. coli* serotypes. In one embodiment, the composition includes an O-polysaccharide from 5 different *E. coli* serotypes. In one embodiment, the composition includes an O-polysaccharide from 6 different *E. coli* serotypes. In one embodiment, the composition includes an O-polysaccharide from 7 different *E. coli* serotypes. In one embodiment, the composition includes an O-polysaccharide from 8 different *E. coli* serotypes. In one embodiment, the composition includes an O-polysaccharide from 9 different *E. coli* serotypes. In one embodiment, the composition includes an O-polysaccharide from 10 different *E. coli* serotypes. In one embodiment, the composition includes an O-polysaccharide from 11 different *E. coli* serotypes. In one embodiment, the composition includes an O-polysaccharide from 12 different serotypes. In one embodiment, the composition includes an O-polysaccharide from 13 different serotypes. In one embodiment, the composition includes an O-polysaccharide from 14 different serotypes. In one embodiment, the composition includes an O-polysaccharide from 15 different serotypes. In one embodiment, the composition includes an O-polysaccharide from 16 different serotypes. In one embodiment, the composition includes an O-polysaccharide from 17 different serotypes. In one embodiment, the composition includes an O-polysaccharide from 18 different serotypes. In one embodiment, the composition includes an O-polysaccharide from 19 different serotypes. In one embodiment, the composition includes an O-polysaccharide from 20 different serotypes.

In a preferred embodiment, the composition includes an O-polysaccharide from at least one *E. coli* serotype, wherein the O-polysaccharide is conjugated to a carrier protein. In a preferred embodiment, the composition includes an O-polysaccharide from more than 1 *E. coli* serotype, wherein each O-polysaccharide is conjugated to a carrier protein. For example, the composition may include an O-polysaccharide from two different *E. coli* serotypes to 12 different *E. coli* serotypes, wherein each O-polysaccharide is conjugated to a carrier protein. In one embodiment, the composition includes an O-polysaccharide from 3 different *E. coli* serotypes, wherein each O-polysaccharide is conjugated to a carrier protein. In one embodiment, the composition includes an O-polysaccharide from 4 different *E. coli* serotypes, wherein each O-polysaccharide is conjugated to a carrier protein. In one embodiment, the composition includes an O-polysaccharide from 5 different *E. coli* serotypes, wherein each O-polysaccharide is conjugated to a carrier protein. In one embodiment, the composition includes an O-polysaccharide from 6 different *E. coli* serotypes, wherein each O-polysaccharide is conjugated to a carrier protein. In one embodiment, the composition includes an O-polysaccharide from 7 different *E. coli* serotypes, wherein each O-polysaccharide is conjugated to a carrier protein. In one embodiment, the composition includes an O-polysaccharide from 8 different *E. coli* serotypes, wherein each O-polysaccharide is conjugated to a carrier protein. In one embodiment, the composition includes an O-polysaccharide from 9 different *E. coli* serotypes, wherein each O-polysaccharide is conjugated to a carrier protein. In one embodiment, the composition includes an O-polysaccharide from 10 different *E. coli* serotypes, wherein each O-polysaccharide is conjugated to a carrier protein. In one embodiment, the composition includes an O-polysaccharide from 11 different *E. coli* serotypes, wherein each O-polysaccharide is conjugated to a carrier protein. In one embodiment, the composition includes an O-polysaccharide from 12 different serotypes, wherein each O-polysaccharide is conjugated to a carrier protein. In one embodiment, the composition includes an O-polysaccharide from 13 different serotypes, wherein each O-polysaccharide is conjugated to a carrier protein. In one embodiment, the composition includes an O-polysaccharide from 14 different serotypes, wherein each O-polysaccharide is conjugated to a carrier protein. In one embodiment, the composition includes an O-polysaccharide from 15 different serotypes, wherein each O-polysaccharide is conjugated to a carrier protein. In one embodiment, the composition includes an O-polysaccharide from 16 different serotypes, wherein each O-polysaccharide is conjugated to a carrier protein. In one embodiment, the composition includes an O-polysaccharide from 17 different serotypes, wherein each O-polysaccharide is conjugated to a carrier protein. In one embodiment, the composition includes an O-polysaccharide from 18 different serotypes, wherein each O-polysaccharide is conjugated to a carrier protein. In one embodiment, the composition includes an O-polysaccharide from 19 different serotypes, wherein each O-polysaccharide is conjugated to a carrier protein. In one embodiment, the composition includes an O-polysaccharide from 20 different serotypes, wherein each O-polysaccharide is conjugated to a carrier protein.

In a most preferred embodiment, the composition includes an O-polysaccharide from at least one *E. coli* serotype, wherein the O-polysaccharide is conjugated to a carrier protein, and wherein the O-polysaccharide includes the O-antigen and core saccharide. In a preferred embodiment, the composition includes an O-polysaccharide from more than 1 *E. coli* serotype, wherein each O-polysaccharide is conjugated to a carrier protein, and wherein the O-polysaccharide includes the O-antigen and core saccharide. For example, the composition may include an O-polysaccharide from two different *E. coli* serotypes to 12 different *E. coli* serotypes, wherein each O-polysaccharide is conjugated to a carrier protein, and wherein the O-polysaccharide includes the O-antigen and core saccharide. In one embodiment, the composition includes an O-polysaccharide from 3 different *E. coli* serotypes, wherein each O-polysaccharide is conjugated to a carrier protein, and wherein the O-polysaccharide includes the O-antigen and core saccharide. In one embodiment, the composition includes an O-polysaccharide from 4 different *E. coli* serotypes, wherein each O-polysaccharide is conjugated to a carrier protein, and wherein the O-polysaccharide includes the O-antigen and core saccharide. In one embodiment, the composition includes an O-polysaccharide from 5 different *E. coli* serotypes, wherein each O-polysaccharide is conjugated to a carrier protein, and wherein the O-polysaccharide includes the O-antigen and core saccharide. In one embodiment, the composition includes an O-polysaccharide from 6 different *E. coli* serotypes, wherein each O-polysaccharide is conjugated to a carrier protein, and wherein the O-polysaccharide includes the O-antigen and core saccharide. In one embodiment, the composition includes an O-polysaccharide from 7 different *E. coli* serotypes, wherein each O-polysaccharide is conjugated to a carrier protein, and wherein the O-polysaccharide includes the O-antigen and core saccharide. In one embodiment, the composition includes an O-polysaccharide from 8 different *E. coli* serotypes, wherein each O-polysaccharide is conjugated to a carrier protein, and wherein the O-polysaccharide includes the O-antigen and core saccharide. In one embodiment, the composition includes an O-polysaccharide from 9 different *E. coli* serotypes, wherein each O-polysaccharide is conjugated to a carrier protein, and wherein the O-polysaccharide includes the O-antigen and core saccharide. In one embodiment, the composition includes an O-polysaccharide from 10 different *E. coli* serotypes, wherein each O-polysaccharide is conjugated to a carrier protein, and wherein the O-polysaccharide includes the O-antigen and core saccharide. In one embodiment, the composition includes an O-polysaccharide from 11 different *E. coli* serotypes, wherein each O-polysaccharide is conjugated to a carrier protein, and wherein the O-polysaccharide includes the O-antigen and core saccharide. In one embodiment, the composition includes an O-polysaccharide from 12 different serotypes, wherein each O-polysaccharide is conjugated to a carrier protein, and wherein the O-polysaccharide includes the O-antigen and core saccharide. In one embodiment, the composition includes an O-polysaccharide from 13 different serotypes, wherein each O-polysaccharide is conjugated to a carrier protein, and wherein the O-polysaccharide includes the O-antigen and core saccharide. In one embodiment, the composition includes an O-polysaccharide from 14 different serotypes, wherein each O-polysaccharide is conjugated to a carrier protein, and wherein the O-polysaccharide includes the O-antigen and core saccharide. In one embodiment, the composition includes an O-polysaccharide from 15 different serotypes, wherein each O-polysaccharide is conjugated to a carrier protein, and wherein the O-polysaccharide includes the O-antigen and core saccharide. In one embodiment, the composition includes an O-polysaccharide from 16 different serotypes, wherein each O-polysaccharide is conjugated to a carrier protein, and wherein the O-polysaccharide includes the O-antigen and core saccharide. In one embodiment, the composition includes an O-polysaccharide from 17 different serotypes, wherein each O-polysaccharide is conjugated to a carrier protein, and wherein the O-polysaccharide includes the O-antigen and core saccharide. In one embodiment, the composition includes an O-polysaccharide from 18 different serotypes, wherein each O-polysaccharide is conjugated to a carrier protein, and wherein the O-polysaccharide includes the O-antigen and core saccharide. In one embodiment, the composition includes an O-polysaccharide from 19 different serotypes, wherein each O-polysaccharide is conjugated to a carrier protein, and wherein the O-polysaccharide includes the O-antigen and core saccharide. In one embodiment, the composition includes an O-polysaccharide from 20 different serotypes, wherein each O-polysaccharide is conjugated to a carrier protein, and wherein the O-polysaccharide includes the O-antigen and core saccharide. In a preferred embodiment, the carrier protein is $CRM_{197}$.

In another preferred embodiment, the composition includes a polypeptide derived from *E. coli* or a fragment thereof; and an O-polysaccharide conjugated to $CRM_{197}$, wherein the O-polysaccharide includes Formula O25a, wherein n is at least 40, and the core saccharide. In a preferred embodiment, the composition further includes an O-polysaccharide conjugated to $CRM_{197}$, wherein the O-polysaccharide includes Formula O25b, wherein n is at least 40, and the core saccharide. In another embodiment, the composition further includes an O-polysaccharide conjugated to $CRM_{197}$, wherein the O-polysaccharide includes Formula O1a, wherein n is at least 40, and the core saccharide. In another embodiment, the composition further includes an O-polysaccharide conjugated to $CRM_{197}$, wherein the O-polysaccharide includes Formula O2, wherein n is at least 40, and the core saccharide. In another embodiment, the composition further includes an O-polysaccharide conjugated to CRM 197, wherein the O-polysaccharide includes Formula O6, wherein n is at least 40, and the core saccharide.

In another embodiment, the composition further includes an O-polysaccharide conjugated to $CRM_{197}$, wherein the O-polysaccharide includes Formula O17, wherein n is at least 40, and the core saccharide. In another embodiment, the composition further includes an O-polysaccharide conjugated to CRM 197, wherein the O-polysaccharide includes Formula O15, wherein n is at least 40, and the core saccharide. In another embodiment, the composition further includes an O-polysaccharide conjugated to CRM 197, wherein the O-polysaccharide includes Formula O18A, wherein n is at least 40, and the core saccharide. In another embodiment, the composition further includes an O-polysaccharide conjugated to $CRM_{197}$, wherein the O-polysaccharide includes Formula O75, wherein n is at least 40, and the core saccharide. In another embodiment, the composition further includes an O-polysaccharide conjugated to $CRM_{197}$, wherein the O-polysaccharide includes Formula O4, wherein n is at least 40, and the core saccharide. In another embodiment, the composition further includes an O-polysaccharide conjugated to $CRM_{197}$, wherein the O-polysaccharide includes Formula O16, wherein n is at least 40, and the core saccharide. In another embodiment, the composition further includes an O-polysaccharide conjugated to $CRM_{197}$, wherein the O-polysaccharide includes Formula O13, wherein n is at least 40, and the core saccharide. In another embodiment, the composition further includes an O-polysaccharide conjugated to $CRM_{197}$, wherein the O-polysaccharide includes Formula O7, wherein n is at least 40, and the core saccharide.

In another embodiment, the composition further includes an O-polysaccharide conjugated to $CRM_{197}$, wherein the O-polysaccharide includes Formula O8, wherein n is at least 40, and the core saccharide. In another embodiment, the O-polysaccharide includes Formula O8, wherein n is 1-20, preferably 2-5, more preferably 3. Formula O8 is shown, e.g., in FIG. 10B. In another embodiment, the composition further includes an O-polysaccharide conjugated to $CRM_{197}$, wherein the O-polysaccharide includes Formula O9, wherein n is at least 40, and the core saccharide. In another embodiment, the O-polysaccharide includes Formula O9, wherein n is 1-20, preferably 4-8, more preferably 5. Formula O9 is shown, e.g., in FIG. 10B. In another embodiment, the O-polysaccharide includes Formula O9a, wherein n is 1-20, preferably 4-8, more preferably 5. Formula O9a is shown, e.g., in FIG. 10B.

In some embodiments, the O-polysaccharide includes selected from any one of Formula O20ab, Formula O20ac, Formula O52, Formula O97, and Formula O101, wherein n is 1-20, preferably 4-8, more preferably 5. See, e.g., FIG. 10B.

As described above, the composition may include a polypeptide derived from *E. coli* or a fragment thereof; and any combination of conjugated O-polysaccharides (antigens). In one exemplary embodiment, the composition includes a polysaccharide that includes Formula O25b, a polysaccharide that includes Formula O1A, a polysaccharide that includes Formula O2, and a polysaccharide that includes Formula O6. More specifically, such as a composition that includes: (i) an O-polysaccharide conjugated to $CRM_{197}$, wherein the O-polysaccharide includes Formula O25b, wherein n is at least 40, and the core saccharide; (ii) an O-polysaccharide conjugated to $CRM_{197}$, wherein the O-polysaccharide includes Formula O1a, wherein n is at least 40, and the core saccharide; (iii) an O-polysaccharide conjugated to $CRM_{197}$, wherein the O-polysaccharide includes Formula O2, wherein n is at least 40, and the core saccharide; and (iv) an O-polysaccharide conjugated to $CRM_{197}$, wherein the O-polysaccharide includes Formula 06, wherein n is at least 40, and the core saccharide.

In one embodiment, the composition includes a polypeptide derived from *E. coli* or a fragment thereof; and at least one O-polysaccharide derived from any *E. coli* serotype, wherein the serotype is not O25a. For example, in one embodiment, the composition does not include a saccharide that includes the Formula O25a. Such a composition may include, for example, an O-polysaccharide that includes Formula O25b, an O-polysaccharide that includes Formula O1A, an O-polysaccharide that includes Formula O2, and an O-polysaccharide that includes Formula O6.

In one embodiment, the composition includes a polypeptide derived from *E. coli* or a fragment thereof; and an O-polysaccharide from 2 different *E. coli* serotypes, wherein each O-polysaccharide is conjugated to $CRM_{197}$, and wherein the O-polysaccharide includes the O-antigen and core saccharide. In one embodiment, the composition includes a polypeptide derived from *E. coli* or a fragment thereof; and an O-polysaccharide from 3 different *E. coli* serotypes, wherein each O-polysaccharide is conjugated to $CRM_{197}$, and wherein the O-polysaccharide includes the O-antigen and core saccharide. In one embodiment, the composition includes a polypeptide derived from *E. coli* or a fragment thereof; and an O-polysaccharide from 4 different *E. coli* serotypes, wherein each O-polysaccharide is conjugated to $CRM_{197}$, and wherein the O-polysaccharide includes the O-antigen and core saccharide. In one embodiment, the composition includes a polypeptide derived from *E. coli* or a fragment thereof; and an O-polysaccharide from 5 different *E. coli* serotypes, wherein each O-polysaccharide is conjugated to $CRM_{197}$, and wherein the O-polysaccharide includes the O-antigen and core saccharide. In one embodiment, the composition includes a polypeptide derived from *E. coli* or a fragment thereof; and an O-polysaccharide from 6 different *E. coli* serotypes, wherein each O-polysaccharide is conjugated to $CRM_{197}$, and wherein the O-polysaccharide includes the O-antigen and core saccharide. In one embodiment, the composition includes a polypeptide derived from *E. coli* or a fragment thereof; and an O-polysaccharide from 7 different *E. coli* serotypes, wherein each O-polysaccharide is conjugated to $CRM_{197}$, and wherein the O-polysaccharide includes the O-antigen and core saccharide. In one embodiment, the composition includes a polypeptide derived from *E. coli* or a fragment thereof; and an O-polysaccharide from 8 different *E. coli* serotypes, wherein each O-polysaccharide is conjugated to $CRM_{197}$, and wherein the O-polysaccharide includes the O-antigen and core saccharide. In one embodiment, the composition includes a polypeptide derived from *E. coli* or a fragment thereof; and an O-polysaccharide from 9 different *E. coli* serotypes, wherein each O-polysaccharide is conjugated to $CRM_{197}$, and wherein the O-polysaccharide includes the O-antigen and core saccharide. In one embodiment, the composition includes a polypeptide derived from *E. coli* or a fragment thereof; and an O-polysaccharide from 10 different *E. coli* serotypes, wherein each O-polysaccharide is conjugated to CRM 197, and wherein the O-polysaccharide includes the O-antigen and core saccharide. In one embodiment, the composition includes a polypeptide derived from *E. coli* or a fragment thereof; and an O-polysaccharide from 11 different *E. coli* serotypes, wherein each O-polysaccharide is conjugated to $CRM_{197}$, and wherein the O-polysaccharide includes the O-antigen and core saccharide. In one embodiment, the composition includes a polypeptide derived from *E. coli* or a fragment thereof; and an O-polysaccharide from 12 different serotypes, wherein each O-polysaccharide is conjugated to $CRM_{197}$, and wherein the O-polysaccharide includes the O-antigen and core saccharide. In one embodiment, the composition includes a polypeptide derived from *E. coli* or a fragment thereof; and an O-polysaccharide from 13 different serotypes, wherein each O-polysaccharide is conjugated to $CRM_{197}$ and wherein the O-polysaccharide includes the O-antigen and core saccharide. In one embodiment, the composition includes a polypeptide derived from *E. coli* or a fragment thereof; and an O-polysaccharide from 14 different serotypes, wherein each O-polysaccharide is conjugated to $CRM_{197}$, and wherein the O-polysaccharide includes the O-antigen and core saccharide. In one embodiment, the composition includes a polypeptide derived from *E. coli* or a fragment thereof; and an O-polysaccharide from 15 different serotypes, wherein each O-polysaccharide is conjugated to $CRM_{197}$, and wherein the O-polysaccharide includes the O-antigen and core saccharide. In one embodiment, the composition includes a polypeptide derived from *E. coli* or a fragment thereof; and an O-polysaccharide from 16 different serotypes, wherein each O-polysaccharide is conjugated to $CRM_{197}$, and wherein the O-polysaccharide includes the O-antigen and core saccharide. In one embodiment, the composition includes a polypeptide derived from *E. coli* or a fragment thereof; and an O-polysaccharide from 17 different serotypes, wherein each O-polysaccharide is conjugated to $CRM_{197}$, and wherein the O-polysaccharide includes the O-antigen and core saccharide. In one embodiment, the composition includes a polypeptide derived from *E. coli* or a fragment thereof; and an O-polysaccharide from 18 different serotypes, wherein each O-polysaccharide is conjugated to $CRM_{197}$, and wherein the O-polysaccharide includes the O-antigen and core saccharide. In one embodiment, the composition includes a polypeptide derived from *E. coli* or a fragment thereof; and an O-polysaccharide from 19 different serotypes, wherein each O-polysaccharide is conjugated to $CRM_{197}$, and wherein the O-polysaccharide includes the O-antigen and core saccharide. In one embodiment, the composition includes a polypeptide derived from *E. coli* or a fragment thereof; and an O-polysaccharide from 20 different serotypes, wherein each O-polysaccharide is conjugated to $CRM_{197}$, and wherein the O-polysaccharide includes the O-antigen and core saccharide.

In one aspect, the invention relates to a composition that includes a polypeptide derived from *E. coli* or a fragment thereof; and a conjugate including a saccharide covalently bound to a carrier protein, wherein the saccharide includes Formula O25b, wherein n is 15±2. In one aspect, the invention relates to a composition that includes a polypeptide derived from *E. coli* or a fragment thereof; and a conjugate including a saccharide covalently bound to a carrier protein, wherein the saccharide includes Formula O25b, wherein n is 17±2. In one aspect, the invention relates to a composition that includes a polypeptide derived from *E. coli* or a fragment thereof; and a conjugate including a saccharide covalently bound a carrier protein, wherein the saccharide includes Formula O25b, wherein n is 55±2. In another aspect, the invention relates to a composition that includes a polypeptide derived from *E. coli* or a fragment thereof; and a conjugate including a saccharide covalently bound a carrier protein, wherein the saccharide includes Formula O25b, wherein n is 51±2. In one embodiment, the saccharide further includes the *E. coli* R1 core saccharide moiety. In another embodiment, the saccharide further includes the *E. coli* K12 core saccharide moiety. In another embodiment, the saccharide further includes the KDO moiety. Preferably, the carrier protein is $CRM_{197}$. In one embodiment, the conjugate is prepared by single end linked conjugation. In one embodiment, the conjugate is prepared by reductive amination chemistry, preferably in DMSO buffer. In one embodiment, the saccharide is conjugated to the carrier protein through a (2-((2-oxoethyl)thio)ethyl)carbamate (eTEC) spacer. Preferably, the composition further includes a pharmaceutically acceptable diluent.

In one embodiment, the immunogenic composition elicits IgG antibodies in humans, said antibodies being capable of binding an *E. coli* serotype O25B polysaccharide at a concentration of at least 0.2 pg/ml, 0.3 pg/ml, 0.35 pg/ml, 0.4 pg/ml or 0.5 pg/ml as determined by ELISA assay. Therefore, comparison of OPA activity of pre- and post-immunization serum with the immunogenic composition of the invention can be conducted and compared for their response to serotype O25B to assess the potential increase of responders. In one embodiment, the immunogenic composition elicits IgG antibodies in humans, said antibodies being capable of killing *E. coli* serotype O25B as determined by in vitro opsonophagocytic assay. In one embodiment, the immunogenic composition elicits functional antibodies in humans, said antibodies being capable of killing *E. coli* serotype O25B as determined by in vitro opsonophagocytic assay. In one embodiment, the immunogenic composition of the invention increases the proportion of responders against *E. coli* serotype O25B (i.e., individual with a serum having a titer of at least 1:8 as determined by in vitro OPA) as compared to the pre-immunized population. In one embodiment, the immunogenic composition elicits a titer of at least 1:8 against *E. coli* serotype O25B in at least 50% of the subjects as determined by in vitro opsonophagocytic killing assay. In one embodiment, the immunogenic composition of the invention elicits a titer of at least 1:8 against *E. coli* serotype O25B in at least 60%, 70%, 80%, or at least 90% of the subjects as determined by in vitro opsonophagocytic killing assay. In one embodiment, the immunogenic composition of the invention significantly increases the proportion of responders against *E. coli* serotypes O25B (i.e., individual with a serum having a titer of at least 1:8 as determined by in vitro OPA) as compared to the pre-immunized population. In one embodiment, the immunogenic composition of the invention significantly increases the OPA titers of human subjects against *E. coli* serotype O25B as compared to the pre-immunized population.

In one aspect, the invention relates to a composition that includes a polypeptide derived from *E. coli* or a fragment thereof; and a conjugate including a saccharide covalently bound a carrier protein, wherein the saccharide includes Formula O1a, wherein n is 39+2. In another aspect, the invention relates to a composition that includes a polypeptide derived from *E. coli* or a fragment thereof; and a conjugate including a saccharide covalently bound a carrier protein, wherein the saccharide includes Formula O1a, wherein n is 13+2. In one embodiment, the saccharide further includes the *E. coli* R1 core saccharide moiety. In one embodiment, the saccharide further includes the KDO moiety. Preferably, the carrier protein is $CRM_{197}$. In one embodiment, the conjugate is prepared by single end linked conjugation. In one embodiment, the conjugate is prepared by reductive amination chemistry, preferably in DMSO buffer. In one embodiment, the saccharide is conjugated to the carrier protein through a (2-((2-oxoethyl)thio)ethyl) carbamate (eTEC) spacer. Preferably, the composition further includes a pharmaceutically acceptable diluent.

In one embodiment, the immunogenic composition elicits IgG antibodies in humans, said antibodies being capable of binding an *E. coli* serotype O1A polysaccharide at a concentration of at least 0.2 pg/ml, 0.3 pg/ml, 0.35 pg/ml, 0.4 pg/ml or 0.5 pg/ml as determined by ELISA assay. Therefore, comparison of OPA activity of pre- and post-immunization serum with the immunogenic composition of the invention can be conducted and compared for their response to serotype O1A to assess the potential increase of responders. In one embodiment, the immunogenic composition elicits IgG antibodies in humans, said antibodies being capable of killing *E. coli* serotype O1A as determined by in vitro opsonophagocytic assay. In one embodiment, the immunogenic composition elicits functional antibodies in humans, said antibodies being capable of killing *E. coli* serotype O1A as determined by in vitro opsonophagocytic assay. In one embodiment, the immunogenic composition of the invention increases the proportion of responders against *E. coli* serotype O1A (i.e., individual with a serum having a titer of at least 1:8 as determined by in vitro OPA) as compared to the pre-immunized population. In one embodiment, the immunogenic composition elicits a titer of at least 1:8 against *E. coli* serotype O1A in at least 50% of the subjects as determined by in vitro opsonophagocytic killing assay. In one embodiment, the immunogenic composition of the invention elicits a titer of at least 1:8 against *E. coli* serotype 01A in at least 60%, 70%, 80%, or at least 90% of the subjects as determined by in vitro opsonophagocytic killing assay. In one embodiment, the immunogenic composition of the invention significantly increases the proportion of responders against *E. coli* serotypes O1A (i.e., individual with a serum having a titer of at least 1:8 as determined by in vitro OPA) as compared to the pre-immunized population. In one embodiment, the immunogenic composition of the invention significantly increases the OPA titers of human subjects against *E. coli* serotype O1A as compared to the pre-immunized population.

In one aspect, the invention relates to a composition that includes a polypeptide derived from *E. coli* or a fragment thereof; and a conjugate including a saccharide covalently bound a carrier protein, wherein the saccharide includes Formula O2, wherein n is 43±2. In another aspect, the invention relates to a composition that includes a polypeptide derived from *E. coli* or a fragment thereof; and a conjugate including a saccharide covalently bound a carrier protein, wherein the saccharide includes Formula O2, wherein n is 47±2. In another aspect, the invention relates to a composition that includes a conjugate including a saccharide covalently bound a carrier protein, wherein the saccharide includes Formula O2, wherein n is 17±2. In another aspect, the invention relates to a composition that includes a conjugate including a saccharide covalently bound a carrier protein, wherein the saccharide includes Formula O2, wherein n is 18±2. In one embodiment, the saccharide further includes the *E. coli* R1 core saccharide moiety. In another embodiment, the saccharide further includes the *E. coli* R4 core saccharide moiety. In another embodiment, the saccharide further includes the KDO moiety. Preferably, the carrier protein is $CRM_{197}$. In one embodiment, the conjugate is prepared by single end linked conjugation. In one embodiment, the conjugate is prepared by reductive amination chemistry, preferably in DMSO buffer. In one embodiment, the saccharide is conjugated to the carrier protein through a (2-((2-oxoethyl)thio)ethyl) carbamate (eTEC) spacer. Preferably, the composition further includes a pharmaceutically acceptable diluent.

In one embodiment, the immunogenic composition elicits IgG antibodies in humans, said antibodies being capable of binding an *E. coli* serotype O2 polysaccharide at a concentration of at least 0.2 pg/ml, 0.3 pg/ml, 0.35 pg/ml, 0.4 pg/ml or 0.5 pg/ml as determined by ELISA assay. Therefore, comparison of OPA activity of pre- and post-immunization serum with the immunogenic composition of the invention can be conducted and compared for their response to serotype O2 to assess the potential increase of responders. In one embodiment, the immunogenic composition elicits IgG antibodies in humans, said antibodies being capable of killing *E. coli* serotype O2 as determined by in vitro opsonophagocytic assay. In one embodiment, the immunogenic composition elicits functional antibodies in humans, said antibodies being capable of killing *E. coli* serotype O2 as determined by in vitro opsonophagocytic assay. In one embodiment, the immunogenic composition of the invention increases the proportion of responders against *E. coli* serotype O2 (i.e., individual with a serum having a titer of at least 1:8 as determined by in vitro OPA) as compared to the pre-immunized population. In one embodiment, the immunogenic composition elicits a titer of at least 1:8 against *E. coli* serotype O2 in at least 50% of the subjects as determined by in vitro opsonophagocytic killing assay. In one embodiment, the immunogenic composition of the invention elicits a titer of at least 1:8 against *E. coli* serotype O2 in at least 60%, 70%, 80%, or at least 90% of the subjects as determined by in vitro opsonophagocytic killing assay. In one embodiment, the immunogenic composition of the invention significantly increases the proportion of responders against *E. coli* serotypes O2 (i.e., individual with a serum having a titer of at least 1:8 as determined by in vitro OPA) as compared to the pre-immunized population. In one embodiment, the immunogenic composition of the invention significantly increases the OPA titers of human subjects against *E. coli* serotype O2 as compared to the pre-immunized population.

In one aspect, the invention relates to a composition that includes a polypeptide derived from *E. coli* or a fragment thereof; and a conjugate including a saccharide covalently bound a carrier protein, wherein the saccharide includes Formula O6, wherein n is 42±2. In another aspect, the invention relates to a composition that includes a polypeptide derived from *E. coli* or a fragment thereof; and a conjugate including a saccharide covalently bound a carrier protein, wherein the saccharide includes Formula O6, wherein n is 50±2. In another aspect, the invention relates to a composition that includes a conjugate including a saccharide covalently bound a carrier protein, wherein the saccharide includes Formula O6, wherein n is 17±2. In another aspect, the invention relates to a composition that includes a conjugate including a saccharide covalently bound a carrier protein, wherein the saccharide includes Formula O6, wherein n is 18±2. In one embodiment, the saccharide further includes the *E. coli* R1 core saccharide moiety. In one embodiment, the saccharide further includes the KDO moiety. Preferably, the carrier protein is $CRM_{197}$. In one embodiment, the conjugate is prepared by single end linked conjugation. In one embodiment, the conjugate is prepared by reductive amination chemistry, preferably in DMSO buffer. In one embodiment, the saccharide is conjugated to the carrier protein through a (2-((2-oxoethyl)thio)ethyl) carbamate (eTEC) spacer. Preferably, the composition further includes a pharmaceutically acceptable diluent.

In one embodiment, the immunogenic composition elicits IgG antibodies in humans, said antibodies being capable of binding an *E. coli* serotype O6 polysaccharide at a concentration of at least 0.2 pg/ml, 0.3 pg/ml, 0.35 pg/ml, 0.4 pg/ml or 0.5 pg/ml as determined by ELISA assay. Therefore, comparison of OPA activity of pre- and post-immunization serum with the immunogenic composition of the invention can be conducted and compared for their response to serotype O6 to assess the potential increase of responders. In one embodiment, the immunogenic composition elicits IgG antibodies in humans, said antibodies being capable of killing *E. coli* serotype O6 as determined by in vitro opsonophagocytic assay. In one embodiment, the immunogenic composition elicits functional antibodies in humans, said antibodies being capable of killing *E. coli* serotype O6 as determined by in vitro opsonophagocytic assay. In one embodiment, the immunogenic composition of the invention increases the proportion of responders against *E. coli* serotype O6 (i.e., individual with a serum having a titer of at least 1:8 as determined by in vitro OPA) as compared to the pre-immunized population. In one embodiment, the immunogenic composition elicits a titer of at least 1:8 against *E. coli* serotype O6 in at least 50% of the subjects as determined by in vitro opsonophagocytic killing assay. In one embodiment, the immunogenic composition of the invention elicits a titer of at least 1:8 against *E. coli* serotype O6 in at least 60%, 70%, 80%, or at least 90% of the subjects as determined by in vitro opsonophagocytic killing assay. In one embodiment, the immunogenic composition of the invention significantly increases the proportion of responders against *E. coli* serotypes O6 (i.e., individual with a serum having a titer of at least 1:8 as determined by in vitro OPA) as compared to the pre-immunized population. In one embodiment, the immunogenic composition of the invention significantly increases the OPA titers of human subjects against *E. coli* serotype O6 as compared to the pre-immunized population.

In one aspect, the composition includes a polypeptide derived from *E. coli* or a fragment thereof; and a conjugate including a saccharide covalently bound to a carrier protein, wherein the saccharide includes a structure selected from any one of Formula O1 (e.g., Formula O1A, Formula O1B, and Formula O1C), Formula O2, Formula O3, Formula O4 (e.g., Formula O4: K52 and Formula O4: K6), Formula O5 (e.g., Formula O5ab and Formula O5ac (strain 180/C3)), Formula O6 (e.g., Formula O6: K2; K13; K15 and Formula O6: K54), Formula O7, Formula O8, Formula O9, Formula O10, Formula O11, Formula O12, Formula O13, Formula O14, Formula O15, Formula O16, Formula O17, Formula O18 (e.g., Formula O18A, Formula O18ac, Formula O18A1, Formula O18B, and Formula O18B1), Formula O19, Formula O20, Formula O21, Formula O22, Formula O23 (e.g., Formula O23A), Formula O24, Formula O25 (e.g., Formula O25a and Formula O25b), Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45 (e.g., Formula O45 and Formula O45rel), Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula $62D_1$, Formula O63, Formula O64, Formula O65, Formula O66, Formula O68, Formula O69, Formula O70, Formula O71, Formula O73 (e.g., Formula O73 (strain 73-1)), Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144, Formula O145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, and Formula O187, wherein n is an integer from 1 to 100. In one embodiment, the saccharide further includes the *E. coli* R1 core saccharide moiety. In one embodiment, the saccharide further includes the *E. coli* R2 core saccharide moiety. In one embodiment, the saccharide further includes the *E. coli* R3 core saccharide moiety. In another embodiment, the saccharide further includes the *E. coli* R4 core saccharide moiety. In one embodiment, the saccharide further includes the *E. coli* K12 core saccharide moiety. In another embodiment, the saccharide further includes the KDO moiety. Preferably, the carrier protein is $CRM_{197}$. In one embodiment, the conjugate is prepared by single end linked conjugation. In one embodiment, the conjugate is prepared by reductive amination chemistry, preferably in DMSO buffer. In one embodiment, the saccharide is conjugated to the carrier protein through a (2-((2-oxoethyl)thio) ethyl) carbamate (eTEC) spacer. Preferably, the composition further includes a pharmaceutically acceptable diluent. In one embodiment, the composition further includes at least 1, 2, 3, 4, 5, 6, 7, 8, 9, 10, 11, 12, 13, 14, 15, 16, 17, 18, 19, 20, 21, 22, 23, 24, 25, 26, 27, 28, 29 additional conjugates to at most 30 additional conjugates, each conjugate including a saccharide covalently bound to a carrier protein, wherein the saccharide includes a structure selected from any one of said Formulas.

A. Saccharide

In one embodiment, the saccharide is produced by expression (not necessarily overexpression) of different Wzz proteins (e.g., WzzB) to control of the size of the saccharide.

As used herein, the term "saccharide" refers to a single sugar moiety or monosaccharide unit as well as combinations of two or more single sugar moieties or monosaccharide units covalently linked to form disaccharides, oligosaccharides, and polysaccharides. The saccharide may be linear or branched.

In one embodiment, the saccharide is produced in a recombinant Gram-negative bacterium. In one embodiment, the saccharide is produced in a recombinant *E. coli* cell. In one embodiment, the saccharide is produced in a recombinant *Salmonella* cell. Exemplary bacteria include *E. coli* O25K5H1, *E. coli* BD559, *E. coli* GAR2831, *E. coli* GAR865, *E. coli* GAR868, *E. coli* GAR869, *E. coli* GAR872, *E. coli* GAR878, *E. coli* GAR896, *E. coli* GAR1902, *E. coli* O25a ETC NR-5, *E. coli* O157: H7: K-, *Salmonella enterica* serovar *Typhimurium* strain LT2, *E. coli* GAR2401, *Salmonella enterica* serotype *Enteritidis* CVD 1943, *Salmonella enterica* serotype *Typhimurium* CVD 1925, *Salmonella enterica* serotype Paratyphi A CVD 1902, and *Shigella flexneri* CVD 1208S. In one embodiment, the bacterium is not *E. coli* GAR2401. This genetic approach towards saccharide production allows for efficient production of O-polysaccharides and O-antigen molecules as vaccine components.

The term "wzz protein," as used herein, refers to a chain length determinant polypeptide, such as, for example, wzzB, wzz, WZZSF, WZZST, fepE, WZZłepE, wzzl and wzz2. The GenBank accession numbers for the exemplary wzz gene sequences are AF011910 for E4991/76, AF011911 for F186, AF011912 for M70/1-1, AF011913 for 79/311, AF011914 for Bi7509-41, AF011915 for C664-1992, AF011916 for C258-94, AF011917 for C722-89, and AF011919 for EDL933. The GenBank accession numbers for the G7 and Bi316-41 wzz genes sequences are U39305 and U39306, respectively. Further GenBank accession numbers for exemplary wzz gene sequences are NP_459581 for *Salmonella enterica* subsp. *enterica* serovar *Typhimurium* str. LT2 FepE; AIG66859 for *E. coli* O157: H7 Strain EDL933 FepE; NP_461024 for *Salmonella enterica* subsp. *enterica* serovar *Typhimurium* str. LT2 WzzB. NP_416531 for *E. coli* K-12 substr. MG1655 WzzB, NP_415119 for *E. coli* K-12 substr. MG 1655 FepE. In preferred embodiments, the wzz family protein is any one of wzzB, wzz, WZZSF, WZZST, fepE, WZZfepE, wZZ1 and wzz2, most preferably wzzB, more preferably fepE.

Exemplary wzzB sequences include sequences set forth in SEQ ID Nos: 30-34. Exemplary FepE sequences include sequences set forth in SEQ ID Nos: 35-39.

In some embodiments, a modified saccharide (modified as compared to the corresponding wild-type saccharide) may be produced by expressing (not necessarily overexpressing) a wzz family protein (e.g., fepE) from a Gram-negative bacterium in a Gram-negative bacterium and/or by switching off (i.e., repressing, deleting, removing) a second wzz gene (e.g., wzzB) to generate high molecular weight saccharides, such as lipopolysaccharides, containing intermediate or long O-antigen chains. For example, the modified saccharides may be produced by expressing (not necessarily overexpressing) wzz2 and switching off wzzl. Or, in the alternative, the modified saccharides may be produced by expressing (not necessarily overexpressing) wzzfepE and switching off wzzB. In another embodiment, the modified saccharides may be produced by expressing (not necessarily overexpressing) wzzB but switching off wzzfepE. In another embodiment, the modified saccharides may be produced by expressing fepE. Preferably, the wzz family protein is derived from a strain that is heterologous to the host cell.

In some embodiments, the saccharide is produced by expressing a wzz family protein having an amino acid sequence that is at least 30%, 50%, 70%, 75%, 80%, 85%, 90%, 95%, 98%, 99% or 100% sequence identity to any one of SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, and SEQ ID NO: 39. In one embodiment, the wzz family protein includes a sequence selected from any one of SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, and SEQ ID NO: 39. Preferably, the wzz family protein has at least 30%, 50%, 70%, 75%, 80%, 85%, 90%, 95%, 98%, 99% or 100% sequence identity to SEQ ID NO: 30, SEQ ID NO: 31, SEQ ID NO: 32, SEQ ID NO: 33, SEQ ID NO: 34. In some embodiments, the saccharide is produced by expressing a protein having an amino acid sequence that is at least 30%, 50%, 70%, 75%, 80%, 85%, 90%, 95%, 98%, 99% or 100% sequence identity to an fepE protein.

In one aspect, the invention relates to saccharides produced by expressing a wzz family protein, preferably fepE, in a Gram-negative bacterium to generate high molecular weight saccharides containing intermediate or long O-antigen chains, which have an increase of at least 1, 2, 3, 4, or 5 repeating units, as compared to the corresponding wild-type O-polysaccharide. In one aspect, the invention relates to saccharides produced by a Gram-negative bacterium in culture that expresses (not necessarily overexpresses) a wzz family protein (e.g., wzzB) from a Gram-negative bacterium to generate high molecular weight saccharides containing short or intermediate or long O-antigen chains, which have an increase of at least 1, 2, 3, 4, or 5 repeating units, as compared to the corresponding wild-type O-antigen. See description of O-polysaccharides and O-antigens below for additional exemplary saccharides having increased number of repeat units, as compared to the corresponding wild-type saccharides. A desired chain length is the one which produces improved or maximal immunogenicity in the context of a given vaccine construct.

In another embodiment, the saccharide includes any one Formula selected from Table 1, wherein the number of repeat units n in the saccharide is greater than the number of repeat units in the corresponding wild-type O-polysaccharide by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more repeat units. Preferably, the saccharide includes an increase of at least 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 repeat units, as compared to the corresponding wild-type O-polysaccharide. See, for example, Table 24. Methods of determining the length of saccharides are known in the art. Such methods include nuclear magnetic resonance, mass spectroscopy, and size exclusion chromatography, as described in Example 13.

In a preferred embodiment, the invention relates to a saccharide produced in a recombinant *E. coli* host cell, wherein the gene for an endogenous wzz O-antigen length regulator (e.g., wzzB) is deleted and is replaced by a (second) wzz gene from a Gram-negative bacterium heterologous to the recombinant *E. coli* host cell (e.g., *Salmonella* fepE) to generate high molecular weight saccharides, such as lipopolysaccharides, containing intermediate or long O-antigen chains. In some embodiments, the recombinant *E. coli* host cell includes a wzz gene from *Salmonella*, preferably from *Salmonella enterica*. In other embodiments, the invention is applicable to all *E. coli* strains expressing O-antigens regulated by wzzB. In one aspect, *E. coli* serotype O8 and O9 strains which produce O-antigens comprised of homopolymeric mannans are not produced according to this embodiment as they employ different mechanisms for chain length regulation and transport of LPS to the outer membrane (J Biol Chem 2009; 284:30662-72; J Biol Chem 2012; 287:35078-91; Proceedings of the National Academy of Sciences 2014; 111:6407-12). In a further embodiment, the homopolymeric galactans polysaccharides of *Klebsiella* serotypes 01 and O2 are produced according to the method set forth in this embodiment.

In one embodiment, the host cell includes the heterologous gene for a wzz family protein as a stably maintained plasmid vector. In another embodiment, the host cell includes the heterologous gene for a wzz family protein as an integrated gene in the chromosomal DNA of the host cell. Methods of stably expressing a plasmid vector in an *E. coli* host cell and methods of integrating a heterologous gene into the chromosome of an *E. coli* host cell are known in the art. In one embodiment, the host cell includes the heterologous genes for an O-antigen as a stably maintained plasmid vector. In another embodiment, the host cell includes the heterologous genes for an O-antigen as an integrated gene in the chromosomal DNA of the host cell. Methods of stably expressing a plasmid vector in an *E. coli* host cell and a *Salmonella* host cell are known in the art. Methods of integrating a heterologous gene into the chromosome of an *E. coli* host cell and a *Salmonella* host cell are known in the art.

In one aspect, the recombinant host cell is cultured in a medium that comprises a carbon source. Carbon sources for culturing *E. coli* are known in the art. Exemplary carbon sources include sugar alcohols, polyols, aldol sugars or keto sugars including but not limited to arabinose, cellobiose, fructose, glucose, glycerol, inositol, lactose, maltose, mannitol, mannose, rhamnose, raffinose, sorbitol, sorbose, sucrose, trehalose, pyruvate, succinate and methylamine. In a preferred embodiment, the medium includes glucose. In some embodiments, the medium includes a polyol or aldol sugar, for example, mannitol, inositol, sorbose, glycerol, sorbitol, lactose and arabinose as the carbon source. All of the carbon sources may be added to the medium before the start of culturing, or it may be added step by step or continuously during culturing.

An exemplary culture medium for the recombinant host cell includes an element selected from any one of $KH_2PO_4$, $K_2HPO_4$, $(NH_4)_2SO_4$, sodium citrate, $Na_2SO_4$, aspartic acid, glucose, $MgSO_4$, $FeSO_4$-$7H_2O$, $Na_2MoO_4$-$2H_2O$, $H_3BO_3$, $CoCl_2$-$6H_2O$, $CuCl_2$-$2H_2O$, $MnCl_2$-$4H_2O$, $ZnCl_2$ and $CaCl_2)$-$2H_2O$. Preferably, the medium includes $KH_2PO_4$, $K_2HPO_4$, $(NH_4)_2SO_4$, sodium citrate, $Na_2SO_4$, aspartic acid, glucose, $MgSO_4$, $FeSO_4$-7H2O, $Na_2MoO_4$-$2H_2O$, $H_3BO_3$, $CoCl_2$-$6H_2O$, $CuCl_2$-$2H_2O$, $MnCl_2$-$4H_2O$, $ZnCl_2$ and $CaCl_2)$-$2H_2O$.

The medium used herein may be solid or liquid, synthetic (i.e. man-made) or natural, and may include sufficient nutrients for the cultivation of the recombinant host cell. Preferably, the medium is a liquid medium.

In some embodiments, the medium may further include suitable inorganic salts. In some embodiments, the medium may further include trace nutrients. In some embodiments, the medium may further include growth factors. In some embodiments, the medium may further include an additional carbon source. In some embodiments, the medium may further include suitable inorganic salts, trace nutrients, growth factors, and a supplementary carbon source. Inorganic salts, trace nutrients, growth factors, and supplementary carbon sources suitable for culturing *E. coli* are known in the art.

In some embodiments, the medium may include additional components as appropriate, such as peptone, N—Z Amine, enzymatic soy hydrosylate, additional yeast extract, malt extract, supplemental carbon sources and various vitamins. In some embodiments, the medium does not include such additional components, such as peptone, N—Z Amine, enzymatic soy hydrosylate, additional yeast extract, malt extract, supplemental carbon sources and various vitamins.

Illustrative examples of suitable supplemental carbon sources include, but are not limited to other carbohydrates, such as glucose, fructose, mannitol, starch or starch hydrolysate, cellulose hydrolysate and molasses; organic acids, such as acetic acid, propionic acid, lactic acid, formic acid, malic acid, citric acid, and fumaric acid; and alcohols, such as glycerol, inositol, mannitol and sorbitol.

In some embodiments, the medium further includes a nitrogen source. Nitrogen sources suitable for culturing *E. coli* are known in the art. Illustrative examples of suitable nitrogen sources include, but are not limited to ammonia, including ammonia gas and aqueous ammonia; ammonium salts of inorganic or organic acids, such as ammonium chloride, ammonium nitrate, ammonium phosphate, ammonium sulfate and ammonium acetate; urea; nitrate or nitrite salts, and other nitrogen-containing materials, including amino acids as either pure or crude preparations, meat extract, peptone, fish meal, fish hydrolysate, corn steep liquor, casein hydrolysate, soybean cake hydrolysate, yeast extract, dried yeast, ethanol-yeast distillate, soybean flour, cottonseed meal, and the like.

In some embodiments, the medium includes an inorganic salt. Illustrative examples of suitable inorganic salts include, but are not limited to salts of potassium, calcium, sodium, magnesium, manganese, iron, cobalt, zinc, copper, molybdenum, tungsten and other trace elements, and phosphoric acid.

In some embodiments, the medium includes appropriate growth factors. Illustrative examples of appropriate trace nutrients, growth factors, and the like include, but are not limited to coenzyme A, pantothenic acid, pyridoxine-HCl, biotin, thiamine, riboflavin, flavine mononucleotide, flavine adenine dinucleotide, DL-6,8-thioctic acid, folic acid, Vitamin B12, other vitamins, amino acids such as cysteine and hydroxyproline, bases such as adenine, uracil, guanine, thymine and cytosine, sodium thiosulfate, p- or r-aminobenzoic acid, niacinamide, nitriloacetate, and the like, either as pure or partially purified chemical compounds or as present in natural materials. The amounts may be determined empirically by one skilled in the art according to methods and techniques known in the art.

In another embodiment, the modified saccharide (as compared to the corresponding wild-type saccharide) described herein is synthetically produced, for example, in vitro. Synthetic production or synthesis of the saccharides may facilitate the avoidance of cost- and time-intensive production processes. In one embodiment, the saccharide is synthetically synthesized, such as, for example, by using sequential glycosylation strategy or a combination of sequential glycosylations and [3+2] block synthetic strategy from suitably protected monosaccharide intermediates. For example, thioglycosides and glycosyl trichloroacetimidate derivatives may be used as glycosyl donors in the glycosylations. In one embodiment, a saccharide that is synthetically synthesized in vitro has the identical structure to a saccharide produced by recombinant means, such as by manipulation of a wzz family protein described above.

The saccharide produced (by recombinant or synthetic means) includes a structure derived from any *E. coli* serotype including, for example, any one of the following *E. coli* serotypes: O1 (e.g., O1A, O1B, and O1C), O2, O3, O4 (e.g., O4: K52 and O4: K6), O5 (e.g., O5ab and O5ac (strain 180/C3)), O6 (e.g., O6: K2; K13; K15 and O6: K54), O7, O8, O9, O10, O11, O12, O13, O14, O15, O16, O17, O18 (e.g., O18A, O18ac, O18A1, O18B, and O18B1), O19, O20, O21, O22, O23 (e.g., O23A), O24, O25 (e.g., O25a and O25b), O26, O27, O28, O29, O30, O32, O33, O34, O35, O36, O37, O38, O39, O40, O41, O42, O43, O44, O45 (e.g., O45 and O45rel), O46, O48, O49, O5O, 051, O52, O53, O54, O55, O56, O57, O58, O59, O60, O61, O62, 62D1, O63, O64, O65, O66, O68, O69, O7O, O71, O73 (e.g., O73 (strain 73-1)), O74, O75, O76, O77, O78, O79, O8O, O81, O82, O83, O84, O85, O86, O87, O88, O89, O9O, O91, O92, O93, O95, O96, O97, O98, O99, O100, O101, O102, O103, O104, O105, O106, O107, O108, O109, O110, O111, O112, O113, O114, O115, O116, O117, O118, O119, O120, O121, O123, O124, O125, O126, O127, O128, O129, O130, O131, O132, O133, O134, O135, O136, O137, O138, O139, O140, O141, O142, O143, O144, O145, O146, O147, O148, O149, O150, O151, O152, O153, O154, O155, O156, O157, O158, O159, O160, O161, O162, O163, O164, O165, O166, O167, O168, O169, O170, O171, O172, O173, O174, O175, O176, O177, O178, O179, O180, O181, O182, O183, O184, O185, O186, and O187.

The individual polysaccharides are typically purified (enriched with respect to the amount of polysaccharide-protein conjugate) through methods known in the art, such as, for example, dialysis, concentration operations, diafiltration operations, tangential flow filtration, precipitation, elution, centrifugation, precipitation, ultra-filtration, depth filtration, and/or column chromatography (ion exchange chromatography, multimodal ion exchange chromatography, DEAE, and hydrophobic interaction chromatography). Preferably, the polysaccharides are purified through a method that includes tangential flow filtration.

Purified polysaccharides may be activated (e.g., chemically activated) to make them capable of reacting (e.g., either directly to the carrier protein or via a linker such as an eTEC spacer) and then incorporated into glycoconjugates of the invention, as further described herein.

In one preferred embodiment, the saccharide of the invention is derived from an *E. coli* serotype, wherein the serotype is O25a. In another preferred embodiment, the serotype is O25b. In another preferred embodiment, the serotype is O1A. In another preferred embodiment, the serotype is O2. In another preferred embodiment, the serotype is O6. In another preferred embodiment, the serotype is O17. In another preferred embodiment, the serotype is O15. In another preferred embodiment, the serotype is O18A. In another preferred embodiment, the serotype is O75. In another preferred embodiment, the serotype is O4. In another preferred embodiment, the serotype is O16. In another preferred embodiment, the serotype is O13. In another preferred embodiment, the serotype is O7. In another preferred embodiment, the serotype is O8. In another preferred embodiment, the serotype is O9.

As used herein, reference to any of the serotypes listed above, refers to a serotype that encompasses a repeating unit structure (O-unit, as described below) known in the art and is unique to the corresponding serotype. For example, the term "O25a" serotype (also known in the art as serotype "O25") refers to a serotype that encompasses Formula O25 shown in Table 1. As another example, the term "O25b" serotype refers to a serotype that encompasses Formula O25b shown in Table 1.

As used herein, the serotypes are referred generically herein unless specified otherwise such that, for example, the term Formula "O18" refers generically to encompass Formula O18A, Formula O18ac, Formula 18A1, Formula O18B, and Formula O18B1.

As used herein, the term "O1" refers generically to encompass the species of Formula that include the generic term "O1" in the Formula name according to Table 1, such as any one of Formula O1A, Formula O1A1, Formula O1B, and Formula O1C, each of which is shown in Table 1. Accordingly, an "O1 serotype" refers generically to a serotype that encompasses any one of Formula O1A, Formula O1A1, Formula O1B, and Formula O1C.

As used herein, the term "6" refers generically to species of Formula that include the generic term "O6" in the Formula name according to Table 1, such as any one of Formula O6: K2; K13; K15; and O6: K54, each of which is shown in Table 1. Accordingly, an "O6 serotype" refers generically to a serotype that encompasses any one of Formula O6: K2; K13; K15; and O6: K54.

Other examples of terms that refer generically to species of a Formula that include the generic term in the Formula name according to Table 1Table 1 include: "O4", "O5", "O18", and "O45".

As used herein, the term "O2" refers to Formula O2 shown in Table 1. The term "O2 O-antigen" refers to a saccharide that encompasses Formula O2 shown in Table 1.

As used herein, reference to an O-antigen from a serotype listed above refers to a saccharide that encompasses the formula labeled with the corresponding serotype name. For example, the term "O25B O-antigen" refers to a saccharide that encompasses Formula O25B shown in Table 1.

As another example, the term "O1 O-antigen" generically refers to a saccharide that encompasses a Formula including the term "O1," such as the Formula O1A, Formula O1A1, Formula O1B, and Formula O1C, each of which are shown in Table 1.

As another example, the term "O6 O-antigen" generically refers to a saccharide that encompasses a Formula including the term "O6," such as Formula O6: K2; Formula O6: K13; Formula O6: K15 and Formula O6: K54, each of which are shown in Table 1.

B. O-Polysaccharide

As used herein, the term "O-polysaccharide" refers to any structure that includes an O-antigen, provided that the structure does not include a whole cell or Lipid A. For example, in one embodiment, the O-polysaccharide includes a lipopolysaccharide wherein the Lipid A is not bound. The step of removing Lipid A is known in the art and includes, as an example, heat treatment with addition of an acid. An exemplary process includes treatment with 1% acetic acid at 100° C. for 90 minutes. This process is combined with a process of isolating Lipid A as removed. An exemplary process for isolating Lipid A includes ultracentrifugation.

In one embodiment, the O-polysaccharide refers to a structure that consists of the O-antigen, in which case, the O-polysaccharide is synonymous with the term O-antigen. In one preferred embodiment, the O-polysaccharide refers to a structure that includes repeating units of the O-antigen, without the core saccharide. Accordingly, in one embodiment, the O-polysaccharide does not include an *E. coli* R1 core moiety. In another embodiment, the O-polysaccharide does not include an *E. coli* R2 core moiety. In another embodiment, the O-polysaccharide does not include an *E. coli* R3 core moiety. In another embodiment, the O-polysaccharide does not include an *E. coli* R4 core moiety. In another embodiment, the O-polysaccharide does not include an *E. coli* $K_{12}$ core moiety. In another preferred embodiment, the O-polysaccharide refers to a structure that includes an O-antigen and a core saccharide. In another embodiment, the O-polysaccharide refers to a structure that includes an O-antigen, a core saccharide, and a KDO moiety.

Methods of purifying an O-polysaccharide, which includes the core oligosaccharide, from LPS are known in the art. For example, after purification of LPS, purified LPS may be hydrolyzed by heating in 1% (v/v) acetic acid for 90 minutes at 100 degrees Celsius, followed by ultracentrifugation at 142,000×g for 5 hours at 4 degrees Celsius. The supernatant containing the O-polysaccharide is freeze-dried and stored at 4 degrees Celsius. In certain embodiments, deletion of capsule synthesis genes to enable simple purification of O-polysaccharide is described.

The O-polysaccharide can be isolated by methods including, but not limited to mild acid hydrolysis to remove lipid A from LPS. Other embodiments may include use of hydrazine as an agent for O-polysaccharide preparation. Preparation of LPS can be accomplished by known methods in the art.

In certain embodiments, the O-polysaccharides purified from wild-type, modified, or attenuated Gram-negative bacterial strains that express (not necessarily overexpress) a Wzz protein (e.g., wzzB) are provided for use in conjugate vaccines. In preferred embodiments, the O-polysaccharide chain is purified from the Gram-negative bacterial strain expressing (not necessarily overexpressing) wzz protein for use as a vaccine antigen either as a conjugate or complexed vaccine.

In one embodiment, the O-polysaccharide has a molecular weight that is increased by about 1-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 21-fold, 22-fold, 23-fold, 24-fold, 25-fold, 26-fold, 27-fold, 28-fold, 29-fold, 30-fold, 31-fold, 32-fold, 33-fold, 34-fold, 35-fold, 36-fold, 37-fold, 38-fold, 39-fold, 40-fold, 41-fold, 42-fold, 43-fold, 44-fold, 45-fold, 46-fold, 47-fold, 48-fold, 49-fold, 50-fold, 51-fold, 52-fold, 53-fold, 54-fold, 55-fold, 56-fold, 57-fold, 58-fold, 59-fold, 60-fold, 61-fold, 62-fold, 63-fold, 64-fold, 65-fold, 66-fold, 67-fold, 68-fold, 69-fold, 70-fold, 71-fold, 72-fold, 73-fold, 74-fold, 75-fold, 76-fold, 77-fold, 78-fold, 79-fold, 80-fold, 81-fold, 82-fold, 83-fold, 84-fold, 85-fold, 86-fold, 87-fold, 88-fold, 89-fold, 90-fold, 91-fold, 92-fold, 93-fold, 94-fold, 95-fold, 96-fold, 97-fold, 98-fold, 99-fold, 100-fold or more, as compared to the corresponding wild-type O-polysaccharide. In a preferred embodiment, the O-polysaccharide has a molecular weight that is increased by at least 1-fold and at most 5-fold, as compared to the corresponding wild-type O-polysaccharide. In another embodiment, the O-polysaccharide has a molecular weight that is increased by at least 2-fold and at most 4-fold, as compared to the corresponding wild-type O-polysaccharide. An increase in molecular weight of the O-polysaccharide, as compared to the corresponding wild-type O-polysaccharide, is preferably associated with an increase in number of O-antigen repeat units. In one embodiment, the increase in molecular weight of the O-polysaccharide is due to the wzz family protein.

In one embodiment, the O-polysaccharide has a molecular weight that is increased by about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 kDa or more, as compared to the corresponding wild-type O-polysaccharide. In one embodiment, the O-polysaccharide of the invention has a molecular weight that is increased by at least 1 and at most 200 kDa, as compared to the corresponding wild-type O-polysaccharide. In one embodiment, the molecular weight is increased by at least 5 and at most 200 kDa. In one embodiment, the molecular weight is increased by at least 10 and at most 200 kDa. In one embodiment, the molecular weight is increased by at least 12 and at most 200 kDa. In one embodiment, the molecular weight is increased by at least 15 and at most 200 kDa. In one embodiment, the molecular weight is increased by at least 18 and at most 200 kDa. In one embodiment, the molecular weight is increased by at least 20 and at most 200 kDa. In one embodiment, the molecular weight is increased by at least 21 and at most 200 kDa. In one embodiment, the molecular weight is increased by at least 22 and at most 200 kDa. In one embodiment, the molecular weight is increased by at least 30 and at most 200 kDa. In one embodiment, the molecular weight is increased by at least 1 and at most 100 kDa. In one embodiment, the molecular weight is increased by at least 5 and at most 100 kDa. In one embodiment, the molecular weight is increased by at least 10 and at most 100 kDa. In one embodiment, the molecular weight is increased by at least 12 and at most 100 kDa. In one embodiment, the molecular weight is increased by at least 15 and at most 100 kDa. In one embodiment, the molecular weight is increased by at least 20 and at most 100 kDa. In one embodiment, the molecular weight is increased by at least 1 and at most 75 kDa. In one embodiment, the molecular weight is increased by at least 5 and at most 75 kDa. In one embodiment, the molecular weight is increased by at least 10 and at most 75 kDa. In one embodiment, the molecular weight is increased by at least 12 and at most 75 kDa. In one embodiment, the molecular weight is increased by at least 15 and at most 75 kDa. In one embodiment, the molecular weight is increased by at least 18 and at most 75 kDa. In one embodiment, the molecular weight is increased by at least 20 and at most 75 kDa. In one embodiment, the molecular weight is increased by at least 30 and at most 75 kDa. In one embodiment, the molecular weight is increased by at least 10 and at most 90 kDa. In one embodiment, the molecular weight is increased by at least 12 and at most 85 kDa. In one embodiment, the molecular weight is increased by at least 10 and at most 75 kDa. In one embodiment, the molecular weight is increased by at least 10 and at most 70 kDa. In one embodiment, the molecular weight is increased by at least 10 and at most 60 kDa. In one embodiment, the molecular weight is increased by at least 10 and at most 50 kDa. In one embodiment, the molecular weight is increased by at least 10 and at most 49 kDa. In one embodiment, the molecular weight is increased by at least 10 and at most 48 kDa. In one embodiment, the molecular weight is increased by at least 10 and at most 47 kDa. In one embodiment, the molecular weight is increased by at least 10 and at most 46 kDa. In one embodiment, the molecular weight is increased by at least 20 and at most 45 kDa. In one embodiment, the molecular weight is increased by at least 20 and at most 44 kDa. In one embodiment, the molecular weight is increased by at least 20 and at most 43 kDa. In one embodiment, the molecular weight is increased by at least 20 and at most 42 kDa. In one embodiment, the molecular weight is increased by at least 20 and at most 41 kDa. Such an increase in molecular weight of the O-polysaccharide, as compared to the corresponding wild-type O-polysaccharide, is preferably associated with an increase in number of O-antigen repeat units. In one embodiment, the increase in molecular weight of the O-polysaccharide is due to the wzz family protein. See, for example, Table 21.

In another embodiment, the O-polysaccharide includes any one Formula selected from Table 1, wherein the number of repeat units n in the O-polysaccharide is greater than the number of repeat units in the corresponding wild-type O-polysaccharide by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more repeat units. Preferably, the saccharide includes an increase of at least 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 repeat units, as compared to the corresponding wild-type O-polysaccharide. See, for example, Table 21.

C. O-Antigen

The O-antigen is part of the lipopolysaccharide (LPS) in the outer membrane of Gram-negative bacteria. The O-antigen is on the cell surface and is a variable cell constituent. The variability of the O-antigen provides a basis for serotyping of Gram-negative bacteria. The current *E. coli* serotyping scheme includes O-polysaccharides 1 to 181.

The O-antigen includes oligosaccharide repeating units (O-units), the wild type structure of which usually contains two to eight residues from a broad range of sugars. The O-units of exemplary *E. coli* O-antigens are shown in Table 1, see also FIG. 9A-9C and FIG. 10A-10B.

In one embodiment, saccharide of the invention may be one oligosaccharide unit. In one embodiment, saccharide of the invention is one repeating oligosaccharide unit of the relevant serotype. In such embodiments, the saccharide may include a structure selected from any one of Formula O8, Formula O9a, Formula O9, Formula O20ab, Formula O20ac, Formula O52, Formula O97, and Formula O101.

In one embodiment, saccharide of the invention may be oligosaccharides. Oligosaccharides have a low number of repeat units (typically 5-15 repeat units) and are typically derived synthetically or by hydrolysis of polysaccharides. In such embodiments, the saccharide may include a structure selected from any one of Formula O8, Formula O9a, Formula O9, Formula O20ab, Formula O20ac, Formula O52, Formula O97, and Formula O101.

Preferably, all of the saccharides of the present invention and in the immunogenic compositions of the present invention are polysaccharides. High molecular weight polysaccharides may induce certain antibody immune responses due to the epitopes present on the antigenic surface. The isolation and purification of high molecular weight polysaccharides are preferably contemplated for use in the conjugates, compositions and methods of the present invention.

In some embodiments, the number of repeat O units in each individual O-antigen polymer (and therefore the length and molecular weight of the polymer chain) depends on the wzz chain length regulator, an inner membrane protein. Different wzz proteins confer different ranges of modal lengths (4 to >100 repeat units). The term "modal length" refers to the number of repeating O-units. Gram-negative bacteria often have two different Wzz proteins that confer two distinct OAg modal chain lengths, one longer and one shorter. The expression (not necessarily the overexpression) of wzz family proteins (e.g., wzzB) in Gram-negative bacteria may allow for the manipulation of O-antigen length, to shift or to bias bacterial production of O-antigens of certain length ranges, and to enhance production of high-yield large molecular weight lipopolysaccharides. In one embodiment, a "short" modal length as used herein refers to a low number of repeat O-units, e.g., 1-20. In one embodiment, a "long" modal length as used herein refers to a number of repeat O-units greater than 20 and up to a maximum of 40. In one embodiment, a "very long" modal length as used herein refers to greater than 40 repeat O-units.

In one embodiment, the saccharide produced has an increase of at least 10 repeating units, 15 repeating units, 20 repeating units, 25 repeating units, 30 repeating units, 35 repeating units, 40 repeating units, 45 repeating units, 50 repeating units, 55 repeating units, 60 repeating units, 65 repeating units, 70 repeating units, 75 repeating units, 80 repeating units, 85 repeating units, 90 repeating units, 95 repeating units, or 100 repeating units, as compared to the corresponding wild-type O-polysaccharide.

In another embodiment, the saccharide of the invention has an increase of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more repeat units, as compared to the corresponding wild-type O-polysaccharide. Preferably, the saccharide includes an increase of at least 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 repeat units, as compared to the corresponding wild-type O-polysaccharide. See, for example, Table 21. Methods of determining the length of saccharides are known in the art. Such methods include nuclear magnetic resonance, mass spectroscopy, and size exclusion chromatography, as described in Example 13.

Methods of determining the number of repeat units in the saccharide are also known in the art. For example, the number of repeat units (or "n" in the Formula) may be calculated by dividing the molecular weight of the polysaccharide (without the molecular weight of the core saccharide or KDO residue) by the molecular weight of the repeat unit (i.e., molecular weight of the structure in the corresponding Formula, shown for example in Table 1, which may be theoretically calculated as the sum of the molecular weight of each monosaccharide within the Formula). The molecular weight of each monosaccharide within the Formula is known in the art. The molecular weight of a repeat unit of Formula O25b, for example, is about 862 Da. The molecular weight of a repeat unit of Formula O1a, for example, is about 845 Da. The molecular weight of a repeat unit of Formula O2, for example, is about 829 Da. The molecular weight of a repeat unit of Formula O6, for example, is about 893 Da. When determining the number of repeat units in a conjugate, the carrier protein molecular weight and the protein: polysaccharide ratio is factored into the calculation. As defined herein, "n" refers to the number of repeating units (represented in brackets in Table 1) in a polysaccharide molecule. As is known in the art, in biological macromolecules, repeating structures may be interspersed with regions of imperfect repeats, such as, for example, missing branches. In addition, it is known in the art that polysaccharides isolated and purified from natural sources such as bacteria may be heterogenous in size and in branching. In such a case, n may represent an average or median value for n for the molecules in a population.

In one embodiment, the O-polysaccharide has an increase of at least one repeat unit of an O-antigen, as compared to the corresponding wild-type O-polysaccharide. The repeat units of O-antigens are shown in Table 1. In one embodiment, the O-polysaccharide includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more total repeat units. Preferably, the saccharide has a total of at least 3 to at most 80 repeat units. In another embodiment, the O-polysaccharide has an increase of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more repeat units, as compared to the corresponding wild-type O-polysaccharide.

In one embodiment, the saccharide includes an O-antigen wherein n in any of the O-antigen formulas (such as, for example, the Formulas shown in Table 1 (see also FIG. 9A-9C and FIG. 10A-10B)) is an integer of at least 1, 2, 3, 4, 5, 10, 20, 21, 22, 23, 24, 25, 26, 27, 28, 29, 30, 31, 32, 33, 34, 35, 36, 37, 38, 39, 40, and at most 200, 100, 99, 98, 97, 96, 95, 94, 93, 92, 91, 90, 89, 88, 87, 86, 81, 80, 79, 78, 77, 76, 75, 74, 73, 72, 71, 70, 69, 68, 67, 66, 65, 60, 59, 58, 57, 56, 55, 54, 53, 52, 51, or 50. Any minimum value and any maximum value may be combined to define a range. Exemplary ranges include, for example, at least 1 to at most 1000; at least 10 to at most 500; and at least 20 to at most 80, preferably at most 90. In one preferred embodiment, n is at least 31 to at most 90. In a preferred embodiment, n is 40 to 90, more preferably 60 to 85.

In one embodiment, the saccharide includes an O-antigen wherein n in any one of the O-antigen Formulas is at least 1 and at most 200. In one embodiment, n in any one of the O-antigen Formulas is at least 5 and at most 200. In one embodiment, n in any one of the O-antigen Formulas is at least 10 and at most 200. In one embodiment, n in any one of the O- antigen Formulas is at least 25 and at most 200. In one embodiment, n in any one of the O-antigen Formulas is at least 50 and at most 200. In one embodiment, n in any one of the O- antigen Formulas is at least 75 and at most 200. In one embodiment, n in any one of the O-antigen Formulas is at least 100 and at most 200. In one embodiment, n in any one of the O-antigen Formulas is at least 125 and at most 200. In one embodiment, n in any one of the O-antigen Formulas is at least 150 and at most 200. In one embodiment, n in any one of the O-antigen Formulas is at least 175 and at most 200. In one embodiment, n in any one of the O-antigen Formulas is at least 1 and at most 100. In one embodiment, n in any one of the O-antigen Formulas is at least 5 and at most 100. In one embodiment, n in any one of the O- antigen Formulas is at least 10 and at most 100. In one embodiment, n in any one of the O-antigen Formulas is at least 25 and at most 100. In one embodiment, n in any one of the O-antigen Formulas is at least 50 and at most 100. In one embodiment, n in any one of the O-antigen Formulas is at least 75 and at most 100. In one embodiment, n in any one of the O-antigen Formulas is at least 1 and at most 75. In one embodiment, n in any one of the O-antigen Formulas is at least 5 and at most 75. In one embodiment, n in any one of the O-antigen Formulas is at least 10 and at most 75. In one embodiment, n in any one of the O-antigen Formulas is at least 20 and at most 75. In one embodiment, n in any one of the O-antigen Formulas is at least 25 and at most 75. In one embodiment, n in any one of the O-antigen Formulas is at least 30 and at most 75. In one embodiment, n in any one of the O-antigen Formulas is at least 40 and at most 75. In one embodiment, n in any one of the O-antigen Formulas is at least 50 and at most 75. In one embodiment, n in any one of the O-antigen Formulas is at least 30 and at most 90. In one embodiment, n in any one of the O-antigen Formulas is at least 35 and at most 85. In one embodiment, n in any one of the O-antigen Formulas is at least 35 and at most 75. In one embodiment, n in any one of the O-antigen Formulas is at least 35 and at most 70. In one embodiment, n in any one of the O-antigen Formulas is at least 35 and at most 60. In one embodiment, n in any one of the O-antigen Formulas is at least 35 and at most 50. In one embodiment, n in any one of the O-antigen Formulas is at least 35 and at most 49. In one embodiment, n in any one of the O-antigen Formulas is at least 35 and at most 48. In one embodiment, n in any one of the O-antigen Formulas is at least 35 and at most 47. In one embodiment, n in any one of the O-antigen Formulas is at least 35 and at most 46. In one embodiment, n in any one of the O-antigen Formulas is at least 36 and at most 45. In one embodiment, n in any one of the O-antigen Formulas is at least 37 and at most 44. In one embodiment, n in any one of the O-antigen Formulas is at least 38 and at most 43. In one embodiment, n in any one of the O-antigen Formulas is at least 39 and at most 42. In one embodiment, n in any one of the O-antigen Formulas is at least 39 and at most 41.

For example, in one embodiment, n in the saccharide is 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90, most preferably 40. In another embodiment, n is at least 35 to at most 60. For example, in one embodiment, n is any one of 35, 36, 37, 38, 39, 40, 41, 42, 43, 44, 45, 46, 47, 48, 49, 50, 51, 52, 53, 54, 55, 56, 57, 58, 59, and 60, preferably 50. In another preferred embodiment, n is at least 55 to at most 75. For example, in one embodiment, n is 55, 56, 57, 58, 59, 60, 61, 62, 63, 64, 65, 66, 67, 68, or 69, most preferably 60.

The saccharide structure may be determined by methods and tools known art, such as, for example, NMR, including 1D, 1H, and/or 13C, 2D TOCSY, DQF-COSY, NOESY, and/or HMQC.

In some embodiments, the purified polysaccharide before conjugation has a molecular weight of between 5 kDa and 400 kDa. In other such embodiments, the saccharide has a molecular weight of between 10 kDa and 400 kDa; between 5 kDa and 400 kDa; between 5 kDa and 300 kDa; between 5 kDa and 200 kDa; between 5 kDa and 150 kDa; between 10 kDa and 100 kDa; between 10 kDa and 75 kDa; between 10 kDa and 60 kDa; between 10 kDa and 40 kDa; between 10 kDa and 100 kDa; 10 kDa and 200 kDa; between 15 kDa and 150 kDa; between 12 kDa and 120 kDa; between 12 kDa and 75 kDa; between 12 kDa and 50 kDa; between 12 and 60 kDa; between 35 kDa and 75 kDa; between 40 kDa and 60 kDa; between 35 kDa and 60 kDa; between 20 kDa and 60 kDa; between 12 kDa and 20 kDa; or between 20 kDa and 50 kDa. In further embodiments, the polysaccharide has a molecular weight of between 7 kDa to 15 kDa; 8 kDa to 16 kDa; 9 kDa to 25 kDa; 10 kDa to 100; 10 kDa to 60 kDa; 10 kDa to 70 kDa; 10 kDa to 160 kDa; 15 kDa to 600 kDa; 20 kDa to 1000 kDa; 20 kDa to 600 kDa; 20 kDa to 400 kDa; 30 kDa to 1,000 KDa; 30 kDa to 60 kDa; 30 kDa to 50 kDa or 5 kDa to 60 kDa. Any whole number integer within any of the above ranges is contemplated as an embodiment of the disclosure.

As used herein, the term "molecular weight" of polysaccharide or of carrier protein-polysaccharide conjugate refers to molecular weight calculated by size exclusion chromatography (SEC) combined with multiangle laser light scattering detector (MALLS).

A polysaccharide can become slightly reduced in size during normal purification procedures. Additionally, as described herein, polysaccharide can be subjected to sizing techniques before conjugation. Mechanical or chemical sizing maybe employed. Chemical hydrolysis may be conducted using acetic acid. Mechanical sizing may be conducted using High Pressure Homogenization Shearing. The molecular weight ranges mentioned above refer to purified polysaccharides before conjugation (e.g., before activation).

TABLE 1

*E. coli* serogroups/serotypes and O-unit moieties

<table>
<tr><th>Serogroup/ Serotype</th><th>Moiety Structure (O-unit)</th><th>Moiety structure referred to herein as:</th></tr>
<tr><td>O1A, O1A1</td><td>[→3)-α-L-Rha-(1→3)-α-L-Rha-(1→3)-β-L-Rha-(1→4)-β-D-GlcNAc-(1→|β-D-ManNAc-(1→2)]$_n$</td><td>Formula O1A</td></tr>
<tr><td>O1B</td><td>[→3)-α-L-Rha-(1→2)-α-L-Rha-(1→2)-α-D-Gal-(1→3)-β-D-GlcNAc-(1→|3-D-ManNAc-(1→2)]$_n$</td><td>Formula O1B</td></tr>
<tr><td>O1C</td><td>[→3)-α-L-Rha-(1→2)-α-L-Rha-(1→3)-α-D-Gal-(1→3)-β-D-GlcNAc-(1→|β-D-ManNAc-(1→2)]$_n$</td><td>Formula O1C</td></tr>
<tr><td>O2</td><td>[→3)-α-L-Rha-(1-2)-α-L-Rha-(1→3)-β-L-Rha-(1-4)-β-D-GlcNAc-(1→|α-D-Fuc3NAc-(1→2)]$_n$</td><td>Formula O2</td></tr>
<tr><td>O3</td><td>[β-L-RhaNAc(1-4)a-D-Glc-(1→4)|→3)-β-D-GlcNAc-(1→3)-α-D-Gal-(1→3)-β-D-GlcNAc-(1→]$_n$</td><td>Formula O3</td></tr>
<tr><td>O4:K52</td><td>[→2)-α-L-Rha-(1→6)-α-D-Glc-(1→3)-α-L-FucNAc-(1→3)-β-D-GlcNAc(1→]$_n$</td><td>Formula O4:K52</td></tr>
<tr><td>O4:K6</td><td>[α-D-Glc-(1→3)|→2)-α-L-Rha-(1→6)-α-D-Glc-(1→3)-α-L-FucNAc-(1→3)-β-D-GlcNAc(1→]$_n$</td><td>Formula O4:K6</td></tr>
<tr><td>O5ab</td><td>[→4)-β-D-Qui3NAc-(1→3)-β-D-Ribf-(1→4)-β-D-Gal-(1→3)-α-D-GalNAc(1→]$_n$</td><td>Formula O5ab</td></tr>
<tr><td>O5ac (strain 180/C3)</td><td>[→2)-β-D-Qui3NAc-(1→3)-β-D-Ribf-(1→4)-β-D-Gal-(1→3)-α-D-GalNAc(1→]$_n$</td><td>Formula O5ac (strain 180/C3)</td></tr>
<tr><td>O6:K2; K13; K15</td><td>[→4)-α-D-GalNAc-(1→3)-β-D-Man-(1→4)-β-D-Man-(1→3)-α-D-GlcNAc-(1→|β-D-Glc-(1→2)]$_n$</td><td>Formula O6:K2; K13; K15</td></tr>
<tr><td>O6:K54</td><td>[→4)-α-D-GalNAc-(1→3)-β-D-Man-(1→4)-β-D-Man-(1→3)-α-D-GlcNAc-(1→|β-D-GlcNAc-(1→2)]$_n$</td><td>Formula O6:K54</td></tr>
<tr><td>O7</td><td>[α-L-Rha-(1→3)|→3)-β-D-Qui4NAc-(1→2)-α-D-Man-(1-4)-β-D-Gal-(1→3)-α-D-GlcNAc-(1→]$_n$</td><td>Formula O7</td></tr>
<tr><td>O10</td><td>[→3)-α-L-Rha-(1→3)-α-L-Rha-(1→3)-α-D-Gal-(1→3)-β-D-GlcNAc-(1→|α-D-Fuc4NAcyl-(1→2)Acyl = acetyl(60%)or(R)-3-hydroxybutyryl (40%)]$_n$</td><td>Formula O10</td></tr>
</table>

TABLE 1-continued

*E. coli* serogroups/serotypes and O-unit moieties

| Serogroup/ Serotype | Moiety Structure (O-unit) | Moiety structure referred to herein as: |
|---|---|---|
| O16 | [→2)-β-D-Galf-(1→6)-α-D-Glc-(1→3)-α-L-Rha2Ac-(1→3)-α-D-GlcNAc-(1→]$_n$ | Formula O16 |
| O17 | [α-D-Glc-(1→6)\|→6)-α-D-Man-(1→2)-α-D-Man-(1→2)-β-D-Man-(1→3)-α-D-GlcNAc(1→]$_n$ | Formula O17 |
| O18A, O18ac | [→2)-α-L-Rha-(1→6)-α-D-Glc-(1→4)-α-D-Gal-(1→3)-α-D-GlcNAc-(1→\|β-D-GlcNAc-(1→3)]$_n$ | Formula O18A, Formula O18ac |
| O18A1 | [α-D-Glc-(1→6)\|→2)-α-L-Rha-(1→6)-α-D-Glc-(1→4)-α-D-Gal-(1)3)-α-D-GlcNAc-(1→\|β-D-GlcNAc-(1→3)]$_n$ | Formula O18A1 |
| O18B | [→3)-α-L-Rha-(1→6)-α-D-Glc-(1→4)-α-D-Gal-(1→3)-α-D-GlcNAc-(1→\|β-D-Glc-(1→3)]$_n$ | Formula O18B |
| O18B1 | [α-D-Glc-(1→4)\|→3)-α-L-Rha-(1→6)-α-D-Glc-(1→4)-α-D-Gal-(1→3)-α-D-GlcNAc-(1→\|β-D-Glc-(1→3)]$_n$ | Formula O18B1 |
| O21 | [β-D-Gal-(1→4)\|→3)-β-D-Gal-(1-4)-β-D-Glc-(1→3)-β-D-GalNAc-(1→\|β-D-GlcNAc-(1→2)]$_n$ | Formula O21 |
| O23A | [α-D-Glc-(1→6)\|→6)-α-D-Glc-(1→4)-β-D-Gal-(1→3)-α-D-GalNAc-(1→3)-β-D-GlcNAc-(1→\|β-D-GlcNAc(1→3)]$_n$ | Formula O23A |
| O24 | [→7)-α-Neu5Ac-(2→3)-β-D-Glc-(1→3)-β-D-GalNAc-(1→\|α-D-Glc-(1→2)]$_n$ | Formula O24 |
| O25/O25a | [β-D-Glc-(1→6)\|→4)-α-D-Glc-(1→3)-α-L-FucNAc-(1→3)-β-D-GlcNAc-(1→\|α-L-Rha-(1→3)]$_n$ | Formula O25a |
| O25b | β-Glcp-<br>1<br>↓<br>6<br>[α-Rhap-(1→3)-α-Glcp-(1→3)-α-Rhap2OAc-(1→3)-β-GlcpNAc-]$_n$ | Formula O25b |
| O26 | [→3)-α-L-Rha-(1→4)-α-L-FucNAc-(1→3)-β-D-GlcNAc-(1→]$_n$ | Formula O26 |
| O28 | [→2)-(R)-Gro-1-P→4)-β-D-GlcNAc-(1→3)-β-D-Galf2Ac-(1→3)-α-D-GlcNAc-(1→]$_n$ | Formula O28 |
| O36 | [α-L-Rhap-(1→2)-α-L-Fucp<br>1<br>↓<br>3<br>→4)-α-D-Manp-(1→3)-α-L-Fucp-(1→3)-β-D-GlcpNAc-(1→]n | Formula O36 |
| O44 | [α-D-Glc-(1→4)\|→6)-α-D-Man-(1→2)-α-D-Man-(1→2)-β-D-Man-(1→3)-α-D-GlcNAc(1→]$_n$ | Formula O44 |
| O45 | [→2)-β-D-Glc-(1→3)-α-L-6dTal2Ac-(1→3)-α-D-FucNAc-(1→]$_n$ | Formula O45 |
| O45rel | [→2)-β-D-Glc-(1→3)-α-L-6dTal2Ac-(1→3)-β-D-GlcNAc-(1→]$_n$ | Formula O45rel |
| O54 | [→4)-α-d-GalpA-(1→2)-α-I-Rhap-(1→2)-β-d-Ribf-(1→4)-β-d-Galp-(1→3)-β-d-GlcpNAc-(1→]$_n$ | Formula O54 |
| O55 | [→6)-β-D-GlcNAc-(1→3)-α-D-Gal-(1→3)-β-D-GalNAc-(1→\|α-Col-(1→2)-β-D-Gal-(1→3)]$_n$ | Formula O55 |
| O56 | [→7)-α-Neu5Ac-(2→3)-β-D-Glc-(1→3)-β-D-GlcNAc-(1→\|α-D-Gal-(1→2)]$_n$ | Formula O56 |
| O57 | [→3)-α-D-Galp-(1→3)-α-L-FucpNAc-(1→3)-α-D-GlcpNAc-(1→]n<br>2 4<br>↑ ↑<br>1 1<br>α-D-GalpA2/3Ac β-D-Glcp | Formula O57 |
| O58 | [3-O-[(R)-1-carboxyethyl]-α-L-Rha-(1→3)\|→4)-α-D-Man-(1→4)-α-D-Man2Ac-(1→3)-β-D-GlcNAc-(1→]$_n$ | Formula O58 |
| O64 | [β-D-Gal-(1→6)\|→3)-α-D-ManNAc-(1→3)-β-D-GlcA-(1→3)-β-D-Gal-(1→3)-β-D-GlcNAc(1→]$_n$ | Formula O64 |
| O68 | [α-L-Rhap α-D-Glcp<br>1 1<br>↓ ↓<br>3 3<br>→6)-α-D-Manp-(1→2)-α-D-Manp-(1→2)-α-D-Manp-(1→2)-β-D-Manp-(1→3)-α-D-GlcpNAC-(1→]n | Formula O68 |

TABLE 1-continued

*E. coli* serogroups/serotypes and O-unit moieties

| Serogroup/ Serotype | Moiety Structure (O-unit) | Moiety structure referred to herein as: |
|---|---|---|
| O69 | [→2)-α-L-Rha-(1→2)-α-L-Rha-(1→2)-α-D-Gal-(1→3)-β-D-GlcNAc-(1→]$_n$ | Formula O69 |
| O73 (Strain 73-1) | [α-D-Glc-(1→3)\|→4)-α-D-Man-(1→2)-α-D-Man-(1→2)-β-D-Man-(1→3)-α-D-GalNAc(1→]$_n$ | Formula O73 (Strain 73-1) |
| O74 | →6)-α-D-GlcpNAc-(1→4)-β-D-GalpA-(1→3)-β-D-GlcpNAc-(1→]n<br>\|<br>[β-D-Fucp3NAc-(1→3) | Formula O74 |
| O75 | [β-D-Man-(1-4)\|→3)-α-D-Gal-(1→4)-α-L-Rha-(1→3)-β-D-GlcNAc-(1→]$_n$ | Formula O75 |
| O76 | [→4)-β-D-GlcpA-(1→4)-β-D-GalpNAc3Ac-(1→4)-α-D-GalpNAc-(1→3)-β-D-GalpNAc-(1→→]$_n$ | Formula O76 |
| O77 | [→6)-α-D-Man-(1→2)-α-D-Man-(1→2)-β-D-Man-(1→3)-α-D-GlcNAc(1→]$_n$ | Formula O77 |
| O78 | [→4)-β-D-GlcNAc-(1→4)-β-D-Man-(1→4)-α-D-Man-(1→3)-β-D-GlcNAc-(1→]$_n$ | Formula O78 |
| O86 | [α-D-Gal-(1→3)\|→4)-α-L-Fuc-(1→2)-β-D-Gal-(1→3)-α-D-GalNAc-(1→3)-β-D-GalNAc-(1→]$_n$ | Formula O86 |
| O88 | [α-L-6dTal-(1→3)\|→4)-α-D-Man-(1→3)-α-D-Man-(1→3)-β-D-GlcNAc-(1→]$_n$ | Formula O88 |
| O90 | [→4)-α-L-Fuc2/3Ac-(1→2)-β-D-Gal-(1→3)-α-D-GalNAc-(1→3)-β-D-GalNAc-(1→]$_n$ | Formula O90 |
| O98 | [→3)-α-L-QuiNAc-(1→4)-α-D-GalNAcA-(1→3)-α-L-QuiNAc-(1→3)-β-D-GlcNAc-(1→]$_n$ | Formula O98 |
| O104 | [→4)-α-D-Gal-(1→4)-α-Neu5,7,9AC3-(2→3)-β-D-Gal-(1→3)-β-D-GalNAc-(1→]$_n$ | Formula O104 |
| O111 | [α-Col-(1→6)\|→4)-α-D-Glc-(1-4)-α-D-Gal-(1→3)-β-D-GlcNAc-(1→\|α-Col-(1→3)]$_n$ | Formula O111 |
| O113 | [→4)-α-D-GalNAc-(1→4)-α-D-GalA-(1→3)-α-D-Gal-(1→3)-β-D-GlcNAc-(1→\|β-D-Gal-(1→3)]$_n$ | Formula O113 |
| O114 | [→4)-β-D-Qui3N(N-acetyl-L-seryl)-(1→3)-β-D-Ribf-(1→4)-β-D-Gal-(1→3)-α-D-GlcNAc(1→]$_n$ | Formula O114 |
| O119 | [β-D-RhaNAc3NFo-(1→3)\|→2)-β-D-Man-(1→3)-α-D-Gal-(1→4)-α-L-Rha-(1→3)-α-D-GlcNAc-(1→]$_n$ | Formula O119 |
| O121 | [→3)-β-D-Qui4N(N-acetyl-glycyl)-(1→4)-α-D-GalNAc3AcA6N-(1→4)-α-D-GalNAcA-(1→3)-α-D-GlcNAc-(1→]$_n$ | Formula O121 |
| O124 | [4-O-[(R)-1-carboxyethyl]-β-D-Glc-(1→6)-α-D-Glc(1→4)\|→3)-α-D-Gal-(1→6)-β-D-Galf-(1→3)-β-D-GalNAc-(1→]$_n$ | Formula O124 |
| O125 | [α-D-Glc-(1→3)\|→4)-β-D-GalNAc-(1→2)-α-D-Man-(1→3)-α-L-Fuc-(1→3)-α-D-GalNAc-(1→\|β-D-Gal-(1→3)]$_n$ | Formula O125 |
| O126 | [→2)-β-D-Man-(1→3)-β-D-Gal-(1→3)-α-D-GlcNAc-(1→3)-β-D-GlcNAc-(1→\|α-L-Fuc-(1→2)]$_n$ | Formula O126 |
| O127 | [→2)-α-L-Fuc-(1→2)-β-D-Gal-(1→3)-α-D-GalNAc-(1→3)-α-D-GalNAc-(1→]$_n$ | Formula O127 |
| O128 | [α-L-Fuc-(1→2)\|→6)-β-D-Gal-(1→3)-β-D-GalNAc-(1-4)-α-D-Gal-(1→3)-β-D-GalNAc-(1→]$_n$ | Formula O128 |
| O136 | [→4)-β-Pse5Ac7Ac-(2→4)-β-D-Gal-(1→4)-β-D-GlcNAc-(1→β-Pse5Ac7Ac = 5,7-diacetamido-3,5,7,9-tetradeoxy-L-glycero-β-L-manno-nonulosonicacid]$_n$ | Formula O136 |
| O138 | [→2)-α-L-Rha-(1→3)-α-L-Rha-(1→4)-α-D-GalNAcA-(1→3)-β-D-GlcNAc-(1→]$_n$ | Formula O138 |
| O140 | [α-D-Galf-(1→2)-α-L-Rhap<br>1<br>↓<br>4<br>→3)-β-D-Galp-(1→4)-α-D-Glcp-(1→4)-β-D-GlcpA-(1→3)-<br>β-D-GalpNAc-(1→]n | Formula O140 |
| O141 | [α-L-Rha-(1→3)\|→→4)-α-D-Man-(1→3)-α-D-Man6Ac-(1→3)-β-D-GlcNAc-(1→\|β-D-GlCA-(1→2)]$_n$ | Formula O141 |
| O142 | [→2)-α-L-Rha-(1→6)-α-D-GalNAc-(1→4)-α-D-GalNAc-(1→3)-α-D-GalNAc-(1→\|β-D-GlcNAc-(1→3)]$_n$ | Formula O142 |
| O143 | [→2)-β-D-GalA6R3,4Ac-(1→3)-α-D-GalNAc-(1→4)-β-D-GlcA-(1→3)-β-D-GlcNAc-(1→R = 1,3-dihydroxy-2-propylamino]$_n$ | Formula O143 |
| O147 | [→2)-α-L-Rha-(1→2)-α-L-Rha-(1-4)-β-D-GalA-(1→3)-β-D-GalNAc-(1→]$_n$ | Formula O147 |
| O149 | [→3)-β-D-GlcNAc-(S)-4,6Py-(1→3)-β-L-Rha-(1→4)-β-D-GlcNAc-(1→(S)-4,6Py = 4,6-O-[(S)-1-carboxyethylidene]-]$_n$ | Formula O149 |
| O152 | [β-L-Rha-(1-4)\|→3)-α-D-GlcNAc-(1-P→6)-α-D-Glc-(1→2)-β-D-Glc-(1→3)-β-D-GlcNAc-(1→]$_n$ | Formula O152 |

TABLE 1-continued

*E. coli* serogroups/serotypes and O-unit moieties

| Serogroup/ Serotype | Moiety Structure (O-unit) | Moiety structure referred to herein as: |
|---|---|---|
| O157 | [→2)-α-D-Rha4NAc-(1→3)-α-L-Fuc-(1→4)-β-D-Glc-(1→3)-α-D-GalNAc-(1→]$_n$ | Formula O157 |
| O158 | [α-D-Glc-(1→6)\|→4)-α-D-Glc-(1→3)-α-D-GalNAc-(1→3)-β-D-GalNAc-(1→\|α-L-Rha-(1→3)]$_n$ | Formula O158 |
| O159 | [α-L-Fuc-(1→4)\|→3)-β-D-GlcNAc-(1→4)-α-D-GalA-(1→3)-α-L-Fuc-(1→3)-β-D-GlcNAc-(1→]$_n$ | Formula O159 |
| O164 | [β-D-Glc-(1→6)-α-D-Glc(1→4)\|→3)-β-D-Gal-(1→6)-β-D-Galf-(1→3)-β-D-GalNAc-(1→]$_n$ | Formula O164 |
| O173 | [α-L-Fuc-(1→4)\|→3)-α-D-Glc-(1-P→6)-α-D-Glc-(1→2)-β-D-Glc-(1→3)-β-D-GlcNAc-(1→]$_n$ | Formula O173 |
| 62D$_1$ Suggested as *Erwinia herbicola* | [α-D-Gal(1→6)\|→2)-β-D-Qui3NAc-(1→3)-α-L-Rha-(1→3)-β-D-Gal-(1→3)-α-D-FucNAc-(1→]$_n$ | Formula 62D$_1$ |
| O22 | [→6)-α-D-Glc-(1→4)-β-D-GlcA-(1→4)-β-D-GalNAc3Ac-(1→3)-α-D-Gal-(1→3)-β-D-GalNAc-(1→]$_n$ | Formula O22 |
| O35 | [→3)-α-L-Rha-(1→2)-α-L-Rha-(1→3)-α-L-Rha-(1→2)-α-L-Rha-(1→3)-β-D-GlcNAc-(1→\|α-D-GalNAcA6N-(1→2)]$_n$ | Formula O35 |
| O65 | [→2)-β-D-Qui3NAc-(1→4)-α-D-GalA6N-(1→4)-α-D-GalNAc-(1→4)-β-D-GalA-(1→3)-α-D-GlcNAc-(1→]$_n$ | Formula O65 |
| O66 | [→2)-β-D-Man-(1→3)-α-D-GlcNAc-(1→2)-β-D-Glc3Ac-(1→3)-α-L-6dTal-(1→3)-α-D-GlcNAc(1→]$_n$ | Formula O66 |
| O83 | [→→6)-α-D-Glc-(1→4)-β-D-GlcA-(1→6)-β-D-Gal-(1→4)-β-D-Gal-(1→4)-β-D-GlcNAc-(1→]$_n$ | Formula O83 |
| O91 | [→4)-α-D-Qui3NAcyl-(1→4)-β-D-Gal-(1→4)-β-D-GlcNAc-(1→4)-β-D-GlcA6NGly-(1→3)-β-D-GlcNAc-(1→Acyl = (R)-3-hydroxybutyryl]$_n$ | Formula O91 |
| O105 | [β-D-Ribf-(1→3)\|→4)-α-D-GlcA2Ac3Ac-(1→2)-α-L-Rha4Ac-(1→3)-β-L-Rha-(1→4)-β-L-Rha-(1→3)-β-D-GlcNAc6Ac-(1→]$_n$ | Formula O105 |
| O116 | [→2)-β-D-Qui4NAc-(1→6)-α-D-GlcNAc-(1→4)-α-D-GalNAc-(1→4)-α-D-GalA-(1→3)-β-D-GlcNAc-(1→]$_n$ | Formula O116 |
| O117 | [→4)-β-D-GalNAc-(1→3)-α-L-Rha-(1→4)-α-D-Glc-(1→4)-β-D-Gal-(1→3)-α-D-GalNAc-(1→]$_n$ | Formula O117 |
| O139 | [β-D-Glc-(1→3)\|→3)-α-L-Rha-(1→4)-α-D-GalA-(1→2)-α-L-Rha-(1→3)-α-L-Rha-(1→2)-α-L-Rha-(1→3)-α-D-GlcNAc-(1→]$_n$ | Formula O139 |
| O153 | [→2)-β-D-Ribf-(1→4)-β-D-Gal-(1→4)-α-D-GlcNAc-(1→4)-β-D-Gal-(1→3)-α-D-GlcNAc-(1→]$_n$ | Formula O153 |
| O167 | [α-D-Galf-(1→4)\|→2)-β-D-GalA6N(L)Ala-(1→3)-α-D-GlcNAc-(1→2)-β-D-Galf-(1→5)-β-D-Galf-(1→3)-β-D-GlcNAc-(1→]$_n$ | Formula O167 |
| O172 | [→3)-α-L-FucNAc-(1→4)-α-D-Glc6Ac-(1-P→→4)-α-D-Glc-(1→3)-α-L-FucNAc-(1→3)-α-D-GlcNAc-(1→]$_n$ | Formula O172 |
| O8 | [→2)-α-D-Man-(1→2)-α-D-Man-(1→3)-β-D-Man-(1→]$_n$ | Formula O8 |
| O9a | [→2)-α-D-Man-(1→2)-α-D-Man-(1→3)-α-D-Man-(1→3)-α-D-Man-(1→]$_n$ | Formula O9a |
| O9 | [→2]-[α-D-Man-(1→2)]2-α-D-Man-(1→3)-α-D-Man-(1→3)-α-D-Man-(1→]$_n$ | Formula O9 |
| O2Oab | [→2)-β-D-Ribf-(1→4)-α-D-Gal-(1→]$_n$ | Formula O20ab |
| O2Oac | [α-D-Gal-(1→3)\|→2)-β-D-Ribf-(1→4)-α-D-Gal-(1→]$_n$ | Formula O20ac |
| O52 | [→3)-β-D-Fucf-(1→3)-β-D-6dmanHep2Ac-(1→]$_n$ | Formula O52 |
| O97 | [→3)-α-L-Rha-(1→3)-β-L-Rha-(1→\|\|β-D-Xulf-(2→2)β-D-Xulf-(2→2)]$_n$ | Formula O97 |

†β-D-6dmanHep2Ac is 2-O-acetyl-6-deoxy-β-D-manno-heptopyranosyl.
‡β-D-Xulf is β-D-threo-pentofuranosyl.

5 D. Core Oligosaccharide

The core oligosaccharide is positioned between Lipid A and the O-antigen outer region in wild-type *E. coli* LPS. More specifically, the core oligosaccharide is the part of the polysaccharide that includes the bond between the O-antigen and the lipid A in wild type *E. coli*. This bond includes a ketosidic bond between the hemiketal function of the innermost 3-deoxy-d-manno-oct-2-ulosonic acid (KDO)) residue and a hydroxyl-group of a GicNAc-residue of the lipid A. The core oligosaccharide region shows a high degree of similarity among wild-type *E. coli* strains. It usually includes a limited number of sugars. The core oligosaccharide includes an inner core region and an outer core region.

More specifically, the inner core is composed primarily of L-glycero-D-manno-heptose (heptose) and KDO residues. The inner core is highly conserved. A KDO residue includes the following Formula KDO:

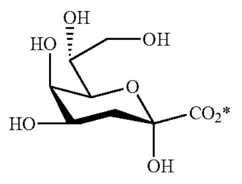

Figure 24:
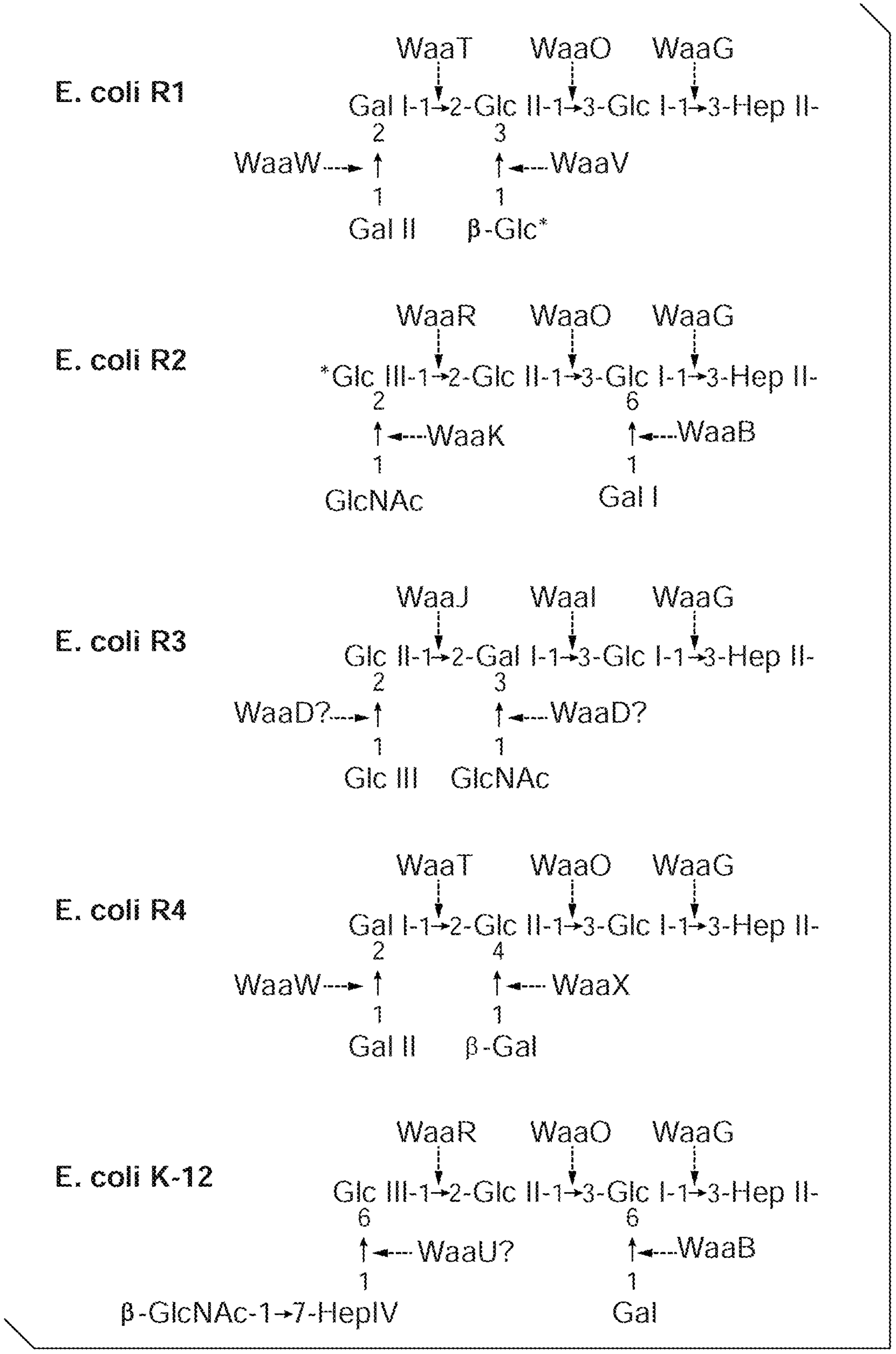
FIG. 24—depicts generalized structures of the carbohydrate backbone of the outer core oligosaccharides of the five known chemotypes. All glycoses are in the α-anomeric configuration unless otherwise indicated. The genes whose products catalyse formation of each linkage are indicated in dashed arrows. An asterisk denotes the residue of the core oligosaccharide to which attachment of O-antigen occurs.

The outer region of the core oligosaccharide displays more variation than the inner core region, and differences in this region distinguish the five chemotypes in *E. coli*: R1, R2, $R^3$, R4, and K-12. See FIG. 24, which illustrates generalized structures of the carbohydrate backbone of the outer core oligosaccharides of the five known chemotypes. Hepll is the last residue of the inner core oligosaccharide. While all of the outer core oligosaccharides share a structural theme, with a (hexose) 3 carbohydrate backbone and two side chain residues, the order of hexoses in the backbone and the nature, position, and linkage of the side chain residues can all vary. The structures for the R1 and R4 outer core oligosaccharides are highly similar, differing in only a single β-linked residue.

The core oligosaccharides of wild-type *E. coli* are categorized in the art based on the structures of the distal oligosaccharide, into five different chemotypes: *E. coli* R1, *E. coli* R2, *E. coli* R3, *E. coli* R4, and *E. coli* K12.

In a preferred embodiment, the compositions described herein include glycoconjugates in which the O-polysaccharide includes a core oligosaccharide bound to the O-antigen. In one embodiment, the composition induces an immune response against at least any one of the core *E. coli* chemotypes *E. coli* R1, *E. coli* R2, *E. coli* R3, *E. coli* R4, and *E. coli* K12. In another embodiment, the composition induces an immune response against at least two core *E. coli* chemotypes. In another embodiment, the composition induces an immune response against at least three core *E. coli* chemotypes. In another embodiment, the composition induces an immune response against at least four core *E. coli* chemotypes. In another embodiment, the composition induces an immune response against all five core *E. coli* chemotypes.

In another preferred embodiment, the compositions described herein include glycoconjugates in which the O-polysaccharide does not include a core oligosaccharide bound to the O-antigen. In one embodiment, such a composition induces an immune response against at least any one of the core *E. coli* chemotypes *E. coli* R1, *E. coli* R2, *E. coli* R3, *E. coli* R4, and *E. coli* K12, despite the glycoconjugate having an O-polysaccharide that does not include a core oligosaccharide.

*E. coli* serotypes may be characterized according to one of the five chemotypes. Table 2 lists exemplary serotypes characterized according to chemotype. The serotypes in bold represent the serotypes that are most commonly associated with the indicated core chemotype. Accordingly, in a preferred embodiment, the composition induces an immune response against at least any one of the core *E. coli* chemotypes *E. coli* R1, *E. coli* R2, *E. coli* R3, *E. coli* R4, and *E. coli* $K_{12}$, which includes an immune response against any one of the respective corresponding *E. coli* serotypes.

TABLE 2

Core Chemotype and associated *E. coli* Serotype

| Core chemotype | Serotype |
| --- | --- |
| R1 | O25a, O6, **O2**, **O1**, O75, O4, **O16**, O8, O18, O9, O13, O20, O21, O91, and O163. |
| R2 | O21, O44, O11, O89, O162, O9 |
| R3 | O25b, O15, O153, O21, O17, O11, O159, O22 O86, O93 |
| R4 | O2, O1, O86, O7, O102, O160, O166 |
| K-12 | **O25b**, O16 |

In some embodiments, the composition includes a saccharide that includes a structure derived from a serotype having an R1 chemotype, e.g., selected from a saccharide having Formula O25a, Formula O6, Formula O2, Formula O1, Formula O75, Formula O4, Formula O16, Formula O8, Formula O18, Formula O9, Formula O13, Formula O20, Formula O21, Formula O91, and Formula O163, wherein n is 1 to 100. In some embodiments, the saccharide in said composition further includes an *E. coli* R1 core moiety, e.g., shown in FIG. 24.

In some embodiments, the composition includes a saccharide that includes a structure derived from a serotype having an R1 chemotype, e.g., selected from a saccharide having Formula O25a, Formula O6, Formula O2, Formula O1, Formula O75, Formula O4, Formula O16, Formula O18, Formula O13, Formula O20, Formula O21, Formula O91, and Formula O163, wherein n is 1 to 100, preferably 31 to 100, more preferably 35 to 90, most preferably 35 to 65. In some embodiments, the saccharide in said composition further includes an *E. coli* R1 core moiety in the saccharide.

In some embodiments, the composition includes a saccharide that includes a structure derived from a serotype having an R2 chemotype, e.g., selected from a saccharide having Formula O21, Formula O44, Formula O11, Formula O89, Formula O162, and Formula O9, wherein n is 1 to 100, preferably 31 to 100, more preferably 35 to 90, most preferably 35 to 65. In some embodiments, the saccharide in said composition further includes an *E. coli* R2 core moiety, e.g., shown in FIG. 24.

In some embodiments, the composition includes a saccharide that includes a structure derived from a serotype having an R3 chemotype, e.g., selected from a saccharide having Formula O25b, Formula O15, Formula O153, Formula O21, Formula O17, Formula O11, Formula O159, Formula O22, Formula O86, and Formula O93, wherein n is 1 to 100, preferably 31 to 100, more preferably 35 to 90, most preferably 35 to 65. In some embodiments, the saccharide in said composition further includes an *E. coli* R3 core moiety, e.g., shown in FIG. 24.

In some embodiments, the composition includes a saccharide that includes a structure derived from a serotype having an R4 chemotype, e.g., selected from a saccharide having Formula O2, Formula O1, Formula O86, Formula O7, Formula O102, Formula O160, and Formula O166, wherein n is 1 to 100, preferably 31 to 100, more preferably 35 to 90, most preferably 35 to 65. In some embodiments, the saccharide in said composition further includes an *E. coli* R4 core moiety, e.g., shown in FIG. 24.

In some embodiments, the composition includes a saccharide that includes a structure derived from a serotype having an K-12 chemotype (e.g., selected from a saccharide having Formula O25b and a saccharide having Formula O16), wherein n is 1 to 1000, preferably 31 to 100, more preferably 35 to 90, most preferably 35 to 65. In some embodiments, the saccharide in said composition further includes an *E. coli* K-12 core moiety, e.g., shown in FIG. 24.

In some embodiments, the saccharide includes the core saccharide. Accordingly, in one embodiment, the O-polysaccharide further includes an *E. coli* R1 core moiety. In another embodiment, the O-polysaccharide further includes an *E. coli* R2 core moiety. In another embodiment, the O-polysaccharide further includes an *E. coli* R3 core moiety. In another embodiment, the O-polysaccharide further includes an *E. coli* R4 core moiety. In another embodiment, the O-polysaccharide further includes an *E. coli* $K_{12}$ core moiety.

In some embodiments, the saccharide does not include the core saccharide. Accordingly, in one embodiment, the O-polysaccharide does not include an *E. coli* R1 core moiety. In another embodiment, the O-polysaccharide does not include an *E. coli* R2 core moiety. In another embodiment, the O-polysaccharide does not include an *E. coli* R3 core moiety. In another embodiment, the O-polysaccharide does not include an *E. coli* R4 core moiety. In another embodiment, the O-polysaccharide does not include an *E. coli* $K_{12}$ core moiety.

E. Conjugated O-Antigens

Chemical linkage of O-antigens or preferably O-polysaccharides to protein carriers may improve the immunogenicity of the O-antigens or O-polysaccharides. However, variability in polymer size represents a practical challenge for production. In commercial use, the size of the saccharide can influence the compatibility with different conjugation synthesis strategies, product uniformity, and conjugate immunogenicity. Controlling the expression of a Wzz family protein chain length regulator through manipulation of the O-antigen synthesis pathway allows for production of a desired length of O-antigen chains in a variety of Gram-negative bacterial strains, including *E. coli.*

In one embodiment, the purified saccharides are chemically activated to produce activated saccharides capable of reacting with the carrier protein. Once activated, each saccharide is separately conjugated to a carrier protein to form a conjugate, namely a glycoconjugate. As used herein, the term "glycoconjugate" refers to a saccharide covalently linked to a carrier protein. In one embodiment a saccharide is linked directly to a carrier protein. In another embodiment, a saccharide is linked to a protein through a spacer/linker. Conjugates may be prepared by schemes that bind the carrier to the O-antigen at one or at multiple sites along the O-antigen, or by schemes that activate at least one residue of the core oligosaccharide.

In one embodiment, each saccharide is conjugated to the same carrier protein. If the protein carrier is the same for 2 or more saccharides in the composition, the saccharides may be conjugated to the same molecule of the carrier protein (e.g., carrier molecules having 2 or more different saccharides conjugated to it).

In a preferred embodiment, the saccharides are each individually conjugated to different molecules of the protein carrier (each molecule of protein carrier only having one type of saccharide conjugated to it). In said embodiment, the saccharides are said to be individually conjugated to the carrier protein.

The chemical activation of the saccharides and subsequent conjugation to the carrier protein can be achieved by the activation and conjugation methods disclosed herein. After conjugation of the polysaccharide to the carrier protein, the glycoconjugates are purified (enriched with respect to the amount of polysaccharide-protein conjugate) by a variety of techniques. These techniques include concentration/diafiltration operations, precipitation/elution, column chromatography, and depth filtration. After the individual glycoconjugates are purified, they are compounded to formulate the immunogenic composition of the present invention.

Activation. The present invention further relates to activated polysaccharides produced from any of the embodiments described herein wherein the polysaccharide is activated with a chemical reagent to produce reactive groups for conjugation to a linker or carrier protein. In some embodiments, the saccharide of the invention is activated prior to conjugation to the carrier protein. In some embodiments, the degree of activation does not significantly reduce the molecular weight of the polysaccharide. For example, in some embodiments, the degree of activation does not cleave the polysaccharide backbone. In some embodiments, the degree of activation does not significantly impact the degree of conjugation, as measured by the number of lysine residues modified in the carrier protein, such as, $CRM_{197}$ (as determined by amino acid analysis). For example, in some embodiments, the degree of activation does not significantly increase the number of lysine residues modified (as determined by amino acid analysis) in the carrier protein by 3-fold, as compared to the number of lysine residues modified in the carrier protein of a conjugate with a reference polysaccharide at the same degree of activation. In some embodiments, the degree of activation does not increase the level of unconjugated free saccharide. In some embodiments, the degree of activation does not decrease the optimal saccharide/protein ratio.

In some embodiments, the activated saccharide has a percentage of activation wherein moles of thiol per saccharide repeat unit of the activated saccharide is between 1-100%, such as, for example, between 2-80%, between 2-50%, between 3-30%, and between 4-25%. The degree of activation is at least 1%, 2%, 3%, 4%, 5%, 6%, 7%, 8%, 9%, 10%, 11%, 12%, 13%, 14%, 15%, 16%, 17%, 18%, 19%, ≥20%, ≥30%, ≥40%, ≥50%, ≥60%, ≥70%, ≥80%, or ≥90%, or about 100%. Preferably, the degree of activation is at most 50%, more preferably at most 25%. In one embodiment, the degree of activation is at most 20%. Any minimum value and any maximum value may be combined to define a range.

In one embodiment, the polysaccharide is activated with 1-cyano-4-dimethylamino pyridinium tetrafluoroborate (CDAP) to form a cyanate ester. The activated polysaccharide is then coupled directly or via a spacer (linker) group to an amino group on the carrier protein (preferably $CRM_{197}$ or tetanus toxoid).

For example, the spacer may be cystamine or cysteamine to give a thiolated polysaccharide which could be coupled to the carrier via a thioether linkage obtained after reaction with a maleimide-activated carrier protein (for example using N-[Y-maleimidobutyrloxy]succinimide ester (GMBS)) or a haloacetylated carrier protein (for example using iodoacetimide, N-succinimidyl bromoacetate (SBA; SIB), N-succinimidyl (4-iodoacetyl)aminobenzoate (SIAB), sulfosuccinimidyl (4-iodoacetyl)aminobenzoate (sulfo-SIAB), N-succinimidyl iodoacetate (SIA), or succinimidyl 3-[bromoacetamido]proprionate (SBAP)). In one embodiment, the cyanate ester (optionally made by CDAP chemistry) is coupled with hexane diamine or adipic acid dihydrazide (ADH) and the amino-derivatised saccharide is conjugated to the carrier protein (e.g., $CRM_{197}$) using carbodiimide (e.g., EDAC or EDC) chemistry via a carboxyl group on the protein carrier.

Other suitable techniques for conjugation use carbodiimides, hydrazides, active esters, norborane, p-nitrobenzoic acid, N-hydroxysuccinimide, S-NHS, EDC, TSTU. Conjugation may involve a carbonyl linker which may be formed by reaction of a free hydroxyl group of the saccharide with CDI followed by reaction with a protein to form a carbamate linkage. This may involve reduction of the anomeric terminus to a primary hydroxyl group, optional protection/deprotection of the primary hydroxyl group, reaction of the primary hydroxyl group with CDI to form a CDI carbamate intermediate and coupling the CDI carbamate intermediate with an amino group on a protein (CDI chemistry).

Molecular weight. In some embodiments, the glycoconjugate comprises a saccharide having a molecular weight of between 10 kDa and 2,000 kDa. In other embodiments, the saccharide has a molecular weight of between 50 kDa and 1,000 kDa. In other embodiments, the saccharide has a molecular weight of between 70 kDa and 900 kDa. In other embodiments, the saccharide has a molecular weight of between 100 kDa and 800 kDa. In other embodiments, the saccharide has a molecular weight of between 200 kDa and 600 kDa. In further embodiments, the saccharide has a molecular weight of 100 kDa to 1000 kDa; 100 kDa to 900 kDa; 100 kDa to 800 kDa; 100 kDa to 700 kDa; 100 kDa to 600 kDa; 100 kDa to 500 kDa; 100 kDa to 400 kDa; 100 kDa to 300 kDa; 150 kDa to 1,000 kDa; 150 kDa to 900 kDa; 150 kDa to 800 kDa; 150 kDa to 700 kDa; 150 kDa to 600 kDa; 150 kDa to 500 kDa; 150 kDa to 400 kDa; 150 kDa to 300 kDa; 200 kDa to 1,000 kDa; 200 kDa to 900 kDa; 200 kDa to 800 kDa; 200 kDa to 700 kDa; 200 kDa to 600 kDa; 200 kDa to 500 kDa; 200 kDa to 400 kDa; 200 kDa to 300; 250 kDa to 1,000 kDa; 250 kDa to 900 kDa; 250 kDa to 800 kDa; 250 kDa to 700 kDa; 250 kDa to 600 kDa; 250 kDa to 500 kDa; 250 kDa to 400 kDa; 250 kDa to 350 kDa; 300 kDa to 1,000 kDa; 300 kDa to 900 kDa; 300 kDa to 800 kDa; 300 kDa to 700 kDa; 300 kDa to 600 kDa; 300 kDa to 500 kDa; 300 kDa to 400 kDa; 400 kDa to 1,000 kDa; 400 kDa to 900 kDa; 400 kDa to 800 kDa; 400 kDa to 700 kDa; 400 kDa to 600 kDa; 500 kDa to 600 kDa. In one embodiment, the glycoconjugate having such a molecular weight is produced by single-end conjugation. In another embodiment, the glycoconjugate having such a molecular weight is produced by reductive amination chemistry (RAC) prepared in aqueous buffer. Any whole number integer within any of the above ranges is contemplated as an embodiment of the disclosure.

In some embodiments, the glycoconjugate of the invention has a molecular weight of between 400 kDa and 15,000 kDa; between 500 kDa and 10,000 kDa; between 2,000 kDa and 10,000 kDa; between 3,000 kDa and 8,000 kDa; or between 3,000 kDa and 5,000 kDa. In other embodiments, the glycoconjugate has a molecular weight of between 500 kDa and 10,000 kDa. In other embodiments, glycoconjugate has a molecular weight of between 1,000 kDa and 8,000 kDa. In still other embodiments, the glycoconjugate has a molecular weight of between 2,000 kDa and 8,000 kDa or between 3,000 kDa and 7,000 kDa. In further embodiments, the glycoconjugate of the invention has a molecular weight of between 200 kDa and 20,000 kDa; between 200 kDa and 15,000 kDa; between 200 kDa and 10,000 kDa; between 200 kDa and 7,500 kDa; between 200 kDa and 5,000 kDa; between 200 kDa and 3,000 kDa; between 200 kDa and 1,000 kDa; between 500 kDa and 20,000 kDa; between 500 kDa and 15,000 kDa; between 500 kDa and 12,500 kDa; between 500 kDa and 10,000 kDa; between 500 kDa and 7,500 kDa; between 500 kDa and 6,000 kDa; between 500 kDa and 5,000 kDa; between 500 kDa and 4,000 kDa; between 500 kDa and 3,000 kDa; between 500 kDa and 2,000 kDa; between 500 kDa and 1,500 kDa; between 500 kDa and 1,000 kDa; between 750 kDa and 20,000 kDa; between 750 kDa and 15,000 kDa; between 750 kDa and 12,500 kDa; between 750 kDa and 10,000 kDa; between 750 kDa and 7,500 kDa; between 750 kDa and 6,000 kDa; between 750 kDa and 5,000 kDa; between 750 kDa and 4,000 kDa; between 750 kDa and 3,000 kDa; between 750 kDa and 2,000 kDa; between 750 kDa and 1,500 kDa; between 1,000 kDa and 15,000 kDa; between 1,000 kDa and 12,500 kDa; between 1,000 kDa and 10,000 kDa; between 1,000 kDa and 7,500 kDa; between 1,000 kDa and 6,000 kDa; between 1,000 kDa and 5,000 kDa; between 1,000 kDa and 4,000 kDa; between 1,000 kDa and 2,500 kDa; between 2,000 kDa and 15,000 kDa; between 2,000 kDa and 12,500 kDa; between 2,000 kDa and 10,000 kDa; between 2,000 kDa and 7,500 kDa; between 2,000 kDa and 6,000 kDa; between 2,000 kDa and 5,000 kDa; between 2,000 kDa and 4,000 kDa; or between 2,000 kDa and 3,000 kDa. In one embodiment, the glycoconjugate having such a molecular weight is produced by eTEC conjugation described herein. In another embodiment, the glycoconjugate having such a molecular weight is produced by reductive amination chemistry (RAC). In another embodiment, the glycoconjugate having such a molecular weight is produced by reductive amination chemistry (RAC) prepared in DMSO.

In further embodiments, the glycoconjugate of the invention has a molecular weight of between 1,000 kDa and 20,000 kDa; between 1,000 kDa and 15,000 kDa; between 2,000 kDa and 10,000 kDa; between 2000 kDa and 7,500 kDa; between 2,000 kDa and 5,000 kDa; between 3,000 kDa and 20,000 kDa; between 3,000 kDa and 15,000 kDa; between 3,000 kDa and 12,500 kDa; between 4,000 kDa and 10,000 kDa; between 4,000 kDa and 7,500 kDa; between 4,000 kDa and 6,000 kDa; or between 5,000 kDa and 7,000 kDa. In one embodiment, the glycoconjugate having such a molecular weight is produced by reductive amination chemistry (RAC). In another embodiment, the glycoconjugate having such a molecular weight is produced by reductive amination chemistry (RAC) prepared in DMSO. In another embodiment, the glycoconjugate having such a molecular weight is produced by eTEC conjugation described herein.

In further embodiments, the glycoconjugate of the invention has a molecular weight of between 5,000 kDa and 20,000 kDa; between 5,000 kDa and 15,000 kDa; between 5,000 kDa and 10,000 kDa; between 5,000 kDa and 7,500 kDa; between 6,000 kDa and 20,000 kDa; between 6,000 kDa and 15,000 kDa; between 6,000 kDa and 12,500 kDa; between 6,000 kDa and 10,000 kDa or between 6,000 kDa and 7,500 kDa.

The molecular weight of the glycoconjugate may be measured by SEC-MALLS. Any whole number integer within any of the above ranges is contemplated as an embodiment of the disclosure. The glycoconjugates of the invention may also be characterized by the ratio (weight/weight) of saccharide to carrier protein. In some embodiments, the ratio of polysaccharide to carrier protein in the glycoconjugate (w/w) is between 0.5 and 3 (e.g., about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, or about 3.0). In other embodiments, the saccharide to carrier protein ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the saccharide to carrier protein ratio (w/w) is between 0.8 and 1.2. In a preferred embodiment, the ratio of polysaccharide to carrier protein in the conjugate is between 0.9 and 1.1. In some such embodiments, the carrier protein is $CRM_{197}$.

The glycoconjugates may also be characterized by their molecular size distribution ($K_d$). Size exclusion chromatography media (CL-4B) can be used to determine the relative molecular size distribution of the conjugate. Size Exclusion Chromatography (SEC) is used in gravity fed columns to profile the molecular size distribution of conjugates. Large molecules excluded from the pores in the media elute more quickly than small molecules. Fraction collectors are used to collect the column eluate. The fractions are tested colorimetrically by saccharide assay. For the determination of $K_d$, columns are calibrated to establish the fraction at which molecules are fully excluded ($V_0$), ($K_d$=0), and the fraction representing the maximum retention ($V_i$), ($K_d$=1). The fraction at which a specified sample attribute is reached ($V_e$), is related to Kd by the expression, $K_d=(V_e-V_o)/(V_i-V_o)$.

Free saccharide. The glycoconjugates and immunogenic compositions of the invention may include free saccharide that is not covalently conjugated to the carrier protein, but is nevertheless present in the glycoconjugate composition. The free saccharide may be non-covalently associated with (i.e., non-covalently bound to, adsorbed to, or entrapped in or with) the glycoconjugate. In a preferred embodiment, the glycoconjugate comprises at most 50%, 45%, 40%, 35%, 30%, 25%, 20% or 15% of free polysaccharide compared to the total amount of polysaccharide. In a preferred embodiment the glycoconjugate comprises less than about 25% of free polysaccharide compared to the total amount of polysaccharide. In a preferred embodiment the glycoconjugate comprises at most about 20% of free polysaccharide compared to the total amount of polysaccharide. In a preferred embodiment the glycoconjugate comprises at most about 15% of free polysaccharide compared to the total amount of polysaccharide. In another preferred embodiment, the glycoconjugate comprises at most about 20%, 19%, 18%, 17%, 16%, 15%, 14%, 13%, 12%, 11%, 10%, 9%, 8%, 7%, 6%, 5%, 4%, 3%, 2%, or 1% of free polysaccharide compared to the total amount of polysaccharide. In a preferred embodiment the glycoconjugate comprises less than about 8% of free polysaccharide compared to the total amount of polysaccharide. In a preferred embodiment the glycoconjugate comprises at most about 6% of free polysaccharide compared to the total amount of polysaccharide. In a preferred embodiment the glycoconjugate comprises at most about 5% of free polysaccharide compared to the total amount of polysaccharide. See, for example, Table 19, Table 20, Table 21, Table 22, Table 23, Table 24, and Table 26.

Covalent linkage. In other embodiments, the conjugate comprises at least one covalent linkage between the carrier protein and saccharide for every 5 to 10 saccharide repeat units; every 2 to 7 saccharide repeat units; every 3 to 8 saccharide repeat units; every 4 to 9 saccharide repeat units; every 6 to 1 1 saccharide repeat units; every 7 to 12 saccharide repeat units; every 8 to 13 saccharide repeat units; every 9 to 14 saccharide repeat units; every 10 to 15 saccharide repeat units; every 2 to 6 saccharide repeat units, every 3 to 7 saccharide repeat units; every 4 to 8 saccharide repeat units; every 6 to 10 saccharide repeat units; every 7 to 1 1 saccharide repeat units; every 8 to 12 saccharide repeat units; every 9 to 13 saccharide repeat units; every 10 to 14 saccharide repeat units; every 10 to 20 saccharide repeat units; every 4 to 25 saccharide repeat units or every 2 to 25 saccharide repeat units. In frequent embodiments, the carrier protein is $CRM_{197}$. In another embodiment, at least one linkage between carrier protein and saccharide occurs for every 2, 3, 4, 5, 6, 7, 8, 9, 10, 11, 12, 13, 14, 15, 16, 17, 18, 19, 20, 21, 22, 23, 24 or 25 saccharide repeat units of the polysaccharide. In one embodiment, the carrier protein is $CRM_{197}$. Any whole number integer within any of the above ranges is contemplated as an embodiment of the disclosure.

Lysine residues. Another way to characterize the glycoconjugates of the invention is by the number of lysine residues in the carrier protein (e.g., $CRM_{197}$) that become conjugated to the saccharide which can be characterized as a range of conjugated lysines (degree of conjugation). The evidence for lysine modification of the carrier protein, due to covalent linkages to the polysaccharides, can be obtained by amino acid analysis using routine methods known to those of skill in the art. Conjugation results in a reduction in the number of lysine residues recovered, compared to the carrier protein starting material used to generate the conjugate materials. In a preferred embodiment, the degree of conjugation of the glycoconjugate of the invention is between 2 and 15, between 2 and 13, between 2 and 10, between 2 and 8, between 2 and 6, between 2 and 5, between 2 and 4, between 3 and 15, between 3 and 13, between 3 and 10, between 3 and 8, between 3 and 6, between 3 and 5, between 3 and 4, between 5 and 15, between 5 and 10, between 8 and 15, between 8 and 12, between 10 and 15 or between 10 and 12. In one embodiment, the degree of conjugation of the glycoconjugate of the invention is about 2, about 3, about 4, about 5, about 6, about 7, about 8, about 9, about 10, about 1 1, about 12, about 13, about 14 or about 15. In a preferred embodiment, the degree of conjugation of the glycoconjugate of the invention is between 4 and 7. In some such embodiments, the carrier protein is $CRM_{197}$.

The frequency of attachment of the saccharide chain to a lysine on the carrier protein is another parameter for characterizing the glycoconjugates of the invention. For example, in some embodiments, at least one covalent linkage between the carrier protein and the polysaccharide for every 4 saccharide repeat units of the polysaccharide. In another embodiment, the covalent linkage between the carrier protein and the polysaccharide occurs at least once in every 10 saccharide repeat units of the polysaccharide. In another embodiment, the covalent linkage between the carrier protein and the polysaccharide occurs at least once in every 15 saccharide repeat units of the polysaccharide. In a further embodiment, the covalent linkage between the carrier protein and the polysaccharide occurs at least once in every 25 saccharide repeat units of the polysaccharide.

O-acetylation. In some embodiments, the saccharides of the invention are O-acetylated. In some embodiments, the glycoconjugate comprises a saccharide which has a degree of O-acetylation of between 10-100%, between 20-100%, between 30-100%, between 40-100%, between 50-100%, between 60-100%, between 70-100%, between 75-100%, 80-100%, 90-100%, 50-90%, 60-90%, 70-90% or 80-90%. In other embodiments, the degree of O-acetylation is ≥10%, ≥20%, ≥30%, ≥40%, ≥50%, ≥60%, ≥70%, ≥80%, or ≥90%, or about 100%. By % of O-acetylation it is meant the percentage of a given saccharide relative to 100% (where each repeat unit is fully acetylated relative to its acetylated structure).

In some embodiments, the glycoconjugate is prepared by reductive amination. In some embodiments, the glycoconjugate is a single-end-linked conjugated saccharide, wherein the saccharide is covalently bound to a carrier protein directly. In some embodiments, the glycoconjugate is covalently bound to a carrier protein through a (2-((2-oxoethyl) thio)ethyl) carbamate (eTEC) spacer.

REDUCTIVE AMINATION. In one embodiment, the saccharide is conjugated to the carrier protein by reductive amination (such as described in U.S. Patent Appl. Pub. Nos. 2006/0228380, 2007/0231340, 2007/0184071 and 2007/0184072, WO 2006/110381, WO 2008/079653, and WO 2008/143709).

Reductive amination includes (1) oxidation of the saccharide, (2) reduction of the activated saccharide and a carrier protein to form a conjugate. Before oxidation, the saccharide is optionally hydrolyzed. Mechanical or chemical hydrolysis may be employed. Chemical hydrolysis may be conducted using acetic acid.

The oxidation step may involve reaction with periodate. The term "periodate" as used herein refers to both periodate and periodic acid. The term also includes both metaperiodate ($IO_4^-$) and orthoperiodate ($IO_6^{5-}$) and the various salts of periodate (e.g., sodium periodate and potassium periodate).

In one embodiment the polysaccharide is oxidized in the presence of metaperiodate, preferably in the presence of sodium periodate ($NaIO_4$). In another embodiment the polysaccharide is oxidized in the presence of orthoperiodate, preferably in the presence of periodic acid.

In one embodiment, the oxidizing agent is a stable nitroxyl or nitroxide radical compound, such as piperidine-N-oxy or pyrrolidine-N-oxy compounds, in the presence of an oxidant to selectively oxidize primary hydroxyls. In said reaction, the actual oxidant is the N-oxoammonium salt, in a catalytic cycle. In an aspect, said stable nitroxyl or nitroxide radical compound are piperidine-N-oxy or pyrrolidine-N-oxy compounds. In an aspect, said stable nitroxyl or nitroxide radical compound bears a TEMPO (2,2,6,6-tetramethyl-1-piperidinyloxy) or a PROXYL (2,2,5,5-tetramethyl-1-pyrrolidinyloxy) moiety. In an aspect, said stable nitroxyl radical compound is TEMPO or a derivative thereof. In an aspect, said oxidant is a molecule bearing a N-halo moiety. In an aspect, said oxidant is selected from any one of N-ChloroSuccinimide, N-Bromosuccinimide, N-Iodosuccinimide, Dichloroisocyanuric acid, 1,3,5-trichloro-1,3,5-triazinane-2,4,6-trione, Dibromoisocyanuric acid, 1,3,5-tribromo-1,3,5-triazinane-2,4,6-trione, Diiodoisocyanuric acid and 1,3,5-triiodo-1,3,5-triazinane-2,4,6-trione. Preferably said oxidant is N-Chlorosuccinimide.

Following the oxidation step of the saccharide, the saccharide is said to be activated and is referred to as "activated" herein below. The activated saccharide and the carrier protein may be lyophilised (freeze-dried), either independently (discrete lyophilization) or together (co-lyophilized). In one embodiment the activated saccharide and the carrier protein are co-lyophilized. In another embodiment the activated polysaccharide and the carrier protein are lyophilized independently.

In one embodiment the lyophilization takes place in the presence of a non-reducing sugar, possible non-reducing sugars include sucrose, trehalose, raffinose, stachyose, melezitose, dextran, mannitol, lactitol and palatinit.

The next step of the conjugation process is the reduction of the activated saccharide and a carrier protein to form a conjugate (so-called reductive amination), using a reducing agent. Suitable reducing agents include the cyanoborohydrides, such as sodium cyanoborohydride, sodium triacetoxyborohydride or sodium or zinc borohydride in the presence of Bronsted or Lewis acids), amine boranes such as pyridine borane, 2-Picoline Borane, 2,6-diborane-methanol, dimethylamine-borane, t-BuMe'PrN-BH3, benzylamine-BH3 or 5-ethyl-2-methylpyridine borane (PEMB), borane-pyridine, or borohydride exchange resin. In one embodiment the reducing agent is sodium cyanoborohydride.

In an embodiment, the reduction reaction is carried out in aqueous solvent (e.g., selected from PBS, MES, HEPES, Bis-tris, ADA, PIPES, MOPSO, BES, MOPS, DIPSO, MOBS, HEPPSO, POPSO, TEA, EPPS, Bicine or HEPB, at a pH between 6.0 and 8.5, 7.0 and 8.0, or 7.0 and 7.5), in another embodiment the reaction is carried out in aprotic solvent. In an embodiment, the reduction reaction is carried out in DMSO (dimethylsulfoxide) or in DMF (dimethylformamide) solvent. The DMSO or DMF solvent may be used to reconstitute the activated polysaccharide and carrier protein which has been lyophilized.

At the end of the reduction reaction, there may be unreacted aldehyde groups remaining in the conjugates, these may be capped using a suitable capping agent. In one embodiment this capping agent is sodium borohydride ($NaBH_4$). Following the conjugation (the reduction reaction and optionally the capping), the glycoconjugates may be purified (enriched with respect to the amount of polysaccharide-protein conjugate) by a variety of techniques known to the skilled person. These techniques include dialysis, concentration/diafiltration operations, tangential flow filtration precipitation/elution, column chromatography (DEAE or hydrophobic interaction chromatography), and depth filtration. The glycoconjugates maybe purified by diafiltration and/or ion exchange chromatography and/or size exclusion chromatography. In an embodiment, the glycoconjugates are purified by diafiltration or ion exchange chromatography or size exclusion chromatography. In one embodiment the glycoconjugates are sterile filtered.

In a preferred embodiment, a glycoconjugate from an *E. coli* serotype is selected from any one of O25B, O1, O2, and O6 is prepared by reductive amination. In a preferred embodiment, the glycoconjugates from *E. coli* serotypes O25B, O1, O2, and O6 are prepared by reductive amination.

In one aspect, the invention relates to a conjugate that includes a carrier protein, e.g., $CRM_{197}$, linked to a saccharide of Formula O25B, presented by

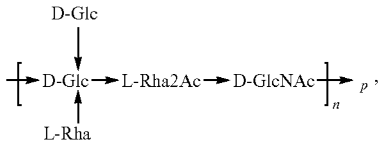

wherein n is any integer greater than or equal to 1. In a preferred embodiment, n is an integer of at least 31, 32, 33, 34, 35, 36, 37, 38, 39, 40, and at most 200, 100, 99, 98, 97, 96, 95, 94, 93, 92, 91, 90, 89, 88, 87, 86, 81, 80, 79, 78, 77, 76, 75, 74, 73, 72, 71, 70, 69, 68, 67, 66, 65, 60, 59, 58, 57, 56, 55, 54, 53, 52, 51, or 50. Any minimum value and any maximum value may be combined to define a range. Exemplary ranges include, for example, at least 1 to at most 1000; at least 10 to at most 500; and at least 20 to at most 80. In one preferred embodiment, n is at least 31 to at most 90, more preferably 40 to 90, most preferably 60 to 85.

In another aspect, the invention relates to a conjugate that includes a carrier protein, e.g., $CRM_{197}$, linked to a saccharide having any one of the following structures shown in Table 1 (see also FIG. 9A-9C and FIG. 10A-10B), wherein n is an integer greater than or equal to 1.

Without being bound by theory or mechanism, in some embodiments, a stable conjugate is believed to require a level of saccharide antigen modification that is balanced against preserving the structural integrity of the critical immunogenic epitopes of the antigen.

Activation and formation of an Aldehyde. In some embodiments, the saccharide of the invention is activated and results in the formation of an aldehyde. In such embodiments wherein the saccharide is activated, the percentage (%) of activation (or degree of oxidation (DO)) (see, e.g., Example 31) refers to moles of a saccharide repeat unit per moles of aldehyde of the activated polysaccharide. For example, in some embodiments, the saccharide is activated by periodate oxidation of vicinal diols on a repeat unit of the polysaccharide, resulting in the formation of an aldehyde. Varying the molar equivalents (meq) of sodium periodate relative to the saccharide repeat unit and temperature during oxidation results in varying levels of degree of oxidation (DO).

The saccharide and aldehyde concentrations are typically determined by colorimetric assays. An alternative reagent is TEMPO (2,2,6,6-tetramethylpiperidine 1-oxyl radical)-N-chlorosuccinimide (NCS) combination, which results in the formation of aldehydes from primary alcohol groups.

In some embodiments, the activated saccharide has a degree of oxidation wherein the moles of a saccharide repeat unit per moles of aldehyde of the activated saccharide is between 1-100, such as, for example, between 2-80, between 2-50, between 3-30, and between 4-25. The degree of activation is at least 1, 2, 3, 4, 5, 6, 7, 8, 9, 10, 11, 12, 13, 14, 15, 16, 17, 18, 19, ≥20, ≥30, ≥40, ≥50, ≥60, ≥70, ≥80, or ≥ 90, or about 100. Preferably, the degree of oxidation (DO) is at least 5 and at most 50, more preferably at least 10 and at most 25. In one embodiment, the degree of activation is at least 10 and at most 25. Any minimum value and any maximum value may be combined to define a range. A degree of oxidation value may be represented as percentage (%) of activation. For example, in one embodiment, a DO value of 10 refers to one activated saccharide repeat unit out of a total of 10 saccharide repeat units in the activated saccharide, in which case the DO value of 10 may be represented as 10% activation.

In some embodiments, the conjugate prepared by reductive amination chemistry includes a carrier protein and a saccharide, wherein the saccharide includes a structure selected from any one of Formula O1 (e.g., Formula O1A, Formula O1B, and Formula O1C), Formula O2, Formula O3, Formula O4 (e.g., Formula O4: K52 and Formula O4: K6), Formula O5 (e.g., Formula O5ab and Formula O5ac (strain 180/C3)), Formula O6 (e.g., Formula O6: K2; K13; K15 and Formula O6: K54), Formula O7, Formula O8, Formula O9, Formula O10, Formula O11, Formula O12, Formula O13, Formula O14, Formula O15, Formula O16, Formula O17, Formula O18 (e.g., Formula O18A, Formula O18ac, Formula O18A1, Formula O18B, and Formula O18B1), Formula O19, Formula O20, Formula O21, Formula O22, Formula O23 (e.g., Formula O23A), Formula O24, Formula O25 (e.g., Formula O25a and Formula O25b), Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45 (e.g., Formula O45 and Formula O45rel), Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula $62D_1$, Formula O63, Formula O64, Formula O65, Formula O66, Formula O68, Formula O69, Formula O70, Formula O71, Formula O73 (e.g., Formula O73 (strain 73-1)), Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144, Formula O145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, and Formula O187. In some embodiments, the saccharide in the conjugate includes a Formula, wherein n is an integer from 1 to 1000, from 5 to 1000, preferably 31 to 100, more preferably 35 to 90, most preferably 35 to 65.

SINGLE-END LINKED CONJUGATES. In some embodiments, the conjugate is single-end-linked conjugated saccharide, wherein the saccharide is covalently bound at one end of the saccharide to a carrier protein. In some embodiments, the single-end-linked conjugated polysaccharide has a terminal saccharide. For example, a conjugate is single-end linked if one of the ends (a terminal saccharide residue) of the polysaccharide is covalently bound to a carrier protein. In some embodiments, the conjugate is single-end linked if a terminal saccharide residue of the polysaccharide is covalently bound to a carrier protein through a linker. Such linkers may include, for example, a cystamine linker (A1), a 3,3'-dithio bis (propanoic dihydrazide) linker (A4), and a 2,2'-dithio-N,N'-bis (ethane-2,1-diyl) bis(2-(aminooxy) acetamide) linker (A6).

In some embodiments, the saccharide is conjugated to the carrier protein through a 3-deoxy-d-manno-oct-2-ulosonic acid (KDO) residue to form a single-end linked conjugate. See, for example, Example 26, Example 27, Example 28, and FIG. 17.

In some embodiments, the conjugate is preferably not a bioconjugate. The term "bioconjugate" refers to a conjugate between a protein (e.g., a carrier protein) and an antigen, e.g., an O antigen (e.g., O25B) prepared in a host cell background, wherein host cell machinery links the antigen to the protein (e.g., N-links). Glycoconjugates include bioconjugates, as well as sugar antigen (e.g., oligo- and polysaccharides)-protein conjugates prepared by means that do not require preparation of the conjugate in a host cell, e.g., conjugation by chemical linkage of the protein and saccharide.

Thiol Activated Saccharides. In some embodiments, the saccharide of the invention is thiol activated. In such embodiments wherein the saccharide is thiol activated, the percentage (%) of activation refers to moles of thiol per saccharide repeat unit of the activated polysaccharide. The saccharide and thiol concentrations are typically determined by Ellman's assay for quantitation of sulfhydryls. For example, in some embodiments, the saccharide includes activation of 2-Keto-3-deoxyoctanoic acid (KDO) with a disulfide amine linker. See, for example, Example 10 and FIG. 31. In some embodiments, the saccharide is covalently bound to a carrier protein through a bivalent, heterobifunctional linker (also referred to herein as a "spacer"). The linker preferably provides a thioether bond between the saccharide and the carrier protein, resulting in a glycoconjugate referred to herein as a "thioether glycoconjugate." In some embodiments, the linker further provides carbamate and amide bonds, such as, for example, (2-((2-oxoethyl) thio)ethyl) carbamate (eTEC). See, for example, Example 21.

In some embodiments, the single-end linked conjugate includes a carrier protein and a saccharide, wherein the saccharide includes a structure selected from any one of Formula O1 (e.g., Formula O1A, Formula O1B, and Formula O1C), Formula O2, Formula O3, Formula O4 (e.g., Formula O4: K52 and Formula O4: K6), Formula O5 (e.g., Formula O5ab and Formula O5ac (strain 180/C3)), Formula O6 (e.g., Formula O6: K2; K13; K15 and Formula O6: K54), Formula O7, Formula O8, Formula O9, Formula O10, Formula O11, Formula O12, Formula O13, Formula O14, Formula O15, Formula O16, Formula O17, Formula O18 (e.g., Formula O18A, Formula O18ac, Formula O18A1, Formula O18B, and Formula O18B1), Formula O19, Formula O20, Formula O21, Formula O22, Formula O23 (e.g., Formula O23A), Formula O24, Formula O25 (e.g., Formula O25a and Formula O25b), Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45 (e.g., Formula O45 and Formula O45rel), Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula $62D_1$, Formula O63, Formula O64, Formula O65, Formula O66, Formula O68, Formula O69, Formula O70, Formula O71, Formula O73 (e.g., Formula O73 (strain 73-1)), Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144, Formula O145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, and Formula O187. In some embodiments, the saccharide in the conjugate includes a Formula, wherein n is an integer from 1 to 1000, from 5 to 1000, preferably 31 to 100, more preferably 35 to 90, most preferably 35 to 65.

For example, in one embodiment, the single-end linked conjugate includes a carrier protein and a saccharide having a structure selected from Formula O8, Formula O9a, Formula O9, Formula O20ab, Formula O20ac, Formula O52, Formula O97, and Formula O101, wherein n is an integer from 1 to 10.

F. eTEC Conjugates

In one aspect, the invention relates generally to glycoconjugates comprising a saccharide derived from *E. coli* described above covalently conjugated to a carrier protein through a (2-((2-oxoethyl)thio)ethyl) carbamate (eTEC) spacer (as described, for example, in U.S. Pat. No. 9,517,274 and International Patent Application Publication WO2014027302, incorporated by reference herein in their entireties), including immunogenic compositions comprising such glycoconjugates, and methods for the preparation and use of such glycoconjugates and immunogenic compositions. Said glycoconjugates comprise a saccharide covalently conjugated to a carrier protein through one or more eTEC spacers, wherein the saccharide is covalently conjugated to the eTEC spacer through a carbamate linkage, and wherein the carrier protein is covalently conjugated to the eTEC spacer through an amide linkage. The eTEC spacer includes seven linear atoms (i.e., $—C(O)NH(CH_2)_2SCH_2C(O)—$) and provides stable thioether and amide bonds between the saccharide and carrier protein.

The eTEC linked glycoconjugates of the invention may be represented by the general formula (I):

(I)

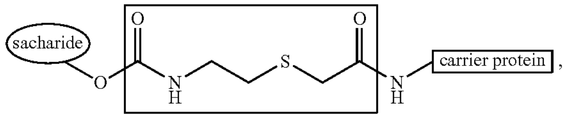

where the atoms that comprise the eTEC spacer are contained in the central box.

In said glycoconjugates of the invention, the saccharide may be a polysaccharide or an oligosaccharide.

The carrier proteins incorporated into the glycoconjugates of the invention are selected from the group of carrier proteins generally suitable for such purposes, as further described herein or known to those of skill in the art. In particular embodiments, the carrier protein is $CRM_{197}$.

In another aspect, the invention provides a method of making a glycoconjugate comprising a saccharide described herein conjugated to a carrier protein through an eTEC spacer, comprising the steps of a) reacting a saccharide with a carbonic acid derivative in an organic solvent to produce an activated saccharide; b) reacting the activated saccharide with cystamine or cysteamine or a salt thereof, to produce a thiolated saccharide; c) reacting the thiolated saccharide with a reducing agent to produce an activated thiolated saccharide comprising one or more free sulfhydryl residues; d) reacting the activated thiolated saccharide with an activated carrier protein comprising one or more a-haloacetamide groups, to produce a thiolated saccharide-carrier protein conjugate; and e) reacting the thiolated saccharide-carrier protein conjugate with (i) a first capping reagent capable of capping unconjugated a-haloacetamide groups of the activated carrier protein; and/or (ii) a second capping reagent capable of capping unconjugated free sulfhydryl residues of the activated thiolated saccharide; whereby an eTEC linked glycoconjugate is produced.

In frequent embodiments, the carbonic acid derivative is 1,1'-carbonyl-di-(1,2,4-triazole) (CDT) or 1,1'-carbonyl-diimidazole (CDI). Preferably, the carbonic acid derivative is CDT and the organic solvent is a polar aprotic solvent, such as dimethylsulfoxide (DMSO). In preferred embodiments, the thiolated saccharide is produced by reaction of the activated saccharide with the bifunctional symmetric thioalkylamine reagent, cystamine or a salt thereof. Alternatively, the thiolated saccharide may be formed by reaction of the activated saccharide with cysteamine or a salt thereof. The eTEC linked glycoconjugates produced by the methods of the invention may be represented by general Formula (I).

In frequent embodiments, the first capping reagent is N-acetyl-L-cysteine, which reacts with unconjugated a-haloacetamide groups on lysine residues of the carrier protein to form an S-carboxymethylcysteine (CMC) residue covalently linked to the activated lysine residue through a thioether linkage.

In other embodiments, the second capping reagent is iodoacetamide (IAA), which reacts with unconjugated free sulfhydryl groups of the activated thiolated saccharide to provide a capped thioacetamide. Frequently, step e) comprises capping with both a first capping reagent and a second capping reagent. In certain embodiments, step e) comprises capping with N-acetyl-L-cysteine as the first capping reagent and IAA as the second capping reagent.

In some embodiments, the capping step e) further comprises reaction with a reducing agent, for example, DTT, TCEP, or mercaptoethanol, after reaction with the first and/or second capping reagent.

The eTEC linked glycoconjugates and immunogenic compositions of the invention may include free sulfhydryl residues. In some instances, the activated thiolated saccharides formed by the methods provided herein will include multiple free sulfhydryl residues, some of which may not undergo covalent conjugation to the carrier protein during the conjugation step. Such residual free sulfhydryl residues are capped by reaction with a athiol-reactive capping reagent, for example, iodoacetamide (IAA), to cap the potentially reactive functionality. Other thiol-reactive capping reagents, e.g., maleimide containing reagents and the like are also contemplated.

In addition, the eTEC linked glycoconjugates and immunogenic compositions of the invention may include residual unconjugated carrier protein, which may include activated carrier protein which has undergone modification during the capping process steps.

In some embodiments, step d) further comprises providing an activated carrier protein comprising one or more a-haloacetamide groups prior to reacting the activated thiolated saccharide with the activated carrier protein. In frequent embodiments, the activated carrier protein comprises one or more a-bromoacetamide groups.

In another aspect, the invention provides an eTEC linked glycoconjugate comprising a saccharide described herein conjugated to a carrier protein through an eTEC spacer produced according to any of the methods disclosed herein.

In some embodiments, the carrier protein is $CRM_{197}$ and the covalent linkage via an eTEC spacer between the $CRM_{197}$ and the polysaccharide occurs at least once in every 4, 10, 15 or 25 saccharide repeat units of the polysaccharide.

For each of the aspects of the invention, in particular embodiments of the methods and compositions described herein, the eTEC linked glycoconjugate comprises a saccharide described herein, such as, a saccharide derived from *E. coli.*

In another aspect, the invention provides a method of preventing, treating or ameliorating a bacterial infection, disease or condition in a subject, comprising administering to the subject an immunologically effective amount of an immunogenic composition of the invention, wherein said immunogenic composition comprises an eTEC linked glycoconjugate comprising a saccharide described herein. In some embodiments, the saccharide is derived from *E. coli.*

In some embodiments, the eTEC linked glycoconjugate comprises a carrier protein and a saccharide, in which said saccharide comprises a structure selected from any one of Formula O1 (e.g., Formula O1A, Formula O1B, and Formula O1C), Formula O2, Formula O3, Formula O4 (e.g., Formula O4: K52 and Formula O4: K6), Formula O5 (e.g., Formula O5ab and Formula O5ac (strain 180/C3)), Formula O6 (e.g., Formula 06: K2; K13; K15 and Formula O6: K54), Formula O7, Formula O8, Formula O9, Formula O10, Formula O11, Formula O12, Formula O13, Formula O14, Formula O15, Formula O16, Formula O17, Formula O18 (e.g., Formula O18A, Formula O18ac, Formula O18A1, Formula O18B, and Formula O18B1), Formula O19, Formula O20, Formula O21, Formula O22, Formula O23 (e.g., Formula O23A), Formula O24, Formula O25 (e.g., Formula O25a and Formula O25b), Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45 (e.g., Formula O45 and Formula O45rel), Formula O46, Formula O48, Formula O49, Formula O50, Formula O51, Formula O52, Formula O53, Formula O54, Formula O55, Formula O56, Formula O57, Formula O58, Formula 059, Formula O60, Formula O61, Formula O62, Formula $62D_1$, Formula O63, Formula O64, Formula O65, Formula O66, Formula O68, Formula O69, Formula O70, Formula O71, Formula O73 (e.g., Formula O73 (strain 73-1)), Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144, Formula O145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, and Formula O187. In some embodiments, the saccharide in the conjugate includes a Formula, wherein n is an integer from 1 to 1000, from 5 to 1000, preferably 31 to 100, more preferably 35 to 90, most preferably 35 to 65.

The number of lysine residues in the carrier protein that become conjugated to the saccharide can be characterized as a range of conjugated lysines. For example, in some embodiments of the immunogenic compositions, the CRM 197 may comprise 4 to 16 lysine residues out of 39 covalently linked to the saccharide. Another way to express this parameter is that about 10% to about 41% of $CRM_{197}$ lysines are covalently linked to the saccharide. In other embodiments, the $CRM_{197}$ may comprise 2 to 20 lysine residues out of 39 covalently linked to the saccharide. Another way to express this parameter is that about 5% to about 50% of $CRM_{197}$ lysines are covalently linked to the saccharide.

In frequent embodiments, the carrier protein is $CRM_{197}$ and the covalent linkage via an eTEC spacer between the CRM 197 and the polysaccharide occurs at least once in every 4, 10, 15 or 25 saccharide repeat units of the polysaccharide.

In other embodiments, the conjugate comprises at least one covalent linkage between the carrier protein and saccharide for every 5 to 10 saccharide repeat units; every 2 to 7 saccharide repeat units; every 3 to 8 saccharide repeat units; every 4 to 9 saccharide repeat units; every 6 to 11 saccharide repeat units; every 7 to 12 saccharide repeat units; every 8 to 13 saccharide repeat units; every 9 to 14 saccharide repeat units; every 10 to 15 saccharide repeat units; every 2 to 6 saccharide repeat units, every 3 to 7 saccharide repeat units; every 4 to 8 saccharide repeat units; every 6 to 10 saccharide repeat units; every 7 to 11 saccharide repeat units; every 8 to 12 saccharide repeat units; every 9 to 13 saccharide repeat units; every 10 to 14 saccharide repeat units; every 10 to 20 saccharide repeat units; or every 4 to 25 saccharide repeat units.

In another embodiment, at least one linkage between carrier protein and saccharide occurs for every 2, 3, 4, 5, 6, 7, 8, 9, 10, 11, 12, 13, 14, 15, 16, 17, 18, 19, 20, 21, 22, 23, 24 or 25 saccharide repeat units of the polysaccharide.

G. Carrier Proteins

A component of the glycoconjugate of the invention is a carrier protein to which the saccharide is conjugated. The terms "protein carrier" or "carrier protein" or "carrier" may be used interchangeably herein. Carrier proteins should be amendable to standard conjugation procedures.

One component of the conjugate is a carrier protein to which the O-polysaccharide is conjugated. In one embodiment, the conjugate includes a carrier protein conjugated to the core oligosaccharide of the O-polysaccharide (see FIG. 24). In one embodiment, the conjugate includes a carrier protein conjugated to the O-antigen of the O-polysaccharide.

The terms "protein carrier" or "carrier protein" or "carrier" may be used interchangeably herein. Carrier proteins should be amendable to standard conjugation procedures.

In a preferred embodiment, the carrier protein of the conjugates is independently selected from any one of TT, DT, DT mutants (such as $CRM_{197}$), *H. influenzae* protein D, PhtX, PhtD, PhtDE fusions (particularly those described in WO 01/98334 and WO 03/54007), detoxified pneumolysin, PorB, N19 protein, PspA, OMPC, toxin A or B of C. *Difficile* and PsaA. In an embodiment, the carrier protein of the conjugates of the invention is DT (Diphtheria toxoid). In another embodiment, the carrier protein of the conjugates of the invention is TT (tetanus toxoid). In another embodiment, the carrier protein of the conjugates of the invention is PD (*Haemophilus influenzae* protein D-see, e.g., EP 0 594 610 B). In some embodiments, the carrier protein includes poly (L-lysine) (PLL). In a further embodiment, the carrier protein of the conjugates of the invention is SCP (Streptococcal C5a peptidase) (Brown, C. K. et al., 2005, PNAS 102 (51): 18391-18396).

In a preferred embodiment, the saccharides are conjugated to $CRM_{197}$ protein. The $CRM_{197}$ protein is a nontoxic form of diphtheria toxin but is immunologically indistinguishable from the diphtheria toxin. $CRM_{197}$ is produced by *C. diphtheriae* infected by the nontoxigenic phage β197tox created by nitrosoguanidine mutagenesis of the toxigenic corynephage beta. The $CRM_{197}$ protein has the same molecular weight as the diphtheria toxin but differs therefrom by a single base change (guanine to adenine) in the structural gene. This single base change causes an amino acid substitution glutamic acid for glycine) in the mature protein and eliminates the toxic properties of diphtheria toxin. The $CRM_{197}$ protein is a safe and effective T-cell dependent carrier for saccharides.

Accordingly, in some embodiments, the conjugates of the invention include CRM 197 as the carrier protein, wherein the saccharide is covalently linked to $CRM_{197}$.

In a preferred embodiment, the carrier protein of the glycoconjugates is selected in the group consisting of DT (Diphtheria toxin), TT (tetanus toxoid) or fragment C of TT, $CRM_{197}$ (a nontoxic but antigenically identical variant of diphtheria toxin), other DT mutants (such as CRM176, CRM228, CRM 45 (Uchida et al J. Biol. Chem. 218; 3838-3844, 1973), CRM9, CRM45, CRM102, CRM103 or CRM107; and other mutations described by Nicholls and Youle in Genetically Engineered Toxins, Ed: Frankel, Marcel Dekker Inc, 1992; deletion or mutation of Glu-148 to Asp, Gln or Ser and/or Ala 158 to Gly and other mutations disclosed in U.S. Pat. No. 4,709,017 or U.S. Pat. No. 4,950,740; mutation of at least one or more residues Lys 516, Lys 526, Phe 530 and/or Lys 534 and other mutations disclosed in U.S. Pat. No. 5,917,017 or U.S. Pat. No. 6,455,673; or fragment disclosed in U.S. Pat. No. 5,843, 711), pneumococcal pneumolysin (Kuo et al (1995) Infect Immun 63; 2706-13) including ply detoxified in some fashion for example dPLY-GMBS (WO 04081515, PCT/EP2005/010258) or dPLY-formol, PhtX, including PhtA, PhtB, PhtD, PhtE (sequences of PhtA, PhtB, PhtD or PhtE are disclosed in WO 00/37105 or WO 00/39299) and fusions of Pht proteins for example PhtDE fusions, PhtBE fusions, Pht A-E (WO O1/98334, WO 03/54007, WO2009/000826), OMPC (meningococcal outer membrane protein-usually extracted from *N. meningitidis* serogroup B-EP0372501), PorB (from *N. meningitidis*), PD (*Haemophilus influenzae* protein D-see, e.g., EP 0 594 610 B), or immunologically functional equivalents thereof, synthetic peptides (EP0378881, EP0427347), heat shock proteins (WO 93/17712, WO 94/03208), pertussis proteins (WO 98/58668, EP0471 177), cytokines, lymphokines, growth factors or hormones (WO 91/01146), artificial proteins comprising multiple human CD4+ T cell epitopes from various pathogen derived antigens (Falugi et al (2001) Eur J Immunol 31; 3816-3824) such as N19 protein (Baraldoi et al (2004) Infect Immun 72; 4884-7) pneumococcal surface protein PspA (WO 02/091998), iron uptake proteins (WO O1/72337), toxin A or B of *C. difficile* (WO 00/61761), transferrin binding proteins, pneumococcal adhesion protein (PsaA), recombinant *Pseudomonas aeruginosa* exotoxin A (in particular non-toxic mutants thereof (such as exotoxin A bearing a substitution at glutamic acid 553 (Uchida Cameron D M, R J Collier. 1987. J. Bacteriol. 169:4967-4971)). Other proteins, such as ovalbumin, keyhole limpet hemocyanin (KLH), bovine serum albumin (BSA) or purified protein derivative of tuberculin (PPD) also can be used as carrier proteins. Other suitable carrier proteins include inactivated bacterial toxins such as cholera toxoid (e.g., as described in Int'l Patent Application No. WO 2004/083251), *E. coli* LT, *E. coli* ST, and exotoxin A from *Pseudomonas aeruginosa*.

In some embodiments, the carrier protein is selected from any one of, for example, $CRM_{197}$, diphtheria toxin fragment B (DTFB), DTFB C8, Diphtheria toxoid (DT), tetanus toxoid (TT), fragment C of TT, pertussis toxoid, cholera toxoid, or exotoxin A from *Pseudomonas aeruginosa*; detoxified Exotoxin A of *P. aeruginosa* (EPA), maltose binding protein (MBP), flagellin, detoxified hemolysin A of *S. aureus*, clumping factor A, clumping factor B, Cholera toxin B subunit (CTB), *Streptococcus pneumoniae* Pneumolysin and detoxified variants thereof, *C. jejuni* AcrA, and *C. jejuni* natural glycoproteins. In one embodiment, the carrier protein is detoxified *Pseudomonas* exotoxin (EPA). In another embodiment, the carrier protein is not detoxified *Pseudomonas* exotoxin (EPA). In one embodiment, the carrier protein is flagellin. In another embodiment, the carrier protein is not flagellin.

In a preferred embodiment, the carrier protein of the glycoconjugates is independently selected from the group consisting of TT, DT, DT mutants (such as $CRM_{197}$), *H. influenzae* protein D, PhtX, PhtD, PhtDE fusions (particularly those described in WO O1/98334 and WO 03/54007), detoxified pneumolysin, PorB, N19 protein, PspA, OMPC, toxin A or B of C. *Difficile* and PsaA. In an embodiment, the carrier protein of the glycoconjugates of the invention is DT (Diphtheria toxoid). In another embodiment, the carrier protein of the glycoconjugates of the invention is TT (tetanus toxoid). In another embodiment, the carrier protein of the glycoconjugates of the invention is PD (*Haemophilus influenzae* protein D-see, e.g., EP 0 594 610 B).

In a preferred embodiment, the capsular saccharides of the invention are conjugated to $CRM_{197}$ protein. The $CRM_{197}$ protein is a nontoxic form of diphtheria toxin but is immunologically indistinguishable from the diphtheria toxin. $CRM_{197}$ is produced by *C. diphtheriae* infected by the nontoxigenic phage β197tox-created by nitrosoguanidine mutagenesis of the toxigenic corynephage beta (Uchida, T. et al. 1971, Nature New Biology 233:8-11). The CRM 197 protein has the same molecular weight as the diphtheria toxin but differs therefrom by a single base change (guanine to adenine) in the structural gene. This single base change causes an amino acid substitution glutamic acid for glycine) in the mature protein and eliminates the toxic properties of diphtheria toxin. The $CRM_{197}$ protein is a safe and effective T-cell dependent carrier for saccharides. Further details about $CRM_{197}$ and production thereof can be found e.g. in U.S. Pat. No. 5,614,382

Accordingly, in frequent embodiments, the glycoconjugates of the invention comprise $CRM_{197}$ as the carrier protein, wherein the capsular polysaccharide is covalently linked to $CRM_{197}$.

H. Dosages of the Compositions

Dosage regimens may be adjusted to provide the optimum desired response. For example, a single dose of the polypeptide derived from *E. coli* or fragment thereof may be administered, several divided doses may be administered over time, or the dose may be proportionally reduced or increased as indicated by the exigencies of the situation. It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. Determining appropriate dosages and regiments for administration of the therapeutic protein are well-known in the relevant art and would be understood to be encompassed by the skilled artisan once provided the teachings disclosed herein.

In some embodiments, the amount of the polypeptide derived from *E. coli* or fragment thereof in the composition, may range from about 10 μg to about 300 μg of each protein antigen. In some embodiments, the amount of the polypeptide derived from *E. coli* or fragment thereof in the composition may range from about 20 μg to about 200 μg of each protein antigen.

The amount of glycoconjugate(s) in each dose is selected as an amount which induces an immunoprotective response without significant, adverse side effects in typical vaccines. Such amount will vary depending upon which specific immunogen is employed and how it is presented.

The amount of a particular glycoconjugate in an immunogenic composition can be calculated based on total polysaccharide for that conjugate (conjugated and non-conjugated). For example, a glycoconjugate with 20% free polysaccharide will have about 80 g of conjugated polysaccharide and about 20 g of non-conjugated polysaccharide in a 100 g polysaccharide dose. The amount of glycoconjugate can vary depending upon the *E. coli* serotype. The saccharide concentration can be determined by the uronic acid assay.

The "immunogenic amount" of the different polysaccharide components in the immunogenic composition, may diverge and each may comprise about 1.0 g, about 2.0 g, about 3.0 g, about 4.0 g, about 5.0 g, about 6.0 g, about 7.0 g, about 8.0 g, about 9.0 g, about 10.0 g, about 15.0 g, about 20.0 g, about 30.0 g, about 40.0 pg, about 50.0 pg, about 60.0 pg, about 70.0 pg, about 80.0 pg, about 90.0 pg, or about 100.0 g of any particular polysaccharide antigen. Generally, each dose will comprise 0.1 g to 100 g of polysaccharide for a given serotype, particularly 0.5 g to 20 g, more particularly 1 g to 10 g, and even more particularly 2 g to 5 g. Any whole number integer within any of the above ranges is contemplated as an embodiment of the disclosure. In one embodiment, each dose will comprise 1 g, 2 g, 3 g, 4 g, 5 g, 6 g, 7 g, 8 g, 9 g, 10 g, 15 g or 20 g of polysaccharide for a given serotype.

Carrier protein amount. Generally, each dose will comprise 5 g to 150 g of carrier protein, particularly 10 g to 100 g of carrier protein, more particularly 15 g to 100 g of carrier protein, more particularly 25 to 75 g of carrier protein, more particularly 30 g to 70 g of carrier protein, more particularly 30 to 60 g of carrier protein, more particularly 30 g to 50 g of carrier protein and even more particularly 40 to 60 g of carrier protein. In one embodiment, said carrier protein is $CRM_{197}$. In one embodiment, each dose will comprise about 25 g, about 26 g, about 27 g, about 28 g, about 29 g, about 30 g, about 31 g, about 32 g, about 33 g, about 34 g, about 35 g, about 36 g, about 37 g, about 38 g, about 39 g, about 40 g, about 41 g, about 42 g, about 43 g, about 44 g, about 45 g, about 46 g, about 47 g, about 48 g, about 49 g, about 50 g, about 51 g, about 52 g, about 53 g, about 54 g, about 55 g, about 56 g, about 57 g, about 58 g, about 59 g, about 60 g, about 61 g, about 62 g, about 63 g, about 64 g, about 65 g, about 66 g, about 67 g, 68 g, about 69 g, about 70 g, about 71 g, about 72 g, about 73 g, about 74 g or about 75 g of carrier protein. In one embodiment, said carrier protein is $CRM_{197}$.

I. Adjuvant

In some embodiments, the immunogenic compositions disclosed herein may further comprise at least one, two or three adjuvants. The term "adjuvant" refers to a compound or mixture that enhances the immune response to an antigen. Antigens may act primarily as a delivery system, primarily as an immune modulator or have strong features of both. Suitable adjuvants include those suitable for use in mammals, including humans.

Examples of known suitable delivery-system type adjuvants that can be used in humans include, but are not limited to, alum (e.g., aluminum phosphate, aluminum sulfate or aluminum hydroxide), calcium phosphate, liposomes, oil-in-water emulsions such as MF59 (4.3% w/v squalene, 0.5% w/v polysorbate 80 (Tween 80), 0.5% w/v sorbitan trioleate (Span 85)), water-in-oil emulsions such as Montanide, and poly (D,L-lactide-co-glycolide) (PLG) microparticles or nanoparticles.

In an embodiment, the immunogenic compositions disclosed herein comprise aluminum salts (alum) as adjuvant (e.g., aluminum phosphate, aluminum sulfate or aluminum hydroxide). In a preferred embodiment, the immunogenic compositions disclosed herein comprise aluminum phosphate or aluminum hydroxide as adjuvant. In an embodiment, the immunogenic compositions disclosed herein comprise from 0.1 mg/mL to 1 mg/mL or from 0.2 mg/mL to 0.3 mg/ml of elemental aluminum in the form of aluminum phosphate. In an embodiment, the immunogenic compositions disclosed herein comprise about 0.25 mg/ml of elemental aluminum in the form of aluminum phosphate. Examples of known suitable immune modulatory type adjuvants that can be used in humans include, but are not limited to, saponin extracts from the bark of the Aquilla tree (QS21, Quil A), TLR4 agonists such as MPL (Monophosphoryl Lipid A), 3DMPL (3-O-deacylated MPL) or GLA-AQ, LT/CT mutants, cytokines such as the various interleukins (e.g., IL-2, IL-12) or GM-CSF, ASO1, and the like.

Examples of known suitable immune modulatory type adjuvants with both delivery and immune modulatory features that can be used in humans include, but are not limited to, ISCOMS (see, e.g., Sjölander et al. (1998) J. Leukocyte Biol. 64:713; WO 90/03184, WO 96/11711, WO 00/48630, WO 98/36772, WO 00/41720, WO 2006/134423 and WO 2007/026190) or GLA-EM which is a combination of a TLR4 agonist and an oil-in-water emulsion.

For veterinary applications including but not limited to animal experimentation, one can use Complete Freund's Adjuvant (CFA), Freund's Incomplete Adjuvant (IFA), Emulsigen, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion.

Further exemplary adjuvants to enhance effectiveness of the immunogenic compositions disclosed herein include, but are not limited to (1) oil-in-water emulsion formulations (with or without other specific immunostimulating agents such as muramyl peptides (see below) or bacterial cell wall components), such as for example (a) SAF, containing 10% Squalane, 0.4% Tween 80, 5% pluronic-blocked polymer L121, and thr-MDP either microfluidized into a submicron emulsion or vortexed to generate a larger particle size emulsion, and (b) RIBI™ adjuvant system (RAS), (Ribi Immunochem, Hamilton, Mont.) containing 2% Squalene, 0.2% Tween 80, and one or more bacterial cell wall components such as monophosphorylipid A (MPL), trehalose dimycolate (TDM), and cell wall skeleton (CWS), preferably MPL+CWS (DETOX™); (2) saponin adjuvants, such as QS21, STIMULON™ (Cambridge Bioscience, Worcester, Mass.), ABISCO® (Isconova, Sweden), or ISCOMATRIX® (Commonwealth Serum Laboratories, Australia), may be used or particles generated therefrom such as ISCOMs (immunostimulating complexes), which ISCOMS may be devoid of additional detergent (e.g., WO 00/07621); (3) Complete Freund's Adjuvant (CFA) and Incomplete Freund's Adjuvant (IFA); (4) cytokines, such as interleukins (e.g., IL-1, IL-2, IL-4, IL-5, IL-6, IL-7, IL-12 (e.g., WO 99/44636)), interferons (e.g., gamma interferon), macrophage colony stimulating factor (M-CSF), tumor necrosis factor (TNF), etc.; (5) monophosphoryl lipid A (MPL) or 3-O-deacylated MPL (3dMPL) (see, e.g., GB2220211, EP0689454) (see, e.g., WO 00/56358); (6) combinations of 3dMPL with, for example, QS21 and/or oil-in-water emulsions (see, e.g., EP0835318, EP0735898, EP0761231); (7) a polyoxyethylene ether or a polyoxyethylene ester (see, e.g., WO 99/52549); (8) a polyoxyethylene sorbitan ester surfactant in combination with an octoxynol (e.g., WO O1/21207) or a polyoxyethylene alkyl ether or ester surfactant in combination with at least one additional non-ionic surfactant such as an octoxynol (e.g., WO O1/21152); (9) a saponin and an immunostimulatory oligonucleotide (e.g., a CpG oligonucleotide) (e.g., WO 00/62800); (10) an immunostimulant and a particle of metal salt (see, e.g., WO 00/23105); (11) a saponin and an oil-in-water emulsion (e.g., WO 99/11241); (12) a saponin (e.g., QS21)+3dMPL+IM2 (optionally+a sterol) (e.g., WO 98/57659); (13) other substances that act as immunostimulating agents to enhance the efficacy of the composition. Muramyl peptides include N-acetyl-muramyl-L-threonyl-D-isoglutamine (thr-MDP), N-25 acetyl-normuramyl-L-alanyl-D-isoglutamine (nor-MDP), N-acetylmuramyl-L-alanyI-D-isoglutarninyl-L-alanine-2-(1'-2'-dipalmitoyl-sn-glycero-3-hydroxyphosphoryloxy)-ethylamine MTP-PE), etc.

In an embodiment of the present invention, the immunogenic compositions as disclosed herein comprise a CpG Oligonucleotide as adjuvant. A CpG oligonucleotide as used herein refers to an immunostimulatory CpG oligodeoxynucleotide (CpG ODN), and accordingly these terms are used interchangeably unless otherwise indicated. Immunostimulatory CpG oligodeoxynucleotides contain one or more immunostimulatory CpG motifs that are unmethylated cytosine-guanine dinucleotides, optionally within certain preferred base contexts. The methylation status of the CpG immunostimulatory motif generally refers to the cytosine residue in the dinucleotide. An immunostimulatory oligonucleotide containing at least one unmethylated CpG dinucleotide is an oligonucleotide which contains a 5' unmethylated cytosine linked by a phosphate bond to a 3' guanine, and which activates the immune system through binding to Toll-like receptor 9 (TLR-9). In another embodiment the immunostimulatory oligonucleotide may contain one or more methylated CpG dinucleotides, which will activate the immune system through TLR9 but not as strongly as if the CpG motif(s) was/were unmethylated. CpG immunostimulatory oligonucleotides may comprise one or more palindromes that in turn may encompass the CpG dinucleotide. CpG oligonucleotides have been described in a number of issued patents, published patent applications, and other publications, including U.S. Pat. Nos. 6,194,388; 6,207,646; 6,214,806; 6,218,371; 6,239,116; and 6,339,068.

In an embodiment of the present invention, the immunogenic compositions as disclosed herein comprise any of the CpG Oligonucleotide described at page 3, line 22, to page 12, line 36, of WO 2010/125480.

Different classes of CpG immunostimulatory oligonucleotides have been identified. These are referred to as A, B, C and P class, and are described in greater detail at page 3, line 22, to page 12, line 36, of WO 2010/125480. Methods of the invention embrace the use of these different classes of CpG immunostimulatory oligonucleotides.

VII. Nanoparticles

In another aspect, disclosed herein is an immunogenic complex that includes 1) a nanostructure; and 2) at least one fimbrial polypeptide antigen or fragment thereof. Preferably, the fimbrial polypeptide or fragment thereof is derived from *E. coli* fimbrial H (fimH). In a preferred embodiment, the fimbrial polypeptide is selected from any one of the fimbrial polypeptides described above. For example, the fimbrial polypeptide may comprise any one amino acid sequence selected from SEQ ID NOs: 1-10, 18, 20, 21, 23, 24, and 26-29.

In some embodiments, the antigen is fused or conjugated to the nanostructure exterior to stimulate development of adaptive immune responses to the displayed epitopes. In some embodiments, the immunogenic complex further includes an adjuvant or other immunomodulatory compounds attached to the exterior and/or encapsulated in the cage interior to help tailor the type of immune response generated for each pathogen.

In some embodiments, the nanostructure includes a single assembly including a plurality of identical first nanostructure-related polypeptides.

In alternative embodiments, the nanostructure includes a plurality assembly, including a plurality of identical first nanostructure-related polypeptides and a plurality of second assemblies, each second assembly comprising a plurality of identical second nanostructure-related polypeptides.

Various nanostructure platforms can be employed in generating the immunogenic compositions described herein. In some embodiments, the nanostructures employed are formed by multiple copies of a single subunit. In some embodiments, the nanostructures employed are formed by multiple copies of multiple different subunits.

The nanostructures are typically ball-like shaped, and/or have rotational symmetry (e.g., with 3-fold and 5-fold axis), e.g., with an icosahedral structure exemplified herein.

In some embodiments, the antigen is presented on self-assembling nanoparticles such as self-assembling nanostructures derived from ferritin (FR), E2p, Qβ, and 13-01. E2p is a redesigned variant of dihydrolipoyl acyltransferase from *Bacillus stearothermophilus.* 13-01 is an engineered protein that may self-assemble into hyperstable nanoparticles. Sequences of the subunits of these proteins are known in the art. In a first apsect, disclosed herein is a nanostructure-related polypeptide comprising an amino acid sequence that is at least 75% identical over its length, and identical at least at one identified interface position, to the amino acid sequence of a nanostructure-related polypeptide selected from the group consisting of SEQ ID NOS: 59-92. The nanostructure-related polypeptides can be used, for example, to prepare the nanostructures. The nanostructure-related polypeptides were designed for their ability to self-assemble in pairs to form nanostructures, such as icosahedral nanostructures.

In some embodiments, the nanostructure includes (a) a plurality of first assemblies, each first assembly comprising a plurality of identical first nanostructure-related polypeptides, wherein the first nanostructure-related polypeptides comprise the amino acid sequence of a nanostructure-related polypeptide selected from the group consisting of SEQ ID NOS: 59-92; and (b) a plurality of second assemblies, each second assembly comprising a plurality of identical second nanostructure-related polypeptides, wherein the second nanostructure-related polypeptides comprise the amino acid sequence of a nanostructure-related polypeptide selected from the group consisting of SEQ ID NOS: 59-92, and wherein the second nanostructure-related polypeptide differs from the first nanostructure-related polypeptide; wherein the plurality of first assemblies non-covalently interact with the plurality of second assemblies to form a nanostructure;

The nanostructures include symmetrically repeated, non-natural, non-covalent polypeptide-polypeptide interfaces that orient a first assembly and a second assembly into a nanostructure, such as one with an icosahedral symmetry.

SEQ ID NOS: 59-92 provide the amino acid sequence of exemplary nanostructure-related polypeptides. The number of interface residues for the exemplary nanostructure-related polypeptides of SEQ ID NO:59-92 range from 4-13 residues. In various embodiments, the nanostructure-related polypeptides comprise an amino acid sequence that is at least 75%, 80%, 85%, 90%, 91%, 92%, 93%, 94%, 95%, 96%, 97%, 98%, or 99% identical over its length, and identical at least at 1, 2, 3, 4, 5, 6, 7, 8, 9, 10, 11, 12, or 13 identified interface positions (depending on the number of interface residues for a given nanostructure-related polypeptide), to the amino acid sequence of a nanostructure-related polypeptide selected from the group consisting of SEQ ID NOS: 59-92. In other embodiments, the nanostructure-related polypeptides comprise an amino acid sequence that is at least 75%, 80%, 85%, 90%, 91%, 92%, 93%, 94%, 95%, 96%, 97%, 98%, or 99% identical over its length, and identical at least at 20%, 25%, 33%, 40%, 50%, 60%, 70%, 75%, 80%, 90%, or 100% of the identified interface positions, to the amino acid sequence of a nanostructure-related polypeptide selected from the group consisting of SEQ ID NOS: 59-92. In further embodiments, the nanostructure-related polypeptides include a nanostructure-related polypeptide having the amino acid sequence of a nanostructure-related polypeptide selected from the group consisting of SEQ ID NOS: 59-98.

In one non-limiting embodiment, the nanostructure-related polypeptides can be modified to facilitate covalent linkage to a "cargo" of interest. In one non-limiting example, the nanostructure-related polypeptides can be modified, such as by introduction of various cysteine residues at defined positions to facilitate linkage to one or more antigens of interest, such that a nanostructure of the nanostructure-related polypeptides would provide a scaffold to provide a large number of antigens for delivery as a vaccine to generate an improved immune response.

In some embodiments, some or all native cysteine residues that are present in the nanostructure-related polypeptides but not intended to be used for conjugation may be mutated to other amino acids to facilitate conjugation at defined positions. In another non-limiting embodiment, the nanostructure-related polypeptides may be modified by linkage (covalent or non-covalent) with a moiety to help facilitate "endosomal escape." For applications that involve delivering molecules of interest to a target cell, such as targeted delivery, a critical step can be escape from the endosome—a membrane-bound organelle that is the entry point of the delivery vehicle into the cell. Endosomes mature into lysosomes, which degrade their contents. Thus, if the delivery vehicle does not somehow “escape” from the endosome before it becomes a lysosome, it will be degraded and will not perform its function. There are a variety of lipids or organic polymers that disrupt the endosome and allow escape into the cytosol. Thus, in this embodiment, the nanostructure-related polypeptides can be modified, for example, by introducing cysteine residues that will allow chemical conjugation of such a lipid or organic polymer to the monomer or resulting assembly surface. In another non-limiting example, the nanostructure-related polypeptides can be modified, for example, by introducing cysteine residues that will allow chemical conjugation of fluorophores or other imaging agents that allow visualization of the nanostructures in vitro or in vivo.

Surface amino acid residues on the nanostructure-related polypeptides can be mutated in order to improve the stability or solubility of the protein subunits or the assembled nanostructures. As will be known to one of skill in the art, if the nanostructure-related polypeptide has significant sequence homology to an existing protein family, a multiple sequence alignment of other proteins from that family can be used to guide the selection of amino acid mutations at non-conserved positions that can increase protein stability and/or solubility, a process referred to as consensus protein design (9).

Surface amino acid residues on the nanostructure-related polypeptides can be mutated to positively charged (Arg, Lys) or negatively charged (Asp, Glu) amino acids in order to endow the protein surface with an overall positive or overall negative charge. In one non-limiting embodiment, surface amino acid residues on the nanostructure-related polypeptides can be mutated to endow the interior surface of the self-assembling nanostructure with a high net charge. Such a nanostructure can then be used to package or encapsulate a cargo molecule with the opposite net charge due to the electrostatic interaction between the nanostructure interior surface and the cargo molecule. In one non-limiting embodiment, surface amino acid residues on the nanostructure-related polypeptides can be mutated primarily to Arginine or Lysine residues in order to endow the interior surface of the self-assembling nanostructure with a net positive charge. Solutions containing the nanostructure-related polypeptides can then be mixed in the presence of a nucleic acid cargo molecule such as a dsDNA, ssDNA, dsRNA, ssRNA, cDNA, miRNA., siRNA, shRNA, piRNA, or other nucleic acid in order to encapsulate the nucleic acid inside the self-assembling nanostructure. Such a nanostructure could be used, for example, to protect, deliver, or concentrate nucleic acids.

In one embodiment, the nanostructure has icosahedral symmetry. In this embodiment, the nanostructure may comprise 60 copies of the first nanostructure-related polypeptide and 60 copies of the second nanostructure-related polypeptide. In one such embodiment, the number of identical first nanostructure-related polypeptides in each first assembly is different than the number of identical second nanostructure-related polypeptides in each second assembly. For example, in one embodiment, the nanostructure comprises twelve first assemblies and twenty second assemblies; in this embodiment, each first assembly may; for example, comprise five copies of the identical first nanostructure-related polypeptide, and each second assembly may, for example, comprise three copies of the identical second nanostructure-related polypeptide. In another embodiment, the nanostructure comprises twelve first assemblies and thirty second assemblies; in this embodiment, each first assembly may, for example, comprise five copies of the identical first nanostructure-related polypeptide, and each second assembly may, for example, comprise two copies of the identical second nanostructure-related polypeptide. In a further embodiment, the nanostructure comprises twenty first assemblies and thirty second assemblies; in this embodiment, each first assembly may, for example, comprise three copies of the identical first nanostructure-related polypeptide, and each second assembly may, for example, comprise two copies of the identical second nanostructure-related polypeptide. All of these embodiments are capable of forming synthetic nanomaterials with regular icosahedral symmetry.

VIII. Combination with a Saccharide and/or Polypeptide or Fragment Thereof Derived from *Klebsiella Pneumoniae*

*Klebsiella pneumoniae* is a Gram-negative pathogen, known to cause urinary tract infections, bacteremia, and sepsis. In one aspect, any of the compositions disclosed herein may further include at least one saccharide that is, or derived from, at least one *K. pneumoniae* serotype selected from O1 (and d-Gal-III variants), O2 (and d-Gal-III variants), O2ac, O3, O4, O5, O7, O8, and O12. In a preferred embodiment, any of the compositions disclosed herein may further include a polypeptide derived from *K. pneumoniae* selected from a polypeptide derived from *K. pneumoniae* Type I fimbrial protein or an immunogenic fragment thereof; and a polypeptide derived from *K. pneumoniae* Type III fimbrial protein or an immunogenic fragment thereof.

As is known in the art, *K. pneumoniae O*1 and O2 antigens contain homopolymer galactose units (or galactans). *K. pneumoniae O*1 and O2 antigens each contain D-galactan I units (sometimes referred to as the O2a repeat unit), but O1 antigens differ in that O1 antigens have a D-galactan II cap structure. D-galactan III (d-Gal-III) is a variant of D-galactan I. In some embodiments, the saccharide derived from *K. pneumoniae O*1 includes a repeat unit of [→3)-β-D-Galf-(1→3)-α-D-Galp-(1→]. In some embodiments, the saccharide derived from *K. pneumoniae O*1 includes a repeat unit of [→3)-α-D-Galp-(1→3)-3-D-Galp-(1→]. In some embodiments, the saccharide derived from *K. pneumoniae O*1 includes a repeat unit of [→3)-β-D-Galf-(1→3)-α-D-Galp-(1→], and a repeat unit of [→3)-α-D-Galp-(1→3)-β-D-Galp-(1→]. In some embodiments, the saccharide derived from *K. pneumoniae O*1 includes a repeat unit of →3)-β-D-Galf-(1→3)-[α-D-Galp-(1→4)]-α-D-Galp-(1→] (referred to as the D-Gal-Ill repeat unit).

In some embodiments, the saccharide derived from *K. pneumoniae O*2 includes a repeat unit of [→3)-α-D-Galp-(1→3)-β-D-Galf-(1→] (which may be an element of *K. pneumoniae* serotype O2a antigen). In some embodiments, the saccharide derived from *K. pneumoniae* O2 includes a repeat unit of [→3)-β-D-GlcpNAc-(1→5)-β-D-Galf-(1→] (which may be an element of *K. pneumoniae* serotype O2c antigen). In some embodiments, the saccharide derived from *K. pneumoniae O*2 includes a modification of the O2a repeat unit by side chain addition of (1→4)-linked Galp residues (which may be an element of the *K. pneumoniae* O2afg antigen). In some embodiments, the saccharide derived from *K. pneumoniae O*2 includes a modification of the O2a repeat unit by side chain addition of (1→2)-linked Galp residues (which may be an element of the *K. pneumoniae* O2aeh antigen).

Without being bound by mechanism or theory, O-antigen polysaccharide structure of *K. pneumoniae* serotypes O3 and O5 are disclosed in the art to be identical to those of *E. coli* serotypes O9a (Formula O9a) and O8 (Formula O8), respectively.

In some embodiments, the saccharide derived from *K. pneumoniae* O4 includes a repeat unit of [→4)-α-D-Galp-(1→2)-β-D-Ribf-(1→)]. In some embodiments, the saccharide derived from *K. pneumoniae* O7 includes a repeat unit of [→2-a-L-Rhap-(1→2)-β-D)-Ribf-(1→3)-α-L-Rhap-(1→3)-α-L-Rhap-(1→]. In some embodiments, the saccharide derived from *K. pneumoniae O*8 serotype includes the same repeat-unit structure as *K. pneumoniae* 02a, but is nonstoichiometrically O-acetylated. In some embodiments, the saccharide derived from *K. pneumoniae O*12 serotype includes a repeat unit of [α-Rhap-(1→3)-β-GicpNAc] disaccharide repeat unit.

In one aspect, the invention includes a composition including a polypeptide derived from *E. coli* FimH or a fragment thereof; and at least one saccharide that is, or derived from, at least one *K. pneumoniae* serotype selected from O1 (and d-Gal-III variants), O2 (and d-Gal-III variants), O2ac, O3, O4, O5, O7, O8, and O12. In some embodiments, the composition includes saccharides from or derived from one or more of serotypes O1, O2, O3, and O5, or a combination thereof. In some embodiments, the composition includes saccharides from or derived from each of serotypes O1, O2, O3, and O5.

In another aspect, the invention includes a composition including at least one saccharide that is, or derived from, at least one *K. pneumoniae* serotype selected from O1 (and d-Gal-Ill variants), O2 (and d-Gal-Ill variants), O2ac, O3, O4, O5, O7, O8, and 012; and a saccharide having a structure selected from any one of Formula O1 (e.g., Formula O1A, Formula O1B, and Formula O1C), Formula O2, Formula O3, Formula O4 (e.g., Formula O4: K52 and Formula O4: K6), Formula O5 (e.g., Formula O5ab and Formula O5ac (strain 180/C3)), Formula O6 (e.g., Formula O6: K2; K13; K15 and Formula O6: K54), Formula O7, Formula O8, Formula O9, Formula O10, Formula O11, Formula O12, Formula O13, Formula O14, Formula O15, Formula O16, Formula O17, Formula O18 (e.g., Formula O18A, Formula O18ac, Formula O18A1, Formula O18B, and Formula O18B1), Formula O19, Formula O20, Formula O21, Formula O22, Formula O23 (e.g., Formula O23A), Formula O24, Formula O25 (e.g., Formula O25a and Formula O25b), Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45 (e.g., Formula O45 and Formula O45rel), Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula $62D_1$, Formula O63, Formula O64, Formula O65, Formula O66, Formula O68, Formula O69, Formula O70, Formula O71, Formula O73 (e.g., Formula O73 (strain 73-1)), Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144, Formula O145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, and Formula O187, wherein n is an integer from 1 to 100. In some embodiments, the composition includes a saccharide from or derived from one or more of *K. pneumoniae* serotypes O1, O2, O3, and O5, or a combination thereof. In some embodiments, the composition includes a saccharide from or derived from each of *K. pneumoniae* serotypes O1, O2, O3, and O5. In some embodiments, the composition includes a saccharide having Formula O9 and does not include a saccharide derived from *K. pneumoniae* serotype O3. In some embodiments, the composition includes a saccharide having Formula O8 and does not include a saccharide derived from *K. pneumoniae* serotype O5.

In another aspect, the invention relates to a composition including a composition including a polypeptide derived from *E. coli* FimH or a fragment thereof; at least one saccharide that is, or derived from, at least one *K. pneumoniae* serotype selected from O1 (and d-Gal-III variants), O2 (and d-Gal-III variants), O2ac, O3, O4, O5, O7, O8, and O12; and a saccharide having a structure selected from any one of Formula O1 (e.g., Formula O1A, Formula O1B, and Formula O1C), Formula O2, Formula O3, Formula O4 (e.g., Formula O4: K52 and Formula O4: K6), Formula O5 (e.g., Formula O5ab and Formula O5ac (strain 180/C3)), Formula O6 (e.g., Formula O6: K2; K13; K15 and Formula O6: K54), Formula O7, Formula O8, Formula O9, Formula O10, Formula O11, Formula O12, Formula O13, Formula O14, Formula O15, Formula O16, Formula O17, Formula O18 (e.g., Formula O18A, Formula O18ac, Formula O18A1, Formula O18B, and Formula O18B1), Formula O19, Formula O20, Formula O21, Formula O22, Formula O23 (e.g., Formula O23A), Formula O24, Formula O25 (e.g., Formula O25a and Formula O25b), Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45 (e.g., Formula O45 and Formula O45rel), Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula $62D_1$, Formula O63, Formula O64, Formula O65, Formula O66, Formula O68, Formula O69, Formula O70, Formula O71, Formula O73 (e.g., Formula O73 (strain 73-1)), Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144, Formula O145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, and Formula O187, wherein n is an integer from 1 to 100. In some embodiments, the composition includes a saccharide having Formula O9 and does not include a saccharide derived from *K. pneumoniae* serotype 03. In some embodiments, the composition includes a saccharide having Formula O8 and does not include a saccharide derived from *K. pneumoniae* serotype O5.

In some embodiments, the composition includes at least one saccharide derived from any one *K. pneumoniae* type selected from the group consisting of O1, O2, O3, and O5. In some embodiments, the composition includes at least one saccharide derived from *K. pneumoniae* type O1. In some embodiments, the composition includes at least one saccharide derived from *K. pneumoniae* type O2.

In some embodiments, the composition includes a combination of saccharides derived from *K. pneumoniae*, wherein a first saccharide is derived from any one of *K. pneumoniae* types selected from the group consisting of O1, O2, O3, and O5; and a second saccharide is derived from a saccharide is derived from any one of *K. pneumoniae* types selected from the group consisting of O1 (and d-Gal-III variants), O2 (and d-Gal-Ill variants), O2ac, O3, O4, O5, O7, O8, and O12. For example, in some embodiments, the composition includes at least one saccharide derived from *K. pneumoniae* type O1 and at least one saccharide derived from *K. pneumoniae* type O2. In a preferred embodiment, the saccharide derived from *K. pneumoniae* is conjugated to a carrier protein; and the saccharide derived from *E. coli* is conjugated to a carrier protein.

In another aspect, the invention includes a composition including a polypeptide derived from *E. coli* FimH or a fragment thereof; and at least one saccharide derived from any one *K. pneumoniae* type selected from the group consisting of O1, O2, O3, and O5.

In another aspect, the invention includes at least one saccharide derived from any one *K. pneumoniae* type selected from the group consisting of O1, O2, O3, and O5; and at least one saccharide derived from *E. coli* having a structure selected from any one of Formula O1 (e.g., Formula O1A, Formula O1B, and Formula O1C), Formula O2, Formula O3, Formula O4 (e.g., Formula O4: K52 and Formula O4: K6), Formula O5 (e.g., Formula O5ab and Formula O5ac (strain 180/C3)), Formula O6 (e.g., Formula O6: K2; K13; K15 and Formula O6: K54), Formula O7, Formula O8, Formula O9, Formula O10, Formula O11, Formula O12, Formula O13, Formula O14, Formula O15, Formula O16, Formula O17, Formula O18 (e.g., Formula O18A, Formula O18ac, Formula O18A1, Formula O18B, and Formula O18B1), Formula O19, Formula O20, Formula O21, Formula O22, Formula O23 (e.g., Formula O23A), Formula O24, Formula O25 (e.g., Formula O25a and Formula O25b), Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45 (e.g., Formula O45 and Formula O45rel), Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula $62D_1$, Formula O63, Formula O64, Formula O65, Formula O66, Formula O68, Formula O69, Formula O70, Formula O71, Formula O73 (e.g., Formula O73 (strain 73-1)), Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144, Formula O145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, and Formula O187. In some embodiments, the composition includes a saccharide having Formula O9 and does not include a saccharide derived from *K. pneumoniae* serotype O3. In some embodiments, the composition includes a saccharide having Formula O8 and does not include a saccharide derived from *K. pneumoniae* serotype O5.

In some embodiments, the composition includes at least one saccharide derived from *K. pneumoniae* type O1; and at least one saccharide derived from *E. coli* having a structure selected from the group consisting of Formula O8 and Formula O9. In another embodiment, the composition includes at least one saccharide derived from *K. pneumoniae* type O2; and at least one saccharide derived from *E. coli* having a structure selected from the group consisting of Formula O8 and Formula O9. In another embodiment, the composition includes at least one saccharide derived from *K.*

*pneumoniae* type O1; at least one saccharide derived from *K. pneumoniae* type O2; and at least one saccharide derived from *E. coli* having a structure selected from the group consisting of Formula O8 and Formula O9.

In some embodiments, the composition includes at least one saccharide that is, or derived from, at least one *K. pneumoniae* serotype selected from O1 (and d-Gal-Ill variants), O2 (and d-Gal-III variants), O2ac, O3, O4, O5, O7, O8, and O12; at least one saccharide derived from *E. coli* having a structure selected from the group consisting of Formula O8 and Formula O9. In some embodiments, the composition includes at least one saccharide that is, or derived from, at least one *K. pneumoniae* serotype selected from O1 (and d-Gal-III variants), O2 (and d-Gal-Ill variants), O2ac, O3, O4, O5, O7, O8, and O12; at least one saccharide derived from *E. coli* having a structure selected from the group consisting of Formula O1A, Formula O1B, Formula O2, Formula O6, and Formula O25B.

In some embodiments, the composition further includes a polypeptide derived from *K. pneumoniae* selected from a polypeptide derived from *K. pneumoniae* Type I fimbrial protein or an immunogenic fragment thereof; and a polypeptide derived from *K. pneumoniae* Type III fimbrial protein or an immunogenic fragment thereof. The sequences of such polypeptides are known in the art.

EXAMPLES

In order that this invention may be better understood, the following examples are set forth. These examples are for purposes of illustration only and are not to be construed as limiting the scope of the invention in any manner. The following Examples illustrate some embodiments of the invention.

Example 1: Summary of Constructs

TABLE 3

| Construct | Plasmid | Signal sequence | Protein Description | Linker | Additional protein variant | Backbone | Mass |
|---|---|---|---|---|---|---|---|
| FimH lectin domain | pSB01877 | FimH signal sequence | FimH J96 F22 . . . G181 | none | none | pcDNA3.1(+) or pCAG vector | |
| FimH lectin domain | pSB01878 | mIgK signal sequence | FimH J96 F22 . . . G181 | none | none | pcDNA3.1(+) or pCAG vector | Fully reduced mass, with His-tag: 18117.48 Observed non-reduced mass, with His-tag: 18117.90 Mass without tag: 17022.08 |
| FimH/C | pSB01879 | FimH signal sequence | FimH J96 F22 . . . Q300 | none | none | pBudCE4.1 Dual promoter vector (CMV & EF1α) | |
| FimH/C | pSB01880 | mIgK signal sequence | FimH J96 F22 . . . Q300 | none | none | pBudCE4.1 Dual promoter vector (CMV & EF1α) | |
| FimH/C | pSB01881 | mIgK signal sequence | FimC G37 . . . E241 (according to SEQ ID NO: 18) | none | none | pBudCE4.1 Dual promoter vector (CMV & EF1α) | |
| FimH-dscG | pSB01882 | FimH signal sequence | FimH J96 F22 . . . Q300 | DNKQ | FimG A1 . . . K14 (SEQ ID NO: 17) | | |
| FimH-dscG | pSB01883 | FimH signal sequence | FimH J96 F22 . . . Q300 | GGSGG | FimG A1 . . . K14 (SEQ ID NO: 17) | | |
| FimH-dscG | pSB01884 | FimH signal sequence | FimH J96 F22 . . . Q300 | GGSSGG | FimG A1 . . . K14 (SEQ ID NO: 17) | | |

TABLE 3-continued

| Construct | Plasmid | Signal sequence | Protein Description | Linker | Additional protein variant | Backbone | Mass |
|---|---|---|---|---|---|---|---|
| FimH-dscG | pSB01885 | FimH signal sequence | FimH J96 F22 . . . Q300 | GGSSGGG | FimG A1 . . . K14 (SEQ ID NO: 17) | N-terminus residue at W20, and therefore does not appear to have been processed at preferred position; a small amount of protein present exhibiting preferred processing as indicated by the small amount of the FACK peptide being detected | |
| FimH-dscG | pSB01886 | Fim H signal sequence | FimH J96 F22 . . . Q300 | GGGSSGGG | FimG A1 . . . K14 (SEQ ID NO: 17) | | |
| FimH-dscG | pSB01887 | FimH signal sequence | FimH J96 F22 . . . Q300 | GGGSGSGGG | FimG A1 . . . K14 (SEQ ID NO: 17) | | |
| FimH-dscG | pSB01888 | FimH signal sequence | FimH J96 F22 . . . Q300 | GGGSGGSGGG | FimG A1 . . . K14 (SEQ ID NO: 17) | | |
| FimH-dscG | pSB01889 | mIgK signal sequence | FimH J96 F22 . . . Q300 | DNKQ | FimG A1 . . . K14 (SEQ ID NO: 17) | | |
| FimH-dscG | pSB01890 | mIgK signal sequence | FimH J96 F22 . . . Q300 | GGSGG | FimG A1 . . . K14 (SEQ ID NO: 17) | | |
| FimH-dscG | pSB01891 | mIgK signal sequence | FimH J96 F22 . . . Q300 | GGSSGG | FimG A1 . . . K14 (SEQ ID NO: 17) | | |
| FimH-dscG | pSB01892 | mIgK signal sequence | FimH J96 F22 . . . Q300 | GGSSGGG | FimG A1 . . . K14 (SEQ ID NO: 17) | appears to have had the signal peptide processed with the F22 being the preferred N-terminal residue; identity of the peptide was confirmed by MS/MS | |
| FimH-dscG | pSB01893 | mIgK signal sequence | FimH J96 F22 . . . Q300 | GGGSSGGG | FimG A1 . . . K14 (SEQ ID NO: 17) | | |
| FimH-dscG | pSB01894 | mIgK signal sequence | FimH J96 F22 . . . Q300 | GGGSGSGGG | FimG A1 . . . K14 (SEQ ID NO: 17) | | |
| FimH-dscG | pSB01895 | mIgK signal sequence | FimH J96 F22 . . . Q300 | GGGSGGSGGG | FimG A1 . . . K14 (SEQ ID NO: 17) | | |

TABLE 3-continued

| Construct | Plasmid | Signal sequence | Protein Description | Linker | Additional protein variant | Backbone | Mass |
|---|---|---|---|---|---|---|---|
| FimH lectin domain | pSB02081 | mIgK signal sequence | F22 . . . G181 J96 FimH/ N28Q N91S His8 in pcDNA3.1(+) | | | | |
| FimH lectin domain | pSB02082 | mIgK signal sequence | F22 . . . G181 J96 FimH N28Q N91S/ His8 in pcDNA3.1(+) | | | | |
| FimH lectin domain | pSB02083 | mIgK signal sequence | F22 . . . G181 J96 FimH N28S N91S/ His8 in pcDNA3.1(+) | | | | |
| FimH lectin domain | pSB02088 | mIgK signal sequence | F22 . . . G181 J96 FimH V48C L55C/ His8 in pcDNA3.1(+) | | | | |
| FimH lectin domain | pSB02089 | mIgK signal sequence | F22 . . . G181 J96 FimH N28Q V48C L55C N91S/ His8 in pcDNA3.1(+) | | | | |
| FimH lectin domain | pSB02158 | mIgK signal sequence | F22 . . . G181 J96 FimH N28S V48C L55C N91S/ His8 in pcDNA3.1(+) | | | | |
| FimH-dscG | pSB02159 | | | | | | |
| FimH-dscG | pSB02198 | mIgK signal sequence | FimH mIgK signal pept/ F22 . . . Q300 J96 FimH N28S V48C L55C N91S N249Q/7 AA linker/FimG A1 . . . K14/ GGHis8 in pcDNA3.1(+) | | | | |
| FimH-dscG | pSB02199 | mIgK signal sequence | FimH mIgK signal pept/ F22 . . . Q300 J96 FimH N28S V48C L55C N91S N256Q/7 AA linker/FimG A1 . . . K14/ GGHis8 in pcDNA3.1(+) | | | | |
| FimH-dscG | pSB02200 | mIgK signal sequence | FimH mIgK signal pept/ F22 . . . Q300 J96 FimH N28S V48C L55C N91S N249Q N256Q/7 AA linker/FimG A1 . . . K14/ GGHis8 in pcDNA3.1(+) | | | | |
| FimH-dscG | pSB02304 | mIgK signal sequence | FimH mIgK signal pept/ F22 . . . Q300 J96 FimH N28S V48C L55C N91S T251A/7 AA linker/FimG | | | | |

TABLE 3-continued

| Construct | Plasmid | Signal sequence | Protein Description | Linker | Additional protein variant | Backbone | Mass |
|---|---|---|---|---|---|---|---|
| | | | A1 . . . K14/ GGHis8 in pcDNA3.1(+) | | | | |
| FimH-dscG | pSB02305 | mIgK signal sequence | FimH mIgK signal pept/ F22 . . . Q300 J96 FimH N28S V48C L55C N91S T258A/7 AA linker/FimG A1 . . . K14/ GGHis8 in pcDNA3.1(+) | | | | |
| FimH-dscG | pSB02306 | mIgK signal sequence | FimH mIgK signal pept/ F22 . . . Q300 J96 FimH N28S V48C L55C N91S T251A T258A/ 7 AA linker/ FimG A1 . . . K14/ GGHis8 in pcDNA3.1(+) | | | | |
| FimH-dscG | pSB02307 | mIgK signal sequence | FimH mIgK signal pept/ F22 . . . Q300 J96 FimH N28S N91S N249Q/7 AA linker/FimG A1 . . . K14/ GGHis8 in pcDNA3.1(+) | | | | |
| FimH-dscG | pSB02308 | mIgK signal sequence | FimH mIgK signal pept/ F22 . . . Q300 J96 FimH N28S N91S N256Q/7 AA linker/FimG A1 . . . K14/ GGHis8 in pcDNA3.1(+) | | | | |

All of the FimH constructs studied were monomeric proteins of expected molecular weight.

TABLE 4

| Protein | Sedimentation Coefficient, S | $M_{w, app}$ | $M_{w, expected}$ | Homogeneity |
|---|---|---|---|---|
| *E. coli* expression | | | | |
| Cytosolic FimH-LD | 1.9 S | 18 kDa | 18 kDa | 98% |
| Periplasmic FimH-LD | 1.9 S | 18 kDa | 18 kDa | 98% |
| FimH-LD lock mutant | 2.0 S | 19 kDa | 18 kDa | 97% |
| Mammalian expression | | | | |
| FimH-LD | 1.9 S | 18 kDa | 18 kDa | >99% |
| FimH-LD lock mutant | 1.9 S | 18 kDa | 18 kDa | 98% |
| FimH wild type | 2.7 S | 36 kDa | 34 kDa | 96% |
| FimH lock mutant | 2.7 S | 34 kDa | 34 kDa | 94% |

Expected molecular weight of FimC-FimH complex is 53.1 kDa;

Expected molecular weight of FimC is 24 kDa.

Example 2: Mammalian Expression of FimH Lectin Binding Domain

The present non-limiting example relates to producing a polypeptide derived from *E. coli* or a fragment thereof in a HEK cell line. The yields were relatively high, as compared to expression of the polypeptide derived from *E. coli* or a fragment thereof in an *E. coli* host cell.

To accomplish the production of FimH variants from mammalian cells, a SignalP prediction algorithm was used to analyze different heterologous signal sequences for secretion of proteins and fragments. The wild type FimH leader sequence was also analyzed. The predictions indicated that the wild type FimH leader sequence may work for secretion of the FimH variants in mammalian cells, however, the secreted variant was predicted to be cleaved at the W20 residue of the full-length wild type FimH (see SEQ ID NO: 1), rather than the F22 residue of the full-length wild type FimH (see SEQ ID NO: 1). A hemagglutinin signal sequence was predicted not to work. The murine IgK signal sequence was predicted to produce an N-terminus of F22 of SEQ ID NO: 1, or F1 residue of the mature protein.

Based on these analyses, DNA was synthesized and recombinantly produced constructs to express the FimH lectin binding domain with the wild-type FimH leader. Constructs were also prepared to express the FimH lectin binding domain with the mlgK signal sequence. Affinity purification tags, such as His tag, were introduced to the C-terminus of the polypeptide derived from *E. coli* or a fragment thereof to facilitate purification.

The expression plasmid was transfected into HEK host cells, namely EXPI293 mammalian cells.

The polypeptides or fragments thereof derived from *E. coli* were successfully expressed. For example, the preferred N-terminal processing using the mlgK signal sequence fused to the mature start of FimH at F22 was demonstrated for the pSB01892 FimHdscG construct by MS. The processing is believed correct for the lectin domain construct pSB01878 and the mass spec data supports this.

The preferred N-terminal processing (i.e., processing at F22 of SEQ ID NO: 1) was not shown with the native FimH leader peptide.

pSB01877 and pSB01878 constructs are in pcDNA3.1 (+) mammalian expression vectors. The cells were diluted and subsequently used in 20 ml transfections. 1 μg/ml DNA for each construct was used and transfected cells in 125 ml flasks using Expifectamine protocol. After 72 hours, the cell viability was still good so the expression was allowed to continue until 96 hours. Samples were taken at 72 hours and ran 10 ul of each on SDS PAGE gels to check for expression.

Figure 4:
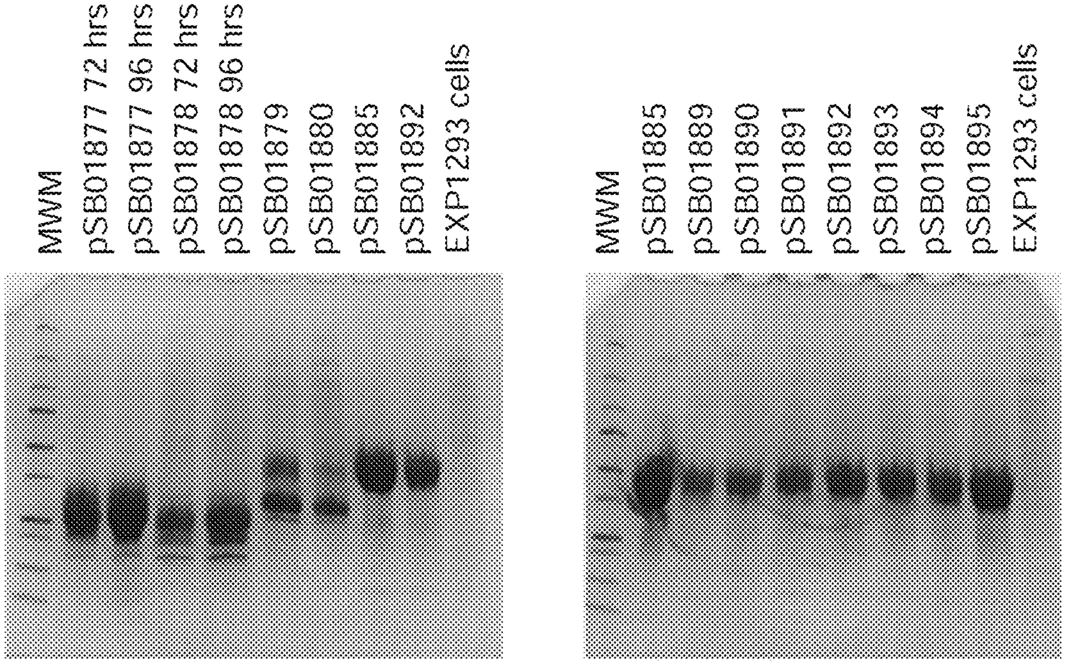
FIG. 4—depicts results from expression and purification.

After 96 hours, conditioned media was harvested and 0.25 ml of Nickel Excel resin was added with batch binding O/N at 4° C. with rotation. Eluted in TrisCl pH8.0, NaCl, imidazole. See FIG. 4.

pSB01878 has expected mass consistent with N-terminal F22. Glycosylation present on 1 or 2 sites (+1 mass from each deamidation of N-D).

Figure 5:
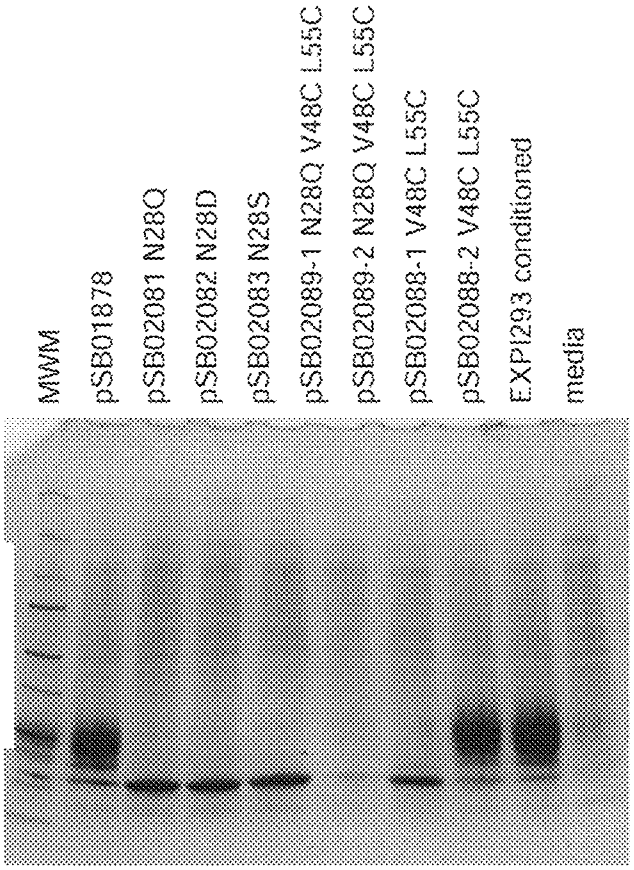
FIG. 5—depicts results from expression.

Glycosylation mutants were constructed. See, for example, pSB02081, pSB02082, pSB02083, pSB02088, and pSB02089. The glycosylation mutants expressed the polypeptides of interest. See FIG. 5 for results.

Figure 6A:
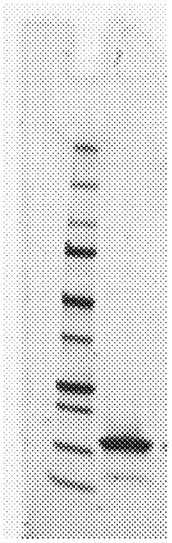
FIG. 6A-6C—depict pSB02083 and pSB02158 SEC pools and affinities; including yields.
Figure 6B:
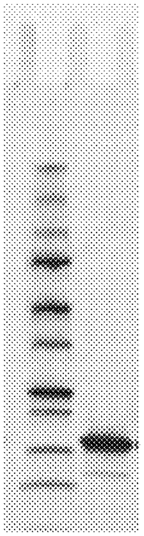

A FimH lectin domain lock mutant was also constructed. See, for example, pSB02158. Results of the expression of the pSB02158 construct is shown in FIG. 6B.

Figure 6C:
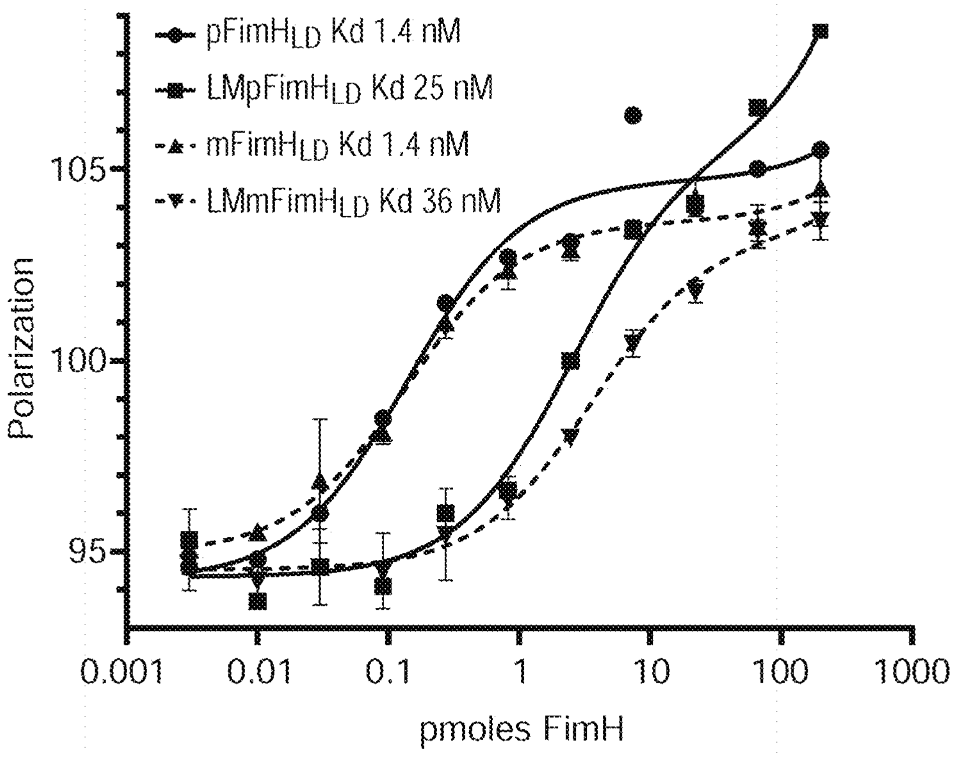

Fluorescence polarization assay using 0.5 pmoles fluorescein-conjugated aminophenyl-mannopyranoside (APMP). The assay was performed at room temperature, 300 RPM for 64 hrs. Results shown in FIG. 6C.

Example 3: Mammalian Expression of FimH/C Complex, pSB01879 and pSB01880

For production of the FimH/C complex, dual expression constructs of the FimC under the EF1alpha promoter and the FimH with either the wild type or migK signal peptide were prepared. These were cloned into a pBudCE4.1 mammalian expression vector (ThermoFisher) and a C-term His tag was added to the FimC. The FimC variant was designed for secretion using the mlgK signal peptide as it resulted in a positive prediction to yield the G37 FimC as the first residue of the mature protein based on SignalP analysis.

More specifically, these constructs were designed to have the FimC fragment under the EF 1alpha promoter in the vector pBudCE4.1 and the FimH fragment inserts under the CMV promoter in the same vector. The vector pBudCE4.1 is an expression vector from Thermo Fisher that has 2 promoters for expression in mammalian cells. The FimC fragment insert (pSB01881 insert) was subcloned by digesting with Notl and Xhol and subcloning into the pBudCE4.1 vector at the same sites. These were plated onto 2xYT zeocin 50 μg/ml plates. Colonies were inoculated into 2xYT with zeocin 50 μg/ml, grew overnight at 37° C. and plasmid prepped. These were digested with Notl and Xhol to check for insert and all colonies had insert size of ~722 bp.

pSB01881 was digested with HindIII and BamHI and the pSB01879 insert and pSB01880 insert DNA was digested with HindIII and BamHI. These fragments were gel isolated and subcloned into the pSB01881 vector and plated onto 2xYTzeo50 μg/ml plates. Colonies from each were inoculated into 2xYT zeo50 μg/ml, grown overnight at 37° C., plasmid prepped and digested with Notl and Xhol to test for FimC insert and HindIII and BamHI to test for FimH inserts. All clones had expected sized inserts at both cloning sites. The pSB01879-1 and pSB01880-1 clones were subsequently used for expression.

The FimH/FimC complex has been demonstrated to express in EXPI293 cells as well. Expression may be optimized by switching promoters, such as EF1a, CAG, Ub, Tub, or other promoters.

The preferred N-terminal processing (i.e., processing at F22 of SEQ ID NO: 1) was not shown with the native FimH leader peptide.

Exemplary results from SignalP 4.1 (DTU Bioinformatics) used for signal peptide predictions are shown below. Additional signal peptides are predicted to produce the preferred N-terminus of Phe at position 1 of the mature FimH polypeptide or fragment thereof. The following is only a representative sample set of 4 common signal sequences.

The following signal peptide sequences were predicted to yield the preferred N-terminus of Phe at position 1 of the mature FimH polypeptide or fragment thereof:

TABLE 5

| | signal peptide sequence | SEQ ID NO: |
|---|---|---|
| >sp\|P55899\|FCGRN_HUMAN IgG receptor FcRn large subunit p51 OS = *Homo sapiens* OX = 9606 GN = FCGRT PE = 1 SV = 1 | MGVPRPQPWALGLLLFLLPGSLG | SEQ ID NO: 55 |
| >tr\|Q6FGW4\|Q6FGW4_HUMAN IL10 protein OS = *Homo sapiens* OX = 9606 GN = IL10 PE = 2 SV = 1 | MHSSALLCCLVLLTGVRA | SEQ ID NO: 56 |

The following signal peptide sequences were NOT predicted to yield the preferred N-terminus of Phe at position 1 of the mature FimH polypeptide or fragment thereof:

TABLE 6

| | signal peptide sequence | SEQ ID NO: |
|---|---|---|
| >sp\|P03420\|FUS_HRSVA Fusion glycoprotein F0 OS = Human respiratory syncytial virus A (strain A2) OX = 11259 GN = F PE = 1 SV = 1 | MELLILKANAITTILTAVTFCFASG | SEQ ID NO: 57 |
| >sp\|P03451\|HEMA_157A0 Hemagglutinin OS = Influenza A virus (strain A/Japan/305/1957 H2N2) OX = 387161 GN = HA PE = 1 SV = 1 | MAIIYLILLFTAVRG | SEQ ID NO: 58 |

TABLE 7

| SignalP 4.1 used for predictions | |
|---|---|
| | Fusion sequence |
| >sp\|P55899\|FCGRN_HUMAN IgG receptor FcRn large subunit p51 OS = *Homo sapiens* OX = 9606 GN = FCGRT PE = 1 SV = 1 MGVPRPQPWALGLLLFLLPGSLGAESHLSLLY HLTAVSSPAPGTPAFWVSGWLGPQQYLS YNSLRGEAEPCGAWVWENQVSWYWEKETT DLRIKEKLFLEAFKALGGKGPYTLQGLLGCE LGPDNTSVPTAKFALNGEEFMNFDLKQGTWG GDWPEALAISQRWQQQDKAANKELTFLLF SCPHRLREHLERGRGNLEWKEPPSMRLKARPS SPGFSVLTCSAFSFYPPELQLRFLRNGL AAGTGQGDFGPNSDGSFHASSSLTVKSGDEH HYCCIVQHAGLAQPLRVELESPAKSSVLV VGIVIGVLLLTAAVGGALLWRRMRSGLPAP WISLRGDDTGVLLPTPGEAQDADLKDVNV IPATA (SEQ ID NO: 102) | The signal peptide from the protein listed in the respective left column is shown below in CAPITAL LETTERS. The N-terminus of FimH is depicted in lower case. MGVPRPQPWALGLLLFLLPGSLGfacktangtaipigggs anvyvnlapvvnvgqnlvvdls (SEQ ID NO: 103) # Measure Position Value Cutoff signal peptide? max. C 24 0.664 max. Y 24 0.788 max. S 9 0.966 mean S 1-23 0.935 D 1-23 0.867 0.450 YES Name = Sequence SP = 'YES' Cleavage site between pos. 23 and 24: SLG-FA D = 0.867 D-cutoff = 0.450 Networks = SignalP-noTM |
| >sp\|P03420\|FUS_HRSVA Fusion glycoprotein FO OS = Human respiratory syncytial virus A (strain A2) OX = 11259 GN = F PE = 1 SV = 1 MELLILKANAITTILTAVTFCFASGQNITEEFYQ STCSAVSKGYLSALRTGWYTSVITIE LSNIKENKCNGTDAKVKLIKQELDKYKNAVTE LQLLMQSTPPTNNRARRELPRFMNYTLN NAKKTNVTLSKKRKRRFLGFLLGVGSAIASG VAVSKVLHLEGEVNKIKSALLSTNKAVVS LSNGVSVLTSKVLDLKNYIDKQLLPIVNKQSC SISNIETVIEFQQKNNRLLEITREFSVN AGVTTPVSTYMLTNSELLSLINDMPITNDQKK LMSNNVQIVRQQSYSIMSIIKEEVLAYV VQLPLYGVIDTPCWKLHTSPLCTTNTKEGSNI CLTRTDRGWYCDNAGSVSFFPQAETCKV QSNRVFCDTMNSLTLPSEINLCNVDIFNPKYD CKIMTSKTDVSSSVITSLGAIVSCYGKT KCTASNKNRGIIKTFSNGCDYVSNKGMDTVS VGNTLYYVNKQEGKSLYVKGEPIINFYDP LVFPSDEFDASISQVNEKINQSLAFIRKSDELL HNVNAGKSTTNIMITTIIIVIIVILLS LIAVGLLLYCKARSTPVTLSKDQLSGINNIAFS N (SEQ ID NO: 104) | The signal peptide from the protein listed in the respective left column is shown below in CAPITAL LETTERS. The N-terminus of FimH is depicted in lower case. MELLILKANAITTILTAVTFCFASGfacktangtaipigggsanvy vnlapvvnvgqnlvvdls (SEQ ID NO: 105) # Measure Position Value Cutoff signal peptide? max. C 28 0.188 max. Y 28 0.263 max. S 11 0.478 mean S 1-27 0.387 D 1-27 0.312 0.500 NO Name = Sequence SP = 'NO' D = 0.312 D-cutoff = 0.500 Networks = SignalP-TM |

TABLE 7-continued

| SignalP 4.1 used for predictions | Fusion sequence |
|---|---|
| >tr\|Q6FGW4\|Q6FGW4_HUMAN IL10 protein OS = *Homo sapiens* OX = 9606 GN = IL10 PE = 2 SV = 1 MHSSALLCCLVLLTGVRASPGQGTQSENSC THFPGNLPNMLRDLRDAFSRVKTFFQMKDQ LDNLLLKESLLEDFKGYLGCQALSEMIQFYLE EVMPQAENQDPDIKAHVNSLGENLKTLR LRLRRCHRFLPCENKSKAVEQVKNAFNKLQE KGIYKAMSEFDIFINYIEAYMTMKIRN (SEQ ID NO: 106) | The signal peptide from the protein listed in the respective left column is shown below in CAPITAL LETTERS. The N-terminus of FimH is depicted in lower case.<br>MHSSALLCCLVLLTGVRAfacktangtaipigggsanvyvnlapvv nvgqnlvvdls (SEQ ID NO: 107)<br># Measure Position Value Cutoff signal peptide?<br>max. C 19 0.726<br>max. Y 19 0.829<br>max. S 0.973<br>mean S 1-18 0.947<br>D 1-18 0.893 0.450 YES<br>Name = Sequence SP = 'YES' Cleavage site between pos. 18 and 19: VRA-FA D = 0.893 D-cutoff = 0.450<br>Networks = SignalP-noTM |
| >sp\|P03451\|HEMA_157A0 Hemagglutinin OS = Influenza A virus (strain A/Japan/305/1957 H2N2) OX = 387161 GN = HA PE = 1 SV = 1 MAIIYLILLFTAVRGDQICIGYHANNSTEKVDT NLERNVTVTHAKDILEKTHNGKLCKLN GIPPLELGDCSIAGWLLGNPECDRLLSVPEW SYIMEKENPRDGLCYPGSFNDYEELKHLL SSVKHFEKVKILPKDRWTQHTTTGGSRACAV SGNPSFFRNMVWLTKEGSDYPVAKGSYNN TSGEQMLIIWGVHHPIDETEQRTLYQNVGTY VSVGTSTLNKRSTPEIATRPKVNGQGGRM EFSWTLLDMWDTINFESTGNLIAPEYGFKISK RGSSGIMKTEGTLENCETKCQTPLGAIN TTLPFHNVHPLTIGECPKYVKSEKLVLATGLR NVPQIESRGLFGAIAGFIEGGWQGMVDG WYGYHHSNDQGSGYAADKESTQKAFDGITN KVNSVIEKMNTQFEAVGKEFGNLERRLENL NKRMEDGFLDVWTYNAELLVLMENERTLDF HDSNVKNLYDKVRMQLRDNVKELGNGCFEF YHKCDDECMNSVKNGTYDYPKYEEESKLNR NEIKGVKLSSMGVYQILAIYATVAGSLSLA IMMAGISFWMCSNGSLQCRICI (SEQ ID NO: 108) | The signal peptide from the protein listed in the respective left column is shown below in CAPITAL LETTERS. The N-terminus of FimH is depicted in lower case.<br>MAIIYLILLFTAVRGfacktangtaipigggsanvyvnlapvvnvgq nlvvdls (SEQ ID NO: 109)<br># Measure Position Value Cutoff signal peptide?<br>max. C 18 0.524<br>max. Y 18 0.690<br>max. S 1 0.951<br>mean S 1-17 0.895<br>D 1-17 0.800 0.450 YES<br>Name = Sequence SP = 'YES' Cleavage site between pos. 17 and 18: GFA-CK D = 0.800 D-cutoff = 0.450<br>Networks = SignalP-noTM |

Example 4: Mammalian Expression of Donor Strand Complement Fusion of FimH with the FimG Peptide Several linker lengths were tested. Recombinant expression with these linkers fusing the FimH to the N-terminal FimG peptide in both the wild type FimH and the migK signal peptide fused to F22 of FimH were prepared.

The FimH donor strand complement FimG constructs have also been shown to have robust expression in EXPI293 cells.

The preferred N-terminal processing (i.e., processing at F22 of SEQ ID NO: 1) was not shown with the native FimH leader peptide.

For the donor strand complement constructs, oligonucleotides were designed to produce base constructs in pcDNA3.1 (+) that contained the various linkers and FimG peptide. A unique BstEII site was incorporated at G294 V295 T296 residues, according to the numbering of SEQ ID NO: 1 of FimH. The same BstEII site was incorporated in the linkers to produce base constructs.

The base constructs for pSB01882-01895 were constructed. Primers were used to PCR amplify pcDNA3.1 (+) with ACCUPRIME PFX DNA Polymerase (Thermo Fisher), digest the PCR products with NdeI (in CMV promoter) and BamHI and cloned into pcDNA3.1 (+) that was digested with NdeI and BamHI and gel isolated to remove the fragment.

Another transient transfection was performed with pSB01877, 01878, 01879, 01880, 01885, and O1892 alongside EXPI293 cells as control.

Figure 3:
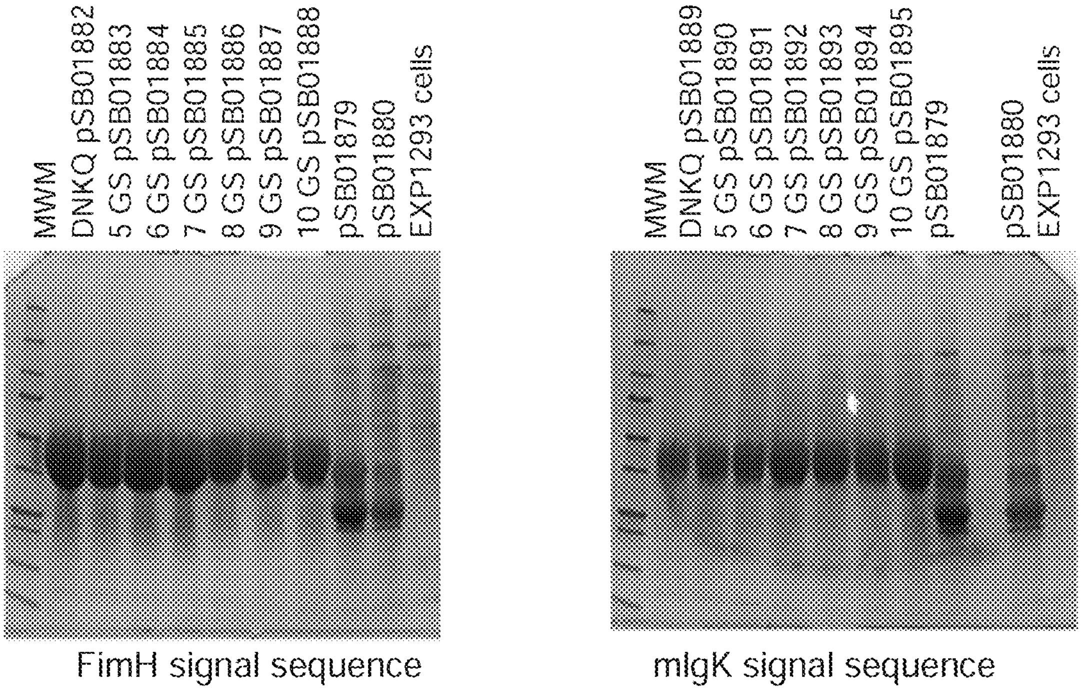
FIG. 3—depicts results from expression and purification.

Constructs pSB01882 through pSB01895 were used in transient transfection expression tests in EXPI293 cells from Thermo Fisher as per the manufacturer's protocol. See FIG. 3, which shows the results following expression in 20 mL EXPI293 cells, 72 hours, 10 ul of conditioned media loaded; high levels of expression observed; the FimH/FimC complex present following expression from pSB01879 & pSB01880 constructs; 20 ml conditioned media batch bound to Nickel Excel, 40 CV wash, elution in Imdidazole.

Figure 7:
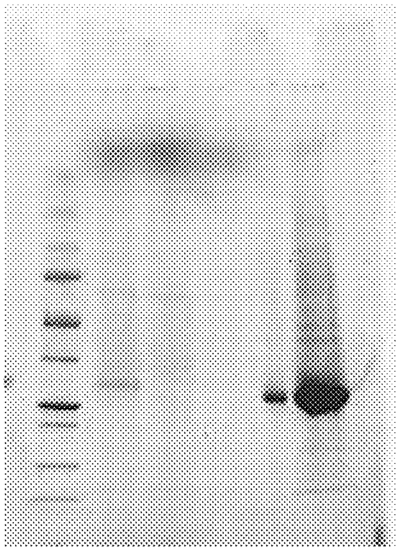
FIG. 7—depicts results from expression of pSB2198 FimH dscG Lock Mutant Construct.
Figure 8:
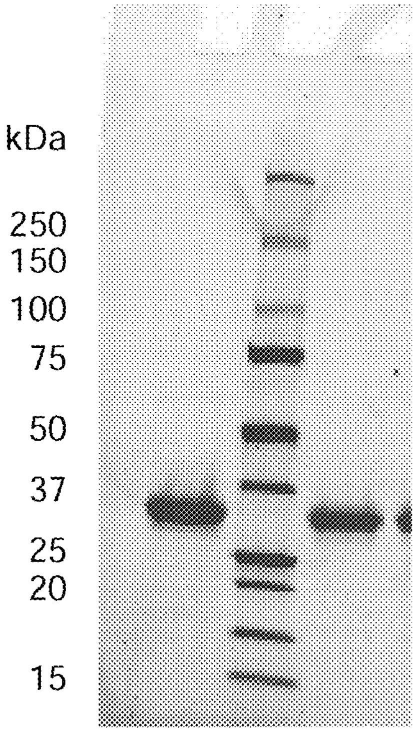
FIG. 8—depicts results from expression of pSB2307 FimH dscG wild type.

Additional FimH-donor strand complement constructs were prepared. See, for example, pSB02198, pSB02199, pSB02200, pSB02304, pSB02305, pSB02306, pSB02307, pSB02308 constructs. The expression of pSB2198 FimH dscG lock mutant construct is shown in FIG. 7. The pSB2198 FimH dscG Lock Mutant yielded 12 mg/L from transient expression.

According to Vi-CELL XR 2.04 (Beckman Coulter, Inc.), the following were observed (actual cell type used for expression was HEK cells):

TABLE 8

| Sample | Cell type parameter entered | Viability (%) | Total cells/ml (×10[6]) | Viable cells/ml (×10[6]) | Avg. diam. (microns) |
|---|---|---|---|---|---|
| EXPI P13 | CHO | 97.8 | 3.56 | 3.48 | 19.33 |
| pSB01882 | CHO | 90.9 | 4.98 | 4.53 | 17.39 |
| pSB01889 | CHO | 89.2 | 5.23 | 4.67 | 17.14 |
| cells | CHO | 88.9 | 6.66 | 5.92 | 16.91 |
| Expi Start | CHO | 93.7 | 3.35 | 3.14 | 18.72 |
| Samples at harvest ~85-86 hours after transfection: | | | | | |
| 1877 | SF-9 | 57.3 | 4.32 | 2.48 | 16.00 |
| pSB01878 | SF-9 | 57.6 | 3.88 | 2.24 | 15.49 |
| pSB01879 | SF-9 | 59.1 | 5.24 | 3.10 | 15.32 |
| pSB01880 | SF-9 | 56.8 | 5.97 | 3.39 | 15.10 |
| pSB01885 | SF-9 | 63.1 | 6.95 | 4.39 | 16.08 |
| pSB01892 | SF-9 | 56.2 | 4.89 | 2.75 | 15.91 |
| 187772 | SF-9 | 79.5 | 5.14 | 4.09 | 18.36 |
| 187872 | SF-9 | 72.6 | 5.26 | 3.81 | 17.35 |
| expicont | SF-9 | 75.5 | 4.95 | 3.74 | 18.62 |

Example 5: Molecular Weight Fragments are with Processed Signal Peptide

TABLE 9 pSB01877 FimH J96 ELL41155.1 [*E. coli* J96] Analysis

| Analysis | Fragment 15-189 | Entire Protein |
|---|---|---|
| Length | 175 aa | 189 aa |
| Molecular Weight | 18948.34 | 20522.36 m.w. |
| 1 microgram= | 52.775 pMoles | 48.727 pMoles |
| Molecular Extinction Coefficient | 35800 | 35800 |
| 1 A(280) corr. to: | 0.53 mg/ml | 0.57 mg/ml |
| A[280] of 1 mg/ml | 1.89 AU | 1.74 AU |
| Isoelectric Point | 6.81 | 8 |
| Charge at pH 7 | −0.48 | 1.52 |

pSB01878 FimH J96 ELL41155.1 [*E. coli* J96] Analysis

| Analysis | Fragment 21-188 | Entire Protein |
|---|---|---|
| Length | 168 aa | 188 aa |
| Molecular Weight | 18117.48 | 20344.08 m.w. |
| 1 microgram= | 55.195 pMoles | 49.154 pMoles |
| Molecular Extinction Coefficient | 24420 | 35800 |
| 1 A(280) corr. to: | 0.74 mg/ml | 0.57 mg/ml |
| A[280] of 1 mg/ml | 1.35 AU | 1.76 AU |
| Isoelectric Point | 6.81 | 6.29 |
| Charge at pH 7 | −0.48 | −2.47 |

pSB01885 FimH J96 ELL41155.1 [*E. coli* J96] Analysis

| Analysis | Fragment 20-331 | Entire Protein |
|---|---|---|
| Length | 312 aa | 331 aa |
| Molecular Weight | 32406.19 | 34537.79 m.w. |
| 1 microgram= | 30.858 pMoles | 28.954 pMoles |
| Molecular Extinction Coefficient | 38030 | 43720 |
| 1 A(280) corr. to: | 0.85 mg/ml | 0.79 mg/ml |
| A[280] of 1 mg/ml | 1.17 AU | 1.27 AU |
| Isoelectric Point | 7.25 | 8.32 |
| Charge at pH 7 | 0.5 | 2.5 |

TABLE 9-continued pSB01892 FimH J96 ELL41155.1 [*E. coli* J96] Analysis

| Analysis | Fragment 21-330 | Entire Protein |
|---|---|---|
| Length | 310 aa | 330 aa |
| Molecular Weight | 32132.91 | 34359.51 m.w. |
| 1 microgram= | 31.121 pMoles | 29.104 pMoles |
| Molecular Extinction Coefficient | 32340 | 43720 |
| 1 A(280) corr. to: | 0.99 mg/ml | 0.79 mg/ml |
| A[280] of 1 mg/ml | 1.01 AU | 1.27 AU |
| Isoelectric Point | 7.25 | 6.51 |
| Charge at pH 7 | 0.5 | −1.49 |

pSB01893 FimH J96 ELL41155.1 [*E. coli* J96] Analysis

| Analysis | Entire Protein |
|---|---|
| Length | 331 aa |
| Molecular Weight | 34416.56 |
| 1 microgram= | 29.056 pMoles |
| Molecular Extinction Coefficient | 43720 |
| 1 A(280) corr. to: | 0.79 mg/ml |
| A[280] of 1 mg/ml | 1.27 AU |
| Isoelectric Point | 6.51 |
| Charge at pH 7 | −1.49 |

pSB01894 FimH J96 ELL41155.1 [*E. coli* J96] Analysis

| Analysis | Fragment 21-332 | Entire Protein |
|---|---|---|
| Length | 312 aa | 332 aa |
| Molecular Weight | 32247.01 | 34473.61 m.w. |
| 1 microgram= | 31.011 pMoles | 29.008 pMoles |
| Molecular Extinction Coefficient | 32340 | 43720 |
| 1 A(280) corr. to: | 1.00 mg/ml | 0.79 mg/ml |
| A[280] of 1 mg/ml | 1.00 AU | 1.27 AU |
| Isoelectric Point | 7.25 | 6.51 |
| Charge at pH 7 | 0.5 | −1.49 |

pSB02083

| Analysis | Fragment 21-188 | Entire Protein |
|---|---|---|
| Length | 168 aa | 188 aa |
| Molecular Weight | 18063.42 | 20290.02 m.w. |
| 1 microgram= | 55.361 pMoles | 49.285 pMoles |
| Molar Extinction coefficient | 24420 | 35800 |

TABLE 9-continued

| | | |
|---|---|---|
| 1 A(280) corr. to: | 0.74 mg/ml | 0.57 mg/ml |
| A[280] of 1 mg/ml | 1.35 AU | 1.76 AU |
| Isoelectric Point | 6.81 | 6.29 |
| Charge at pH 7 | −0.48 | −2.47 |

pSB02198

| | |
|---|---|
| | Sample<br>FimH PSB 2198<br>1.45 mg/ml<br>5 ml<br>20190918 SS |
| Volume (mls) | 25 |
| Conc. (mg/ml) | 1.45 |
| Total Amount (mgs) | 36.25 |
| Aliquots | 5 ml × 5 |
| Yield | 12 mg/L |
| Buffer: 50 mM TrisCl pH 8.0, 300 mM NaCl | |

pSB02307

| | |
|---|---|
| | Sample Name<br>Fim H 2307<br>0.48 mg/ml<br>5 ml<br>20190918 SS |
| Volume (mls) | 22.5 mls |
| Conc. (mg/ml) | 0.48 mg/ml |
| Total Amount (mgs) | 10.8 mg |
| Yield | 3.6 mg/L |
| Buffer: 50 mM TrisCl pH 8.0, 300 mM NaCl | |

Example 6: The N-Terminal α-Amino Group of Phe1 (According to the Numbering of SEQ ID NO: 2) in the FimH Mature Protein Provides Critical Polar Recognition for D-Mannose Without being bound by theory or mechanism, it is suggested that the correct signal peptide cleavage just ahead of Phe1 (according to the numbering of SEQ ID NO: 2) of the FimH mature protein is important to express functional FimH protein. Changes at the N-terminal α-amino group, such as by adding an amino acid at the N-terminus ahead of Phe1 of the FimH protein can abolish the hydrogen bond interactions with O2-, O5- and O6-atoms of the D-mannose and introduce steric repulsion with D-mannose, thereby blocking mannose binding. This is confirmed with our experimental observation that adding an extra Gly residue ahead of the Phe1 of SEQ ID NO: 2 leads to no detection of mannose binding.

Following an analysis of the crystal structure of FimH bound to D-mannose, the following were observed: The N-Terminal a-amino group of Phe1 along with sidechains of Asp54 of the FimH according to the numbering of SEQ ID NO: 2 and Gln133 of the FimH according to the numbering of SEQ ID NO: 2 provide critical polar recognition motifs for D-mannose, and mutations and changes of these polar interactions lead to no mannose binding.

Example 7: The Sidechain of Phe1 in FimH does not Interact Directly with D-Mannose but is Rather Buried Inside of FimH, Suggesting that Phe1 can be Replaced by Other Residues, e.g. Aliphatic Hydrophobic Residues (Lle, Leu, or Val)

Analysis of crystal structures of FimH in complex with D-mannose and its analogs (e.g. PDB ID: 1QUN) shows that the sidechain of Phe1 (according to the numbering of SEQ ID NO: 2) does not interact directly with D-mannose but rather stabilizes the binding pocket by stacking its aromatic rings with the sidechains of Val56, Tyr95, Gln133 and Phe144 (according to the numbering of SEQ ID NO: 2).

Figure 11:
FIG. 11—depicts computational mutagenesis scanning of Phe1 with other amino acids having aliphatic hydrophobic sidechains, e.g. lle, Leu and Val, that may stabilize the FimH protein and accommodate mannose binding.

Alternative N-terminal residue instead of Phe may stabilize the FimH protein, accommodate mannose binding, and allow correct signal peptide cleavage. Such residues may be identified by suitable method known in the art, such as by visual inspection of a crystal structure of FimH, or more quantitative selection using computational protein design software, such as BioLuminate™ [BioLuminate, Schrodinger LLC, New York, 2017], Discovery Studio™ [Discovery Studio Modeling Environment, Dassault Systèmes, San Diego, 2017], MOET [Molecular Operating Environment, Chemical Computing Group Inc., Montreal, 2017], and Rosetta™ [Rosetta, University of Washington, Seattle, 2017]. An illustrative example is shown FIG. 9A-9C. The replacement amino acids can be aliphatic hydrophobic amino acids (e.g. Ile, Leu and Val). FIG. 11 depicts computational mutagenesis scanning of Phe1 with other amino acids having aliphatic hydrophobic sidechains, e.g. Ile, Leu and Val, which may stabilize the FimH protein and accommodate mannose binding.

Example 8: Mutations of Asn7 According to the Numbering of SEQ ID NO: 2 in a FimH Protein can Remove the Putative N-Glycosylation Site and Prevent Deamidation, without Impacting Mannose, mAb21, or mAb475 Binding Over-expression of secreted *E. coli* FimH from mammalian cell lines may lead to N-linked glycosylation at residue Asn7, according to the numbering of SEQ ID NO: 2. In addition, residue Asn7 is solvent exposed and followed with a Gly residue, making it very prone to deamidation.

Analysis of crystal structures of FimH in complex with D-mannose and its analogs (e.g. PDB ID: 1QUN) indicates that Asn7 is more than 20 Å away from the mannose binding site and a mutation at the site should not impact mannose binding. Thus, mutations of Asn7 to other amino acids (e.g. Ser, Asp and Gln) can effectively remove the putative N-glycosylation site and prevent deamidation.

Example 9: *E. coli* and *S. enterica* Strains

Clinical strains and derivatives are listed in Table 10. Additional reference strains included: O25K5H1, a clinical O25a serotype strain; and *S. enterica* serovar *Typhimurium* strain LT2.

Gene knockouts in *E. coli* strains removing the targeted open-reading frame but leaving a short scar sequence were constructed.

The hydrolyzed O-antigen chain and core sugars are indicated subsequently as O-Polysaccharide (OPS) for simplicity.

TABLE 10

| E. coli Strains | | | |
|---|---|---|---|
| Strain | Strain Alias | Genotype | Serotype |
| GAR2401 | PFEEC0100 | wt (blood isolate) | O25b |
| '2401ΔwzzB | — | ΔwzzB | O25b |
| '2401ΔAraAΔ(OPS) | — | ΔAraA Δ(rflB-wzzB) | OPS- |
| O25K5H1 | PFEEC0101 | wt | O25a |
| O25K5H1ΔwzzB | | ΔwzzB | O25a |
| BD559 | — | W3110 ΔAraA ΔfhuA ΔrecA | OPS- |
| BD559ΔwzzB | — | W3110ΔAraA ΔfhuA ΔrecAΔwzzB | OPS- |
| BD559Δ(OPS) | — | BD559 Δ(rflB-wzzB) | OPS- |
| GAR2831 | PFEEC0102 | wt (blood isolate) | O25b |
| GAR865 | PFEEC0103 | wt (blood isolate) | O2 |
| GAR868 | PFEEC0104 | wt (blood isolate) | O2 |
| GAR869 | PFEEC0105 | wt (blood isolate) | O15 |
| GAR872 | PFEEC0106 | wt (blood isolate) | O1 |
| GAR878 | PFEEC0107 | wt (blood isolate) | O75 |
| GAR896 | PFEEC0108 | wt (blood isolate) | O15 |
| GAR1902 | PFEEC0109 | wt (blood isolate) | O6 |
| Atlas187913 | PFEEC0068 | wt (blood isolate) | O25b |
| *Salmonella enterica* serovar *Typhimurium* strain LT2 | — | wt | N/A |

Example 10: Oligonucleotide Primers for wzzB, fepE and O-Antigen Gene Cluster Cloning

TABLE 11

| Oligonucleotide Primers | | |
|---|---|---|
| Name | Primer Sequence | Comments |
| LT2wzzB_S | GAAGCAAACCGTACGCGTAAAG (SEQ ID NO: 40) | based on Genbank GCA 000006945.2 *Salmonella enterica serovar Typhimurium* strain LT2 |
| LT2wzzB_AS | CGACCAGCTCTTACACGGCG (SEQ ID NO: 41) | |
| O25bFepE_S | GAAATAGGACCACTAATAAATACACAAATTAATAAC (SEQ ID NO: 42) | Based on Genbank GCA_000285655.3 O25b EC958 strain ST131 assembly and O25b GAR2401 WGS data |
| O25bFepE_A | ATAATTGACGATCCGGTTGCC (SEQ ID NO: 43) | |
| wzzB P1_S | GCTATTTACGCCCTGATTGTCTTTTGT (SEQ ID NO: 44) | based on *E. coli* K-12 strain sequence, Genbank MG1655 NC_000913.3 or W3110 assembly GCA_000010245.1 |
| wzzB P2_AS | ATTGAGAACCTGCGTAAACGGC (SEQ ID NO: 45) | |
| wzzB P3_S | TGAAGAGCGGTTCAGATAACTTCC (SEQ ID NO: 46) (UDP-glucose-6-dehydrogenase) | |
| wzzB P4_AS | CGATCCGGAAACCTCCTACAC (SEQ ID NO: 47) (Phosphoribosyl-AMP cyclohydrolase/ Phosphoribosyl-ATP pyrophosphohydrolase) | |
| O157 FepE_S | GATTATTCGCGCAACGCTAAACAGAT (SEQ ID NO: 48) | *E. coli* O157 fepE (based on Genbank EDL933 strain GCA_000732965.1) |
| O157 FepE_AS | TGATCATTGACGATCCGGTAGCC (SEQ ID NO: 49) | |
| pBAD33_adaptor_S | CGGTAGCTGTAAAGCCAGGGGCGGTAGCGTGGTTTAAACCCAAGCAACAGATCGGCGTCGTCGGTATGGA (SEQ ID NO: 50) | Adaptor has central PmeI site and homology to conserved 5' OAg operon promoter and 3' gnd gene sequences |
| pBAD33_adaptor_AS | AGCTTCCATACCGACGACGCCGATCTGTTGCTTGGGTTTAAACCACGCTACCGCCCCTGGCTTTACAGCTACCGAGCT (SEQ ID NO: 51) | |
| JUMPSTART_r | GGTAGCTGTAAAGCCAGGGGCGGTAGCGTG (SEQ ID NO: 52) | Universal Jumpstart (OAg operon promoter) |
| gnd_f | CCATACCGACGACGCCGATCTGTTGCTTGG (SEQ ID NO: 53) | Universal 3' OAg (gnd) operon antisense primer |

Example 11: Plasmids

Figure 12A:
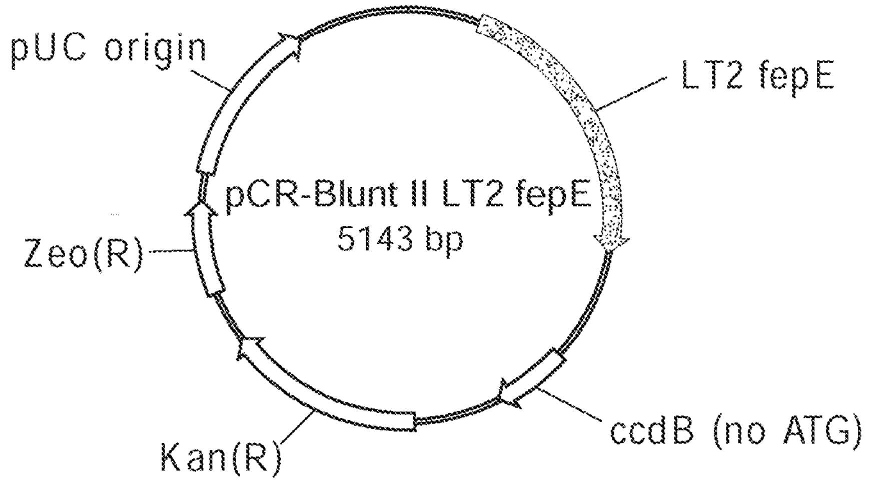
FIG. 12A-12B—depict plasmids: a pUC replicon plasmid, 500-700× copies per cell, Chain length regulator (FIG. 12A); and P15a replicon plasmid, 10-12× copies per cell, O-antigen operon (FIG. 12B).
Figure 12B:
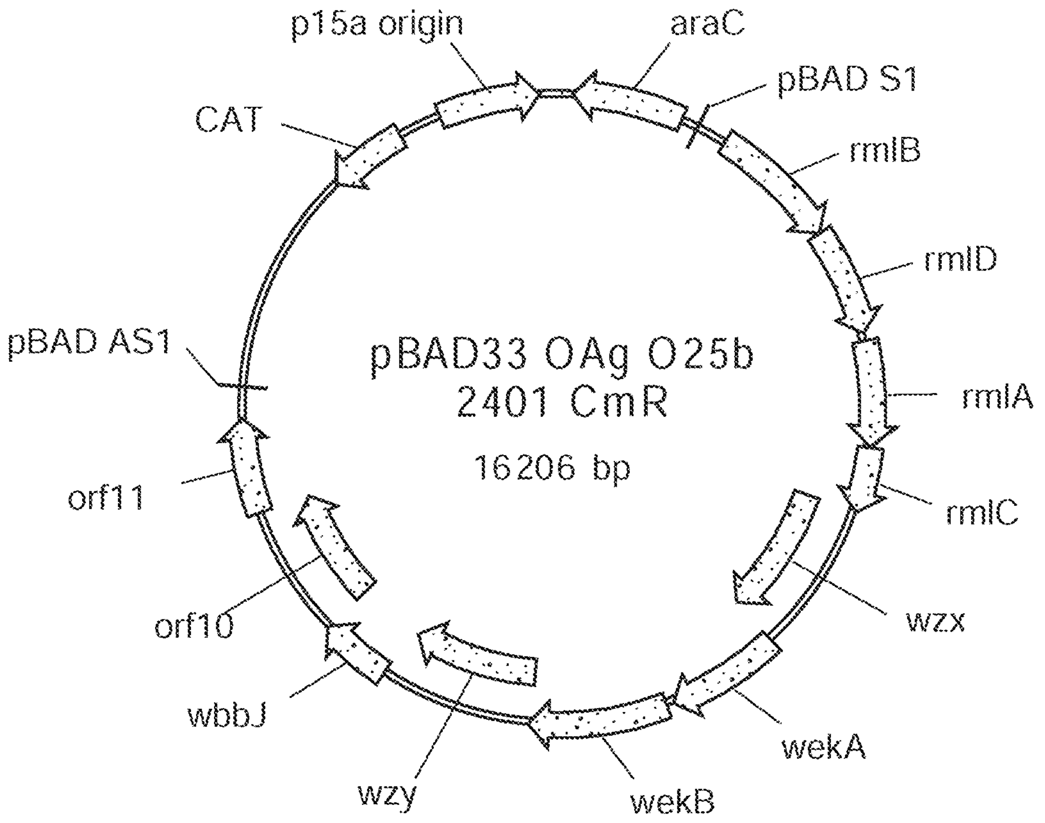

Plasmid vectors and subciones are listed in Table 12. PCR fragments harboring various *E. coli* and *Salmonella* wzzB and fepE genes were amplified from purified genomic DNA and subcloned into the high copy number plasmid provided in the Invitrogen PCR®Blunt cloning kit FIG. 12A-12B. This plasmid is based on the pUC replicon. Primers P3 and P4 were used to amplify *E. coli* wzzB genes with their native promoter, and are designed to bind to regions in proximal and distal genes encoding UDP-glucose-6-dehydrogenase and phosphoribosyladenine nucleotide hydrolase respectively (annotated in Genbank MG1655 NC_000913.3). A PCR fragment containing *Salmonella* fepE gene and promoter were amplified using primers previously described. Analogous *E. coli* fepE primers were designed based on available Genbank genome sequences or whole genome data generated internally (in case of GAR2401 and O25K5H1). Low copy number plasmid pBAD33 was used to express O-antigen biosynthetic genes under control of the arabinose promoter. The plasmid was first modified to facilitate cloning (via Gibson method) of long PCR fragments amplified using universal primers homologous to the 5' promoter and 3' 6-phosphogluconate dehydrogenase (gnd) gene Table 12. The pBAD33 subclone containing the O25b biosynthetic operon is illustrated in FIG. 12A-12B.

TABLE 12

Plasmids

| Name | Replicon | Resistance marker | Comments |
|---|---|---|---|
| PCR®Blunt II TOPO | pUC | KanR | Invitrogen PCR cloning vector |
| pBAD33 | P15a | CamR | Arabinose inducible vector |
| pBAD33-OAg | P15a | CamR | OAg operon Gibson cloning vector |
| pBAD33-O25b | P15a | CamR | O25b OAg expression plasmid |
| pBAD33-O21 | P15a | CamR | O21 OAg expression plasmid |
| pBAD33-O16 | P15a | CamR | O16 OAg expression plasmid |
| pBAD33-O75 | P15a | CamR | O75 OAg expression plasmid |
| pBAD33-O1 | P15a | CamR | O1 OAg expression plasmid |
| pBAD33-O2 | P15a | CamR | O2 OAg expression plasmid |
| pTOPO-O25b 2401 wzzB | pUC | KanR | GAR 2401 gDNA template |
| pTOPO-O25b 2401 fepE | pUC | KanR | |
| pTOPO-K12 wzzB | pUC | KanR | *E. coli* K-12 strain gDNA template |
| pTOPO-O25a wzzB | pUC | KanR | *E. coli* O25a strain O25K5H1 |
| pTOPO-O25a fepE | pUC | KanR | gDNA template |
| pTOPO-*Salmonella* LT2 wzzB | pUC | KanR | *Salmonella enterica* serovar *Typhimurium* strain LT2 gDNA |
| pTOPO-*Salmonella* LT2 fepE | pUC | KanR | template |
| pTOPO-O25a ETEC wzzB | pUC | KanR | O25a ETEC strain gDNA |
| pTOPO-O25a ETEC fepE | pUC | KanR | purchased from ATCC (“NR-5” E2539-C1) |
| pTOPO-O157fepE | pUC | KanR | O157:H7:K- Shigella toxin strain gDNA purchased from ATCC (EDL933 #43895D-5) |

Example 12: O-Antigen Purification

The fermentation broth was treated with acetic acid to a final concentration of 1-2% (final pH of 4.1). The extraction of OAg and delipidation were achieved by heating the acid treated broth to 100° C. for 2 hours. At the end of the acid hydrolysis, the batch was cooled to ambient temperature and 14% $NH_4OH$ was added to a final pH of 6.1. The neutralized broth was centrifuged and the centrate was collected. To the centrate was added $CaCl_2$) in sodium phosphate and the resulting slurry was incubated for 30 mins at room temperature. The solids were removed by centrifugation and the centrate was concentrated 12-fold using a 10 kDa membrane, followed by two diafiltrations against water. The retentate which contained OAg was then purified using a carbon filter. The carbon filtrate was diluted 1:1 (v/v) with 4.0M ammonium sulfate. The final ammonium sulfate concentration was 2M. The ammonium sulfate treated carbon filtrate was further purified using a membrane with 2M ammonium sulfate as the running buffer. The OAg was collected in the flow through. For the long OAg the HIC filtrate was concentrated and then buffer exchanged against water (20 diavolumes) using a 5 kDa membrane. For the short (native) OAg polysaccharide, the MWCO was further reduced to enhance yield.

Example 13: Conjugation of 025b Long O-Antigen to $CRM_{197}$

The first set of long chain O25b polysaccharide-$CRM_{197}$ conjugates were produced using periodate oxidation followed by conjugation using reductive amination chemistry (RAC) (Table 14). Conjugate variants with three activation levels (low, medium and high) by varying the oxidation levels. Conjugates were produced by reacting the lyophilized activated polysaccharides with lyophilized $CRM_{197}$, reconstituted in DMSO medium, using sodium cyanoborohydride as the reducing agent. Conjugation reactions were carried out at 23° C. for 24 hrs, followed by capping using sodium borohydride for 3 hrs. Following the conjugation quenching step, conjugates were purified by ultrafiltration/diafiltration with 100K MWCO regenerated cellulose membrane, using 5 mM Succinate/0.9% NaCl, pH 6.0. Final filtration of the conjugates were performed using a 0.22 μm membrane.

Unless expressly stated otherwise, the conjugates disclosed throughout the following Examples include a core saccharide moiety.

1.1. Long O-Antigen Expression Conferred by Heterologous Polymerase Chain Length Regulators Initial *E. coli* strain construction focused on the O25 serotype. Goal was to overexpress heterologous wzzB or fepE genes to see if they confer longer chain length in O25 wzzB knockout strains. First, blood isolates were screened by PCR to identify strains of the O25a and O25b subtype. Next, strains were screened for sensitivity to ampicilin. A single ampicilin-sensitive O25b isolate GAR2401 was identified into which a wzzB deletion was introduced. Similarly, a wzzB deletion was made in O25a strain O25K5H1. For genetic complementation of these mutations, wzzB genes from GAR 2401 and O25K5H1 were subcloned into the high copy PCR-Blunt II cloning vector and introduced into both strains by electroporation. Additional wzzB genes from *E. coli* K-12 and *S. enterica* serovar *Typhimurium* LT2 were similarly cloned and transferred; likewise fepE genes from *E. coli* O25K5H1, GAR 2401, O25a ETEC NR-5, O157: H7: K- and *S. enterica* serovar *Typhimurium* LT2.

Figure 13A:
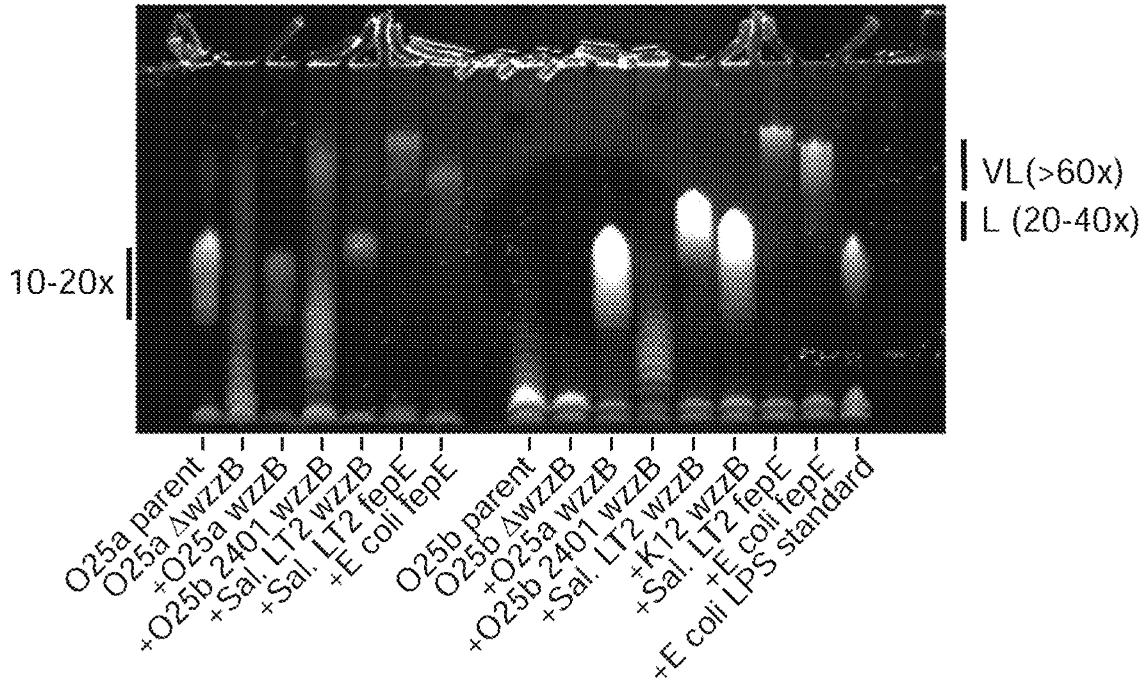
FIG. 13A-13B—depict modulation of O-antigen chain length in serotype O25a and O25b strains by plasmid-based expression of heterologous wzzB and fepE chain length regulators. Genetic complementation of LPS expression in plasmid transformants of wzzB knockout strains O25K5H1 (O25a) and GAR2401 (O25b) is shown. On the left side of FIG. 13A, LPS profiles of plasmid transformants of O25a O25K5HΔwzzB are shown; and on the right, analogous profiles of O25b GAR 2401ΔwzzB transformants. An immunoblot of a replicate gel probed with 025-specific sera (Statens Serum Institut) is shown in FIG. 13B. O25a ΔwxxB (Knock out) background associated with Lanes 1-7; O25b 2401 ΔwzzB (Knock out) background associated with Lanes 8-15.
Figure 13B:
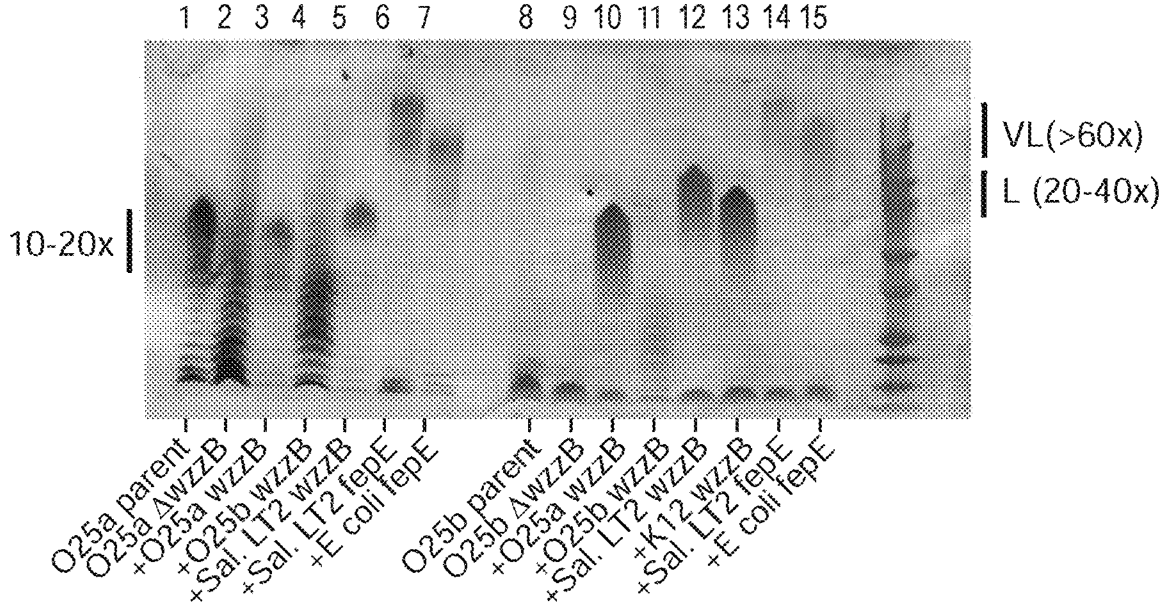

Bacteria were grown overnight in LB medium and LPS was extracted with phenol, resolved by SDS PAGE (4-12% acrylamide) and stained. Each well of the gel was loaded with LPS extracted from the same number of bacterial cells (approximately 2 $OD_{600}$ units). Size of LPS was estimated from an internal native *E. coli* LPS standard and by counting the ladder discernable from a subset of samples showing a broad distribution of chain lengths (differing by one repeat unit). On the left side of FIG. 13A, LPS profiles of plasmid transformants of O25a O25K5HΔwzzB are shown; and on the right, analogous profiles of 025b GAR 2401ΔwzzB transformants. An immunoblot of a replicate gel probed with O25-specific sera is shown in FIG. 13B.

Results from this experiment show that introduction of the homologous wzzB gene into the *E. coli* O25aΔwzzB host restores expression of short O25 LPS (10-20×), as does the *Salmonella* LT2 wzzB. Introduction of the O25b wzzB gene from GAR2401 does not, suggesting the WzzB enzyme from this strain is defective. A comparison of *E. coli* WzzB amino acid sequences suggests that A210E and P253S substitutions may be responsible. Significantly, *Salmonella* LT2 fepE and *E. coli* fepE from O25a O25K5H1 conferred the ability to express very long (VL) OAg LPS, with the *Salmonella* LT2 fepE resulting in OAg exceeding in size that conferred by *E. coli* fepE.

Figure 14:
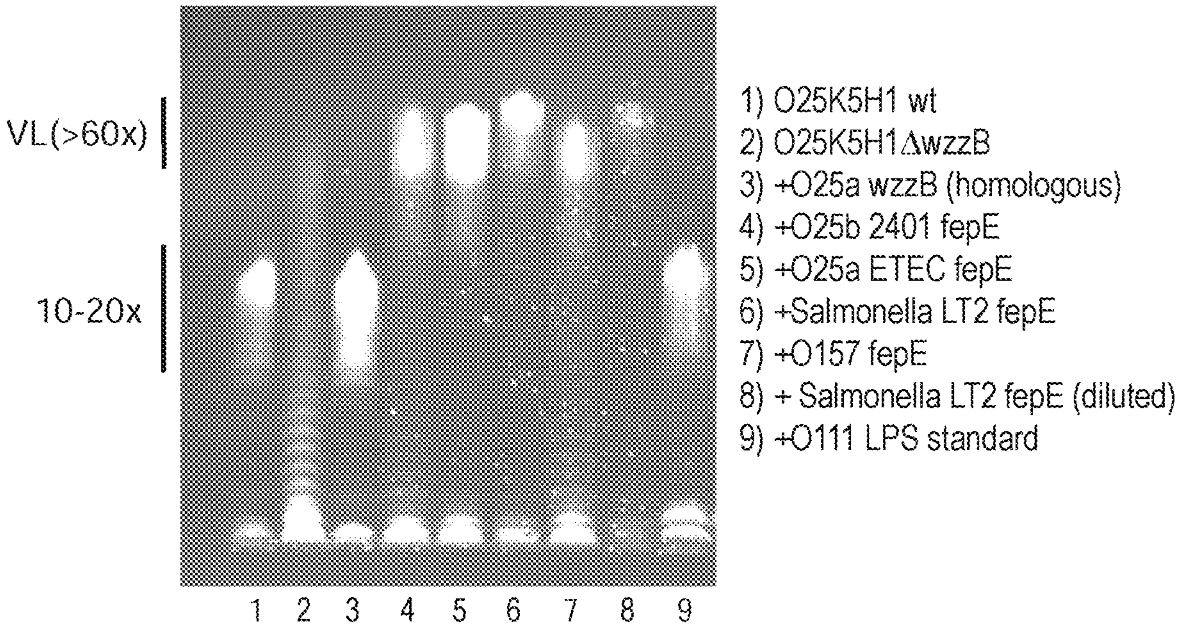
FIG. 14—depicts long chain O-antigen expression conferred by *E. coli* and *Salmonella* fepE plasmids in host O25K5H1ΔwzzB.

A similar pattern of expression was observed with GAR2401ΔwzzB transformants: *E. coli* O25a or K12 strain wzzB restored ability to produce short LPS. The *Salmonella* LT2 fepE generated the longest LPS, the *E. coli* fepE a slightly shorter LPS, while the *Salmonella* LT2 wzzB yielded an intermediate sized long LPS (L). The ability of other *E. coli* fepE genes to produce very long LPS was assessed in a separate experiment with transformants of *E. coli* O25aΔwzzB. The fepE genes from GAR2401, an O25a ETEC strain and an O157 *Shigella* toxin producing strain also conferred the ability to produce very long LPS, but not as long as the LPS generated with the *Salmonella* LT2 fepE (FIG. 14).

Figure 15:
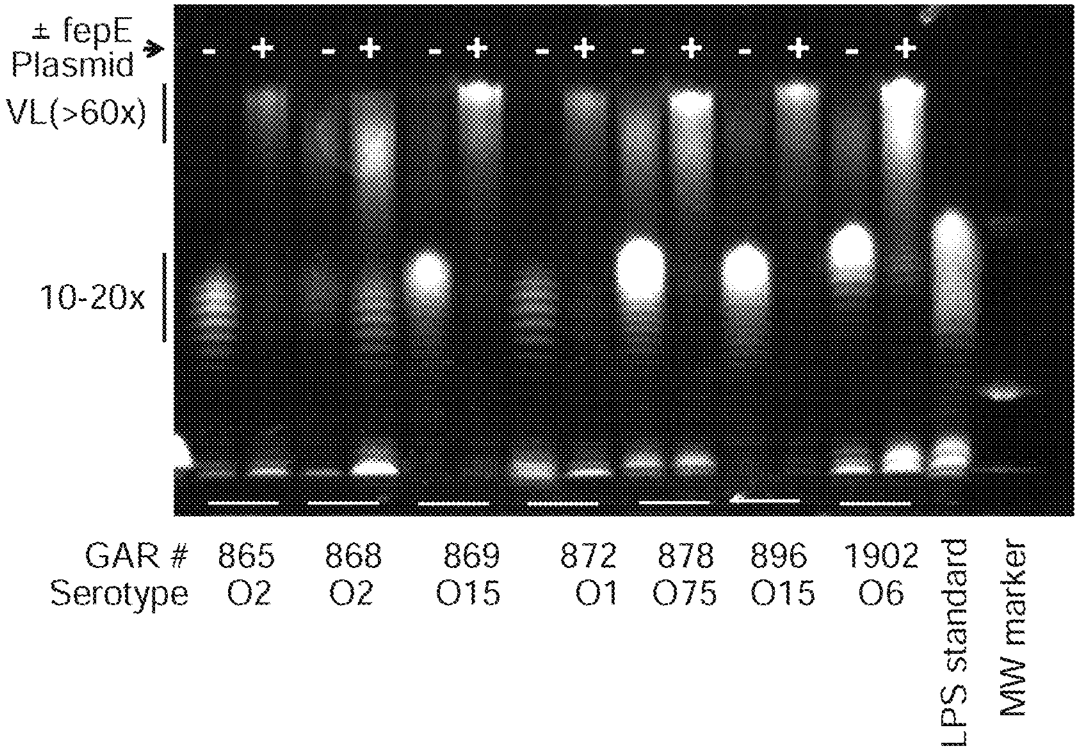
FIG. 15—depicts that *Salmonella* fepE expression generates Long O-antigen LPS in a variety of clinical isolates.

Having established in serotype O25a and O25b strains that *Salmonella* LT2 fepE generates the longest LPS of the polymerase regulators evaluated, we next sought to determine whether it would also produce very long LPS in other *E. coli* serotypes. Wild-type bacteremia isolates of serotype O1, 02, 06, 015 and 075 were transformed with the *Salmonella* fepE plasmid and LPS extracted. The results shown in FIG. 15 confirm that *Salmonella* fepE can confer the ability to make very long LPS in other prevalent serotypes associated with blood-infections. Results also show that plasmid-based expression of *Salmonella* fepE appears to override the control of chain length normally exerted by endogenous wzzB in these strains.

1.2. Plasmid-Based Expression of O-Antigens in a Common *E. coli* Host Strain.

Figure 16A:
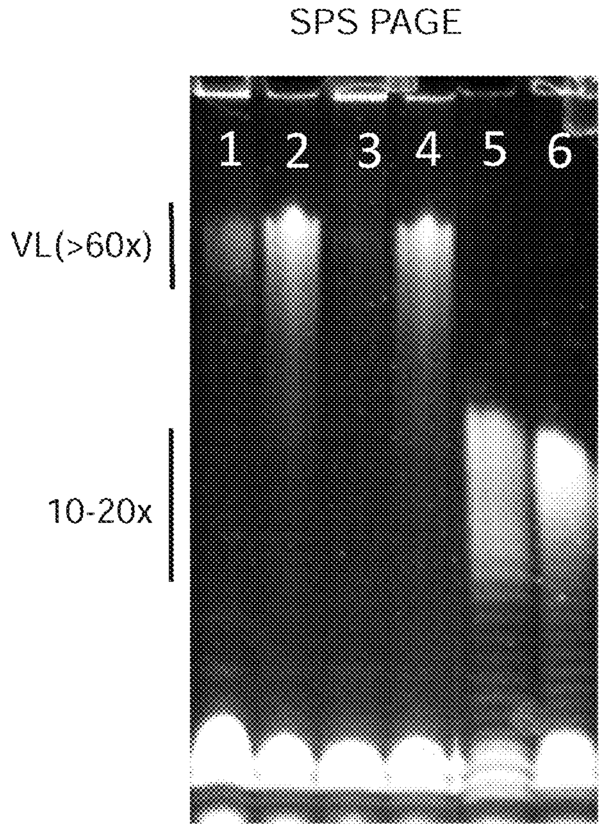
FIG. 16A-16B—depict plasmid-mediated Arabinose-inducible Expression of O25b Long O-antigen LPS in O25b O-antigen knock-out host strain. Results from an SPS PAGE are shown in FIG. 16A and results from an 025 Immuno-Blot are shown in FIG. 16B, wherein Lane 1 is from Clone 1, no arabinose; Lane 2 is from Clone 1, 0.2% arabinose; Lane 3 is from Clone 9, no Arabinose; Lane 4 is from Clone 9, 0.2% Arabinose; Lane 5 is from 055 *E. coli* LPS Standard; and Lane 6 is from 0111 *E. coli* LPS Standard, in both FIG. 16A and in FIG. 16B.
Figure 16B:

From the perspective of bioprocess development, the ability to produce O-antigens of different serotypes in a common *E. coli* host instead of multiple strains would greatly simplify the manufacturing of individual antigens. To this end, O-antigen gene clusters from different serotypes were amplified by PCR and cloned into a low-copy number plasmid (pBAD33) under control of an arabinose regulated promoter. This plasmid is compatible (can coexist) with the *Salmonella* LT2 fepE plasmid in *E. coli* as it harbors a different (p15a) replicon and different selectable marker (chloramphenicol vs kanamycin). In a first experiment, a pBAD33 O25b operon plasmid subclone was cotransfected with the *Salmonella* LT2 fepE plasmid into GAR2401ΔwzzB and transformants grown in the presence or absence of 0.2% arabinose. Results shown in FIG. 16A-16B demonstrated that very long O-antigen LPS was produced in an arabinose-dependent manner.

Figure 17:
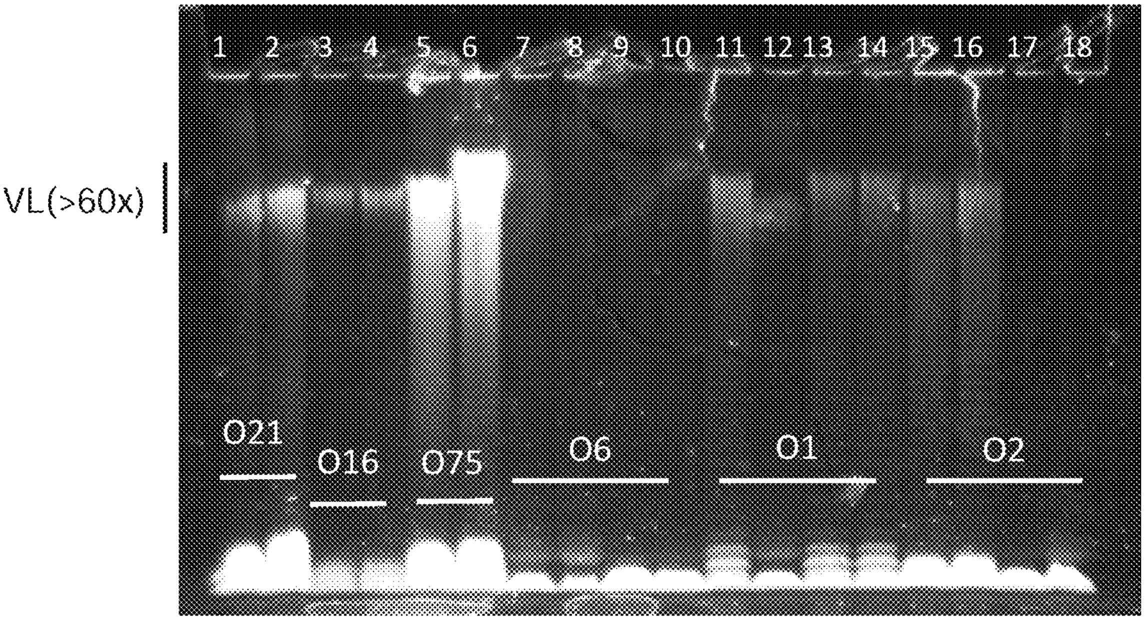
FIG. 17—depicts plasmid-mediated Arabinose-inducible Expression of Long O-antigen LPS in common host strain.

O-antigen gene clusters cloned from other serotypes were similarly evaluated and the results shown in FIG. 17. Co-expression of *Salmonella* LT2 fepE and pBAD33-OAg plasmids resulted in detectable long chain LPS corresponding to O1, O2 (for two out of four clones), O16, O21 and O75 serotypes. For unknown reasons, the pBAD33-O6 plasmid failed to yield detectable LPS in all four isolates tested. Although expression level was variable, results show that expression of long chain O-antigens in a common host is feasible. However, in some cases further optimization to improve expression may be required, for example by modification of plasmid promoter sequences.

Figure 18:
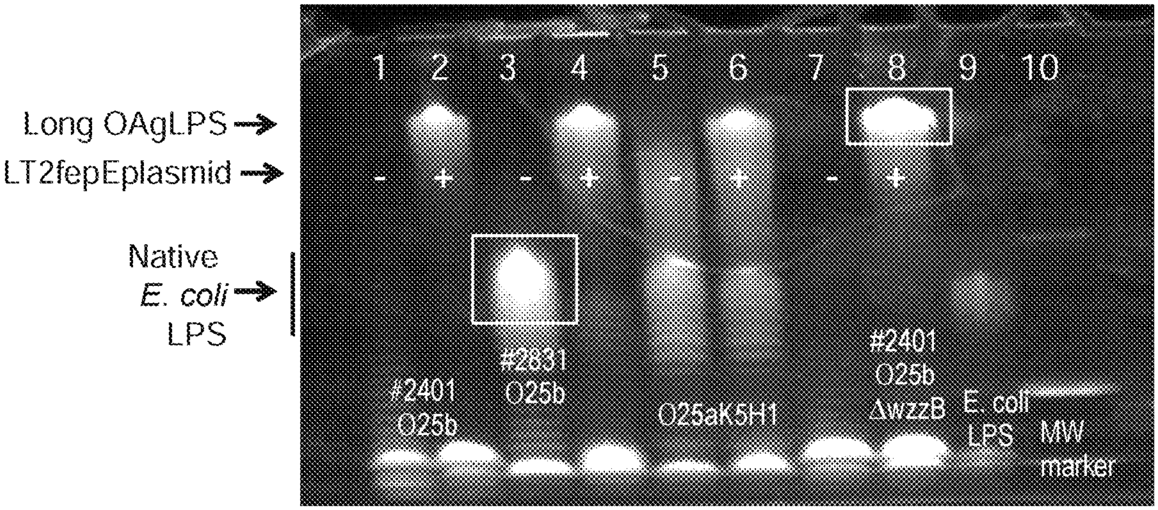
FIG. 18—depicts expression of 025 O-antigen LPS in Exploratory Bioprocess strains.
Figure 19A:
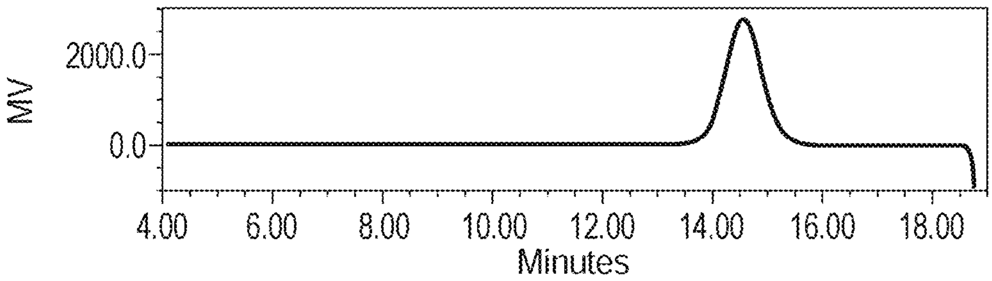
FIG. 19A-19B—depict SEC profiles and properties of short (FIG. 19A, Strain 1 O25b wt 2831) and long O25b O-antigens (FIG. 19B, Strain 2 025b 2401ΔwzzB/LT2 FepE) purified from strains GAR2831 and '2401ΔwzzB/fepE.
Figure 19B:
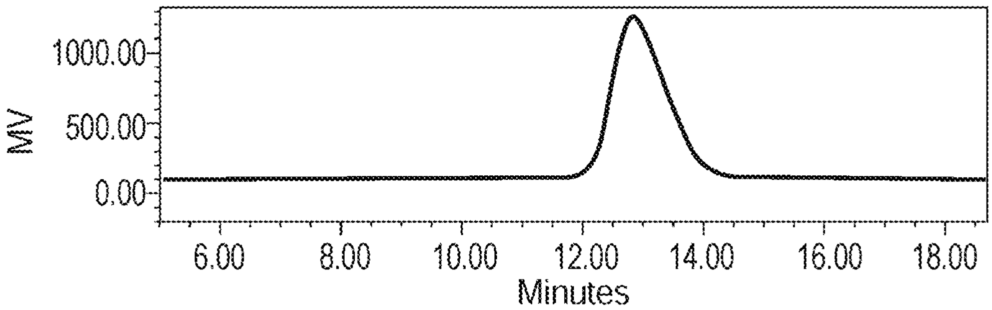

The profiles of LPS from different serotype O25 *E. coli* strains with or without the *Salmonella* LT2 fepE plasmid are shown in FIG. 18. Two strains were studied for fermentation, extraction and purification of O-antigens: GAR2831, for the production of native short O25b OAg; and GAR2401ΔwzzB/fepE, for the production of long O25b OAg. The corresponding short and long form LPSs shown in the FIG. 18 SDS-PAGE gel are highlighted in red. Polysaccharides were extracted directly from fermented bacteria with acetic acid and purified. Size exclusion chromatography profiles of purified short and long or very long O25b polysaccharides are shown in FIG. 19A-19B. The properties of two lots of short polysaccharide (from GAR2831) are compared with a single very long polysaccharide preparation (from strain GAR2401ΔwzzB/fepE). The molecular mass of the long O-antigen is 3.3-fold greater than that of the short O-antigen, and the number of repeat units was estimated to be ~65 (very long) vs ~20. See Table 13.

TABLE 13

| Poly Lot # | Native | Native | Modified (long chain) |
|---|---|---|---|
| Poly Lot # | 709766-24A | 709722-24B | 709766-25A |
| Poly MW (kDa) | 17.3 | 16.3 | 55.3 |
| # Repeat Units | 20 | 19 | 64 |

The very long O25b O-antigen polysaccharide was conjugated to diphtheria toxoid $CRM_{197}$ using a conventional reductive amination process. Three different lots of glycoconjugate were prepared with varying degree of periodate activation: medium (5.5%), low (4.4%) and high (8.3%). The resulting preparations and unconjugated polysaccharide were shown to be free of endotoxin contamination) (Table 14).

Figure 20A:
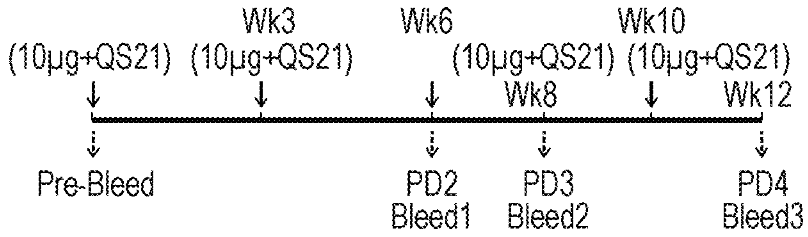
FIG. 20A-20B—depict vaccination schedules in rabbits.

Groups of four rabbits (New Zealand White females) were each vaccinated with 10 mcg of glycoconjugate and 20 mcg of QS21 adjuvant and serum sampled (VAC-2017-PRL-EC-0723) according to the schedule shown in FIG. 20A. It is worth noting that a 10 mcg dose is at the low end of the range customarily given to rabbits in the evaluation of bacterial glycoconjugates (20-50 mcg is more typical). A group of rabbits was also vaccinated in a separate study (VAC-2017-PRL-GB-0698) with unconjugated polysaccharide using the same dose (10 mcg polysaccharide+20 mcg QS21 adjuvant) and identical administration schedule.

Figure 21A:
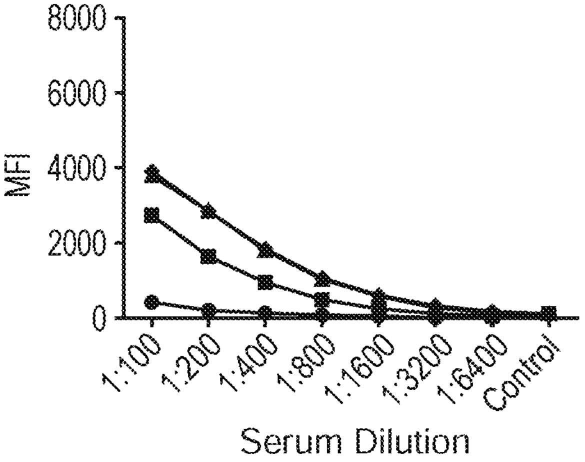
FIG. 21A-21C—depict O25b Glycoconjugate IgG responses, wherein —●— represents results from Prebleed; —■— Bleed 1 (6 wk); —▲— Bleed 2 (8 wk); —♦— Bleed 3 (12 wk).
Figure 21B:
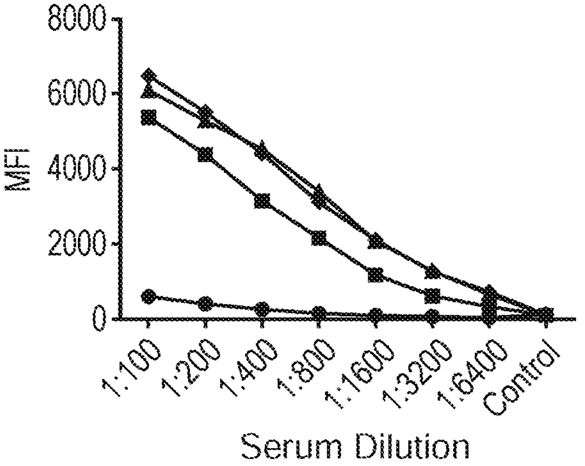
Figure 21C:
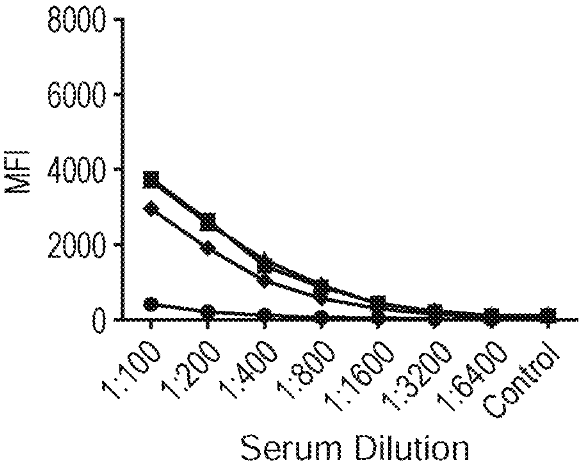

Rabbit antibody responses to the three O25b glycoconjugate preparations were evaluated in a LUMINEX assay in which carboxy beads were coated with methylated human serum albumin prebound with unconjugated O25b long polysaccharide. The presence of 025b-specific IgG antibodies in serum samples was detected with a phycoerythrin (PE)-labelled anti-IgG secondary antibody. The profiles of immune responses observed in sera sampled at week 0 (pre-immune), week 6 (post-dose 2, PD2), week 8 (post-dose 3, PD3) and week 12 (post-dose 4, PD4) in best-responding rabbits (one from each group of four) are shown in FIG. 21A-21C. No significant pre-immune serum IgG titers were detected in any of the 12 rabbits. In contrast, O25b antigen-specific antibody responses were detected in post-vaccination sera from rabbits in all three groups, with the low-activation glycoconjugate group responses trending slightly higher than the medium or high activation glycoconjugate groups. Maximal responses were observed by the post-dose 3 timepoint. One rabbit in the low activation group and one rabbit from the high activation group failed to respond to vaccination (non-responders).

Figure 22A:
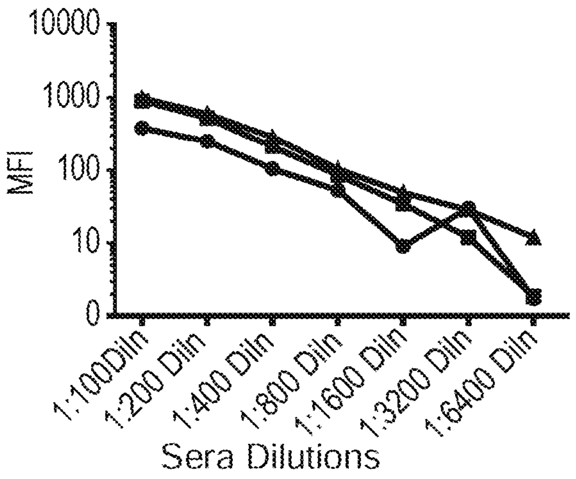
FIG. 22A-22F—depict IgG responses to O25b Long O-antigen Glycoconjugate, i.e., Low activation O25b-$CRM_{197}$ conjugate (FIG. 22D-22F, wherein —■— represents results from Prebleed from Rabbit 2-1, —■— Week 12 Antisera from Rabbit 2-1) vs unconjugated polysaccharide, i.e., free O25b polysaccharide (FIG. 22A-22C, wherein —●— represents results from Prebleed from Rabbit A-1, —■— Week 6 Antisera from Rabbit A-1, —▲— Week 8 Antisera from Rabbit A-1). Note that MFIs are plotted on log scale to highlight differences between pre-immune and immune antibodies in the <1000 MFI range.
Figure 22B:
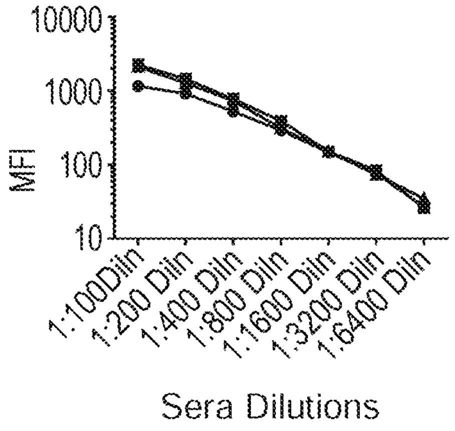
Figure 22C:
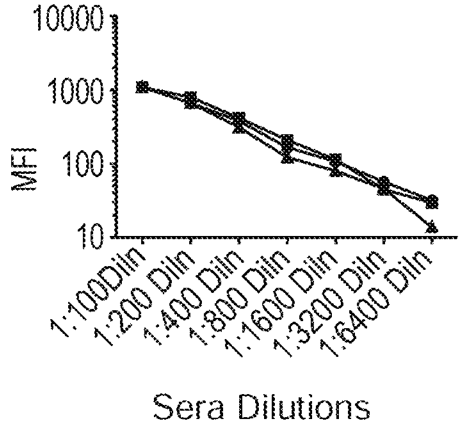
Figure 22D:
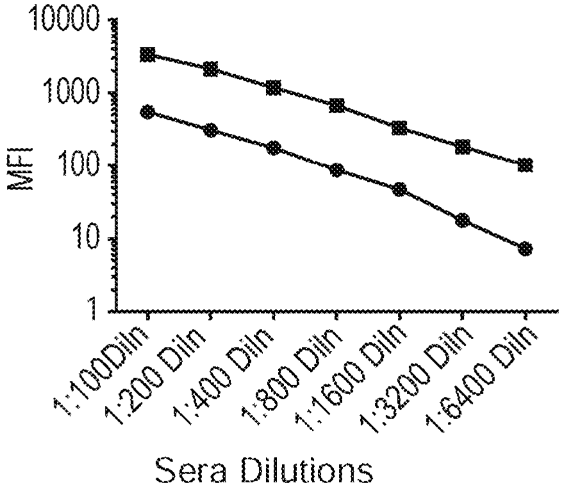
Figure 22E:
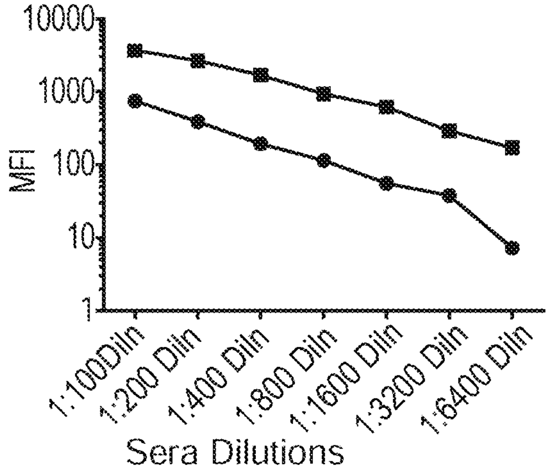
Figure 22F:

To assess the impact of CRM: 97 carrier protein conjugation on immunogenicity of the long O25b OAg polysaccharide, the presence of antibodies in sera from rabbits vaccinated with unconjugated polysaccharide was compared with sera from rabbits vaccinated with the low activation $CRM_{197}$ glycoconjugate FIG. 22A-22F. Remarkably, the free polysaccharide was not immunogenic, eliciting virtually no IgG responses in immune vs preimmune sera (FIG. 22A). In contrast, O25b OAg-specific IgG mean fluorescence intensity values (MFIs) of approximately ten-fold above pre-immune serum levels were observed in PD4 sera from three out of four rabbits vaccinated with O25b OAg-$CRM_{197}$, across a range of serum dilutions (from 1:100 to 1:6400). These results demonstrate the necessity of carrier protein conjugation to generate IgG antibodies to the O25b OAg polysaccharide at the 10 mcg dose level.

Bacteria grown on TSA plates were suspended in PBS, adjusted to $OD_{600}$ of 2.0 and fixed in 4% paraformaldehyde in PBS. After blocking in 4% BSA/PBS for 1h, bacteria were incubated with serial dilutions of pre-immune and PD3 immune sera in 2% BSA/PBS, and bound IgG detected with PE-labeled secondary F (ab) antibody.

Specificity of the O25b antibodies elicited by the O25b OAg-CRM 197 was demonstrated in flow cytometry experiments with intact bacteria. Binding of IgG to whole cells was detected with PE-conjugated $F(ab')_2$ fragment goat anti-rabbit IgG in an Accuri flow cytometer.

Figure 23A:
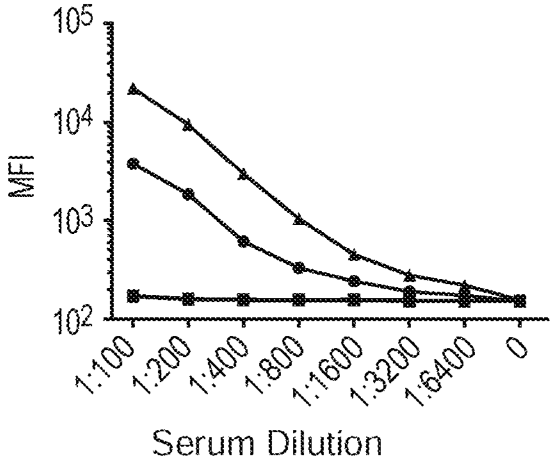
FIG. 23A-23C—depict surface expression of native vs long O25b O-antigen detected with O25b antisera.
Figure 23B:
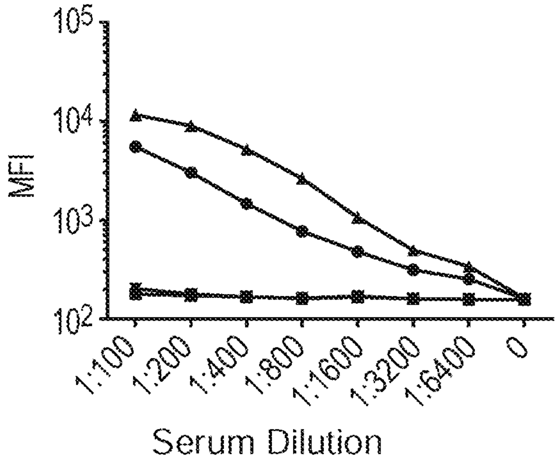
Figure 23C:
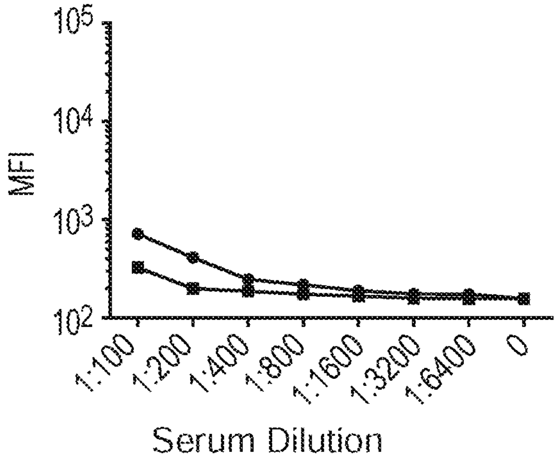

As shown in FIG. 23A-23C, pre-immune rabbit antibodies failed to bind to wild-type serotype O25b isolates GAR2831 and GAR2401 or to a K-12 *E. coli* strain, whereas matched PD3 antibodies stained the O25b bacteria in a concentration dependent manner. Negative control K-12 strain which lacks the ability to express OAg showed only very weak binding of PD3 antibodies, most likely due to the presence of exposed inner core oligosaccharide epitopes on its surface. Introduction of the *Salmonella* fepE plasmid into the wild-type O25b isolates resulted in significantly enhanced staining, consistent with the higher density of immunogenic epitopes provided by the longer OAg polysaccharide.

Conclusion: The results described show that not only is *Salmonella* fepE the determinant of very long O-antigen polysaccharides in *Salmonella* species, but that it also can confer on *E. coli* strains of different O-antigen serotypes the ability to make very long OAgs. This property can be exploited to produce O-antigen vaccine polysaccharides with improved properties for bioprocess development, by facilitating purification and chemical conjugation to appropriate carrier proteins, and by potentially enhancing immunogenicity through the formation of higher molecular weight complexes.

Example 14: Initial Rabbit Studies Generated First Polyclonal Antibody Reagents and IgG Responses to RAC O25b OAg-$CRM_{197}$ Long chain O25b polysaccharide-$CRM_{197}$ conjugates were produced using periodate oxidation followed by conjugation using reductive amination chemistry (RAC) (Table 14). See also Table 24.

TABLE 14

| $CRM_{197}$ conjugate | 132242-28 Medium 5.5% activation | 132242-27 Low 4.5% activation | 132242-29 High 8.3% activation | 709766-29 Free O25b polysaccharide |
|---|---|---|---|---|
| Polysaccharide concentration (mg/mL) | 0.7 | 0.6 | 0.67 | 1 |
| Endotoxin (EU/ug) | 0.02 | 0.02 | 0.02 | <0.6 EU |
| Matrix | 5 um Succinate buffer/saline, pH 6.0 | | | |

Figure 25:
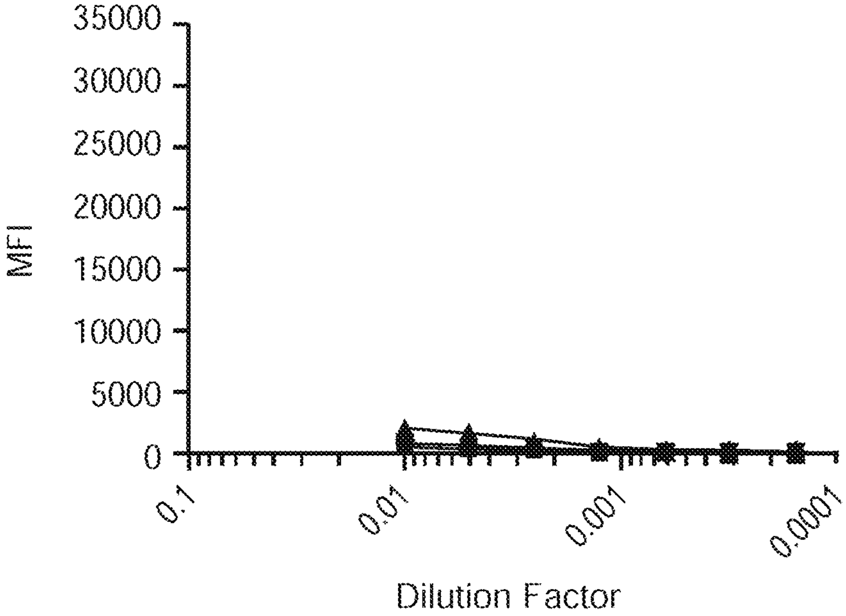
FIG. 25—depicts that unconjugated free O25b polysaccharide is not immunogenic (dLIA), wherein —●— represents results from Week 18 (1wk=PD4) Antisera from 4-1; —■— represents results from Week 18 (1wk=PD4) Antisera from 4-2; —▲— represents results from Week 18 (1wk=PD4) Antisera from 5-1; —▼— represents results from Week 18 (1wk=PD4) Antisera from 5-2; —*—represents results from Week 18 (1wk=PD4) Antisera from 6-1; —▲— represents results from Week 18 (1wk=PD4) Antisera from 6-2.

In Rabbit Study 1 (VAC-2017-PRL-EC-0723) (also described above in Example 13)—five (5) rabbits/group, with 10 μg L-, M- or H-activation RAC (+QS21) received a composition according to the schedule shown in FIG. 20A. Unconjugated free O25b polysaccharide was observed not to be immunogenic in a follow-up rabbit Study (VAC-2017-PRL-GB-0698) (see FIG. 25).

Figure 20B:
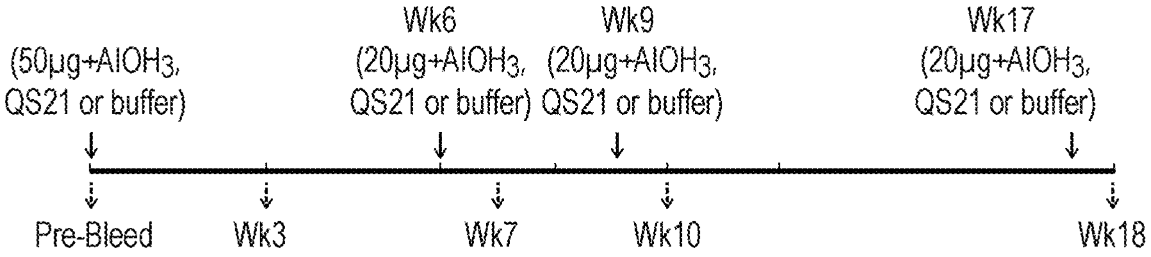

In Rabbit Study 2 (VAC-2018-PRL-EC-077)-2 rabbits/group, with L-RAC ($AlOH_3$, QS21, or no adjuvant) received a composition according to the schedule shown in FIG. 20B.

Rabbits 4-1, 4-2, 5-1, 5-2, 6-1, and 6-2 received the very long unconjugated O25b polysaccharide described in Example 13, and week 18 sera were tested.

More specifically, a composition including 50 μg unconjugated O25b, 100 μg $AlOH_3$ adjuvant was administered to Rabbit 4-1. A composition including 50 μg unconjugated O25b, 100 μg $AlOH_3$ adjuvant was administered to Rabbit 4-2. A composition including 50 μg unconjugated O25b, 50 μg QS-21 adjuvant was administered to Rabbit 5-1. A composition including 50 μg unconjugated O25b, 50 μg QS-21 adjuvant was administered to Rabbit 5-2. A composition including 50 μg unconjugated O25b, no adjuvant was administered to Rabbit 6-1. A composition including 50 μg unconjugated O25b, no adjuvant was administered to Rabbit 6-2.

Example 15: Rabbit Studies with O25b RAC Conjugate: dLIA Serum Dilution Titers Rabbit Study 2 (VAC-2018-PRL-EC-077) O25b dLIA serum dilution titers vs best responding rabbit from study 1

(VAC-2017-PRL-EC-0723). For these experiments a modified direct binding Luminex assay was implemented in which a polylysine conjugate of O25b long O-antigen was passively adsorbed onto the Luminex carboxy beads instead of the methylated serum albumin long O-antigen mixture described previously. The use of the polylysine-O25b conjugate improved the sensitivity of the assay and the quality of IgG concentration dependent responses, permitting determination of serum dilution titers through use of curve-fitting (four parameter non-linear equation). O25b IgG titers in sera from highest titer rabbit from first study is compared with sera from second study rabbits in Table 15.

TABLE 15

| | O25b-CRM Low Activation Conjugate with Alum Adjuvant ($EC_{50}$ as serum dilution) | | O25b-CRM Low Activation Conjugate with QS21 Adjuvant ($EC_{50}$ as serum dilution) | | O25b-CRM Low Activation Conjugate without Adjuvant ($EC_{50}$ as serum dilution) | |
|---|---|---|---|---|---|---|
| | Rabbit 1-1 | Rabbit 1-2 | Rabbit 2-1 | Rabbit 2-2 | Rabbit 3-1 | Rabbit 3-2 |
| Week 3 Antisera (3 wks after primary) | ~1:200 | ~1:200 | <1:100 | <1:100 | ~1:200 | ~1:200 |
| Week 7 Antisera (1 wk after boost 1) | 1:1600 | 1:4000 | 1:250 | 1:500 | 1:250 | 1:1500 |
| Week 10 Antisera (1 wk after boost 2) | 1:1100 | 1:1900 | 1:250 | 1:500 | 1:800 | 1:1200 |
| Week 18 Antisera (1 wk after boost 4) | 1:1600 | 1:4000 | 1:1300 | 1:1200 | 1:1400 | 1:1600 |
| | Average of 6 replicates of best antisera from rabbit 2-3 (assay standard from first study) $EC_{50}$ = 1:1700 | | | | | |

Higher doses in second rabbit study (50/20 μg vs 10 μg) did not improve IgG titers.

Two month rest boosts IgG responses (not observed with shorter intervals).

Alum appears to enhance IgG response in rabbits compared with QS21 or no adjuvant.

An opsonophagocytic assay (OPA) with baby rabbit complement (BRC) and HL60 cells as source of neutrophils was established to measure the functional immunogenicity of O-antigen glycoconjugates. Pre-frozen bacterial stocks of *E. coli* GAR2831 were grown in Luria broth (LB) media at 37° C. Cells were pelleted and suspended to a concentration of 1 $OD_{600}$ unit per ml in PBS supplemented with 20% glycerol and frozen. Pre-titered thawed bacteria were diluted to $0.5\times10^5$ CFU/ml in HBSS (Hank's Balanced Salt Solution) with 1% Gelatin) and 10 μL ($10^3$ CFU) combined with 20 μL of serially diluted sera in a U-bottomed tissue culture microplate and the mixture shaken at 700 rpm BELLCO Shaker) for 30 min at 37° C. in a 5% $CO_2$ incubator. 10 μl of 2.5% complement (Baby Rabbit Serum, PEL-FREEZ 31061-3, prediluted in HBG) and 20 μL of HL-60 cells ($0.75\times10^7$/ml) and 40 μL of HBG added to the U-bottomed tissue culture microplate and the mixture shaken at 700 rpm BELLCO Shaker) for 45 min at 37° C. in a 5% $CO_2$ incubator. Subsequently, 10 μL of each 100 μL reaction was transferred into the corresponding wells of a pre-wetted MILLIPORE MULTISCREENHTS HV filter plate prepared by applying 100 ul water, filter vacuumed, and applying 150 μL of 50% LB. The filter plate was vacuum filtered and incubated overnight at 37° C. in a 5% $CO_2$ incubator. The next day the colonies were enumerated after fixing, staining, and destaining with COOMASSIE dye and Destain solutions, using an IMMUNOSPOT® analyzer and IMMUNOCAPTURE software. To establish the specificity of OPA activity, immune sera were preincubated with 100 μg/mL purified long O25b O-antigen prior to combining with the other assay components in the OPA reaction. The OPA assay includes control reactions without HL60 cells or complement, to demonstrate dependence of any observed killing on these components.

Figure 26A:
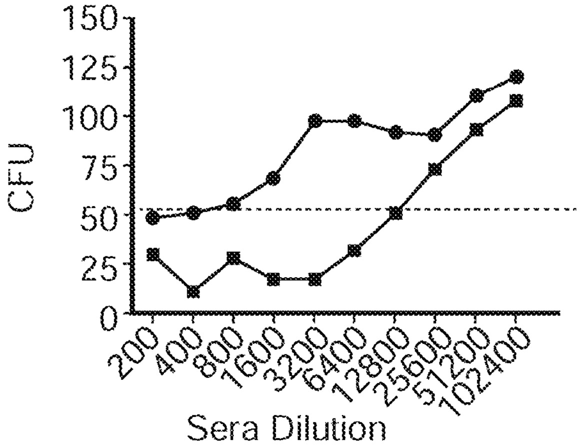
FIG. 26A-26C—depict graphs illustrating the specificity of BRC Rabbit O25b RAC conjugate immune sera OPA titers.
Figure 26B:
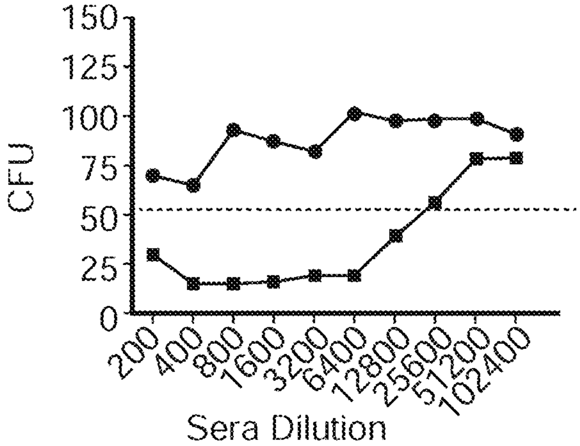

Matched pre-immune and post-vaccination serum samples from representative rabbits from both rabbit studies were evaluated in the assay and serum dilution titers determined (Table 16, FIG. 26A-26B). Preincubation with unconjugated O25b long O-antigen polysaccharide blocked bactericidal activity demonstrating specificity of the OPA (FIG. 19C). Table 16 OPA titers Rabbit 2-3 was dosed as follows: Rabbit 2-3 dosing: Oct. 10, 2010/10 μg RAC conjugate+QS21, post-dose (PD) 4 bleed. Rabbit 1-2 was dosed as follows: 50/20/20/20 μg RAC conjugate+AI (OH) 3, PD4 bleed.

TABLE 16

| Sample | Titer |
|---|---|
| Rabbit 2-3 Pre-immune serum | 537 |
| Rabbit 2-3 wk 13 serum (terminal bleed) | 13686 |
| Rabbit 1-2 Pre-immune serum | <200 |
| Rabbit 1-2 wk 19 serum (terminal bleed) | 22768 |

Figure 27A:
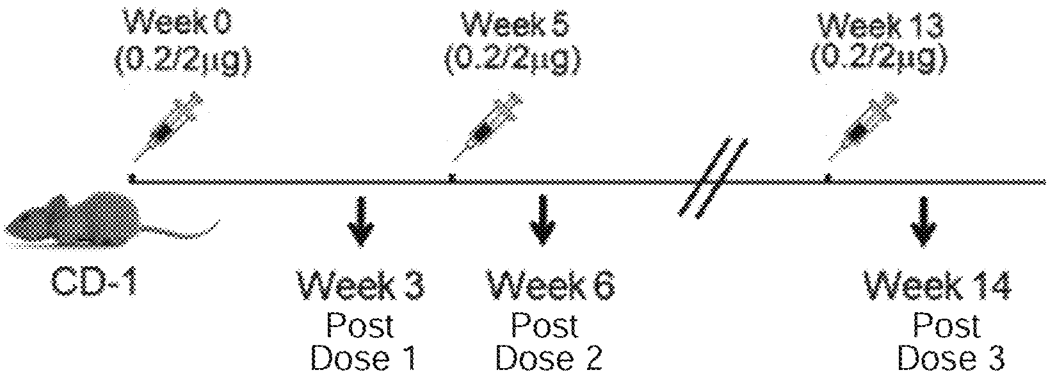
FIG. 27A-27C-FIG. 27A depicts an illustration of an exemplary administration schedule.
Figure 27B:
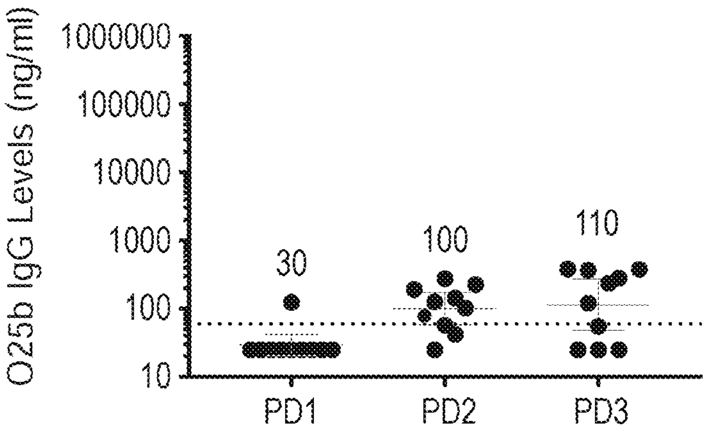
Figure 27C:
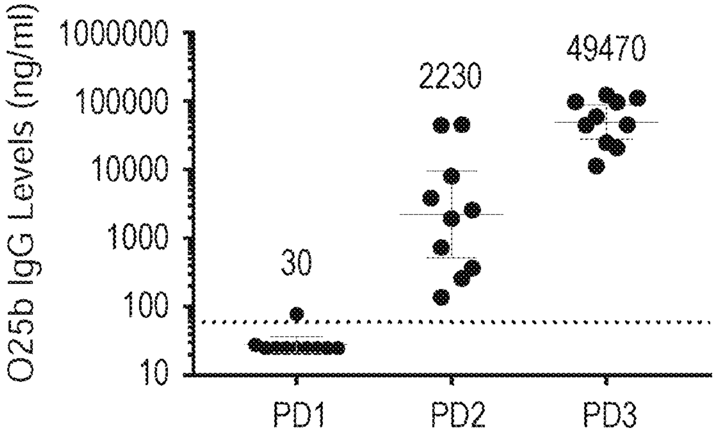

Example 16: O-Antigen O25b IgG Levels Elicited by Unconjugated O25b Long O-Antigen Polysaccharide and Derived 025b RAC/DMSO Long O-Antigen Glycoconjugate Groups of ten CD-1 mice were dosed by sub-cutaneous injection with 0.2 or 2.0 μg/animal of O25b RAC/DMSO long O-antigen glycoconjugate at weeks 0, 5 and 13, with bleeds taken at week 3 (post-dose 1, PD1), week 6 (post-dose 2, PD2) and week 13 (post-dose 3, PD3) timepoints for immunogenicity testing. Levels of antigen-specific IgG were determined by quantitative Luminex assay (see details in Example 15) with O25b-specific mouse mAb as internal standard. Baseline IgG levels (dotted line) were determined in serum pooled from 20× randomly selected unvaccinated mice. The free unconjugated O25b long O-antigen polysaccharide immunogen did not induce IgG above baseline levels at any timepoint. In contrast, IgG responses were observed after two doses of O25b-$CRM_{197}$ RAC long conjugate glycoconjugate: robust uniform IgG responses were observed by PD3, with intermediate and more variable IgG levels at PD2. GMT IgG values (ng/ml) are indicated with 95% CI error bars. See FIG. 27A-27C.

Example 17: Specificity of the 025b Baby Rabbit Complement (BRC) OPA

Figure 26C:
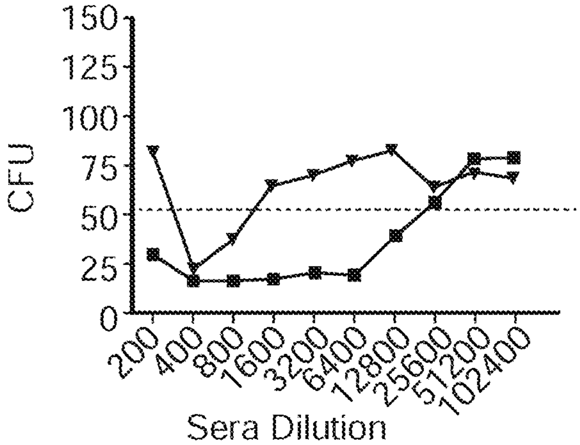

A-B) O25b RAC/DMSO long O-antigen post-immune serum from rabbits 2-3 and 1-2 (but not matched pre-immune control serum) shows bactericidal OPA activity. C) OPA activity of immune serum from rabbit 1-2 was blocked by pre-incubation with 100 μg/mL long O-antigen O25b polysaccharide. Strain GAR2831 bacteria were incubated with HL60s, 2.5% BRC and serial dilutions of serum for 1 h at 37° C. and surviving bacteria enumerated by counting microcolonies (CFUs) on filter plates. See FIG. 26A-26C.

Figure 28A:
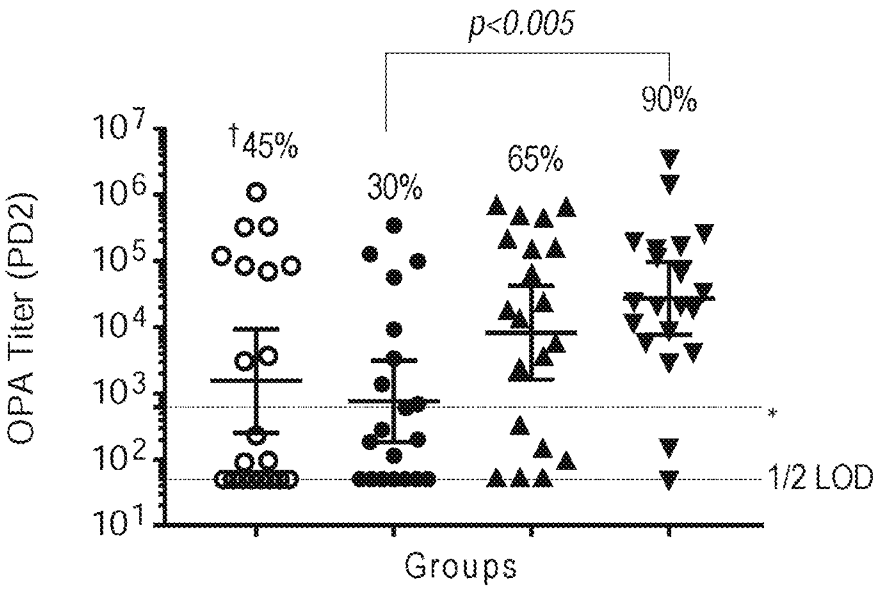
FIG. 28A-28B-depict graphs showing OPA immunogenicity of RAC, eTEC O25b long glycoconjugates, and single end glycoconjugates post dose 2 (FIG. 28A) and post dose 3 (FIG. 28B), wherein —○— represents results from single end short 2 μg; —●— single end long 2 μg; —▲— RAC/DMSO long 2 μg; —▼— eTEC long 2 μg; *Background control (n=20). †Responder rates are % mice with titers >2× unvaccinated baseline.
Figure 28B:
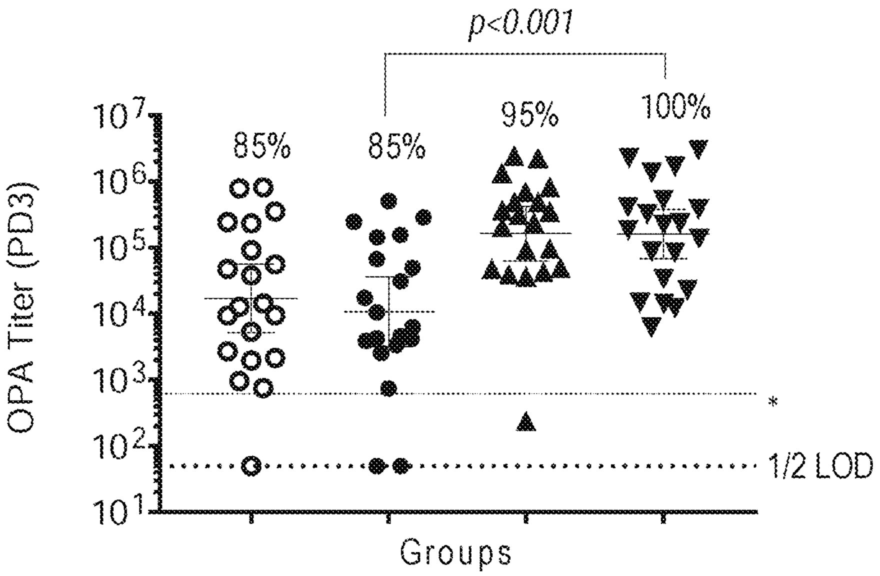

Example 18: RAC and eTEC O25b Long Glycoconjugates are More Immunogenic than Single End Glycoconjugates BRC OPA assay with carbapenem-resistant fluoroquinlone-resistant MDR strain Atlas187913. Groups of 20 CD-1 mice were vaccinated with 2 μg of glycoconjugate according to the same schedule as shown in FIG. 28A-28B and OPA responses determined at post-dose 2 (PD2) (FIG. 28A) and post-dose 3 (PD3) (FIG. 28B) timepoints. Bars indicate GMTs with 95% C1. Responder rates above unvaccinated baseline are indicated. Log transformed data from different groups were evaluated to assess if differences were statistically significant using unpaired t-test with Welch's correction (Graphpad Prism). Results are summarized in the Table 17. See FIG. 28A-28B. In mice that were vaccinated with 2 μg of eTEC O1a long glycoconjugates, OPA titers against O1a, PD2 and PD3 (data not shown), were observed to be greater than the OPA titers against O25b, PD2 and PD3, respectively, shown in Table 17.

TABLE 17

| DESCRIPTION | % Responders (n/N)* | GEO-MEAN TITER PD2 | % Responders (n/N)* | GEO-MEAN TITER PD3 |
|---|---|---|---|---|
| Single end short, 2 μg | 45 (9/20) | 1,552 | 85 (17/20) | 17,070 |
| Single end long, 2 μg | 30 (6/20) | 763 | 85 (17/20) | 10,838 |
| RAC/DMSO long, 2 μg | 65 (13/20) | 8,297 | 95 (19/20) | 163,210 |
| eTEC (10%) long, 2 μg | 90 (18/20) | 27,368 | 100 (19/19) | 161,526 |

Figure 29:
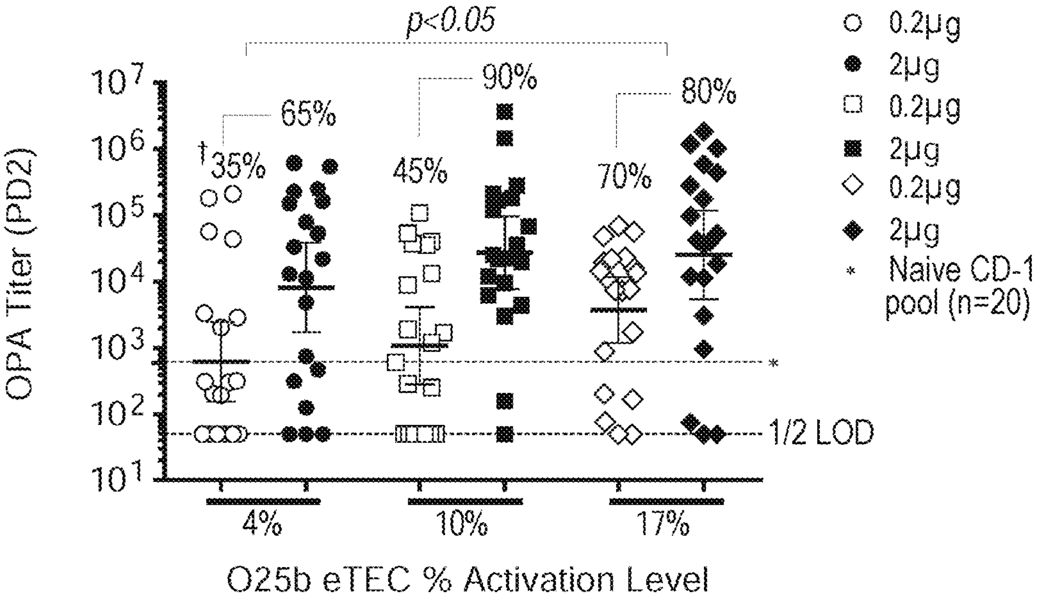
FIG. 29—depicts graph showing OPA immunogenicity of eTEC chemistry and modified levels of polysaccharide activation. †Responder rates are % mice with titers >2× unvaccinated baseline.

Example 19: OPA Immunogenicity of eTEC Chemistry May be Improved by Modifying Levels of Polysaccharide Activation BRC OPA assay with carbapenem-resistant fluoroquinlone-resistant MDR strain Atlas187913. Groups of 20 CD-1 mice were vaccinated with 0.2 μg or 2 μg of the indicated long O25b eTEC glycoconjugate and OPA responses determined at PD2 timepoint. Aggregated log transformed data from 4% activation vs 17% activation groups were evaluated to confirm that differences in OPA responses were statistically significant using unpaired t-test with Welch's correction (Graphpad Prism). GMTs and responder rates for individual groups are summarized in Table 18. See FIG. 29.

TABLE 18

| Description | % Responders (n/N) | GeoMean Titer |
|---|---|---|
| eTEC long 4% activation (0.2 μg) | 35 (7/20) | 628 |
| eTEC long 4% activation (0.2 μg) | 65 (13/20) | 8,185 |
| eTEC long 10% activation (0.2 μg) | 45 (9/20) | 1,085 |
| eTEC long 10% activation (0.2 μg) | 90 (18/20) | 27,368 |
| eTEC long 17% activation (0.2 μg) | 70 (14/20) | 3,734 |
| eTEC long 17% activation (0.2 μg) | 80 (16/20) | 25,461 |

Figure 30A:
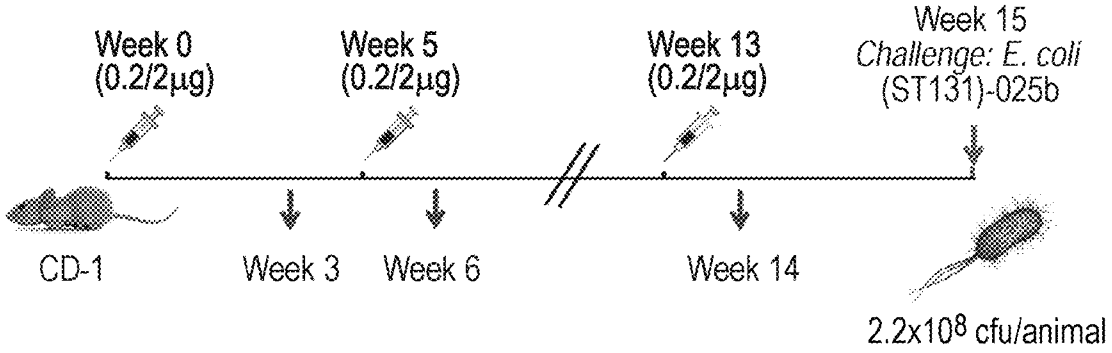
FIG. 30A-30B—depict an illustration of an exemplary administration schedule (FIG. 30A); and a graph depicting protection of mice immunized with doses of *E. coli* eTEC conjugates from lethal challenge with O25b isolate (FIG. 30B), wherein —◇— represents eTEC Long Chain 17% activation; —Δ— eTEC represents Long Chain 10% activation; —∇— represents eTEC Long Chain 4% activation; —□— represents O25b Polysaccharide; —○— represents unvaccinated controls.
Figure 30B:
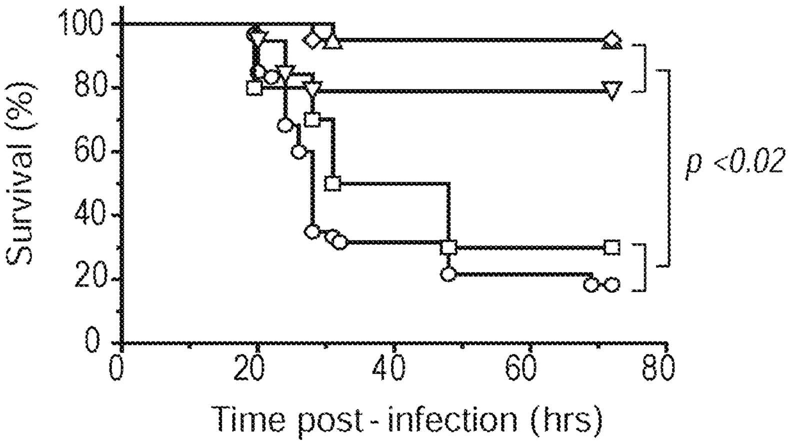

Example 20: Challenge Study Indicates Long *E. coli* 025b eTEC Conjugates Elicit Protection after Three Doses Groups of 20× CD-1 mice immunized with a 2 μg dose according to the indicated schedule were challenged IP with $1\times10^9$ bacteria of strain GAR2831. Subsequent survival was monitored for six days. Groups of mice vaccinated with eTEC glycoconjugates activated at 4%, 10% or 17% levels were protected from lethal infection, whereas unvaccinated control mice or mice vaccinated with 2 μg unconjugated O25b long polysaccharide were not. See FIG. 30A-30B.

Example 21: Process for Preparation of eTEC Linked Glycoconjugates

Activation of Saccharide and Thiolation with Cystamine dihydrochloride. The saccharide is reconstituted in anhydrous dimethylsulfoxide (DMSO). Moisture content of the solution is determined by Karl Fischer (KF) analysis and adjusted to reach a moisture content of 0.1 and 1.0%, typically 0.5%.

To initiate the activation, a solution of 1,1'-carbonyl-di-1,2,4-triazole (CDT) or 1,1'-carbonyldiimidazole (CDI) is freshly prepared at a concentration of 100 mg/mL in DMSO. The saccharide is activated with various amounts of CDT/CDI (1-10 molar equivalents) and the reaction is allowed to proceed for 1-5 hours at rt or 35° C. Water was added to quench any residual CDI/CDT in the activation reaction solution. Calculations are performed to determine the added amount of water and to allow the final moisture content to be 2-3% of total aqueous. The reaction was allowed to proceed for 0.5 hour at rt. Cystamine dihydrochloride is freshly prepared in anhydrous DMSO at a concentration of 50 mg/mL. The activated saccharide is reacted with 1-2 mol. eq. of cystamine dihydrochloride. Alternatively, the activated saccharide is reacted with 1-2 mol. eq. of cysteamine hydrochloride. The thiolation reaction is allowed to proceed for 5-20 hours at rt, to produce a thiolated saccharide. The thiolation level is determined by the added amount of CDT/CDI.

Reduction and Purification of Activated Thiolated Saccharide. To the thiolated saccharide reaction mixture a solution of tris(2-carboxyethyl)phosphine (TCEP), 3-6 mol. eq., is added and allowed to proceed for 3-5 hours at rt. The reaction mixture is then diluted 5-10-fold by addition to pre-chilled 10 mM sodium phosphate monobasic, and filtered through a 5 μm filter. Dialfiltration of thiolated saccharide is performed against 30-40-fold diavolume of pre-chilled 10 mM sodium phosphate monobasic. An aliquot of activated thiolated saccharide retentate is pulled to determine the saccharide concentration and thiol content (Ellman) assays.

Activation and Purification of Bromoacetylated Carrier Protein. Free amino groups of the carrier protein are bromoacteylated by reaction with a bromoacetylating agent, such as bromoacetic acid N-hydroxysuccinimide ester (BAANS), bromoacetylbromide, or another suitable reagent.

The carrier protein (in 0.1M Sodium Phosphate, pH 8.0±0.2) is first kept at 8±3° C., at about pH 7 prior to activation. To the protein solution, the N-hydroxysuccinimide ester of bromoacetic acid (BAANS) as a stock dimethylsulfoxide (DMSO) solution (20 mg/mL) is added in a ratio of 0.25-0.5 BAANS: protein (w/w). The reaction is gently mixed at 5±3° C. for 30-60 minutes. The resulting bromoacetylated (activated) protein is purified, e.g., by ultrafiltration/diafiltration using 10 kDa MWCO membrane using 10 mM phosphate (pH 7.0) buffer. Following purification, the protein concentration of the bromoacetylated carrier protein is estimated by Lowry protein assay.

The extent of activation is determined by total bromide assay by ion-exchange liquid chromatography coupled with suppressed conductivity detection (ion chromatography). The bound bromide on the activated bromoacetylated protein is cleaved from the protein in the assay sample preparation and quantitated along with any free bromide that may be present. Any remaining covalently bound bromine on the protein is released by conversion to ionic bromide by heating the sample in alkaline 2-mercaptoethanol.

Activation and Purification of Bromoacetylated $CRM_{197}$. $CRM_{197}$ was diluted to 5 mg/mL with 10 mM phosphate buffered 0.9% NaCl PH 7 (PBS) and then made 0.1 M $NaHCO_3$ pH 7.0 using 1 M stock solution. BAANS was added at a $CRM_{197}$: BAANS ratio 1:0.35 (w:w) using a BAANS stock solution of 20 mg/mL DMSO. The reaction mixture was incubated at between 3° C. and 11° C. for 30 mins-1 hour then purified by ultrafiltration/diafiltration using a 10K MWCO membrane and 10 mM Sodium Phosphate/0.9% NaCl, pH 7.0. The purified activated CRM 197 was assayed by the Lowry assay to determine the protein concentration and then diluted with PBS to 5 mg/mL. Sucrose was added to 5% wt/vol as a cryoprotectant and the activated protein was frozen and stored at −25° C. until needed for conjugation.

Bromoacetylation of lysine residues of $CRM_{197}$ was very consistent, resulting in the activation of 15 to 25 lysines from 39 lysines available. The reaction produced high yields of activated protein.

Conjugation of Activated Thiolated Saccharide to Bromoacetylated Carrier Protein. Bromoacetylated carrier protein and activated thiolated saccharide are subsequently added. The saccharide/protein input ratio is 0.8±0.2. The reaction pH is adjusted to 9.0±0.1 with 1 M NaOH solution. The conjugation reaction is allowed to proceed at 5° C. for 20±4 hours.

Capping of Residual Reactive Functional Groups. The unreacted bromoacetylated residues on the carrier protein are quenched by reacting with 2 mol. eq. of N-acetyl-L-cysteine as a capping reagent for 3-5 hours at 5° C. Residual free sulfhydryl groups are capped with 4 mol. eq. of iodoacetamide (IAA) for 20-24 hours at 5° C.

Purification of eTEC-linked Glycoconjugate. The conjugation reaction (post-IAA-capped) mixture is filtered through 0.45 μm filter. Ultrafiltration/dialfiltration of the glycoconjugate is performed against 5 mM succinate-0.9% saline, pH 6.0. The glycoconjugate retentate is then filtered through 0.2 μm filter. An aliquot of glycoconjugate is pulled for assays. The remaining glycoconjugate is stored at 5° C. See Table 21, Table 22, Table 23 Table 24, and Table 25.

Example 22: Preparation of *E. coli*-025B ETEC Conjugates

Activation Process-Activation of *E. coli*-025b Lipopolysaccharide. The lyophilized *E. coli*-O25b polysaccharide was reconstituted in anhydrous dimethylsulfoxide (DMSO). Moisture content of the lyophilized O25b/DMSO solution was determined by Karl Fischer (KF) analysis. The moisture content was adjusted by adding WFI to the O25b/DMSO solution to reach a moisture content of 0.5%.

To initiate the activation, 1,1'-carbonyldiimidazole (CDI) was freshly prepared as 100 mg/mL in DMSO solution. *E. coli*-O25b polysaccharide was activated with various amounts of CDI prior to the thiolation step. The CDI activation was carried out at rt or 35° C. for 1-3 hours. Water was added to quench any residual CDI in the activation reaction solution. Calculations are performed to determine the added amount of water and to allow the final moisture content to be 2-3% of total aqueous. The reaction was allowed to proceed for 0.5 hour at rt.

Thiolation of Activated *E. coli*-O25b Polysaccharide. Cystamine-dihydrochloride was freshly prepared in anhydrous DMSO and 1-2 mol. eq. of cystamine dihydrochloride was added to the activated polysaccharide reaction solution. The reaction was allowed to proceed for 20+4 hours at rt.

Figure 32A:
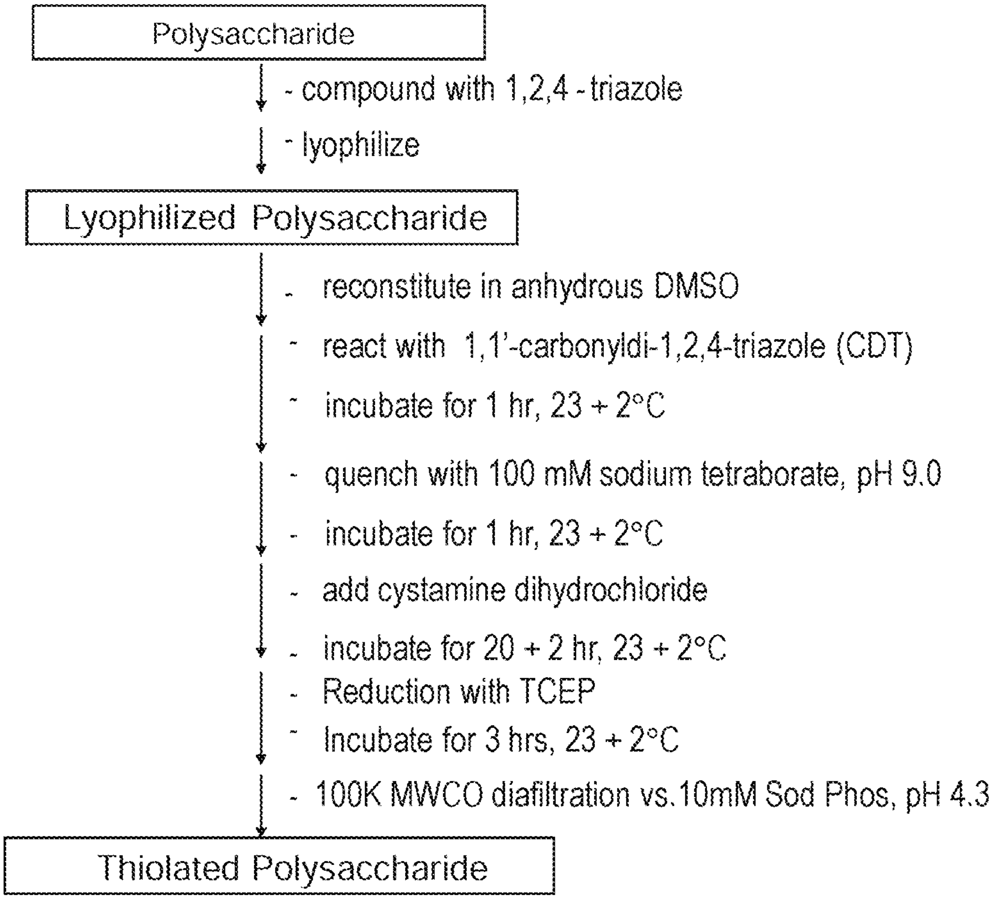
FIG. 32A-32B—depict an exemplary process flow diagram for the activation (FIG. 32A) and conjugation (FIG. 32B) processes used in the preparation of *E. coli* glycoconjugate to $CRM_{197}$.

Reduction and Purification of Activated Thiolated *E. coli*-O25b Polysaccharide. To the thiolated saccharide reaction mixture a solution of tris(2-carboxyethyl)phosphine (TCEP), 3-6 mol. eq., was added and allowed to proceed for 3-5 hours at rt. The reaction mixture was then diluted 5-10-fold by addition to pre-chilled 10 mM sodium phosphate monobasic and filtered through a 5 μm filter. Dialfiltration of thiolated saccharide was performed against 40-fold diavolume of pre-chilled 10 mM sodium phosphate monobasic with 5K MWCO ultrafilter membrane cassettes. The thiolated O25b polysaccharide retentate was pulled for both saccharide concentration and thiol (Ellman) assays. A flow diagram of the activation process is provided in FIG. 32A).

Conjugation Process-Conjugation of Thiolated *E. coli*-O25b Polysaccharide to Bromoacetylated $CRM_{197}$. The $CRM_{197}$ carrier protein was activated separately by bromoacetylation, as described in Example 21, and then reacted with the activated *E. coli*-O25b polysaccharide for the conjugation reaction. Bromoacetylated $CRM_{197}$ and thiolated O25b polysaccharide were mixed together in a reaction vessel. The saccharide/protein input ratio was 0.8±0.2. The reaction pH was adjusted to 8.0-10.0. The conjugation reaction was allowed to proceed at 5° C. for 20±4 hours.

Capping of Reactive Groups on Bromoacetylated $CRM_{197}$ and Thiolated *E. coli*-O25b Polysaccharide. The unreacted bromoacetylated residues on $CRM_{197}$ proteins were capped by reacting with 2 mol. eq. of N-acetyl-L-cysteine for 3-5 hours at 5° C., followed by capping any residual free sulfhydryl groups of the thiolated O25b-polysaccharide with 4 mol. eq. of iodoacetamide (IAA) for 20-24 hours at 5° C.

Purification of eTEC-linked *E. coli*-O25b Glycoconjugate. The conjugation solution was filtered through a 0.45 μm or 5 μm filter. Dialfiltration of the O25b glycoconjugate was carried out with 100K MWCO ultrafilter membrane cassettes. Diafiltration was performed against 5 mM succinate-0.9% saline, pH 6.0. The *E. coli*-O25b glycoconjugate 100K retentate was then filtered through a 0.22 μm filter and stored at 5° C.

Figure 32B:
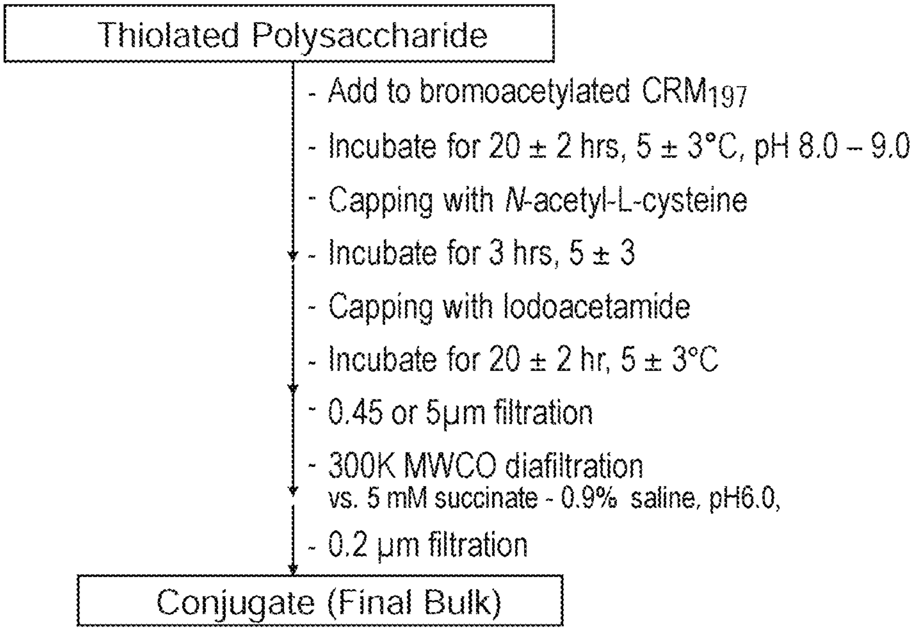

A flow diagram of the conjugation process is provided in FIG. 32B.

Results

The reaction parameters and characterization data for several batches of *E. coli*-O25b eTEC glycoconjugates are shown in Table 19. The CDI activation-thiolation with cystamine dihydrochloride generated glycoconjugates having from 41 to 92% saccharide yields and <5 to 14% free saccharides. See also See Table 21, Table 22, Table 23, Table 24, and Table 25.

TABLE 19

Experimental Parameters and Characterization Data of *E. coli*-O25b eTEC Conjugates

| Conjugate Batch | O25b-1A | O25b-2B | O25b-3C | O25b-4D | O25b-5E | O25b-6F |
|---|---|---|---|---|---|---|
| Activation level (mol of thiol/mol of polysaccharide), % | 10 | 20 | 22 | 17 | 25 | 24 |
| Input Sacc/Prot Ratio | 0.8 | 0.8 | 0.8 | 0.8 | 0.8 | 0.8 |
| Saccharide yield (%) | 56 | 57 | 79 | 92 | 41 | 59 |
| Output Sacc/Prot Ratio | 0.88 | 1 | 1.18 | 1.32 | 2.9 | 1.4 |
| Free Saccharide, % | 8 | <5 | 6 | 5 | 14 | 5 |
| Free Protein, % | <1 | <1 | <1 | <1 | <1 | <1 |
| Conjugate Mw, kDa | 1057 | 4124 | 2259 | 2306 | 1825 | 1537 |
| Total CMCA | 3 | na | na | 7.2 | na | na |

Example 23: Procedure for the Preparation of *E. coli* O-Antigen Polysaccharide-$CRM_{197}$ eTEC Conjugates (Applied to O-Antigens from *E. coli* Serotypes O25b, O1a, O2, and O6

Activation of Polysaccharide.

The *E. coli* O-antigen polysaccharide is reconstituted in anhydrous dimethylsulfoxide (DMSO). To initiate the activation, various amounts of 1,1'-carbonyldiimidazole (CDI) (1-10 molar equivalents) is added to the polysaccharide solution and the reaction is allowed to proceed for 1-5 hours at rt or 35° C. Then, water (2-3%, v/v) was added to quench any residual CDI in the activation reaction solution. After the reaction was allowed to proceed for 0.5 hour at rt, 1-2 mol. eq. of cystamine dihydrochloride is added. The reaction is allowed to proceed for 5-20 hours at rt, and then treated with 3-6 mol. eq of tris (2-carboxyethyl) phosphine (TCEP) to produce a thiolated saccharide. The thiolation level is determined by the added amount of CDI.

The reaction mixture is then diluted 5-10-fold by addition to pre-chilled 10 mM sodium phosphate monobasic, and filtered through a 5 μm filter. Dialfiltration of thiolated saccharide is performed against 30-40-fold diavolume of pre-chilled 10 mM sodium phosphate monobasic. An aliquot of activated thiolated saccharide retentate is pulled to determine the saccharide concentration and thiol content (Ellman) assays.

Activation of Carrier Protein ($CRM_{197}$)

The CRM 197 (in 0.1M Sodium Phosphate, pH 8.0±0.2) is first kept at 8±3° C., at about pH 8 prior to activation. To the protein solution, the N-hydroxysuccinimide ester of bromoacetic acid (BAANS) as a stock dimethylsulfoxide (DMSO) solution (20 mg/mL) is added in a ratio of 0.25-0.5 BAANS: protein (w/w). The reaction is gently mixed at 5±3° C. for 30-60 minutes. The resulting bromoacetylated (activated) protein is purified, e.g., by ultrafiltration/diafiltration using 10 kDa MWCO membrane using 10 mM phosphate (pH 7.0) buffer. Following purification, the protein concentration of the bromoacetylated carrier protein is estimated by Lowry protein assay.

Conjugation

Activated $CRM_{197}$ and activated *E. coli* O-antigen polysaccharide are subsequently added to a reactor and mixed. The saccharide/protein input ratio is 1±0.2. The reaction pH is adjusted to 9.0±0.1 with 1 M NaOH solution. The conjugation reaction is allowed to proceed at 5° C. for 20±4 hours. The unreacted bromoacetylated residues on the carrier protein are quenched by reacting with 2 mol. eq. of N-acetyl-L-cysteine as a capping reagent for 3-5 hours at 5° C. Residual free sulfhydryl groups are capped with 4 mol. eq. of iodoacetamide (IAA) for 20-24 hours at 5° C. Then, the reaction mixture is purified using ultrafiltration/dialfiltration performed against 5 mM succinate-0.9% saline, pH 6.0. The purified conjugate is then filtered through 0.2 μm filter. See Table 21, Table 22, Table 23, Table 24, and Table 25.

Example 24: General Procedure-Conjugation of O-Antigen (from *E. coli* Serotypes O1, O2, O6, 25b) Polysaccharide by Reductive Mination Chemistry (RAC) Conjugation in Dimethylsulfoxide (RAC/DMSO)

Activating Polysaccharide

Polysaccharide oxidation was carried out in 100 mM sodium phosphate buffer (pH 6.0±0.2) by sequential addition of calculated amount of 500 mM sodium phosphate buffer (pH 6.0) and water for injection (WFI) to give final polysaccharide concentration of 2.0 g/L. If required, the reaction pH was adjusted to pH 6.0, approximately. After pH adjustment, the reaction temperature was cooled to 4° C. Oxidation was initiated by the addition of approximately 0.09-0.13 molar equivalents of sodium periodate. The oxidation reaction was performed at 5±3° C. for 20±4 hrs, approximately.

Concentration and diafiltration of the activated polysaccharide was carried out using 5K MWCO ultrafiltration cassettes. Diafiltration was performed against 20-fold diavolumes of WFI. The purified activated polysaccharide was then stored at 5±3° C. The purified activated saccharide is characterized, inter alia, by (i) saccharide concentration by colorimetric assay; (ii) aldehyde concentration by colorimetric assay; (iii) degree of oxidation; and (iv) molecular weight by SEC-MALLS.

Compounding Activated Polysaccharide with Sucrose Excipient, and Lyophilizing

The activated polysaccharide was compounded with sucrose to a ratio of 25 grams of sucrose per gram of activated polysaccharide. The bottle of compounded mixture was then lyophilized. Following lyophilization, bottles containing lyophilized activated polysaccharide were stored at −20±5° C. Calculated amount of $CRM_{197}$ protein was shell-frozen and lyophilized separately. Lyophilized CRM-97 was stored at −20±5° C.

Reconstituting Lyophilized Activated Polysaccharide and Carrier Protein Lyophilized activated polysaccharide was reconstituted in anhydrous dimethyl sulfoxide (DMSO). Upon complete dissolution of polysaccharide, an equal amount of anhydrous DMSO was added to lyophilized CRM 197 for reconstitution.

Conjugating and Capping

Reconstituted activated polysaccharide was combined with reconstituted $CRM_{197}$ in the reaction vessel, followed by mixing thoroughly to obtain a clear solution before initiating the conjugation with sodium cyanoborohydride. The final polysaccharide concentration in reaction solution was approximately 1 g/L. Conjugation was initiated by adding 0.5-2.0 MEq of sodium cyanoborohydride to the reaction mixture and incubating at 23±2° C. for 20-48 hrs. The conjugation reaction was terminated by adding 2 MEq of sodium borohydride ($NaBH_4$) to cap unreacted aldehydes. This capping reaction continued at 23±2° C. for 3±1 hrs.

Purifying the Conjugate

The conjugate solution was diluted 1:10 with chilled 5 mM succinate-0.9% saline (pH 6.0) in preparation for purification by tangential flow filtration using 100-300K MWCO membranes. The diluted conjugate solution was passed through a 5 μm filter, and diafiltration was performed using 5 mM succinate/0.9% saline (pH 6.0) as the medium. After the diafiltration was completed, the conjugate retentate was transferred through a 0.22 μm filter. The conjugate was diluted further with 5 mM succinate/0.9% saline (pH 6), to a target saccharide concentration of approximately 0.5 mg/mL. Alternatively, the conjugate is purified using 20 mM Histidine-0.9% saline (pH 6.5) by tangential flow filtration using 100-300K MWCO membranes. Final 0.22 μm filtration step was completed to obtain the immunogenic conjugate. See Table 21, Table 22, Table 23, Table 24, and Table 25.

Example 25: Conjugation in Aqueous Buffer (RAC/Aqueous), as Applied to from *E. coli* Serotypes O25B, O1A, O2, and O6

Polysaccharides activation and diafiltration was performed in the same manner as the one for DMSO based conjugation.

The filtered activated saccharide was compounded with $CRM_{197}$ at a polysaccharide to protein mass ratio ranging from 0.4 to 2 w/w depending on the serotype. This input ratio was selected to control the polysaccharide to $CRM_{197}$ ratio in the resulting conjugate.

The compounded mixture was then lyophilized. Upon conjugation, the polysaccharide and protein mixture was dissolved in 0.1M sodium phosphate buffer at the polysaccharide concentration ranging from 5 to 25 g/L depending on the serotype, pH was adjusted between 6.0 to 8.0 depending on the serotype. Conjugation was initiated by adding 0.5-2.0 MEq of sodium cyanoborohydride to the reaction mixture and incubating at 23±2° C. for 20-48 hrs. The conjugation reaction was terminated by adding 1-2 MEq of sodium borohydride ($NaBH_4$) to cap unreacted aldehydes.

Alternatively, the filtered activated saccharide and calculated amount of $CRM_{197}$ protein was shell-frozen and lyophilized separately, and then combined upon dissolving in 0.1M sodium phosphate buffer, subsequent conjugation can then be proceeded as described above.

Table 20 Summarizes the Results from Both Conjugations Prepared in DMSO and Aqueous Buffer

| | RAC/DMSO | RAC/Aqueous |
|---|---|---|
| Poly MW (kDa) | 48K | 46K |
| Degree of Oxidation (DO) | 12 | 12 |
| Saccharide/Protein Ratio | 0.8 | 1.0 |

-continued

| | RAC/DMSO | RAC/Aqueous |
|---|---|---|
| % Free Saccharide | <5% | 32% |
| Conjugate MW by SEC-MALLS, kDa | 7950 | 260 |

Figure 31:
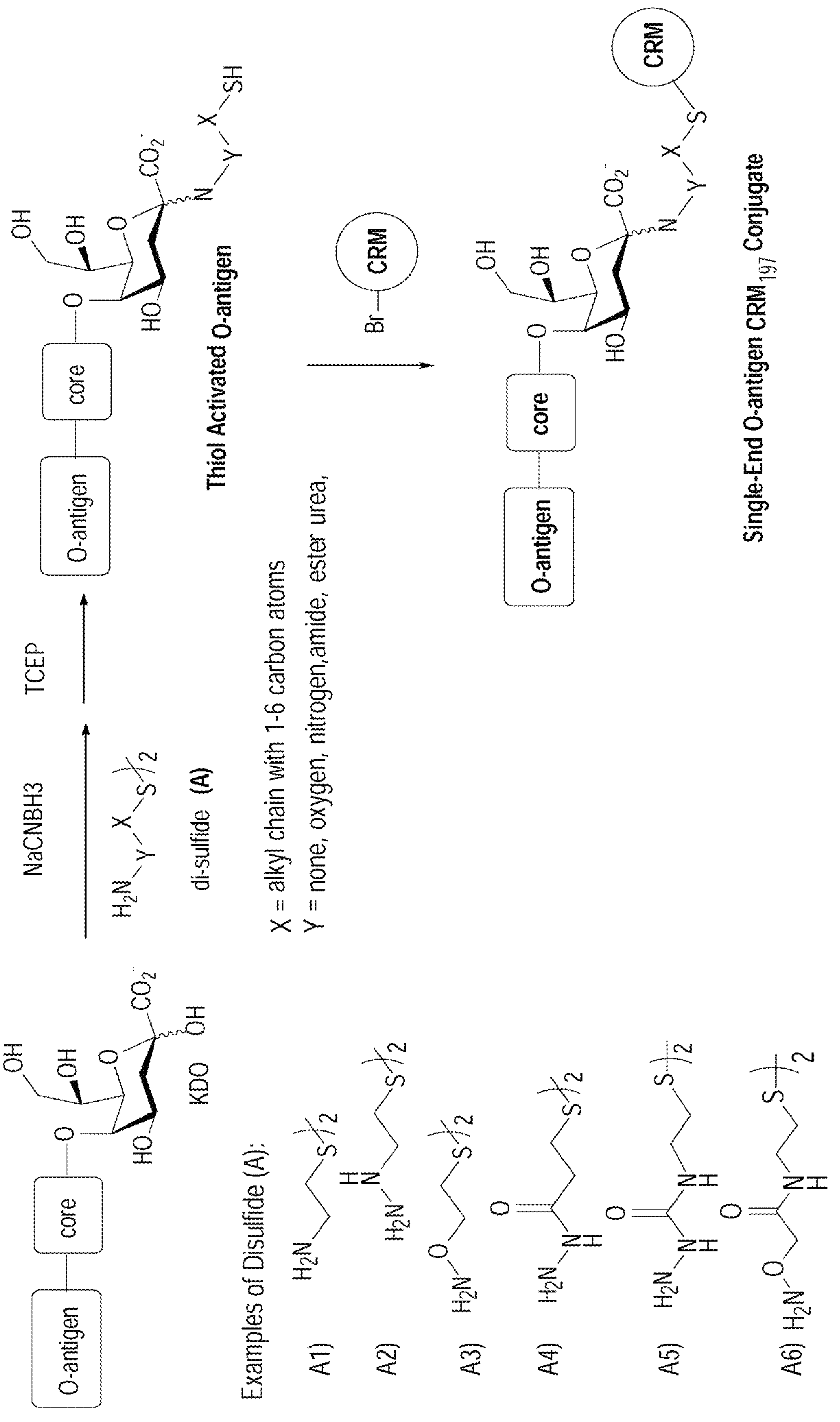
FIG. 31—depicts a schematic illustrating an exemplary preparation of single-ended conjugates, wherein the conjugation process involves selective activation of 2-Keto-3-deoxyoctanoic acid (KDO) with a disulfide amine linker, upon unmasking of a thiol functional group. The KDO is then conjugated to bromo activated $CRM_{197}$ protein as depicted in FIG. 31 (Preparation of Single-Ended Conjugates).

Example 26: Procedure for the Preparation of *E. coli* O-Antigen Polysaccharide-$CRM_{197}$ Single-Ended Conjugates Lipopolysaccharides (LPS), which are common components of the outer membrane of Gram-negative bacteria, comprise lipid A, the core region, and the O-antigen (also refer to as the O-specific polysaccharide or O-polysaccharide). Different serotype of O-antigen repeating units differ in their composition, structure and serological features. The O-antigen used in this invention is attached to the core domain which contains a sugar unit called 2-Keto-3-deoxyoctanoic acid (KDO) at its chain terminus. Unlike some conjugation methods based on random activation of the polysaccharide chain (e.g. activation with sodium periodate, or carbodiimide). This invention discloses a conjugation process involving selective activation of KDO with a disulfide amine linker, upon unmasking of thiol functional group, it is then conjugated to bromo activated $CRM_{197}$ protein as depicted in FIG. 31 (Preparation of Single-Ended Conjugates).

Conjugation Based on Cystamine Linker (A1)

O-antigen polysaccharide and cystamine (50-250 mol. eq of KDO) were mixed in phosphate buffer, adjust pH to 6.0-7.0. To the mixture, sodium cyanoborohydride ($NaCNBH_3$) (5-30 mol. eq of KDO) was added and the mixture was stirred at 37° C. for 48-72 hrs. Upon cooling to room temperature and diluted with equal volume of phosphate buffer, the mixture was treated with tris (2-carboxyethyl) phosphine (TCEP) (1.2 mol, eq of cystamine added). The mixture was then purified through diafiltration using 5 KDa MWCO membrane against 10 mM sodium phosphate monobasic solution, to furnish thiol containing O-antigen polysaccharide. The thiol content can be determined by Ellman assays.

The conjugation was then proceeded by mixing above thiol activated O-antigen polysaccharide with bromo activated $CRM_{197}$ protein at a ratio of 0.5-2.0. The pH of the reaction mixture is adjusted to 8.0-10.0 with 1 M NaOH solution. The conjugation reaction was proceeded at 5° C. for 24±4 hours. The unreacted bromo residues on the carrier protein were quenched by reacting with 2 mol. eq. of N-acetyl-L-cysteine for 3-5 hours at 5° C. The addition of 3 mol. eq. of iodoacetamide (related to N-acetyl-L-Cysteine added) wad then followed to cap the residual free sulfhydryl groups. This capping reaction was proceeded for another 3-5 hours at 5° C., and pH of both capping steps was maintained at 8.0-10.0 by addition of 1M NaOH. The resulting conjugate was obtained after ultrafiltration/dialfiltration using 30 KDa MWCO membrane against 5 mM succinate-0.9% saline, pH 6.0. See Table 21, Table 22, Table 23, Table 24, and Table 25.

Example 27: Conjugation Based on 3,3'-Dithio Bis (Propanoic Dihydrazide) Linker (A4)

O-antigen polysaccharide and 3,3'-dithio bis (propanoic dihydrazide) (5-50 mol. eq of KDO) were mixed in acetate buffer, adjust pH to 4.5-5.5. To the mixture, sodium cyanoborohydride ($NaCNBH_3$) (5-30 mol. eq of KDO) was added and the mixture was stirred at 23-37° C. for 24-72 hrs. The mixture was then treated with tris (2-carboxyethyl) phosphine (TCEP) (1.2 mol, eq of 3,3'-dithio bis (propanoicdihydrazide) linker added). The mixture was then purified through diafiltration using 5 KDa MWCO membrane against 10 mM sodium phosphate monobasic solution, to furnish thiol containing O-antigen polysaccharide. The thiol content can be determined by Ellman assays.

The conjugation was then proceeded by mixing above thiol activated O-antigen polysaccharide with bromo activated $CRM_{197}$ protein at a ratio of 0.5-2.0. The pH of the reaction mixture is adjusted to 8.0-10.0 with 1 M NaOH solution. The conjugation reaction was proceeded at 5° C. for 24±4 hours. The unreacted bromo residues on the carrier protein were quenched by reacting with 2 mol. eq. of N-acetyl-L-cysteine for 3-5 hours at 5° C. The addition of 3 mol. eq. of iodoacetamide (related to N-acetyl-L-Cysteine added) wad then followed to cap the residual free sulfhydryl groups. This capping reaction was proceeded for another 3-5 hours at 5° C., and pH of both capping steps was maintained at 8.0-10.0 by addition of 1M NaOH. The resulting conjugate was obtained after ultrafiltration/dialfiltration using 30 KDa MWCO membrane against 5 mM succinate-0.9% saline, pH 6.0.

Example 28: Conjugation Based on 2,2'-dithio-N, N'-bis (ethane-2,1-diyl)bis(2-(aminooxy)acetamide) linker (A6)

O-antigen polysaccharide and 2,2'-dithio-N,N'-bis (ethane-2,1-diyl)bis(2-(aminooxy) acetamide) (5-50 mol. eq of KDO) were mixed in acetate buffer, adjust pH to 4.5-5.5. The mixture was then stirred at 23-37° C. for 24-72 hrs, followed by the addition of sodium cyanoborohydride ($NaCNBH_3$) (5-30 mol. eq of KDO) and the mixture was stirred for another 3-24 hrs. The mixture was then treated with tris (2-carboxyethyl) phosphine (TCEP) (1.2 mol, eq of linker added). The mixture was then purified through diafiltration using 5 KDa MWCO membrane against 10 mM sodium phosphate monobasic solution, to furnish thiol containing O-antigen polysaccharide. The thiol content can be determined by Ellman assays.

The conjugation was then proceeded by mixing above thiol activated O-antigen polysaccharide with bromo activated CRM 197 protein at a ratio of 0.5-2.0. The pH of the reaction mixture is adjusted to 8.0-10.0 with 1 M NaOH solution. The conjugation reaction was proceeded at 5° C. for 24±4 hours. The unreacted bromo residues on the carrier protein were quenched by reacting with 2 mol. eq. of N-acetyl-L-cysteine for 3-5 hours at 5° C. The addition of 3 mol. eq. of iodoacetamide (related to N-acetyl-L-Cysteine added) was then followed to cap the residual free sulfhydryl groups. This capping reaction was proceeded for another 3-5 hours at 5° C., and PH of both capping steps was maintained at 8.0-10.0 by addition of 1M NaOH. The resulting conjugate was obtained after ultrafiltration/dialfiltration using 30 KDa MWCO membrane against 5 mM succinate-0.9% saline, pH 6.0.

Example 29: Preparation of Bromo Activated $CRM_{197}$

The $CRM_{197}$ was prepared in 0.1M Sodium Phosphate, pH 8.0±0.2 solution, and was cooled to 5±3° C. To the protein solution, the N-hydroxysuccinimide ester of bromoacetic acid (BAANS) as a stock dimethylsulfoxide (DMSO) solution (20 mg/mL) is added in a ratio of 0.25-0.5 BAANS: protein (w/w). The reaction is gently mixed at 5±3° C. for 30-60 minutes. The resulting bromoacetylated (activated) protein is purified, e.g., by ultrafiltration/diafiltration using 10 kDa MWCO membrane using 10 mM phosphate (pH 7.0) buffer. Following purification, the protein concentration of the bromoacetylated carrier protein is estimated by Lowry protein assay.

TABLE 21

| O1a Conjugates | | | | | |
|---|---|---|---|---|---|
| Conjugate Lot# | 132240-112-2 | 132242-106 | 132242-124 | 132242-127 | 132242-130 |
| Poly Lot# | 709756-160 | 709756-160 | 709756-160 | 710958-116 | 710958-116 |
| Poly Type | Long Chain | | | Short Chain | |
| Poly MW (kDa) | 33 | 33 | 33 | 11 | 11 |
| Variant | eTEC | Single-End | RAC/DMSO | Single-End | RAC/DMSO |
| Activation | 8% SH | 2.1% SH | DO: 13 | 6.4% SH | DO: 16 |
| Conjugate Data | | | | | |
| Yield (%) | 30 | 26 | 77 | 45 | 35 |
| SPRatio | 0.6 | 0.5 | 1.0 | 0.7 | 0.6 |
| Free Sacc (%) | 9 | 9 | 20 | 5 | 6 |
| MW (kDa) | 1035 | 331 | 1284 | 280 | 2266 |
| Sacc Conc (mg · mL) | 0.31 | 0.37 | 0.58 | 0.59 | 0.37 |
| Endotoxin (EU/ug) | 0.03 | 0.02 | 0.01 | 0.01 | 0.01 |
| Buffer | 5 mM Succ/Saline, pH 6.0 | | | | |

TABLE 22

| O2 Conjugates | | | | | |
|---|---|---|---|---|---|
| Conjugate Lot# | 00709749-0003-1 | 132242-161 | 132242-152 | 132242-159 | 132242-157 |
| Poly Lot# | 709766-33 | 709766-65 | | 710958-141-2 | |
| Poly Type | | Long Chain | | Short Chain | |
| Poly MW (kDa) | 36 | 39 | | 14 | |
| Variant | eTEC | Single-End | RAC/DMSO | Single-End | RAC/DMSO |
| Activation | 6.8% SH | 1.6% SH | DO: 17 | 6.3% SH | DO: 19 |
| Conjugate Data | | | | | |
| Yield (%) | 26 | 33 | 50 | 38 | 36 |
| SPRatio | 1.5 | 0.8 | 0.8 | 1.0 | 0.6 |
| Free Sacc (%) | 11 | 24% | <5 | <5 | 6 |
| MW (kDa) | 1161 | 422 | 3082 | 234 | 1120 |
| Endotoxin (EU/ug) | 0.025 | 0.02 | 0.01 | 0.01 | 0.01 |
| Buffer | 5 mM Succ/Saline, pH 6.0 | | | | |

TABLE 23

| O6 Conjugates | | | | | |
|---|---|---|---|---|---|
| Conjugate Lot# | 132240-117-1 | 132242-134 | 132242-137 | 132242-146 | 132242-145 |
| Poly Lot# | | 710958-121-1 | | 710958-143-3 | |
| Poly Type | | Long Chain | | Short Chain | |
| Poly MW (kDa) | | 44 | | 15 | |
| Variant | eTEC | Single-End | RAC/DMSO | Single-End | RAC/DMSO |
| Activation | 18% SH | 2.2% SH | DO: 16.5 | 6.1% SH | DO: 22 |
| Conjugate Data | | | | | |
| Yield (%) | 27 | 23 | 58 | 48 | 30 |
| SPRatio | 0.78 | 0.6 | 0.82 | 0.7 | 0.6 |
| Free Sacc (%) | 9 | 4 | 4 | <5 | 8 |
| MW (kDa) | 1050 | 340 | 1910 | 256 | 2058 |
| Sacc Conc (mg · mL) | 0.39 | 0.45 | 0.59 | 0.88 | 0.41 |
| Endotoxin (EU/ug) | 0.03 | 0.02 | 0.01 | 0.004 | 0.005 |
| Buffer | 5 mM Succ/Saline, pH 6.0 | | | | |

TABLE 24

| O25b Conjugates | | | | | | | | | |
|---|---|---|---|---|---|---|---|---|---|
| Conjugate Lot# | 132242-28 | 132242-98 | 132240-73-1-1 | 132240-62-1 | 132240-81 | 132242-116 | 132242-121 | 132242-27 | 132242-29 |
| Poly Lot# | 709766-28 | 709766-29 | 709766-30 | 709766-30 | 709766-30 | 710958-117/118 | 710958-117/118 | 709766-28 | 709766-28 |
| Poly type | | | Long Chain | | | Short Chain | | Long Chain | Long Chain |
| Poly MW (kDa) | 51 | 48 | 48 | 48 | 48 | 14 | 14 | 51 | 51 |
| Variant | RAC/DMSO | Single-End | eTEC | eTEC | eTEC | Single-End | RAC/DMSO | RAC/DMSO | RAC/DMSO |
| Activation | DO: 18 | 2.4% SH | 10% SH | 4% SH | 17% SH | 6.6% SH | DO: 17 | 21 | 12 |
| Conjugate Data | | | | | | | | | |
| Yield (%) | 82 | 26 | 56 | 32 | 92 | 28 | 18 | 71 | 80 |
| SPRatio | 0.9 | 0.82 | 0.88 | 0.64 | 1.32 | 0.7 | 0.36 | 0.81 | 0.84 |
| Free Sacc (%) | 7.2 | 5 | <5 | 11 | <5 | <5 | <5 | 8.3 | <5 |
| Conjugate MW (kDa) | 4415 | 840 | 1057 | 1029 | 2306 | 380 | 9114 | 3303 | 7953 |
| Sacc Conc (mg · mL) | 0.7 | 0.4 | 0.43 | 0.36 | 0.9 | 0.45 | 0.19 | 0.6 | 0.67 |
| Endotoxin (EU/ug) | 0.01 | 0.02 | 0.08 | 0.08 | 0.01 | 0.01 | 0.01 | 0.02 | 0.22 |
| Conjugate (DS) Buffer matrix | 5 mM Succ/Saline, pH 6.0 | | | | | | | | |

TABLE 25

| O25b K-12 Conjugates | | |
|---|---|---|
| Conjugate Lot# | 709749-015-2 | 709744-0016 |
| Poly Lot# | 710958-137 | |
| Poly Type | Long Chain(K12) | |
| Poly MW (kDa) | 44 | |
| Variant | eTEC | RAC/DMSO |
| Activation | SH: 24% | DO: 19 |
| Conjugate Data | | |
| Yield (%) | 59% | 33% |
| SPRatio | 1.4 | 0.83 |
| Free Sacc (%) | 5% | 5.2% |
| MW (kDa) | 1537 | 4775 |
| Sacc Conc (mg · mL) | 0.91 | 0.29 |
| Endotoxin (EU/ug) | 0.08 | 0.01 |
| Buffer | 5 mM Succ/Saline, pH 6.0 | |

Example 29: Preparation of *E. coli* O-Ag-TT Conjugates

*E. coli* serotype O25b long polysaccharide, Lot #709766-30 (about 6.92 mg/mL, MW: about 39 kDa), 50 mg, lyophilized was used for Tetanus Toxoid (TT) conjugation.

*E. coli* serotype O1a long polysaccharide 710958-142-3 (about 6.3 mg/mL, MW: about 44.3 kDa) (50 mg, 7.94 mL) was lyophilized.

*E. coli* serotype O6 long polysaccharide, 710758-121-1 (about 16.8 mg/mL, MW: about 44 kDa) (50 mg, 2.98 mL) was lyophilized.

Each of the lyophilized polysaccharides listed above was dissolved in WFI to make at approx 5-10 mg/mL to it, 0.5 mL (100 mg (1-cyano-4-dimethylaminopyridinum tetrafluoroborate (CDAP) solution in 1 mL acetonitrile) was added and stirred at RT. Triethylamine (TEA) 0.2M (2 mL) was added and stirred at RT.

Preparation of Tetanus toxoid (TT): TT (100 mg, 47 ml) was concentrated to approximately 20 mL and washed twice with saline (2×50 mL) using filteration tubes. After that it was diluted with HEPES and saline to make final HEPES conc as about 0.25M. TT was prepared as described above and pH of the reaction was adjusted to about 9.1-9.2. The reaction mixture was stirred at RT.

After 20-24 hrs the reaction was quenched with Glycine (0.5 mL). After that it was concentrated to using MWCO regenerated cellulose membranes and diafiltration was performed against saline. Filtered and analyzed. See Table 26.

TABLE 26

| Exemplary embodiments: | |
|---|---|
| *E. coli* serotype O25b-TT conjugate | *E. coli* serotype O6-TT conjugate |
| Volume: 41 mL | Volume: 42 mL |
| Sacc Conc (Anthrone): 1.122 mg/mL (92% yield) | Sacc Conc (Anthrone): 0.790 mg/mL (66% yield) |
| Protein Conc (Lowry): 1.133 mg/mL | Protein Conc (Lowry): 1.895 mg/mL |
| SPRatio: 0.99 | SPRatio: 0.42 |
| Free Sacc (DOC): 74.7% | Free Sacc (DOC): <5% |
| The product obtained was concentrated to 15 mL using MWCO regenerated cellulose membranes and diafiltration was performed against saline (40X diavolumes). Filtered through 0.22 um filter and analyzed. | MW (kDa): 1192<br>Endotoxin (EU/ug:) 0.022 |
| Volume: 27 mL | |
| Sacc Conc (Anthrone): 1.041 mg/mL (56% yield) | |
| Protein Conc (Lowry): 1.012 mg/mL | |
| SPRatio: 1.03 | |
| Free Sacc (DOC): 60.6% (poly recovery 100%) | |

Example 30: Additional Results from O-Antigen Fermentation, Purification, and Conjugation The exemplary processes described below is generally applicable to all *E. coli* serotypes. The production of each polysaccharide included a batch production fermentation followed by chemical inactivation prior to downstream purification.

Strains and storage. Strains employed for biosynthesis of short chain O-antigen were clinical wild type strains of *E. coli*. Long chain O-antigen was produced with derivatives of the short chain-producers that had been engineered by the Wanner-Datsenko method to possess a deletion of the native wzzb gene and were complemented by the "long-chain" extender function fepE from *Salmonella*. The fepE function was expressed from its native promoter on either a high copy colE1-based "topo" vector or a low copy derivative of the colE1-based vector pET30a, from which the T7 promoter region had been deleted.

Cell banks were prepared by growing cells in either animal free LB or minimal medium to an OD600 of at least 3.0. The broth was then diluted in fresh medium and combined with 80% glycerol to obtain a 20% glycerol final concentration with 2.0 OD600/mL.

Media used for seed culture and fermentation. The seed and fermentation medium employed share the following formulation: $KH_2PO_4$, K2HPO4, $(NH_4)$ 2SO4, sodium citrate, $Na_2SO_4$, aspartic acid, glucose, $MgSO_4$, $FeSO_4$-$7H_2O$, $Na_2MoO_4$-$2H_2O$, $H_3BO_3$, $CoCl_2$-$6H_2O$, $CuCl_2$-$2H_2O$, $MnCl_2$-$4H_2O$, $ZnCl_2$ and $CaCl_2$)-$2H_2O$.

Seed and fermentation conditions. Seeds were inoculated at 0.1% from a single seed vial. The seed flask was incubated at 37° C. for 16-18 hours and typically achieved 10-20 OD600/mL.

Fermentation was performed in a 10L stainless steel, steam in place fermentor.

Inoculation of the fermentor was typically 1:1000 from a 10 $OD_{600}$ seed. The batch phase, which is the period during which growth proceeds on the 10 g/L batched glucose, typically lasts 8 hours. Upon glucose exhaustion, there was a sudden rise in dissolved oxygen, at which point glucose was fed to the fermentation. The fermentation typically then proceeds for 16-18 hours with harvest giving >120 OD600/mL.

Initial evaluation of short/long chain O-antigen production for serotypes O1a, O2, O6 and O25b. Wild type strains for O1a, O2, O6 and O25b were fermented in a supplemented minimal medium in batch mode to an $OD_{600}$=15-20. Upon glucose exhaustion, which results in a sudden decrease in oxygen consumption, a growth limiting glucose feed was applied from a glucose solution for 16-18 hours. Cell densities of 124-145 $OD_{600}$ units/mL were reached. The pH of the harvest broths was subsequently adjusted to about 3.8 and heated to 95° C. for 2 hours. The hydrolyzed broth was then cooled to 25° C., brought to pH 6.0 and centrifuged to remove solids. The resulting supernatant was then applied to a SEC-HPLC column for quantitation of the O-antigen. Productivities in the range of 2240-4180 mg/L were obtained. The molecular weight of purified short-chain O-antigen from these batches was found to range from 10-15 kDa. It was also noted that SEC chromatography of the O2 and O6 hydrolysates revealed a distinct and separable contaminating polysaccharide that was not evident in the O1a and O25b hydrolysates.

Long chain versions of the O1a, O2, O6 and O25b O-antigens where accessed through fermentation of a wzzb deletion version of each strain which carried a heterologous, complementing fepE gene on a high-copy, kanamycin-selectable topo plasmid. Fermentation was performed as for the short chain, albeit with kanamycin selection. The final cell densities observed at 124-177 $OD_{600}$/mL were associated with O-antigen productivities of 3500-9850 mg/L. The complementation-based synthesis of long chain O-antigen was at least as productive as in the parental short chain strain and in some cases more so. The molecular weights of purified O-antigen polysaccharide were 33-49 kDa or about 3 times the size of the corresponding short chain.

It was noted that the long chain hydrolysates for O2 and O6 showed evidence of a contaminating polysaccharide peak that, in the case of long chain antigen, was observed as a shoulder on the main O-antigen peak; O1 and O25b showed no evidence of production of a contaminating polysaccharide, as was seen earlier with the short chain parent.

Growth rate suppression was found to be associated with the presence of the topo replicon absent the fepE. Additionally, the Δwzzb mutation itself had not adverse effect on growth rate, indicating that the disturbed growth rates were conveyed by the plasmid vector.

Evaluation of strains for production of O11, O13, O16, O21 and O75 O-antigen. Multiple wild-type strains of serotypes O11, O13, O16, O21 and O75 were evaluated for their propensity to produce unwanted polysaccharide in fermentation by SEC-HPLC. Strains for O11, O13, O16, O21 and O75 were selected as absent contaminating polysaccharide, as well as for their ability to produce >1000 mg/L O-antigen and for the display of an antibiotic sensitivity profile that allowed Wanner-Datsenko recombineering for introduction of the Δwzzb trait.

Chloramphenicol-selectable versions of topo-fepE and pET-fepE were constructed that allowed for the introduction of fepE into the O11, O13, O16, O21 and O75 Δwzzb strains that in general were found to be kanamycin-resistant. The resulting topo-fepE and pET-fepE bearing strains were fermented with chloramphenicol selection and the supernatant from acid-hydrolyzed broth was evaluated by SEC-HPLC. Both the high (topo) and low copy (pET) fepE constructs directed the synthesis of O-antigen with productivities for each that were equivalent to the parental wild-type. Expression of potentially interfering polysaccharides was not observed. An evaluation of growth rates for wzzb plasmid-bearing strains showed that the O11, O13 and O21 were retarded by the presence of topo-fepE but not by pET-fepE; strains O16 and O75 strains showed acceptable growth rates irrespective of replicon choice.

TABLE 27

| O-antigen type | IHMA type | short (SC) or long chain (LC) | fep E plasmid type | marker | final cell density $OD_{600}$ | final Oag productivity (mg/L) | MW - kDa | SEC impurity |
|---|---|---|---|---|---|---|---|---|
| O1a | wt | SC | None | None | 125 | 2550 | 11 | N |
| O1a | Δwzzb/fepE | LC | topo | Kana | 130 | 5530 | 33 | N |
| O1a | Δwzzb/fepE | LC | pET | Kana | Not done (ND) | ND | ND | ND |
| O2 | wt | SC | None | None | 127 | 2240 | 13 | Y |

TABLE 27-continued

| O-antigen type | IHMA type | short (SC) or long chain (LC) | fep E plasmid type | marker | final cell density $OD_{600}$ | final Oag productivity (mg/L) | MW - kDa | SEC impurity |
|---|---|---|---|---|---|---|---|---|
| O2 | Δwzzb/fepE | LC | topo | Kana | 177 | 3750 | 49 | Y |
| O2 | x | LC | pET | x | NA | NA | NA | NA |
| O6 | wt | SC | None | None | 145 | 4180 | 16 | Y |
| O6 | Δwzzb/fepE | LC | topo | Kana | 124 | 9850 | 44 | Y |
| O6 | Δwzzb/fepE | LC | pET | Kana | ND | ND | ND | ND |
| O11 | wt | SC | None | None | 194 | 4720 | x | N |
| O11 | Δwzzb/fepE | LC | topo | Kana | 142 | 7220 | x | N |
| O11 | x | LC | pET | x | NA | NA | NA | NA |
| O13 | wt | SC | None | x | 113 | 4770 | x | N |
| O13 | Δwzzb/fepE | LC | topo | cam | 101 | 4680 | x | N |
| O13 | Δwzzb/fepE | LC | pET | cam | 108 | 4600 | x | N |
| O16 | wt | SC | None | x | 154 | 1870 | x | N |
| O16 | Δwzzb/fepE | LC | topo | cam | 129 | 1180 | x | N |
| O16 | Δwzzb/fepE | LC | pET | cam | 137 | 1280 | x | N |
| O21 | wt | SC | None | x | 140 | 1180 | x | N |
| O21 | Δwzzb/fepE | LC | topo | cam | ND | ND | x | N |
| O21 | Δwzzb/fepE | LC | pET | cam | 131 | 820 | x | N |
| O25b | 2831 | SC | None | None | 126 | 3550 | 10 | N |
| O25b | Δwzzb/fepE | LC | topo | Kana | 152 | 3500 | 49 | N |
| O25b | x | LC | pET | x | NA | NA | NA | NA |
| O75 | wt | SC | None | x | 149 | 1690 | x | N |
| O75 | Δwzzb/fepE | LC | topo | cam | 132 | 1500 | x | N |
| O75 | Δwzzb/fepE | LC | pET | cam | 138 | 1520 | x | N |

The purification process for the polysaccharides included acid hydrolysis to release the O-antigens. A crude suspension of serotype specific *E. coli* culture in fermentation reactor was directly treated with acetic acid to the final pH of 3.5±0.5 and the acidified broth was heated to the temperature of 95±5° C. for at least one hour. This treatment cleaves the labile linkage between KDO, at the proximal end of the oligosaccharide and the lipid A, thus releasing the O-Ag chain. The acidified broth that contains the released O-Ag was cooled to 20±10° C. before being neutralized to PH 7±1.0 using $NH_4OH$. The process further included severalcentrifugation, filtration, and concentration/diafiltration operations steps.

TABLE 28

| Serotype (core) | Description | Expected Poly size | Titer (g/L) | Purified Poly M.W. (kDa) | Number of Repeat Units | Increase in M.W. (kDa) over short | NMR | Purified Conjugate M.W. (kDa) | Conjugation Lot # |
|---|---|---|---|---|---|---|---|---|---|
| O25b (R1) | ΔwzzB + LT2FepE | Long | 5.3 | 47 | 55 | 34 | ✓ | 5365 | 132242-28 (RAC/DMSO) |
| | | | | | | | | 1423 | 132242-98 (Single-end) |
| | | | | | | | | 1258 | 132240-73-1-1 (eTEC) |
| | ΔwzzB + O25a wzzB | Short | 2.3 | 13/14 | 15 | NA | ✓ | 380 | 132242-116 (Single-end) |
| | | | | | | | | 9114 | 132242-121 (RAC/DMSO) |
| O25b (K12) | ΔwzzB + LT2FepE | Long | 3.5 | 44 | 51 | 27 | ✓ | 1537 | 709749-015-2 (eTEC) |
| | | | | | | | | 4775 | 709744-0016 (RAC/DMSO |
| | wt | Short | 3.5 | 17 | 17 | NA | ✓ | | |
| O1a (R1) | ΔwzzB + LT2FepE | Long | 5.5 | 33 | 39 | 22 | ✓ | 1035 | 132240-112-2 (eTEC) |
| | | | | | | | | 331 | 132242-106 (Single-end) |
| | | | | | | | | 1284 | 132242-124 (RAC/DMSO) |
| | wt | Short | 2.5 | 11 | 13 | NA | ✓ | 280 | 132242-127 (Single-end) |
| | | | | | | | | 2266 | 132242-130 (RAC/DMSO) |

TABLE 28-continued

| Serotype (core) | Description | Expected Poly size | Titer (g/L) | Purified Poly M.W. (kDa) | Number of Repeat Units | Increase in M.W. (kDa) over short | NMR | Purified Conjugate M.W. (kDa) | Conjugation Lot # |
|---|---|---|---|---|---|---|---|---|---|
| O2 (R1) | ΔwzzB + LT2FepE | Long | 4.9 | 36 | 43 | 22 | ✓ | 1161 | 00707947-0003-1 (eTEC) |
| | | | | 39 | 47 | 25 | | 422 | 132242-161 (single-end) |
| | | | | | | | | 3082 | 132242-152 (RAC/DMSO) |
| | wt | Short | 2.8 | 14 | 17 | NA | ✓ | 234 | 132242-159 (single-end) |
| | | | | | | | | 1120 | 1322421-157 (RAC/DMSO) |
| O2 (R4) | ΔwzzB + LT2FepE | Long | 5.1 | NA | NA | NA | NA | | |
| | wt | Short | 2.1 | 14.7 | 18 | NA | ✓ | | |
| O6 (R1) | ΔwzzB + LT2FepE | Long | 6.9 | 37.2 | 42 | 22.2 | ✓ | | |
| | wt | Short | 3.5 | 15 | 17 | NA | ✓ | 256 | 132242-146 (Single-end__ |
| | | | | | | | | 2058 | 123342-145 (RAC/DMSO) |
| O6 (R1) | ΔwzzB + LT2FepE | Long | 8.4 | 44.4 | 50 | 28.2 | ✓ | 1050 | 132240-117-1 (eTEC) |
| | | | | | | | | 340 | 132242-134 (Single-end) |
| | | | | | | | | 1910 | 132242-137 (RAC/DMSO) |
| | wt | Short | 3.6 | 16.2 | 18 | NA | ✓ | | |

Example 31: Conjugation Towards O-Antigen (O4, O11, O21, O75) Studied (RAC/DMSO)

TABLE 29

| O4 conjugates | | | |
|---|---|---|---|
| Conjugate Lot# | 709744-70 | 709744-73 | 709744-72 |
| Poly Lot# | | 709740-168 | |
| Poly MW (kDa) | | 52 | |
| DO | 26 | 19 | 15 |
| Act poly Mw (kDa) | | 51 | |
| Conjugation | | | |
| Input SP | 1.0 | 1.0 | 1.0 |
| SPRatio | 0.85 | 1.0 | 1.0 |
| Free Sacc (%) | <5% | <5% | <5% |
| MW (kDa) | 4764 | 4758 | 3423 |
| Yield (%) | 72 | 80 | 82 |
| Endotoxin (EU/ug) | 0.003 | 0.001 | 0.005 |

TABLE 30

| O11 conjugates | | | | |
|---|---|---|---|---|
| Conjugate Lot# | 709744-64 | 709744-66 | 709744-65 | 709744-67 |
| Poly Lot# | | 709740-162 | | |
| Poly MW (kDa) | | 39 | | |
| DO | 21 | | 14 | |
| Act poly Mw (kDa) | | 40 | | |
| Conjugation | | | | |
| Input SP | 1.0 | 1.3 | 1.0 | 1.3 |
| SPRatio | 0.5 | 0.64 | 0.65 | 0.75 |
| Free Sacc (%) | <5% | <5% | <5% | <5% |
| MW (kDa) | 10520 | 7580 | 4814 | 4338 |
| Yield (%) | 30 | 30 | 44 | 38 |
| Endotoxin (EU/ug) | 0.005 | 0.005 | 0.005 | 0.005 |

TABLE 31

| O21 conjugates | | | | | |
|---|---|---|---|---|---|
| Conjugate Lot# | 709749-113 | 709749-111 | 709749-112 | 709749-115 | 709749-116 |
| Poly Lot# | | | 709740-165 | | |
| Poly MW (kDa) | | | 40 | | |
| DO | 25 | 18 | | 15 | |
| Act poly Mw (KDa) | 40 | 41 | | 40 | |
| Conjugation | | | | | |
| Input SP | 1.0 | 1.0 | 0.8 | 1.0 | 1.25 |
| SPRatio | 0.6 | 0.6 | 0.5 | 0.9 | 1.1 |
| Free Sacc (%) | 6% | 5% | <5% | 12% | 7% |
| MW (kDa) | 6920 | 5961 | 9729 | 2403 | 1960 |
| Yield (%) | 31 | 36 | 37 | 52 | 54 |
| Endotoxin (EU/ug) | 0.02 | 0.02 | 0.03 | 0.01 | 0.009 |

TABLE 32

| O75 conjugates | | | |
|---|---|---|---|
| Conjugate Lot# | 709749-101 | 709749-102 | 709749-103 |
| Poly Lot# | | 709766-080B | |
| Poly MW (kDa) | | 48 | |
| DO | 18 | | 25 |
| Act poly Mw (kDa) | 43 | | 44 |
| Conjugation | | | |
| Input SP | 1.0 | 0.8 | 1.0 |
| SPRatio | 0.94 | 0.76 | 0.78 |
| Free Sacc (%) | <5% | 6% | 6% |
| MW (kDa) | 2304 | 2427 | 5229 |
| Yield (%) | 62 | 65 | 45 |
| Endotoxin (EU/ug) | 0.02 | 0.01 | 0.01 |

Example 32: PLL Conjugates Prepared

TABLE 33

| Serotype | O11 | O75 | O21 | O4 |
|---|---|---|---|---|
| Conjugate Lot# | 00707779-0413 | 00707779-0414 | 00707779-0415 | 00707779-0416 |
| Poly Lot# | 709740-162 | 709766-080B | 709740-165 | 709740-168 |
| Poly MW (kDa) | 39 | 48 | 40 | 52 |
| Conjugate Data | | | | |
| SPRatio | 13.5 | 16.8 | 18.1 | 21.2 |
| Free Sacc (%) | 9.8% | <5% | <5% | 6.9% |
| Sacc Conc | 789 μg/mL | 676 μg/mL | 978 μg/mL | 837 μg/mL |
| PLL Conc | 58.3 μg/mL | 40.3 μg/mL | 54.0 μg/mL | 39.4 μg/mL |
| Endotoxin (EU/ug) | 0.002 | 0.002 | 0.005 | 0.004 |
| Conjugate (DS) Matrix | | 1X PBS, 1M NaCl | | |

Example 33: Stable Mammalian Cell Expression of *E. coli* Polypeptides

Stable CHO clones expressing FimH GSD or FimH LD were generated using a SSI (Site Specific Integration) stable expression system.

The host CHO cell is an engineered cell line from a CHOK1SV GS-KO background (see, for example, U.S. patent application No. 20200002727, for a description of the CHOK1SV GS-KO host cell line). Briefly a landing pad with green fluorescent protein (GFP) gene surrounded by two FRT sites were targeted into a transcription hot spot in the genome of the host cell. The GFP gene can be exchanged with GS gene and the gene of interest which are also surrounded by FRT sites from the LVEC vector co-expressed with flippase recombinase (FLPe). This system not only has growth and productivity profiles that compare favorably with random integration but also displays genotypic and phenotypic stability to at least 100 generations.

As referred to herein, the term "FRT site" refers to a nucleotide sequence at which the product of the flippase (FLP) gene of the yeast 2 μm plasmid, FLP recombinase, can catalyze a site-specific recombination. A variety of non-identical FRT sites are known to the art. The sequences of the various FRT sites are similar in that they all contain identical 13-base pair inverted repeats flanking an 8-base pair asymmetric core region in which the recombination occurs. It is the asymmetric core region that is responsible for the directionality of the site and for the variation among the different FRT sites. Illustrative (non-limiting) examples of these include the naturally occurring FRT (F), and several mutant or variant FRT sites such as FRT F1 and FRT F2.

As referred to herein, the term "landing pad" refers to a nucleic acid sequence comprising a first recombination target site chromosomally-integrated into a host cell. In some embodiments, a landing site comprises two or more recombination target sites chromosomally-integrated into a host cell. In some embodiments, the cell comprises 1, 2, 3, 4, 5, 6, 7, or 8 landing pads. In some embodiments, the cell comprises 1, 2, or 3 landing pads. In some embodiments, the cell comprises 4 landing pads. In some embodiments, landing pads are integrated at up to 1, 2, 3, 4, 5, 6, 7, or 8 distinct chromosomal loci. In some embodiments, landing pads are integrated at up to 1, 2, or 3 distinct chromosomal loci. In some embodiments, landing pads are integrated at 4 distinct chromosomal loci.

The LVEC expression vector for FimH GSD or FimH LD and the FLPe expression vector were co-transfected into a SSI host cell by electroporation either with BioRad Gene Pulser Xcell or Amaxa 4D-Nucleofector. Then cells were cultured in media without glutamine to select cells that has GS gene integrated at the landing pad site. Usually cells recover in 2-3 weeks. Then single cell cloning were carried out in 96 well plates either by FACS or limiting dilution. Titers from wells with cells were ranked to narrow down to top 48 clones. A second round of fed batch screening in 24 deep-well plates was conducted to narrow down the clones to top 12. A third round of fed batch screening in Ambr15 was executed to narrow down the clones to top 3. Ambr250 experiments were used to identify the best clone. Master cell bank and working cell bank were generated for the top clone after its identification.

Example 34: Cell Line Development and Production Reactor Expression of FimH-DSG WT and $FimH_{LD}$ WT Proteins The example described herein, describes an exemplary production of both FimH-DSG WT and $FimH_{LD}$ WT proteins from stable CHO cell lines, where the coding sequences for each protein has been stably intergraded into the CHO genome.

In a production bioreactor setting, the stable CHO cell lines selected were able to produce the target protein at around 1 gram per liter of culture for FimH-DSG WT, and 250 miligrams per liter of culture for $FimH_{LD}$ WT. The seed train for the production reactor was continuously scaled up from vial thaw of a working cell bank and expanded in shake flasks using an inoculation viable cell density of 0.3×10/\6 cells/ml through three passage cycles in shake flasks to provide enough cells for the production reactor. The cells were grown at 36.5 deg C, at 5% $CO_2$ for three-four days.

The production reactor was seeded from the final shake flask, targeting an inoculation cell density of 1×10/\6 cells/ml. The production reactor was grown at 36.5 deg C. for seven days, using a pH of 7.05 (+/−0.15), and targeting a $CO_2$ saturation of 5-10%. pH is controlled by sodium/potassium bicarbonate for base control, and $CO_2$ sparge for acid control. Dissolved oxygen is controlled at a setpoint of 40% using pure oxygen through the sparge. The temperature was adjusted to 31 deg C. on day seven. The reactor was fed on day 1 using a feed strategy that adds feed in correlation to the viable cell density, this is achieved by using a feed factor of 0.75 in order to ensure feed components do not run out during the run. The feed is then added continuously to provide the desired volume of feed over the course of the day.

The production reactor was harvested on day 13, and the harvest culture was centrifuged and 0.22 μm filtered, prior to downstream processing.

Example 35: Antibodies Elicited by $CRM_{197}$ Conjugates of *E. coli* Serotype O8 and O9 O-Antigens Show Cross-Protective Bactericidal Activity Against *K.Pneumoniae* Serotype O5 and O3 Invasive Isolates This Example demonstrates that antibodies elicited by short single-end native $CRM_{197}$ polymannan conjugates of *E. coli* serotype O8 and O9 O-antigens are bactericidal and cross-protective against *Klebsiella O*5 and O3 strains that express equivalent or related O-antigens.

*E. coli* and *K. pneumoniae* share common polymannan O-antigens which are synthesized by enzymes encoded by highly homologous biosynthetic gene clusters. The *E. coli* O8 and O9 O-antigen polysaccharides are linear mannose homopolymers whose repeat units differ in their monosaccharide linkages and in the number of residues. Their counterparts in *K. pneumoniae* are the serotype O5 and O3 O-antigens. Biosynthesis of the *E. coli* and *K. pneumoniae* polymannan O-antigens involves a different mechanism of O-unit translocation and chain synthesis than other *E. coli* O-antigens. In this case chain elongation is regulated by the biosynthetic WbdA-WbdD complex (King JD, Berry S, et al. Proceedings of the National Academy of Sciences 2014; 111:6407-12), which is distinct from the Wzx/Wzy-dependent pathway where chain length is controlled by WzzB or FepE enzymes. As a consequence, the native polymannan O-antigens can only be produced in their short form, which requires different bioprocesses methods for purification and carrier protein conjugation than the engineered long *E. coli* O-antigens. The same mechanism and limitation applies to the predominant *K. pneumoniae* serotype O1 and O2 O-antigens, which are polygalactans comprised of galactose residues.

The structural relationship between these O-antigens and their subtypes is shown in FIG. 33. The *E. coli O*8 and *K. pneumoniae O*5 O-antigens are identical (Vinogradov E, et al. J Biol Chem 2002; 277:25070-81). *E. coli O*9 and *K. pneumoniae* O3 O-antigens share common tetrameric O9a/O3a and pentameric O9/O3 repeat unit subtypes, while the trimeric O3b subtype is only found in *K. pneumoniae*. These subtypes can be identified serologically and genotypically (Guachalla L M, et al. Scientific Reports 2017; 7:6635). Serotype O3a loci are distinguished by a single point mutation in wbdA (C80R). An analogous point mutation in the *E. coli O*9 wbdA enzyme (C55R) converts the O9 polysaccharide into O9a (Kido N, Kobayashi H. Journal of bacteriology 2000; 182:2567-73). The O3b subtype has sufficient nucleotide divergence in the sequence of the WbdD enzyme to necessitate a separate reference sequence. The Kaptive web algorithm (Wick R R, et al. J Clin Microbiol 2018; 56), implemented into Pfizer's BigSdb whole genome sequencing (WGS) pipeline, designates O3 loci as either O3/O3a (covered by the same reference sequence) or O3b.

Materials and Methods a. Production of *E. coli* Serotype O8 and O9 $CRM_{197}$ Immune Sera in Rabbits Two groups of four female New Zealand White rabbits each were used for the study run at Covance. Animals received 10 μg/animal of serotype O8 or O9 $CRM_{197}$ conjugate per dose with CFA/IFA as adjuvant. Native O8 and O9 O-antigens were conjugated using single-end chemistry. Each 1 mL dose of 10 μg of antigen was split across two subcutaneous vaccination sites. Vaccinations were given at weeks 0, 6 and 14, with blood draws at weeks 7 and 15, which correspond to post-dose two (PD2) and post-dose three (PD3) timepoints.

b. Bacterial Strains

*E. coli* and *K. pneumoniae* clinical isolates were obtained from the Pfizer-sponsored Antimicrobial Testing Leadership and Surveillance (ATLAS) collection which is maintained by the International Health Management Associates (IHMA) clinical lab. Strains were genotypically characterized by whole genome sequencing (WGS) using the Miseq platform (Illumina). WGS data was used to generate multi-locus-sequence type (MLST) information using established *E. coli* and *K. pneumoniae* schemes integrated into the BigDdb platform (Wirth T, et al. Molecular microbiology 2006; 60:1136-51; Jolley K A, et al. Wellcome Open Res 2018; 3:124; Diancourt L, et al. Journal of clinical microbiology 2005; 43:4178-82). Embedded in silico serotyping algorithms for *E. coli* and *K. pneumoniae* were used to predict O-antigen serotype (Wick R R, et al. J Clin Microbiol 2018; 56; Joensen K G, et al. J Clin Microbiol 2015; 53:2410-26).

TABLE 34

Clinical isolates used for O-antigen production or development of bactericidal assays

| ID | Species | MLST ST | Serotype (subtype) | Source |
|---|---|---|---|---|
| EC0130 | *E. coli* | 162 | O8 | Blood |
| EC0423 | *E. coli* | 46 | O9a | Blood |
| EC0305 | *E. coli* | 448 | O8 | Blood |
| KP0121 | *K. pneumoniae* | 279 | O5 | Blood |

TABLE 34-continued

Clinical isolates used for O-antigen production or development of bactericidal assays

| ID | Species | MLST ST | Serotype (subtype) | Source |
|---|---|---|---|---|
| EC0611 | *E. coli* | New | O9a | UTI, Kidney |
| KP0009 | *K. pneumoniae* | 37 | O3b | UTI, Bladder |

c. *E. coli O*8 and O9 $CRM_{197}$ Conjugates

Serotype O8 and O9a O-antigen polysaccharides were extracted and purified from strains EC0130 and EC0423, respectively (Table 34). The conjugation process involves selective activation of the Kdo monosaccharide present on the reducing end of the short native *E. coli O*8 and O9 O-antigens with a disulfide amine linker. Upon unmasking of thiol functional group, it is then conjugated to bromo activated $CRM_{197}$ protein as described Example 26 set forth herein.

d. Bactericidal Assays

Pre-frozen *E. coli* and *K. pneumoniae* stocks were prepared by growing strains in DMEM or LB media to an OD600 of between 0.5 and 1.0 and glycerol was added to a final concentration of 20% prior to freezing. Specific assay conditions varied according to conditions optimized for each bacterial strain. Pre-titered thawed bacteria were diluted to $1\times10^5$ CFU/ml in OPA buffer (Hanks Balanced Salt Solution (Life Technologies) and 0.1% gelatin) and 20 μL ($10^3$ CFU) of the bacterial suspension was opsonized with 20 μL of serially diluted sera for 30 min at RT in a tissue culture microplate. Subsequently, 10 μl of complement (Baby Rabbit Serum or IgG/IgM depleted human serum, Pel-Freez) and 20 μL of HL-60 cells (at 100-200:1 ratio) were added to each well with OPA buffer to a final volume of 100 μL. The reaction mixture was shaken for 60 min at 37° C. in a 5% $CO_2$ incubator. In some cases, bacteria were directly combined with complement and HL60s without the pre-opsonization step and shaken for 60 min at 37° C. under 5% $CO_2$. After the incubation, 10 μL of each reaction was transferred into the corresponding wells of a prewetted Millipore MultiScreen HTS HV filter plate containing 100 μL water. After vacuum filtering the liquid, 100 μL of 50% bacterial growth media was applied and filtered, and the plate incubated overnight at 37° C. in a sealed zip-lock bag. The next day microcolonies were enumerated after staining with Coomassie dye using an ImmunoSpot® analyzer and ImmunoCapture software. In the case of the *E. coli* serotype O9 assay, the OPA was miniaturized for 50 μL reaction reactions volumes in the 384-well format. To establish the specificity of OPA activity, immune sera were preincubated with purified O-antigen polysaccharide prior to the opsonization step. The OPA assay included control reactions without HL60 cells or complement, to demonstrate dependence of any observed killing on these components. For the *Klebsiella* serotype O5 assay where presence of HL60s had no impact, serum bactericidal reactions were run in the absence of effector cells.

Results a. *E. coli* and *K. pneumoniae* Strain Selection for Bactericidal Assays Bacterial clinical strains were initially selected after confirming O-antigen expression by LPS profiling (by SDS-PAGE), and O-antigen surface accessibility by flow cytometry with O-antigen specific rabbit antisera. Next, empiric screening of serum complement was done to identify individual compatible lots across a range of concentrations that provided a suitable balance of low levels of non-specific killing combined with a high degree of susceptibility in the presence of immune sera. Additional assay optimization parameters included adjusting the ratio of HL60 effector cell to bacteria, shaker speed, presence/absence of plate sealer and inclusion of an opsonization preincubation step.

b. *E. coli O*8 and *K. pneumoniae O*5 O-Antigen Immune Serum Cross-Protection and Specificity

Figure 34A:
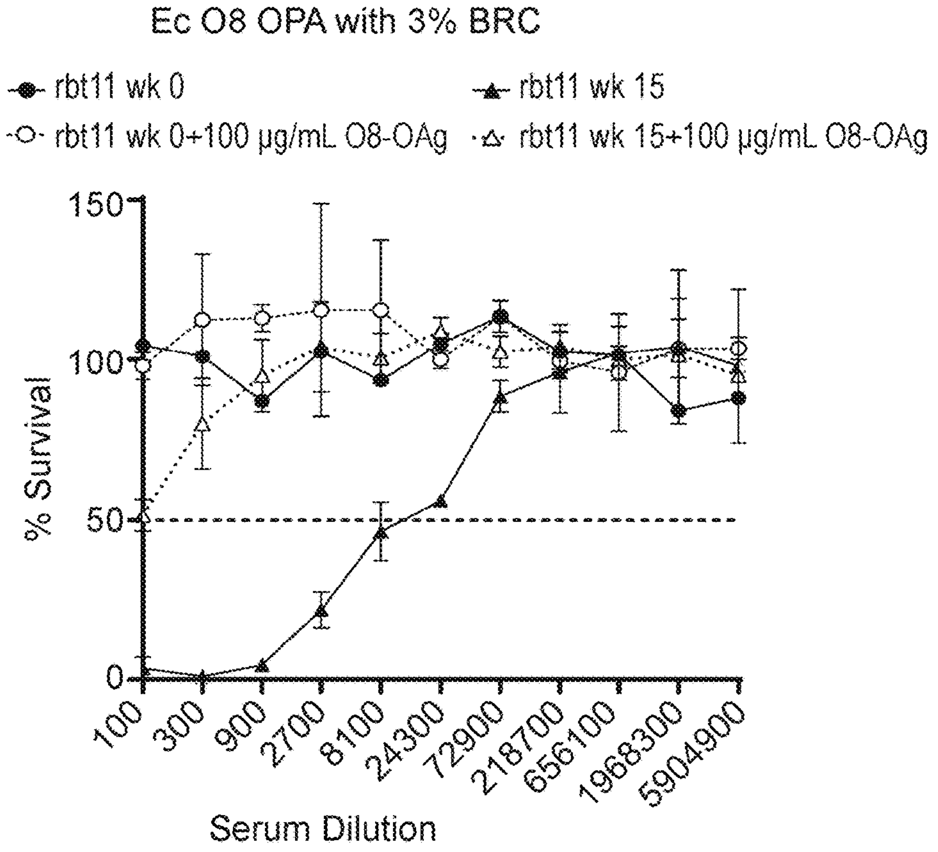
FIG. 34A—34B—depict *E. coli* serotype O8 immune sera is bactericidal against an invasive *K. pneumoniae* serotype O5 strai. Legend: Rabbit immune sera elicited by an *E. coli* serotype O8 O-antigen CRM197 conjugate was evaluated in bactericidal assays with an *E. coli O*8 strain (FIG. 34A) and a *K. pneumoniae O*5 strain (FIG. 34B). Potent opsonophagocytic assay (OPA) activity against an *E. coli O*8 strain was observed after two vaccine doses (week 15) that was absent following preadsorption with unconjugated O8 polysaccharide (O8-OAg), or with matched pre-immune sera (week 0). The same rabbit immune serum showed antigen-specific serum bactericidal activity (SBA) against the *K. pneumoniae O*5 strain. BRC—baby rabbit complement, hC—IgG/IgM depleted human sera as complement source.
Figure 34B:
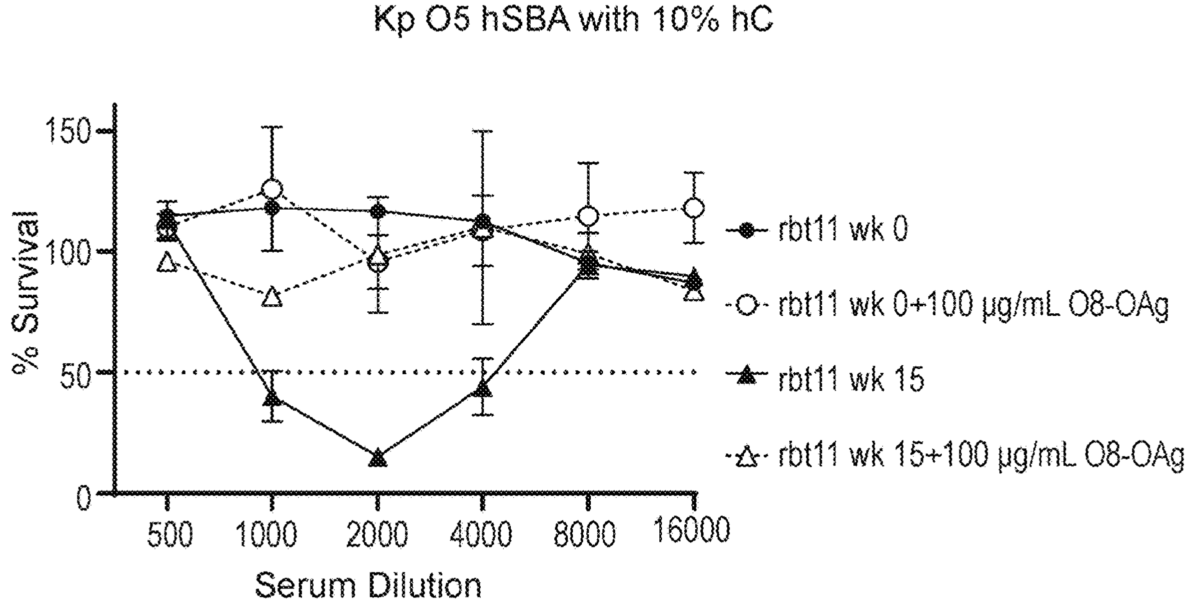

*E. coli O*8 strain EC0305 and *K. pneumoniae O*5 strain KP0121 were selected for assay development. Both are blood isolates. EC0305 is resistant to cephalosporins and tetracycline while KP0121 is resistant to ampicillin. An OPA assay was developed for the *E. coli O*8 strain EC0305 with conditions including 3.0% BRC, a 1:100 bacteria to HL60 ratio, and a single step 60 min OPA incubation reaction. As the bactericidal activity of the *K. pneumoniae O*5 strain KP0121 in the presence if immune sera was found to be independent of HL60 effector cells, an SBA was developed. In this case, the SBA reaction required the use of 10% depleted human serum as source of complement. Results of bactericidal assays with these *E. coli O*8 and *K. pneumoniae O*5 strains are shown in FIG. 34A-34B. In the *E. coli* serotype O8 OPA, rabbit immune serum generated after two doses of 08-$CRM_{197}$ conjugate showed potent O-antigen specific killing that was blocked by preadsorption of the immune serum with free O8 O-antigen polysaccharide. Complete killing was observed at serum dilutions of less than 1:1000. Matched pre-immune sera from the same rabbit was inactive. The same rabbit sera was evaluated in the *K. pneumoniae O*5 SBA, and found to be similarly bactericidal at a 1:2000 serum dilution. Killing was blocked by free O8 O-antigen and absent with the pre-immune serum. In this case a serum matrix prozone masked SBA activity at serum dilutions of less than 1:1000.

c. *E. coli O*9 and *K. pneumoniae O*3 OPA O-Antigen Immune Serum Cross-Protection and Specificity

Figure 35A:
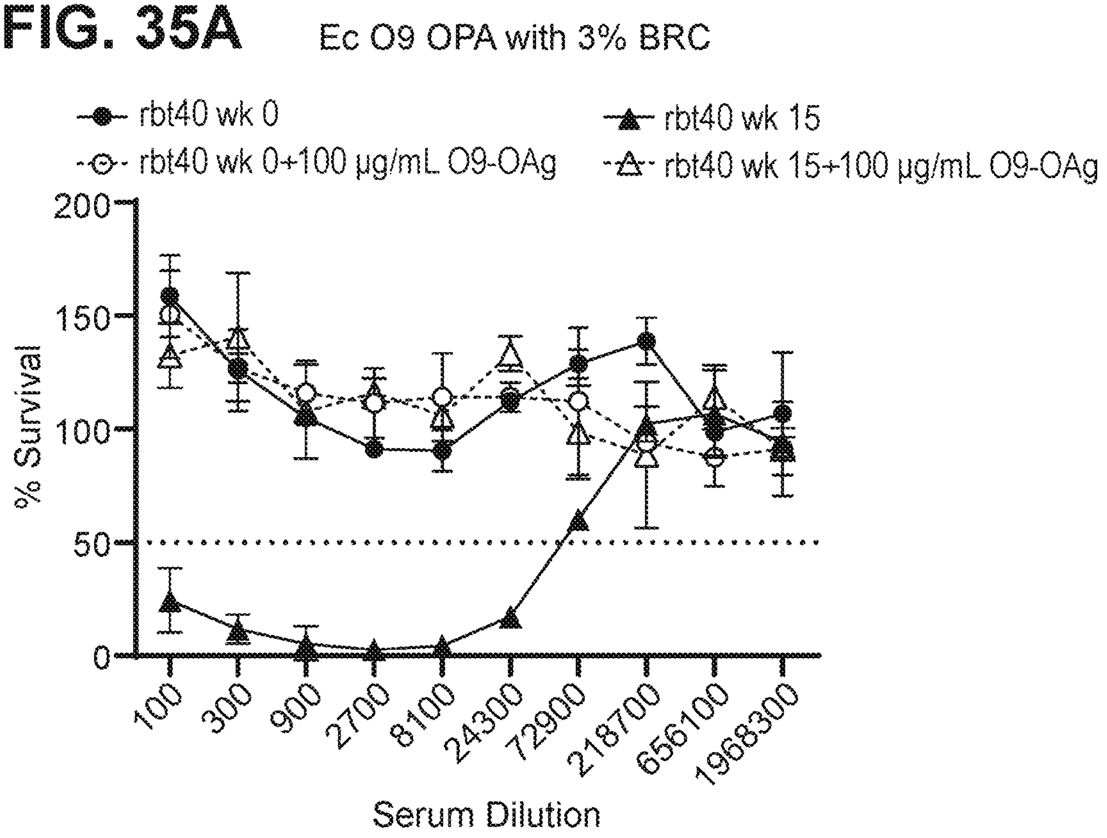
FIG. 35A-35B—depict *E. coli* serotpye O9 O-antugen immune sera is bactericidal against an invasive *K. pneumoniae* 03 isolate. Legend: Rabbit immune sera elicited by an *E. coli* serotype O9a O-antigen CRM197 conjugate was evaluated in opsonophagocytic assays (OPAs) with an *E. coli O*9a strain (FIG. 35A) and a *K. pneumoniae* O3b strain (FIG. 35B). OPA activity against the *E. coli O*9 strain was observed after two vaccine doses (week 15) that was absent following preadsorption with unconjugated O9 polysaccharide (O9-OAg), or with matched pre-immune sera (week 0). The same rabbit immune serum also showed potent antigen-specific serum bactericidal activity (SBA) against the *K. pneumoniae* O3b strain. BRC, baby rabbit complement; hC, IgG/IgM depleted human sera used as complement source.
Figure 35B:
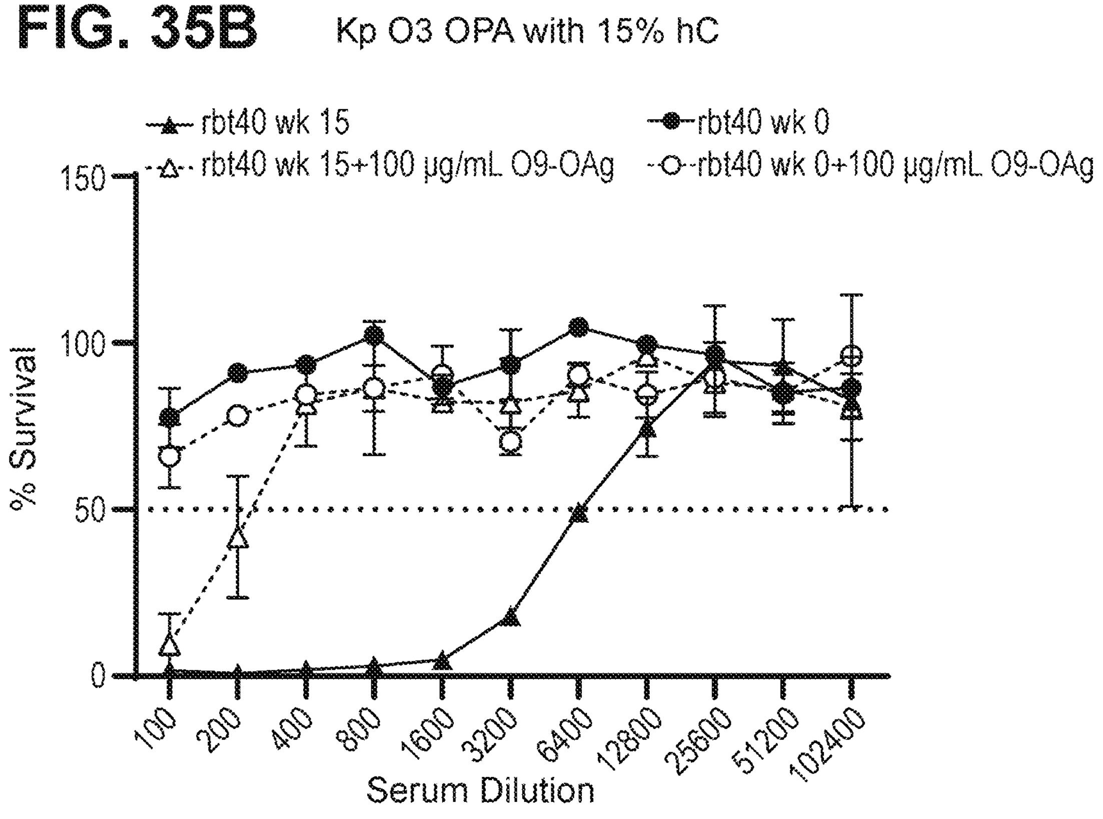

*E. coli O*9a strain EC0611 and *K. pneumoniae* O3b strain KP0009 were selected for assay development. EC0611 is resistant to ampicillin, while KP0009 is resistant to cephalosporins, fluoroquinolones, and tetracycline. Both are UTI isolates from kidney and bladder infections, respectively. The O9a O-antigen used to generate the $CRM_{197}$ conjugate and resulting immune serum has the tetrametic polymannan repeat unit structure and is identical to the O9a EC0611 assay strain O-antigen; however, it is structurally heterologous to the *K. pneumoniae* O3b O-antigen KP0009 assay strain, which is predicted to express the shorter trimeric repeat unit based on the sequence of its wbdD gene (See FIG. 33). Results of OPAs with the *E. coli O*9a and *K. pneumoniae* O3b strains show that anti-*E. coli O*9a immune serum is potent against both (FIG. 35A-35B). Complete killing in the OPAs was observed at serum dilutions of less than 1:8,000 for the *E. coli O*9a strain and at less than 1:1,600 for the *Klebsiella* O3b strain. Specificity was demonstrated by the lack of activity upon preadsorption of serum with free O9a O-antigen and with the matched-pre-immune serum.

CONCLUSION

*E. coli* serotype O8 and O9 polymannan $CRM_{197}$ conjugates elicit functional antibodies that are capable of killing not only homologous *E. coli* clinical strains but also *Klebsiella* serotype O5 and O3 strains in bactericidal assays. Results confirm that these conjugates elicit antibodies that are cross-protective against isolates of both species expressing structurally related polymannan O-antigens.

The Following Clauses Describe Additional Embodiments of the Invention:

C1. A composition comprising a polypeptide derived from FimH or a fragment thereof; and a saccharide comprising a structure selected from any one of Formula O1 (e.g., Formula O1A, Formula O1B, and Formula O1C), Formula O2, Formula O3, Formula O4 (e.g., Formula 04: K52 and Formula O4: K6), Formula O5 (e.g., Formula O5ab and Formula O5ac (strain 180/C3)), Formula O6 (e.g., Formula O6: K2; K13; K15 and Formula O6: K54), Formula O7, Formula O8, Formula O9, Formula O10, Formula O11, Formula O12, Formula O13, Formula O14, Formula O15, Formula O16, Formula O17, Formula O18 (e.g., Formula O18A, Formula O18ac, Formula O18A1, Formula O18B, and Formula O18B1), Formula O19, Formula O20, Formula O21, Formula O22, Formula O23 (e.g., Formula O23A), Formula O24, Formula O25 (e.g., Formula O25a and Formula O25b), Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45 (e.g., Formula O45 and Formula O45rel), Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula $62D_1$, Formula O63, Formula O64, Formula O65, Formula O66, Formula O68, Formula O69, Formula O70, Formula O71, Formula O73 (e.g., Formula O73 (strain 73-1)), Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula 114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144, Formula O145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, and Formula O187, wherein n is an integer from 1 to 100.

C2. The composition according to clause C1, wherein the saccharide comprises a structure selected from Formula O1 (e.g., Formula O1A, Formula O1B, and Formula O1C), Formula O2, Formula O3, Formula O4 (e.g., Formula O4: K52 and Formula O4: K6), Formula O5 (e.g., Formula O5ab and Formula O5ac (strain 180/C3)), Formula O6 (e.g., Formula O6: K2; K13; K15 and Formula O6: K54), Formula O7, Formula O10, Formula O16, Formula O17, Formula O18 (e.g., Formula O18A, Formula O18ac, Formula O18A1, Formula O18B, and Formula O18B1), Formula O21, Formula O23 (e.g., Formula O23A), Formula O24, Formula O25 (e.g., Formula O25a and Formula O25b), Formula O26, Formula O28, Formula O44, Formula O45 (e.g., Formula O45 and Formula O45rel), Formula O55, Formula O56, Formula O58, Formula O64, Formula O69, Formula O73 (e.g., Formula O73 (strain 73-1)), Formula O75, Formula O77, Formula O78, Formula O86, Formula O88, Formula O90, Formula O98, Formula O104, Formula O111, Formula O113, Formula O114, Formula O119, Formula O121, Formula O124, Formula O125, Formula O126, Formula O127, Formula O128, Formula O136, Formula O138, Formula O141, Formula O142, Formula O143, Formula O147, Formula O149, Formula O152, Formula O157, Formula O158, Formula O159, Formula O164, Formula O173, Formula $62D_1$, Formula O22, Formula O35, Formula O65, Formula O66, Formula O83, Formula O91, Formula O105, Formula O116, Formula O117, Formula O139, Formula O153, Formula O167, and Formula O172, wherein n is an integer from 20 to 100.

C3. The composition according to clause C2, wherein the saccharide comprises a structure selected from Formula O1 (e.g., Formula O1A, Formula O1B, and Formula O1C), Formula O2, Formula O3, Formula O4 (e.g., Formula O4: K52 and Formula O4: K6), Formula O5 (e.g., Formula O5ab and Formula O5ac (strain 180/C3)), Formula O6 (e.g., Formula O6: K2; K13; K15 and Formula O6: K54), Formula O7, Formula O10, Formula O16, Formula O17, Formula O18 (e.g., Formula O18A, Formula O18ac, Formula O18A1, Formula O18B, and Formula O18B1), Formula O21, Formula O23 (e.g., Formula O23A), Formula O24, Formula O25 (e.g., Formula O25a and Formula O25b), Formula O26, Formula O28, Formula O44, Formula O45 (e.g., Formula O45 and Formula O45rel), Formula O55, Formula O56, Formula 058, Formula O64, Formula O69, Formula O73 (e.g., Formula O73 (strain 73-1)), Formula O75, Formula O77, Formula O78, Formula O86, Formula O88, Formula O90, Formula O98, Formula O104, Formula O111, Formula O113, Formula O114, Formula O119, Formula O121, Formula O124, Formula O125, Formula O126, Formula O127, Formula O128, Formula O136, Formula O138, Formula O141, Formula O142, Formula O143, Formula O147, Formula O149, Formula O152, Formula O157, Formula O158, Formula O159, Formula O164, Formula O173, and Formula $62D_1$, wherein n is an integer from 20 to 100.

C4. The composition according to clause C2, comprising a structure selected from Formula O1 (e.g., Formula O1A, Formula O1B, and Formula O1C), Formula O2, Formula O6 (e.g., Formula O6: K2; K13; K15 and Formula O6: K54), Formula O15, Formula O16, Formula O21, Formula O25 (e.g., Formula O25a and Formula O25b), and Formula O75.

C5. The composition according to clause C2, comprising a structure selected from Formula O4, Formula O11, Formula O21, and Formula O75.

C6. The composition according to clause C1, wherein the saccharide does not comprise a structure selected from Formula O8, Formula O9a, Formula O9, Formula O20ab, Formula O20ac, Formula O52, Formula O97, and Formula O101.

C7. The composition according to clause C1, wherein the saccharide does not comprise a structure selected from Formula O12.

C8. The composition according to clause C4, wherein the saccharide is produced by expressing a wzz family protein in a Gram-negative bacterium to generate said saccharide.

C9. The composition according to clause C8, wherein the wzz family protein is selected from the group consisting of wzzB, wzz, $WZZ_{SF}$, $WZZ_{ST}$, fepE, $WZZ_{fepE}$, wzZ1 and wzz2.

C10. The composition according to clause C8, wherein the wzz family protein is wzzB.

C11. The composition according to clause C8, wherein the wzz family protein is fepE.

C12. The composition according to clause C8, wherein the wzz family protein is wzzB and fepE.

C13. The composition according to clause C8, wherein the wzz family protein is derived from *Salmonella enterica.*

C14. The composition according to clause C8, wherein the wzz family protein comprises a sequence selected from any one of SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, and SEQ ID NO: 39.

C15. The composition according to clause C8, wherein the wzz family protein comprises a sequence having at least 90% sequence identity to any one of SEQ ID NO: 30, SEQ ID NO: 31, SEQ ID NO: 32, SEQ ID NO: 33, SEQ ID NO: 34.

C16. The composition according to clause C8, wherein the wzz family protein comprises a sequence selected from any one of SEQ ID NO: 35, SEQ ID NO: 36, SEQ ID NO: 37, SEQ ID NO: 38, and SEQ ID NO: 39.

C17. The composition according to clause C1, wherein the saccharide is synthetically synthesized.

C18. The composition according to any one of clauses C1 to C17, wherein the saccharide further comprises an *E. coli* R1 moiety.

C19. The composition according to any one of clauses C1 to C17, wherein the saccharide further comprises an *E. coli* R2 moiety.

C20. The composition according to any one of clauses C1 to C17, wherein the saccharide further comprises an *E. coli* R3 moiety.

C21. The composition according to any one of clauses C1 to C17, wherein the saccharide further comprises an *E. coli* R4 moiety.

C22. The composition according to any one of clauses C1 to C17, wherein the saccharide further comprises an *E. coli* K-12 moiety.

C23. The composition according to any one of clauses C1 to C22, wherein the saccharide further comprises a 3-deoxy-d-manno-oct-2-ulosonic acid (KDO) moiety.

C24. The composition according to any one of clauses C1 to C17, wherein the saccharide does not further comprise an *E. coli* R1 moiety.

C25. The composition according to any one of clauses C1 to C17, wherein the saccharide does not further comprise an *E. coli* R2 moiety.

C26. The composition according to any one of clauses C1 to C17, wherein the saccharide does not further comprise an *E. coli* R3 moiety.

C27. The composition according to any one of clauses C1 to C17, wherein the saccharide does not further comprise an *E. coli* R4 moiety.

C28. The composition according to any one of clauses C1 to C17, wherein the saccharide does not further comprise an *E. coli* K-12 moiety.

C29. The composition according to any one of clauses C1 to C22, wherein the saccharide does not further comprise a 3-deoxy-d-manno-oct-2-ulosonic acid (KDO) moiety.

C30. The composition according to any one of clauses C1 to C23, wherein the saccharide does not comprise a Lipid A.

C31. The composition according to any one of clauses C1 to C30, wherein the polysaccharide has a molecular weight of between 10 kDa and 2,000 kDa, or between 50 kDa and 2,000 kDa.

C32. The composition according to any one of clauses C1 to C31, wherein the saccharide has an average molecular weight of 20-40 kDa.

C33. The composition according to any one of clauses C1 to C32, wherein the saccharide has an average molecular weight of 40,000 to 60,000 kDa.

C34. The composition according to any one of clauses C1 to C33, wherein n is an integer 31 to 90.

C35. A composition comprising a polypeptide derived from FimH or fragment thereof; and a conjugate comprising a saccharide covalently bound to a carrier protein, wherein the saccharide is derived from *E. coli.*

C36. A composition comprising a polypeptide derived from FimH or fragment thereof; and a conjugate comprising a saccharide according to any one of clause C1 to clause C34, covalently bound to a carrier protein.

C37. A composition comprising a polypeptide derived from FimH or fragment thereof; and a conjugate according to any one of clause C35 to clause C36, wherein the carrier protein is selected from any one of poly (L-lysine), $CRM_{197}$, diphtheria toxin fragment B (DTFB), DTFB C8, Diphtheria toxoid (DT), tetanus toxoid (TT), fragment C of TT, pertussis toxoid, cholera toxoid, or exotoxin A from *Pseudomonas aeruginosa*; detoxified Exotoxin A of *P. aeruginosa* (EPA), maltose binding protein (MBP), detoxified hemolysin A of *S. aureus*, clumping factor A, clumping factor B, Cholera toxin B subunit (CTB), *Streptococcus pneumoniae* Pneumolysin and detoxified variants thereof, *C. jejuni* AcrA, *C. jejuni* natural glycoproteins and Streptococcal C5a peptidase (SCP).

C38. The composition according to any one of clause C35 to clause C37, wherein the carrier protein is $CRM_{197}$.

C39. The composition according to any one of clause C35 to clause C37, wherein the carrier protein is tetanus toxoid (TT).

C40. The composition according to any one of clause C35 to clause C37, wherein the carrier protein is poly (L-lysine).

C41. The composition according to any one of clause C35 to clause C39, wherein the conjugate is prepared by reductive amination.

C42. The composition according to any one of clause C35 to clause C39, wherein the conjugate is prepared by CDAP chemistry.

C43. The composition according to any one of clause C35 to clause C39, wherein the conjugate is a single-end linked conjugated saccharide.

C44. The composition according to any one of clause C35 to clause C39, wherein the saccharide is conjugated to the carrier protein through a (2-((2-oxoethyl)thio)ethyl) carbamate (eTEC) spacer.

C45. The composition according to clause C44, wherein the saccharide is conjugated to the carrier protein through a (2-((2-oxoethyl)thio)ethyl) carbamate (eTEC) spacer, wherein the saccharide is covalently linked to the eTEC spacer through a carbamate linkage, and wherein the carrier protein is covalently linked to the eTEC spacer through an amide linkage.

C46. The composition according to any one of clause C44 to clause C45, wherein the $CRM_{197}$ comprises 2 to 20, or 4 to 16, lysine residues covalently linked to the polysaccharide through an eTEC spacer.

C47. The composition according to any one of clause C35 to clause C46, wherein the saccharide: carrier protein ratio (w/w) is between 0.2 and 4.

C48. The composition according to any one of clause C35 to clause C46, wherein the ratio of saccharide to protein is at least 0.5 and at most 2.

C49. The composition according to any one of clause C35 to clause C46, wherein the ratio of saccharide to protein is between 0.4 and 1.7

C50. The composition according to any one of clause C43 to clause C49, wherein the saccharide is conjugated to the carrier protein through a 3-deoxy-d-manno-oct-2-ulosonic acid (KDO) residue.

C51. A composition comprising a polypeptide derived from FimH or fragment thereof; and a conjugate comprising a saccharide covalently bound a carrier protein, wherein the saccharide comprises a structure selected from Formula O8, Formula O9a, Formula O9, Formula O20ab, Formula O20ac, Formula O52, Formula O97, and Formula O101, wherein n is an integer from 1 to 10.

C52. A composition comprising a polypeptide derived from FimH or fragment thereof; and a saccharide according to any one of clause C1 to clause C34, and a pharmaceutically acceptable diluent.

C53. A composition comprising a polypeptide derived from FimH or fragment thereof; and a conjugate according to any one of clause C35 to clause C51, and a pharmaceutically acceptable diluent.

C54. The composition according to clause C53, comprising at most about 25% free saccharide as compared to the total amount of saccharide in the composition.

C55. The composition according to any one of clause C52 to clause C53, further comprising an adjuvant.

C56. The composition according to any one of clause C52 to clause C53, further comprising aluminum.

C57. The composition according to any one of clause C52 to clause C53, further comprising QS-21.

C58. The composition according to any one of clause C52 to clause C53, further comprising a CpG oligonucleotide.

C59. The composition according to any one of clause C52 to clause C53, wherein the composition does not include an adjuvant.

C60. A composition comprising a polypeptide derived from FimH or fragment thereof; and a saccharide derived from *E. coli*, conjugated to a carrier protein through a (2-((2-oxoethyl)thio)ethyl) carbamate (eTEC) spacer, wherein the polysaccharide is covalently linked to the eTEC spacer through a carbamate linkage, and wherein the carrier protein is covalently linked to the eTEC spacer through an amide linkage.

C61. The composition according to clause C60, wherein the saccharide is an O-antigen derived from *E. coli.*

C62. The composition according to clause C60, further comprising a pharmaceutically acceptable excipient, carrier or diluent.

C63. The composition according to clause C60, wherein the saccharide is an O-antigen derived from *E. coli.*

C64. A composition comprising a polypeptide derived from FimH or fragment thereof; and a saccharide according to any one of clause C1 to clause C17, conjugated to a carrier protein through a (2-((2-oxoethyl)thio)ethyl) carbamate (eTEC) spacer, wherein the polysaccharide is covalently linked to the eTEC spacer through a carbamate linkage, and wherein the carrier protein is covalently linked to the eTEC spacer through an amide linkage.

C65. A composition comprising a polypeptide derived from FimH or fragment thereof; and (i) a conjugate of an *E. coli* O25B antigen covalently coupled to a carrier protein, (ii) a conjugate of an *E. coli* O1A antigen covalently coupled to a carrier protein, (iii) a conjugate of an *E. coli* O2 antigen covalently coupled to a carrier protein, and (iv) a conjugate of an O6 antigen covalently coupled to a carrier protein, wherein the *E. coli* O25B antigen comprises the structure of Formula O25B, wherein n is an integer greater than 30.

C66. The composition of clause C65, wherein the carrier protein is selected from any one of poly (L-lysine), $CRM_{197}$, diphtheria toxin fragment B (DTFB), DTFB C8, Diphtheria toxoid (DT), tetanus toxoid (TT), fragment C of TT, pertussis toxoid, cholera toxoid, or exotoxin A from *Pseudomonas aeruginosa*; detoxified Exotoxin A of *P. aeruginosa* (EPA), maltose binding protein (MBP), detoxified hemolysin A of *S. aureus*, clumping factor A, clumping factor B, Cholera toxin B subunit (CTB), *Streptococcus pneumoniae* Pneumolysin and detoxified variants thereof, *C. jejuni* AcrA, and *C. jejuni* natural glycoproteins.

C67. A composition comprising a polypeptide derived from FimH or fragment thereof; and (i) a conjugate of an *E. coli* O25B antigen covalently coupled to a carrier protein, (ii) a conjugate of an *E. coli O*4 antigen covalently coupled to a carrier protein, (iii) a conjugate of an *E. coli* O11 antigen covalently coupled to a carrier protein, and (iv) a conjugate of an 021 antigen covalently coupled to a carrier protein, wherein the *E. coli* O25B antigen comprises the structure of Formula O75, wherein n is an integer greater than 30.

C68. The composition of clause C67, wherein the carrier protein is selected from any one of poly (L-lysine), $CRM_{197}$, diphtheria toxin fragment B (DTFB), DTFB C8, Diphtheria toxoid (DT), tetanus toxoid (TT), fragment C of TT, pertussis toxoid, cholera toxoid, or exotoxin A from *Pseudomonas aeruginosa*; detoxified Exotoxin A of *P. aeruginosa* (EPA), maltose binding protein (MBP), detoxified hemolysin A of *S. aureus*, clumping factor A, clumping factor B, Cholera toxin B subunit (CTB), *Streptococcus pneumoniae* Pneumolysin and detoxified variants thereof, *C. jejuni* AcrA, *C. jejuni* natural glycoproteins and Streptococcal C5a peptidase (SCP).

C69. A method of making a composition comprising a polypeptide derived from FimH or fragment thereof; and a conjugate comprising a saccharide conjugated to a carrier protein through a (2-((2-oxoethyl)thio)ethyl) carbamate (eTEC) spacer, comprising the steps of a) reacting a saccharide with 1,1'-carbonyl-di-(1,2,4-triazole) (CDT) or 1,1'-carbonyldiimidazole (CDI), in an organic solvent to produce an activated saccharide; b) reacting the activated saccharide with cystamine or cysteamine or a salt thereof, to produce a thiolated saccharide; c) reacting the thiolated saccharide with a reducing agent to produce an activated thiolated saccharide comprising one or more free sulfhydryl residues; d) reacting the activated thiolated saccharide with an activated carrier protein comprising one or more a-haloacetamide groups, to produce a thiolated saccharide-carrier protein conjugate; and e) reacting the thiolated saccharide-carrier protein conjugate with (i) a first capping reagent capable of capping unconjugated a-haloacetamide groups of the activated carrier protein; and/or (ii) a second capping reagent capable of capping unconjugated free sulfhydryl residues; whereby an eTEC linked glycoconjugate is produced, wherein the saccharide is derived from *E. coli*; further comprising expressing a polynucleotide encoding a polypeptide derived from FimH or fragment thereof in a recombinant mammalian cell, and isolating said polypeptide or fragment thereof.

C70. The method according to clause C69, comprising making the composition according to any one of clause C1 to clause C34.

C71. The method according to any of one clause C69 to clause C70, wherein the capping step e) comprises reacting the thiolated saccharide-carrier protein conjugate with (i)N-acetyl-L-cysteine as a first capping reagent, and/or (ii) iodoacetamide as a second capping reagent.

C72. The method according to any of one clause C69 to clause C71, further comprising a step of compounding the saccharide by reaction with triazole or imidazole to provide a compounded saccharide, wherein the compounded saccharide is shell frozen, lyophilized and reconstituted in an organic solvent prior to step a).

C73. The method according to any of one clause C69 to clause C72, further comprising purification of the thiolated polysaccharide produced in step c), wherein the purification step comprises diafiltration.

C74. The method according to any of one clause C69 to clause C73, wherein the method further comprises purification of the eTEC linked glycoconjugate by diafiltration.

C75. The method according to any of one clause C69 to clause C74, wherein the organic solvent in step a) is a polar aprotic solvent selected from any one of dimethyl sulfoxide (DMSO), dimethylformamide (DMF), dimethylacetamide (DMA), N-methyl-2-pyrrolidone (NMP), acetonitrile, 1,3-Dimethyl-3,4,5,6-tetrahydro-2 (1H)-pyrimidinone (DMPU) and hexamethylphosphoramide (HMPA), or a mixture thereof.

C76. A medium comprising $KH_2PO_4$, K2HPO4, $(NH_4)_2SO_4$, sodium citrate, $Na_2SO_4$, aspartic acid, glucose, $MgSO_4$, $FeSO_4$-$7H_2O$, $Na_2MoO_4$-$2H_2O$, $H_3BO_3$, $CoCl_2$-$6H_2O$, $CuCl_2$-$2H_2O$, $MnCl_2$-$4H_2O$, $ZnCl_2$ and $CaCl_2$)-$2H_2O$.

C77. The medium according to clause C76, wherein the medium is used for culturing *E. coli*. C78. A method for producing a saccharide according to any one of clause C1 to clause C34, comprising culturing a recombinant *E. coli* in a medium; producing said saccharide by culturing said cell in said medium; whereby said cell produces said saccharide. C79. The method according to clause C78, wherein the medium comprises an element selected from any one of $KH_2PO_4$, K2HPO4, $(NH_4)$ $2SO_4$, sodium citrate, $Na_2SO_4$, aspartic acid, glucose, $MgSO_4$, $FeSO_4$-$7H_2O$, $Na_2MoO_4$-$2H_2O$, $H_3BO_3$, $CoCl_2$-$6H_2O$, $CuCl_2$-$2H_2O$, $MnCl_2$-$4H_2O$, $ZnCl_2$ and $CaCl_2$)-$2H_2O$.

C80. The method according to clause C78, wherein the medium comprises soy hydrolysate. C81. The method according to clause C78, wherein the medium comprises yeast extract.

C82. The method according to clause C78, wherein the medium does not further comprise soy hydrolysate and yeast extract.

C83. The method according to clause C78, wherein the *E. coli* cell comprises a heterologous wzz family protein selected from any one of wzzB, wzz, $WZZ_{SF}$, $WZZ_{ST}$, fepE, $WZZ_{fepE}$, WZZ1 and wzz2.

C84. The method according to clause C78, wherein the *E. coli* cell comprises a *Salmonella enterica* wzz family protein selected from any one of wzzB, wzz, $WZZ_{SF}$, $WZZ_{ST}$, fepE, $WZZ_{fepE}$, wzz1 and wzz2.

C85. The method according to clause C84, wherein the wzz family protein comprises a sequence selected from any one of SEQ ID NO: 20, SEQ ID NO: 21, SEQ ID NO: 22, SEQ ID NO: 23, SEQ ID NO: 24, SEQ ID NO: 15, SEQ ID NO: 16, SEQ ID NO: 17, SEQ ID NO: 18, and SEQ ID NO: 19.

C86. The method according to clause C78, wherein the culturing produces a yield of >120 OD600/mL.

C87. The method according to clause C78, further comprising purifying the saccharide.

C88. The method according to clause C78, wherein the purifying step comprises any one of the following: dialysis, concentration operations, diafiltration operations, tangential flow filtration, precipitation, elution, centrifugation, precipitation, ultra-filtration, depth filtration, and column chromatography (ion exchange chromatography, multimodal ion exchange chromatography, DEAE, and hydrophobic interaction chromatography).

C89. A method for inducing an immune response in a mammal comprising administering to the subject a composition according to any one of clause C1 to clause C68.

C90. The method according to clause C89, wherein the immune response comprises induction of an anti-*E. coli* O-specific polysaccharide serum antibody.

C91. The method according to clause C89, wherein the immune response comprises induction of an anti-*E. coli* IgG antibody.

C92. The method according to clause C89, wherein the immune response comprises induction of bactericidal activity against *E. coli.*

C93. The method according to clause C89, wherein the immune response comprises induction of opsonophagocytic antibodies against *E. coli.*

C94. The method according to clause C89, wherein the immune response comprises a geometric mean titer (GMT) level of at least 1,000 to 200,000 after initial dosing.

C95. The method according to clause C89, wherein the composition comprises a saccharide comprising the Formula O25, wherein n is an integer 40 to 100, wherein the immune response comprises a geometric mean titer (GMT) level of at least 1,000 to 200,000 after initial dosing.

C96. The method according to clause C89, wherein the mammal is at risk of any one of the conditions selected from urinary tract infection, cholecystitis, cholangitis, diarrhea, hemolytic uremic syndrome, neonatal meningitis, urosepsis, intra-abdominal infection, meningitis, complicated pneumonia, wound infection, post-prostate biopsy-related infection, neonatal/infant sepsis, neutropenic fever, and other blood stream infection; pneumonia, bacteremia, and sepsis.

C97. The method according to clause C89, wherein the mammal has any one of the conditions selected from urinary tract infection, cholecystitis, cholangitis, diarrhea, hemolytic uremic syndrome, neonatal meningitis, urosepsis, intra-abdominal infection, meningitis, complicated pneumonia, wound infection, post-prostate biopsy-related infection, neonatal/infant sepsis, neutropenic fever, and other blood stream infection; pneumonia, bacteremia, and sepsis.

C98. A method for (i) inducing an immune response in a subject against extra-intestinal pathogenic *Escherichia coli*, (ii) inducing an immune response in a subject against extra-intestinal pathogenic *Escherichia coli*, or (iii) inducing the production of opsonophagocytic antibodies in a subject that are specific to extra-intestinal pathogenic *Escherichia coli*, wherein the method comprises administering to the subject an effective amount of the composition according to any one of clause C1 to clause C68.

C99. The method of clause C98, wherein the subject is at risk of developing a urinary tract infection.

C100. The method of clause C98, wherein the subject is at risk of developing bacteremia.

C101. The method of clause C98, wherein the subject is at risk of developing sepsis.

C102. A composition comprising a polypeptide derived from FimH or fragment thereof; and a (i) a conjugate of an *E. coli* O25B antigen covalently coupled to a carrier protein, (ii) a conjugate of an *E. coli* O1A antigen covalently coupled to a carrier protein, (iii) a conjugate of an *E. coli O*2 antigen covalently coupled to a carrier protein, and (iv) a conjugate of an 06 antigen covalently coupled to a carrier protein, wherein the *E. coli* O25B antigen comprises the structure of Formula O25B, wherein n is an integer greater than 30.

C103. The composition of clause C102, wherein the carrier protein is selected from the group consisting of poly (L-lysine), detoxified Exotoxin A of *P. aeruginosa* (EPA), $CRM_{197}$, maltose binding protein (MBP). Diphtheria toxoid, Tetanus toxoid, detoxified hemolysin A of *S. aureus*, clumping factor A, clumping factor B, Cholera toxin B subunit (CTB), cholera toxin, detoxified variants of cholera toxin, *Streptococcus pneumoniae* Pneumolysin and detoxified variants thereof, *C. jejuni* AcrA, and *C. jejuni* natural glycoproteins.

C104. A method for (i) inducing an immune response in a subject against extra-intestinal pathogenic *Escherichia coli*, (ii) inducing an immune response in a subject against extra-intestinal pathogenic *Escherichia coli*, or (iii) inducing the production of opsonophagocytic antibodies in a subject that are specific to extra-intestinal pathogenic *Escherichia coli*, wherein the method comprises administering to the subject an effective amount of the composition of clause C1.

C105. The method of clause C104, wherein the subject is at risk of developing a urinary tract infection.

C106. The method of clause C104, wherein the subject is at risk of developing bacteremia.

C107. The method of clause C104, wherein the subject is at risk of developing sepsis.

C108. A composition comprising a polypeptide derived from FimH or fragment thereof; and a saccharide comprising an increase of at least 5 repeating units, compared to the corresponding wild-type O-polysaccharide of an *E. coli.*

C109. The composition according to clause C108, wherein the saccharide comprises Formula O25a and the *E. coli* is an *E. coli* serotype O25a.

C110. The composition according to clause C108, wherein the saccharide comprises Formula O25b and the *E. coli* is an *E. coli* serotype O25b.

C111. The composition according to clause C108, wherein the saccharide comprises Formula 02 and the *E. coli* is an *E. coli* serotype O2.

C112. The composition according to clause C108, wherein the saccharide comprises Formula O6 and the *E. coli* is an *E. coli* serotype 06.

C113. The composition according to clause C108, wherein the saccharide comprises Formula O1 and the *E. coli* is an *E. coli* serotype O1.

C114. The composition according to clause C108, wherein the saccharide comprises Formula O17 and the *E. coli* is an *E. coli* serotype O17.

C115. The composition according to clause C108, wherein the saccharide comprises a structure selected from: Formula O1, Formula O2, Formula O3, Formula O4, Formula O5, Formula O6, Formula O7, Formula O8, Formula O9, Formula O10, Formula O11, Formula O12, Formula O13, Formula O14, Formula O15, Formula O16, Formula O17, Formula O18, Formula O19, Formula O20, Formula O21, Formula O22, Formula O23, Formula O24, Formula O25, Formula O25b, Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45, Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula O63, Formula O64, Formula O65, Formula O66, Formula O68, Formula O69, Formula O70, Formula O71, Formula O73, Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144,0145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, and Formula O187, wherein n is an integer from 5 to 1000.

C116. The composition according to clause C108, wherein the *E. coli* is *E. coli* serotype selected from the group consisting of: O1, O2, O3, O4, O5, O6, O7, O8, O9, O10, O11, O12, O13, O14, O15, O16, O17, O18, O19, O20, O21, O22, O23, O24, O25, O25b, O26, O27, O28, O29, O30, O32, O33, O34, O35, O36, O37, O38, O39, O40, O41, O42, O43, O44, O45, O46, O48, O49, O50, O51, O52, O53, O54, O55, O56, O57, O58, O59, O60, O61, O62, O63, O64, O65, O66, O68, O69, O70, O71, O73, O74, O75, O76, O77, O78, O79, O80, O81, O82, O83, O84, O85, O86, O87, O88, O89, O90, O91, O92, O93, O95, O96, O97, O98, O99, O100, O101, O102, O103, O104, O105, O106, O107, O108, O109, O110, O111, O112, O113, O114, O115, O116, O117, O118, O119, O120, O121, O123, O124, O125, O126, O127, O128, O129, O130, O131, O132, O133, O134, O135, O136, O137, O138, O139, O140, O141, O142, O143, O144, O145, O146, O147, O148, O149, O150, O151, O152, O153, O154, O155, O156, O157, O158, O159, O160, O161, O162, O163, O164, O165, O166, O167, O168, O169, O170, O171, O172, O173, O174, O175, O176, O177, O178, O179, O180, O181, O182, O183, O184, O185,O186, and O187.

C117. The composition according to clause C108, wherein the saccharide is produced by increasing repeating units of O-polysaccharides produced by a Gram-negative bacterium in culture comprising overexpressing wzz family proteins in a Gram-negative bacterium to generate said saccharide.

C118. The composition according to clause C117, wherein the overexpressed wzz family protein is selected from the group consisting of wzzB, wzz, $WZZ_{SF}$, $WZZ_{ST}$, fepE, WZZfepE, WZZ1 and wzz2.

C119. The composition according to clause C117, wherein the overexpressed wzz family protein is wzzB.

C120. The composition according to clause C117, wherein the overexpressed wzz family protein is fepE.

C121. The composition according to clause C117, wherein the overexpressed wzz family protein is wzzB and fepE.

C122. The composition according to clause C108, wherein the saccharide is synthetically synthesized.

C123. A composition comprising a polypeptide derived from FimH or fragment thereof; and a conjugate comprising a saccharide according to clause C108, covalently bound to a carrier protein.

C124. The composition according to clause C123, wherein the carrier protein is CRM 197.

C125. The composition according to clause C123, wherein the saccharide comprises a structure selected from: Formula O1, Formula O2, Formula O3, Formula O4, Formula O5, Formula O6, Formula O7, Formula O8, Formula O9, Formula O10, Formula O11, Formula O12, Formula O13, Formula O14, Formula O15, Formula O16, Formula O17, Formula O18, Formula O19, Formula O20, Formula O21, Formula O22, Formula O23, Formula O24, Formula O25, Formula O25b, Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45, Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula O63, Formula O64, Formula O65, Formula O66, Formula O68, Formula O69, Formula O70, Formula O71, Formula O73, Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144,O145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, and Formula O187, wherein n is an integer from 5 to 1000.

C126. The composition according to clause C123, wherein said saccharide comprises an increase of at least 5 repeating units, compared to the corresponding wild-type O-polysaccharide.

C127. The composition according to clause C1, further comprising a pharmaceutically acceptable diluent.

C128. The composition according to clause C127, further comprising an adjuvant.

C129. The composition according to clause C127, further comprising aluminum.

C130. The composition according to clause C127, further comprising QS-21.

C131. The composition according to clause C127, wherein the composition does not include an adjuvant.

C132. A method for inducing an immune response in a subject comprising administering to the subject a composition according to clause C127.

C133. The composition according to clause C123, further comprising a pharmaceutically acceptable diluent.

C134. A method for inducing an immune response in a subject comprising administering to the subject a composition according to clause C133.

C135. The method according to clauses C132 or C134, wherein the immune response comprises induction of an anti-*E. coli* O-specific polysaccharide serum antibody.

C136. The method according to clause C135, wherein the anti-*E. coli* O-specific polysaccharide serum antibody is an IgG antibody.

C137. The method according to clause C135, wherein the anti-*E. coli* O-specific polysaccharide serum antibody is an IgG antibody has bactericidal activity against *E. coli*.

C138. An immunogenic composition comprising a polypeptide derived from FimH or fragment thereof; and a saccharide derived from *E. coli*, conjugated to a carrier protein through a (2-((2-oxoethyl)thio)ethyl) carbamate (eTEC) spacer, wherein the polysaccharide is covalently linked to the eTEC spacer through a carbamate linkage, and wherein the carrier protein is covalently linked to the eTEC spacer through an amide linkage.

C139. The immunogenic composition according to clause C138, further comprising a pharmaceutically acceptable excipient, carrier or diluent.

C140. The immunogenic composition according to clause C138, wherein the saccharide is an O-antigen derived from *E. coli*.

C141. The immunogenic composition according to clause C138, wherein the saccharide comprises a structure selected from: Formula O1, Formula O2, Formula O3, Formula O4, Formula O5, Formula O6, Formula O7, Formula O8, Formula O9, Formula O10, Formula O11, Formula O12, Formula O13, Formula O14, Formula O15, Formula O16, Formula O17, Formula O18, Formula O19, Formula O20, Formula O21, Formula O22, Formula O23, Formula O24, Formula O25, Formula O25b, Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45, Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula O63, Formula O64, Formula O65, Formula O66, Formula O68, Formula O69, Formula O70, Formula O71, Formula O73, Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144,0145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, and Formula O187, wherein n is an integer from 5 to 1000.

C142. The immunogenic composition according to clause C138, wherein the saccharide has a degree of O-acetylation between 75-100%.

C143. The immunogenic composition according to clause C138, wherein the carrier protein is $CRM_{197}$.

C144. The immunogenic composition according to clause C143, wherein the $CRM_{197}$ comprises 2 to 20 lysine residues covalently linked to the polysaccharide through an eTEC spacer.

C145. The immunogenic composition according to clause C143, wherein the $CRM_{197}$ comprises 4 to 16 lysine residues covalently linked to the polysaccharide through an eTEC spacer.

C146. The immunogenic composition according to clause C138, further comprising an additional antigen.

C147. The immunogenic composition according to clause C138, further comprising an adjuvant.

C148. The immunogenic composition according to clause C147, wherein the adjuvant is an aluminum-based adjuvant selected from the group consisting of aluminum phosphate, aluminum sulfate and aluminum hydroxide.

C149. The immunogenic composition according to clause C138, wherein the composition does not comprise an adjuvant.

C150. An immunogenic composition comprising a polypeptide derived from FimH or fragment thereof; and a glycoconjugate comprising a saccharide derived from *E. coli* conjugated to a carrier protein, wherein the glycoconjugate is prepared using reductive amination.

C151. The immunogenic composition according to clause C150, further comprising a pharmaceutically acceptable excipient, carrier or diluent.

C152. The immunogenic composition according to clause C150, wherein the saccharide is an O-antigen derived from *E. coli*.

C153. The immunogenic composition according to clause C150, wherein the saccharide comprises a structure selected from: Formula O1, Formula O2, Formula O3, Formula O4, Formula O5, Formula O6, Formula O7, Formula O8, Formula O9, Formula O10, Formula 011, Formula O12, Formula O13, Formula O14, Formula O15, Formula O16, Formula O17, Formula O18, Formula O19, Formula O20, Formula O21, Formula O22, Formula O23, Formula O24, Formula O25, Formula O25b, Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45, Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula O63, Formula O64, Formula O65, Formula O66, Formula O68, Formula O69, Formula O70, Formula O71, Formula O73, Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144,0145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, and Formula O187, wherein n is an integer from 5 to 1000.

C154. The immunogenic composition according to clause C150, wherein the saccharide has a degree of O-acetylation between 75-100%.

C155. The immunogenic composition according to clause C150, wherein the carrier protein is $CRM_{197}$.

C156. The immunogenic composition according to clause C150, further comprising an additional antigen.

C157. The immunogenic composition according to clause C150, further comprising an adjuvant.

C158. The immunogenic composition according to clause C157, wherein the adjuvant is an aluminum-based adjuvant selected from the group consisting of aluminum phosphate, aluminum sulfate and aluminum hydroxide.

C159. The immunogenic composition according to clause C150, wherein the composition does not comprise an adjuvant.

C160. A method for inducing an immune response in a subject comprising administering to the subject a composition according to any one of clauses C138-C159.

C161. The method according to clause C160, wherein the immune response comprises induction of an anti-*E. coli* O-specific polysaccharide serum antibody.

C162. The method according to clause C135, wherein the anti-*E. coli* O-specific polysaccharide serum antibody is an IgG antibody.

C163. The method according to clause C135, wherein the anti-*E. coli* O-specific polysaccharide serum antibody is an IgG antibody has bactericidal activity against *E. coli.*

C164. A composition comprising a polypeptide derived from FimH or fragment thereof; and a saccharide comprising a structure selected from any one of Formula O1, Formula O1A, Formula O1B, Formula O1C, Formula O2, Formula O3, Formula O4, Formula O4: K52, Formula O4: K6, Formula O5, Formula O5ab, Formula O5ac, Formula O6, Formula O6: K2; K13; K15, Formula O6: K54, Formula O7, Formula O8, Formula O9, Formula O10, Formula O11, Formula O12, Formula O13, Formula O14, Formula O15, Formula O16, Formula O17, Formula O18, Formula O18A, Formula O18ac, Formula O18A1, Formula O18B, Formula O18B1, Formula O19, Formula O20, Formula O21, Formula O22, Formula O23, Formula O23A, Formula O24, Formula O25, Formula O25a, Formula O25b, Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45, Formula O45, Formula O45rel, Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula $62D_1$, Formula O63, Formula O64, Formula O65, Formula O66, Formula O68, Formula O69, Formula O70, Formula O71, Formula O73, Formula O73, Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144, Formula O145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, Formula O187, wherein n is greater than the number of repeat units in the corresponding wild-type *E. coli* polysaccharide.

C165. The composition according to clause C164, wherein n is an integer from 31 to 100.

C166. The composition according to clause C164, wherein the saccharide comprises a structure according to any one of Formula O1A, Formula O1B, and Formula O1C, Formula O2, Formula O6, and Formula O25B.

C167. The composition according to clause C164, wherein the saccharide is produced in a recombinant host cell that expresses a wzz family protein having at least 90% sequence identity to any one of SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, and SEQ ID NO: 39.

C168. The composition according to clause C167, wherein the protein comprises any one of SEQ ID NO: 30, SEQ ID NO: 31, SEQ ID NO: 32, SEQ ID NO: 33, SEQ ID NO: 34.

C169. The saccharide according to clause C164, wherein the saccharide is synthetically synthesized.

C170. A composition comprising a polypeptide derived from FimH or fragment thereof; and a conjugate comprising a carrier protein covalently bound to a saccharide, said saccharide comprising a structure selected from any one of Formula O1, Formula O1A, Formula O1B, Formula O1C, Formula O2, Formula O3, Formula O4, Formula O4: K52, Formula O4: K6, Formula O5, Formula O5ab, Formula O5ac, Formula O6, Formula O6: K2; K13; K15, Formula O6: K54, Formula O7, Formula O8, Formula O9, Formula O10, Formula O11, Formula O12, Formula O13, Formula O14, Formula O15, Formula O16, Formula O17, Formula O18, Formula O18A, Formula O18ac, Formula O18A1, Formula O18B, Formula O18B1, Formula O19, Formula O20, Formula O21, Formula O22, Formula O23, Formula O23A, Formula O24, Formula O25, Formula O25a, Formula O25b, Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45, Formula O45, Formula O45rel, Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula $62D_1$, Formula O63, Formula O64, Formula O65, Formula O66, Formula O68, Formula O69, Formula O70, Formula O71, Formula O73, Formula O73, Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144, Formula O145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, Formula O187, wherein n is an integer from 1 to 100.

C171. The composition according to clause C170, wherein the saccharide comprises any one of the following Formula O25b, Formula O1A, Formula O2, and Formula O6.

C172. The composition according to clause C170, wherein the saccharide further comprises any one of an *E. coli* R1 moiety, *E. coli* R2 moiety, *E. coli* R3 moiety, *E. coli* R4 moiety, and *E. coli* K-12 moiety.

C173. The composition according to clause C170, wherein the saccharide does not further comprise any one of an *E. coli* R1 moiety, *E. coli* R2 moiety, *E. coli* R3 moiety, *E. coli* R4 moiety, and *E. coli* K-12 moiety. The composition according to clause C170, wherein the saccharide does not further comprise an *E. coli* R2 moiety.

C174. The composition according to clause C170, wherein the saccharide further comprises a 3-deoxy-d-manno-oct-2-ulosonic acid (KDO) moiety.

C175. The composition according to clause C170, wherein the carrier protein is selected from any one of $CRM_{197}$, diphtheria toxin fragment B (DTFB), DTFB C8, Diphtheria toxoid (DT), tetanus toxoid (TT), fragment C of TT, pertussis toxoid, cholera toxoid, or exotoxin A from *Pseudomonas aeruginosa*; detoxified Exotoxin A of *P. aeruginosa* (EPA), maltose binding protein (MBP), detoxified hemolysin A of *S. aureus*, clumping factor A, clumping factor B, Cholera toxin B subunit (CTB), *Streptococcus pneumoniae* Pneumolysin and detoxified variants thereof, *C. jejuni* AcrA, and *C. jejuni* natural glycoproteins.

C176. The composition according to clause C170, wherein the carrier protein is $CRM_{197}$.

C177. The composition according to clause C170, wherein the carrier protein is tetanus toxoid.

C178. The composition according to clause C170, wherein the ratio of saccharide to protein is at least 0.5 to at most 2.

C179. The composition according to clause C170, wherein the conjugate is prepared via reductive amination.

C180. The composition according to clause C170, wherein the saccharide is conjugated to the carrier protein through a (2-((2-oxoethyl)thio)ethyl) carbamate (eTEC) spacer.

C181. The composition according to clause C170, wherein the saccharide is a single-end linked conjugated saccharide.

C182. The composition according to clause C174, wherein the saccharide is conjugated to the carrier protein through a 3-deoxy-d-manno-oct-2-ulosonic acid (KDO) residue.

C183. The composition according to clause C170, wherein the conjugate is prepared via CDAP chemistry.

C184. A composition comprising a polypeptide derived from FimH or fragment thereof; and (a) a conjugate comprising a carrier protein covalently bound to a saccharide comprising Formula O25b, wherein n is an integer from 31 to 90, (b) a conjugate comprising a carrier protein covalently bound to a saccharide comprising Formula O1A, wherein n is an integer from 31 to 90, (c) a conjugate comprising a carrier protein covalently bound to a saccharide comprising Formula O2, wherein n is an integer from 31 to 90, and (d) a conjugate comprising a carrier protein covalently bound to a saccharide comprising and Formula O6, wherein n is an integer from 31 to 90.

C185. The composition according to clause C184, further comprising a conjugate comprising a carrier protein covalently bound to a saccharide comprising a structure selected from any one of the following: Formula O15, Formula O16, Formula O17, Formula O18 and Formula 075, wherein n is an integer from 31 to 90.

C186. The composition according to clause C184, comprising at most 25% free saccharide as compared to the total amount of saccharide in the composition.

C187. A method of eliciting an immune response against *Escherichia coli* in a mammal, comprising administering to the mammal an effective amount of the composition according to any one of clauses C184 to C186.

C188. The method according to clause C187, wherein the immune response comprises opsonophagocytic antibodies against *E. coli.*

C189. The method according to clause C187, wherein the immune response protects the mammal from an *E. coli* infection.

C190. A mammalian cell comprising (a) a first gene of interest encoding a polypeptide derived from *E. coli* or a fragment thereof, wherein the gene is integrated between at least two recombination target sites (RTS).

C191. The embodiment of clause C190, wherein the two RTS are chromosomally-integrated within the NL1 locus or the NL2 locus.

C192. The embodiment of clause C190, wherein the first gene of interest further comprises a reporter gene, a gene encoding a difficult to express protein, an ancillary gene or a combination thereof.

C193. The embodiment of clause C190, further comprising a second gene of interest that is integrated within a second chromosomal locus distinct from the locus of (a), wherein the second gene of interest comprises a reporter gene, a gene encoding a difficult to express protein, an ancillary gene or a combination thereof.

C194. A recombinant mammalian cell, comprising a polynucleotide encoding a polypeptide derived from *E. coli* or a fragment thereof.

C195. The recombinant cell according to C194, wherein the polypeptide is derived from *E. coli* fimbrial H (FimH).

C196. The recombinant cell according to C195, wherein the polypeptide comprises a phenylalanine residue at the N-terminus of the polypeptide.

C197. The recombinant cell according to C195, wherein the polypeptide comprises a phenylalanine residue within the first 20 residue positions of the N-terminus.

C198. The recombinant cell according to C195, wherein the polypeptide comprises a phenylalanine residue at position 1 of the polypeptide.

C199. The recombinant cell according to C198, wherein the polypeptide does not comprise a glycine residue immediately before the phenylalanine residue at position 1 of the polypeptide.

C200. The recombinant cell according to C195, wherein the polypeptide does not comprise an N-glycosylation site at position 7 of the polypeptide.

C201. The recombinant cell according to C199, wherein the polypeptide does not comprise an Asn residue at position 7 of the polypeptide.

C202. The recombinant cell according to C201, wherein the polypeptide comprises a residue selected from the group consisting of Ser, Asp, Thr, and Gln at position 7.

C203. The recombinant cell according to C198, wherein the polypeptide does not comprise an N-glycosylation site at position 70 of the polypeptide.

C204. The recombinant cell according to C203, wherein the polypeptide does not comprise an Asn residue at position 70 of the polypeptide.

C205. The recombinant cell according to C203, wherein the polypeptide does not comprise a Ser residue at position 70 of the polypeptide.

C206. The recombinant cell according to C194, wherein the polypeptide comprises a residue substitution selected from the group consisting of Ser, Asp, Thr, and Gin at an N-glycosylation site of the polypeptide.

C207. The recombinant cell according to C206, wherein the N-glycosylation site comprises position N235 of the polypeptide.

C208. The recombinant cell according to C206, wherein the N-glycosylation site comprises position N228 of the polypeptide.

C209. The recombinant cell according to C206, wherein the N-glycosylation site comprises position N235 and position N228 of the polypeptide.

C210. The recombinant cell according to C195, wherein the polypeptide comprises SEQ ID NO: 3.

C211. The recombinant cell according to C195, wherein the polypeptide comprises SEQ ID NO: 2.

C212. The recombinant cell according to C194, wherein the polypeptide comprises an aliphatic hydrophobic amino acid residue at position 1 of the polypeptide.

C213. The recombinant cell according to C212, wherein the aliphatic hydrophobic amino acid residue is selected from the group consisting of lle, Leu, and Val.

C214. The recombinant cell according to C194, wherein the polypeptide comprises a fragment of FimH.

C215. The recombinant cell according to C214, wherein the polypeptide comprises a lectin domain of FimH.

C216. The recombinant cell according to C215, wherein the lectin domain comprises a mass of about 17022 Daltons.

C217. The recombinant cell according to C194, wherein the polypeptide is complexed with a FimC polypeptide or a fragment thereof.

C218. The recombinant cell according to C217, wherein the FimC polypeptide or a fragment thereof comprises a glycine residue at position 37 of the FimC polypeptide or a fragment thereof.

C219. The recombinant cell according to C195, wherein the polypeptide is in the low affinity conformation.

C220. The recombinant cell according to C195, wherein the polypeptide is stabilized by FimG.

C221. The recombinant cell according to C195, wherein the polypeptide is stabilized by a donor-strand peptide of FimG (DsG).

C222. The recombinant cell according to C221, wherein the polynucleotide sequence further encodes a linker sequence.

C223. The recombinant cell according to C222, wherein the linker comprises at least 4 amino acid residues and at most 15 amino acid residues.

C224. The recombinant cell according to C222, wherein the linker comprises at least 5 amino acid residues and at most 10 amino acid residues.

C225. The recombinant cell according to C222, wherein the linker comprises 7 amino acid residues.

C226. The recombinant cell according to C194, wherein the polypeptide does not comprise a signal peptide selected from the group consisting of a native FimH leader peptide, influenza hemagglutinin signal peptide, and a human respiratory syncytial virus A (strain A2) fusion glycoprotein F0 signal peptide.

C227. The recombinant cell according to C194, wherein the polypeptide comprises a murine IgK signal peptide sequence.

C228. The recombinant cell according to C194, wherein the polypeptide comprises any one signal peptide sequence selected from human IgG receptor FcRn large subunit p51 signal peptide and a human IL10 protein signal peptide.

C229. The recombinant cell according to C195, wherein the polypeptide comprises a mutation of arginine to proline at amino acid position 60 (R60P), according to the numbering of SEQ ID NO: 3.

C230. The recombinant cell according to C194, wherein the expression level of the polypeptide is greater than the expression level of the corresponding wild-type polypeptide expressed in the periplasm of a wild-type *E. coli* cell.

C231. The recombinant cell according to C194, wherein the expression level of the polypeptide is greater than 10 mg/L.

C232. The recombinant cell according to C194, wherein the polynucleotide sequence is integrated into the genomic DNA of said mammalian cell.

C233. The recombinant cell according to C194, wherein the polynucleotide sequence is codon optimized for expression in the cell.

C234. The recombinant cell according to C194, wherein the cell is a human embryonic kidney cell.

C235. The recombinant cell according to C234, wherein the human embryonic kidney cell comprises a HEK293 cell.

C236. The recombinant cell according to C235, wherein the HEK293 cell is selected from any one of HEK293T cells, HEK293TS cells, and HEK293E cells.

C237. The recombinant cell according to C195, wherein the cell is a CHO cell.

C238. The recombinant cell according to C237, wherein said CHO cell is a CHO-K1 cell, CHO-DUXB11, CHO-DG44 cell, or CHO-S cell.

C239. The recombinant cell according to C194, wherein the polypeptide is soluble.

C240. The recombinant cell according to C194, wherein the polypeptide is secreted from the cell.

C241. The recombinant cell according to C195, wherein the polypeptide comprises a N28Q substitution, according to the numbering of SEQ ID NO: 1.

C242. The recombinant cell according to C195, wherein the polypeptide comprises a N28D substitution, according to the numbering of SEQ ID NO: 1.

C243. The recombinant cell according to C195, wherein the polypeptide comprises a N28S substitution, according to the numbering of SEQ ID NO: 1.

C244. The recombinant cell according to C195, wherein the polypeptide comprises a substitution selected from any one of N28Q, V48C, and L55C, according to the numbering of SEQ ID NO: 1.

C245. The recombinant cell according to C195, wherein the polypeptide comprises a substitution N92S according to the numbering of SEQ ID NO: 1.

C246. The recombinant cell according to C194, wherein the polypeptide derived from FimH or fragment thereof comprises a substation selected from any one of V48C and L55C, according to the numbering of SEQ ID NO: 1.

C247. A culture comprising the recombinant cell of C194, wherein said culture is at least 5 liter in size.

C248. The culture according to C242, wherein the yield of the polypeptide or fragment thereof is at least 0.05 g/L.

C249. The culture according to C248, wherein the yield of the polypeptide or fragment thereof is at least 0.10 g/L.

C250. A method for producing a polypeptide derived from *E. coli* or a fragment thereof, comprising culturing a recombinant mammalian cell according to C194 under a suitable condition, thereby expressing the polypeptide or fragment thereof; and harvesting the polypeptide or fragment thereof.

C251. The method according to C250, further comprising purifying the polypeptide or fragment thereof.

C252. The method according to C250, wherein the cell comprises a nucleic acid encoding any one of SEQ ID NO: 5, SEQ ID NO: 6, SEQ ID NO: 7, SEQ ID NO: 8, and SEQ ID NO: 27.

C253. The method according to C250, wherein the yield of the polypeptide or fragment thereof is at least 0.05 g/L.

C254. The method according to C250, wherein the yield of the polypeptide or fragment thereof is at least 0.10 g/L.

C255. A composition comprising a polypeptide having at least 70% identity to any one of SEQ ID NO: 1, SEQ ID NO: 2, SEQ ID NO: 3, SEQ ID NO: 4, SEQ ID NO: 20, SEQ ID NO: 23, SEQ ID NO: 24, SEQ ID NO: 26, SEQ ID NO: 28, and SEQ ID NO: 29.

C256. The composition according to C255, further comprising a saccharide comprising a structure selected from any one Formula in Table 1Table-4.

C257. The composition according to C256, wherein the saccharide is covalently bound a carrier protein.

C258. The composition according to C257, wherein the carrier protein is selected from any one of poly (L-lysine), $CRM_{197}$, diphtheria toxin fragment B (DTFB), DTFB C8, Diphtheria toxoid (DT), tetanus toxoid (TT), fragment C of TT, pertussis toxoid, cholera toxoid, or exotoxin A from *Pseudomonas aeruginosa*; detoxified Exotoxin A of *P. aeruginosa* (EPA), maltose binding protein (MBP), detoxified hemolysin A of *S. aureus*, clumping factor A, clumping factor B, Cholera toxin B subunit (CTB), *Streptococcus pneumoniae* Pneumolysin and detoxified variants thereof, *C. jejuni* AcrA, and *C. jejuni* natural glycoproteins.

C259. The composition according to C257, wherein the carrier protein is CRM 197.

C260. The composition according to C257, wherein the carrier protein is tetanus toxoid (TT).

C261. The composition according to C257, wherein the carrier protein is poly (L-lysine).

C262. The composition according to C257, wherein the saccharide is covalently bound a carrier protein by reductive amination.

C263. The composition according to C257, wherein the saccharide is covalently bound a carrier protein by CDAP chemistry.

C264. The composition according to C257, wherein the saccharide is covalently bound a carrier protein by single-end linked conjugation.

C265. The composition according to C257, wherein the saccharide is covalently bound a carrier protein through a (2-((2-oxoethyl)thio)ethyl) carbamate (eTEC) spacer.

C266. A polypeptide comprising the amino acid sequence selected from the group consisting of SEQ ID NO: 5, SEQ ID NO: 6, SEQ ID NO: 7, SEQ ID NO: 8, and SEQ ID NO: 27.

C267. A composition comprising a polypeptide derived from FimH or a fragment thereof; and a saccharide comprising a structure selected from any one of Formula O1, Formula O1A, Formula O1B, Formula O1C, Formula O2, Formula O3, Formula O4, Formula O4: K52, Formula O4: K6, Formula O5, Formula O5ab, Formula O5ac, Formula O6, Formula O6: K2; K13; K15, Formula O6: K54, Formula O7, Formula O8, Formula O9, Formula O10, Formula O11, Formula O12, Formula O13, Formula O14, Formula O15, Formula O16, Formula O17, Formula O18, Formula O18A, Formula O18ac, Formula O18A1, Formula O18B, Formula O18B1, Formula O19, Formula O20, Formula O21, Formula O22, Formula O23, Formula O23A, Formula O24, Formula O25, Formula O25a, Formula O25b, Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45, Formula O45, Formula O45rel, Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula $62D_1$, Formula O63, Formula O64, Formula O65, Formula O66, Formula O68, Formula O69, Formula O70, Formula O71, Formula O73, Formula O73, Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144, Formula O145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, Formula O187.

C268. The composition according to Clause C267, further comprising at least one saccharide derived from any one *K. pneumoniae* type selected from the group consisting of O1, O2, O3, and O5.

C269. The composition according to Clause C267, further comprising a saccharide derived from *Klebsiella pneumoniae* type O1.

C270. The composition according to Clause C267, further comprising a saccharide derived from *K. pneumoniae* type O2.

C271. The composition according to Clause C267, further comprising a saccharide derived from *K. pneumoniae* type O3.

C272. The composition according to Clause C267, further comprising a saccharide derived from *K. pneumoniae* type O5.

C273. The composition according to Clause C267, further comprising a saccharide derived from *K. pneumoniae* type O1 and a saccharide derived from *K. pneumoniae* type O2.

C274. The composition according to Clause C268, wherein the saccharide derived from *K. pneumoniae* is conjugated to a carrier protein; and the saccharide derived from *E. coli* is conjugated to a carrier protein.

C275. The composition according to Clause C267, further comprising a polypeptide derived from *K. pneumoniae.*

C276. A composition comprising a polypeptide derived from FimH or a fragment thereof; and at least one saccharide derived from any one *K. pneumoniae* type selected from the group consisting of O1, O2, O3, and O5.

C277. The composition according to Clause C276, further comprising at least one saccharide comprising a structure selected from any one of Formula O1, Formula O1A, Formula O1B, Formula O1C, Formula O2, Formula O3, Formula O4, Formula O4: K52, Formula O4: K6, Formula O5, Formula O5ab, Formula O5ac, Formula O6, Formula O6: K2; K13; K15, Formula O6: K54, Formula O7, Formula O8, Formula O9, Formula O10, Formula O11, Formula O12, Formula O13, Formula O14, Formula O15, Formula O16, Formula O17, Formula O18, Formula O18A, Formula O18ac, Formula O18A1, Formula O18B, Formula O18B1, Formula O19, Formula O20, Formula O21, Formula O22, Formula O23, Formula O23A, Formula O24, Formula O25, Formula O25a, Formula O25b, Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45, Formula O45, Formula O45rel, Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula $62D_1$, Formula O63, Formula O64, Formula O65, Formula O66, Formula O68, Formula O69, Formula O70, Formula O71, Formula O73, Formula O73, Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O179, Formula O180, Formula O181, Formula O182, Formula O183, Formula O184, Formula O185, Formula O186, Formula O187. 25 O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144, Formula O145, Formula O146, Formula O147, Formula O148, Formula O149, Formula O150, Formula Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, C278. The composition according to Clause C277, wherein the saccharide derived from *K. pneumoniae* is conjugated to a carrier protein; and the saccharide derived from *E. coli* is conjugated to a carrier protein.

C279. The composition according to Clause C277, further comprising a polypeptide derived from *K. pneumoniae.*

C280. A composition comprising at least one saccharide derived from any one *K. pneumoniae* type selected from the group consisting of O1, O2, O3, and O5; and at least one saccharide comprising a structure selected from any one of Formula O1, Formula O1A, Formula O1B, Formula O1C, Formula O2, Formula O3, Formula O4, Formula O4: K52, Formula O4: K6, Formula O5, Formula O5ab, Formula O5ac, Formula O6, Formula O6: K2; K13; K15, Formula O6: K54, Formula O7, Formula O8, Formula O9, Formula O10, Formula O11, Formula O12, Formula O13, Formula O14, Formula O15, Formula O16, Formula O17, Formula O18, Formula O18A, Formula O18ac, Formula O18A1, Formula O18B, Formula O18B1, Formula O19, Formula O20, Formula O21, Formula O22, Formula O23, Formula O23A, Formula O24, Formula O25, Formula O25a, Formula O25b, Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45, Formula O45, Formula O45rel, Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula $62D_1$, Formula O63, Formula O64, Formula O65, Formula O66, Formula O68, Formula O69, Formula O70, Formula O71, Formula O73, Formula O73, Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144, Formula O145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, Formula O187.

C281. The composition according to Clause C280, further comprising a polypeptide derived from FimH or a fragment thereof.

C282. The composition according to Clause C280, wherein the *E. coli* saccharide comprises Formula O8.

C283. The composition according to Clause C280, wherein the *E. coli* saccharide comprises Formula O9.

C284. The composition according to Clause C280, further comprising a polypeptide derived from *K. pneumoniae.*

C285. The composition according to any of Clauses C267-C284, wherein the saccharide is covalently bound to a carrier protein.

C286. The composition according to Clause C285, wherein the saccharide further comprises a 3-deoxy-d-manno-oct-2-ulosonic acid (KDO) moiety.

C287. The composition according to Clause C285, wherein the saccharide comprises Lipid A.

C288. The composition according to any one of claims C285-C287, wherein the saccharide is synthetically synthesized.

C289. The composition according to Clause C285, wherein the carrier protein is selected from any one of CRM197, diphtheria toxin fragment B (DTFB), DTFB C8, Diphtheria toxoid (DT), tetanus toxoid (TT), fragment C of TT, pertussis toxoid, cholera toxoid, or exotoxin A from *Pseudomonas aeruginosa*; detoxified Exotoxin A of *P. aeruginosa* (EPA), maltose binding protein (MBP), detoxified hemolysin A of *S. aureus*, clumping factor A, clumping factor B, Cholera toxin B subunit (CTB), *Streptococcus pneumoniae* Pneumolysin and detoxified variants thereof, *C. jejuni* AcrA, *C. jejuni* natural glycoproteins and Streptococcal C5a peptidase (SCP). 25

C290. A method of eliciting an immune response against *Escherichia coli* in a mammal, comprising administering to the mammal an effective amount of the composition according to any one of Clauses C267-C289.

C291. The method according to Clause C290, wherein the immune response comprises opsonophagocytic antibodies against *E. coli.*

C292. The method according to Clause C290, wherein the immune response protects the mammal from an *E. coli* infection.

C293. A method of eliciting an immune response against *Klebsiella pneumoniae* in a mammal, comprising administering to the mammal an effective amount of the composition according to any one of Clauses C267-C289.

C294. The method according to Clause C293, wherein the immune response comprises opsonophagocytic antibodies against *Klebsiella pneumoniae.*

C295. The method according to Clause C293, wherein the immune response protects the mammal from a *Klebsiella pneumoniae* infection.

C297. The compositions and methods of Clause C296, wherein the *K. pneumoniae* type O1 comprises variant O1V1 or O1V2.

C296. The compositions and methods according to any one of Clauses C1-C266, further comprising further comprising at least one saccharide derived from any one *K. pneumoniae* type selected from the group consisting of O1, O2, O3, and O5.

C298. The compositions and methods of Clause C296, wherein the *K. pneumoniae* type O2 comprises variant O2V1 or O2V2.

C299. Use of the compositions set forth in any one of Clauses C1-C298 as set forth herein.

What is claimed is:

1. A method of eliciting an immune response against *Escherichia coli* (*E. coli*) and *Klebsiella pneumoniae* (*K. pneumoniae*) in a subject, comprising administering to the subject an effective amount of a composition comprising (a) a saccharide derived from *E. coli* comprising a structure selected from the group consisting of Formula O1A, Formula O2, Formula O6: K2, Formula O6: K13, Formula O6: K15, Formula O6: K54, Formula O25b, and Formula O75, wherein n is an integer consisting of 31 to 100 in the Formula for each saccharide molecule; and (b) a saccharide derived from a *K. pneumoniae* type selected from the group consisting of O3, O4, O5, O7, O8, and O12.

2. The method according to claim 1, wherein the *K. pneumoniae* saccharide is derived from *K. pneumoniae* type O4.

3. The method according to claim 1, wherein the *K. pneumoniae* saccharide is derived from *K. pneumoniae* type O7.

4. The method according to claim 1, wherein the *K. pneumoniae* saccharide is derived from *K. pneumoniae* type O3.

5. The method according to claim 1, wherein the *K. pneumoniae* saccharide is derived from *K. pneumoniae* type O5.

6. The method according to claim 1, wherein the composition comprises a saccharide derived from *K. pneumoniae* type O3 and a saccharide derived from *K. pneumoniae* type O5.

7. The method according to claim 1, wherein the saccharide derived from *K. pneumoniae* is conjugated to a carrier protein; and the saccharide derived from *E. coli* is conjugated to a carrier protein.

8. The method according to claim 1, wherein the *E. coli* saccharide further comprises a 3-deoxy-d-manno-oct-2-ulosonic acid (KDO) moiety.

9. The method according to claim 7, wherein the carrier protein conjugated to the saccharide derived from *E. coli* is selected from the group consisting of $CRM_{197}$, diphtheria toxin fragment B(DTFB), DTFB C8, Diphtheria toxoid (DT), tetanus toxoid (TT), fragment C of TT, pertussis toxoid, cholera toxoid, exotoxin A from *Pseudomonas aeruginosa* (*P. aeruginosa*), detoxified Exotoxin A of *P. aeruginosa* (EPA), maltose binding protein (MBP), detoxified hemolysin A of *Staphylococcus aureus*, clumping factor A, clumping factor B, Cholera toxin B subunit (CTB), *Streptococcus pneumoniae* Pneumolysin, detoxified variants of *Streptococcus pneumoniae* Pneumolysin, *Campylobacter jejuni* (*C. jejuni*) AcrA, and *C. jejuni* natural glycoproteins.

10. The method according to claim 7, wherein the carrier protein conjugated to the saccharide derived from *K. pneumoniae* is selected from the group consisting of $CRM_{197}$, diphtheria toxin fragment B (DTFB), DTFB C8, Diphtheria toxoid (DT), tetanus toxoid (TT), fragment C of TT, pertussis toxoid, cholera toxoid, exotoxin A from *Pseudomonas aeruginosa* (*P. aeruginosa*), detoxified Exotoxin A of *P. aeruginosa* (EPA), maltose binding protein (MBP), detoxified hemolysin A of *Staphylococcus aureus*, clumping factor A, clumping factor B, Cholera toxin B subunit (CTB), *Streptococcus pneumoniae* Pneumolysin, detoxified variants of *Streptococcus pneumoniae* Pneumolysin, *Campylobacter jejuni* AcrA, and *C. jejuni* natural glycoproteins.

11. The method according to claim 1, wherein the immune response comprises opsonophagocytic antibodies against *E. coli.*

12. The method according to claim 1, wherein the immune response protects the subject from an *E. coli* infection.

13. The method according to claim 1, wherein the immune response comprises opsonophagocytic antibodies against *K. pneumoniae.*

14. The method according to claim 1, wherein the immune response protects the subject from a *K. pneumoniae* infection.

* * * * *

SEQUENCE LISTING

```
Sequence total quantity: 109
SEQ ID NO: 1            moltype = AA  length = 300
FEATURE                 Location/Qualifiers
REGION                  1..300
                        note = Synthetic
source                  1..300
                        mol_type = protein
                        organism = synthetic construct
SEQUENCE: 1
MKRVITLFAV LLMGWSVNAW SFACKTANGT AIPIGGGSAN VYVNLAPVVN VGQNLVVDLS  60
TQIFCHNDYP ETITDYVTLQ RGSAYGGVLS NFSGTVKYSG SSYPFPTTSE TPRVVYNSRT  120
DKPWPVALYL TPVSSAGGVA IKAGSLIAVL ILRQTNNYNS DDFQFVWNIY ANNDVVVPTG  180
GCDVSARDVT VTLPDYPGSV PIPLTVYCAK SQNLGYYLSG TTADAGNSIF TNTASFSPAQ  240
GVGVQLTRNG TIIPANNTVS LGAVGTSAVS LGLTANYART GGQVTAGNVQ SIIGVTFVYQ  300

SEQ ID NO: 2            moltype = AA  length = 279
FEATURE                 Location/Qualifiers
REGION                  1..279
                        note = Synthetic
source                  1..279
                        mol_type = protein
                        organism = synthetic construct
SEQUENCE: 2
FACKTANGTA IPIGGGSANV YVNLAPVVNV GQNLVVDLST QIFCHNDYPE TITDYVTLQR  60
GSAYGGVLSN FSGTVKYSGS SYPFPTTSET PRVVYNSRTD KPWPVALYLT PVSSAGGVAI  120
KAGSLIAVLI LRQTNNYNSD DFQFVWNIYA NNDVVVPTGG CDVSARDVTV TLPDYPGSVP  180
IPLTVYCAKS QNLGYYLSGT TADAGNSIFT NTASFSPAQG VGVQLTRNGT IIPANNTVSL  240
GAVGTSAVSL GLTANYARTG GQVTAGNVQS IIGVTFVYQ                        279

SEQ ID NO: 3            moltype = AA  length = 156
FEATURE                 Location/Qualifiers
REGION                  1..156
                        note = Synthetic
source                  1..156
                        mol_type = protein
```

```
                         organism = synthetic construct
SEQUENCE: 3
FACKTANGTA IPIGGGSANV YVNLAPVVNV GQNLVVDLST QIFCHNDYPE TITDYVTLQR  60
GSAYGGVLSN FSGTVKYSGS SYPFPTTSET PRVVYNSRTD KPWPVALYLT PVSSAGGVAI  120
KAGSLIAVLI LRQTNNYNSD DFQFVWNIYA NNDVVV                            156

SEQ ID NO: 4             moltype = AA  length = 120
FEATURE                  Location/Qualifiers
REGION                   1..120
                         note = Synthetic
source                   1..120
                         mol_type = protein
                         organism = synthetic construct
SEQUENCE: 4
GCDVSARDVT VTLPDYPGSV PIPLTVYCAK SQNLGYYLSG TTADAGNSIF TNTASFSPAQ  60
GVGVQLTRNG TIIPANNTVS LGAVGTSAVS LGLTANYART GGQVTAGNVQ SIIGVTFVYQ  120

SEQ ID NO: 5             moltype = AA  length = 330
FEATURE                  Location/Qualifiers
REGION                   1..330
                         note = Synthetic
source                   1..330
                         mol_type = protein
                         organism = synthetic construct
SEQUENCE: 5
VETDTLLLWV LLLWVPGSTG FACKTASGTA IPIGGGSANV YVNLAPCVNV GQNCVVDLST  60
QIFCHNDYPE TITDYVTLQR GSAYGGVLSS FSGTVKYSGS SYPFPTTSET PRVVYNSRTD  120
KPWPVALYLT PVSSAGGVAI KAGSLIAVLI LRQTNNYNSD DFQFVWNIYA NNDVVVPTGG  180
CDVSARDVTV TLPDYPGSVP IPLTVYCAKS QNLGYYLSGT TADAGNSIFT NTASFSPAQG  240
VGVQLTRQGT IIPANNTVSL GAVGTSAVSL GLTANYARTG GQVTAGNVQS IIGVTFVYQG  300
GSSGGGADVT ITVNGKVVAK GGHHHHHHHH                                   330

SEQ ID NO: 6             moltype = AA  length = 330
FEATURE                  Location/Qualifiers
REGION                   1..330
                         note = Synthetic
source                   1..330
                         mol_type = protein
                         organism = synthetic construct
SEQUENCE: 6
METDTLLLWV LLLWVPGSTG FACKTASGTA IPIGGGSANV YVNLAPVVNV GQNLVVDLST  60
QIFCHNDYPE TITDYVTLQR GSAYGGVLSS FSGTVKYSGS SYPFPTTSET PRVVYNSRTD  120
KPWPVALYLT PVSSAGGVAI KAGSLIAVLI LRQTNNYNSD DFQFVWNIYA NNDVVVPTGG  180
CDVSARDVTV TLPDYPGSVP IPLTVYCAKS QNLGYYLSGT TADAGNSIFT NTASFSPAQG  240
VGVQLTRQGT IIPANNTVSL GAVGTSAVSL GLTANYARTG GQVTAGNVQS IIGVTFVYQG  300
GSSGGGADVT ITVNGKVVAK GGHHHHHHHH                                   330

SEQ ID NO: 7             moltype = AA  length = 188
FEATURE                  Location/Qualifiers
REGION                   1..188
                         note = Synthetic
source                   1..188
                         mol_type = protein
                         organism = synthetic construct
SEQUENCE: 7
METDTLLLWV LLLWVPGSTG FACKTASGTA IPIGGGSANV YVNLAPVVNV GQNLVVDLST  60
QIFCHNDYPE TITDYVTLQR GSAYGGVLSS FSGTVKYSGS SYPFPTTSET PRVVYNSRTD  120
KPWPVALYLT PVSSAGGVAI KAGSLIAVLI LRQTNNYNSD DFQFVWNIYA NNDVVVPTGG  180
HHHHHHHH                                                           188

SEQ ID NO: 8             moltype = AA  length = 188
FEATURE                  Location/Qualifiers
REGION                   1..188
                         note = Synthetic
source                   1..188
                         mol_type = protein
                         organism = synthetic construct
SEQUENCE: 8
METDTLLLWV LLLWVPGSTG FACKTASGTA IPIGGGSANV YVNLAPCVNV GQNCVVDLST  60
QIFCHNDYPE TITDYVTLQR GSAYGGVLSS FSGTVKYSGS SYPFPTTSET PRVVYNSRTD  120
KPWPVALYLT PVSSAGGVAI KAGSLIAVLI LRQTNNYNSD DFQFVWNIYA NNDVVVPTGG  180
HHHHHHHH                                                           188

SEQ ID NO: 9             moltype = AA  length = 14
FEATURE                  Location/Qualifiers
REGION                   1..14
                         note = Synthetic
source                   1..14
                         mol_type = protein
```

```
                        organism = synthetic construct
SEQUENCE: 9
ADVTITVNGK VVAK                                                    14

SEQ ID NO: 10           moltype = AA  length = 241
FEATURE                 Location/Qualifiers
REGION                  1..241
                        note = Synthetic
source                  1..241
                        mol_type = protein
                        organism = synthetic construct
SEQUENCE: 10
MSNKNVNVRK SQEITFCLLA GILMFMAMMV AGRAEAGVAL GATRVIYPAG QKQVQLAVTN  60
NDENSTYLIQ SWVENADGVK DGRFIVTPPL FAMKGKKENT LRILDATNNQ LPQDRESLFW  120
MNVKAIPSMD KSKLTENTLQ LAIISRIKLY YRPAKLALPP DQAAEKLRFR RSANSLTLIN  180
PTPYYLTVTE LNAGTRVLEN ALVPPMGEST VKLPSDAGSN ITYRTINDYG ALTPKMTGVM  240
E                                                                  241

SEQ ID NO: 11           moltype = AA  length = 4
FEATURE                 Location/Qualifiers
REGION                  1..4
                        note = Synthetic
source                  1..4
                        mol_type = protein
                        organism = synthetic construct
SEQUENCE: 11
DNKQ                                                               4

SEQ ID NO: 12           moltype = AA  length = 5
FEATURE                 Location/Qualifiers
REGION                  1..5
                        note = Synthetic
source                  1..5
                        mol_type = protein
                        organism = synthetic construct
SEQUENCE: 12
GGSGG                                                              5

SEQ ID NO: 13           moltype = AA  length = 6
FEATURE                 Location/Qualifiers
REGION                  1..6
                        note = Synthetic
source                  1..6
                        mol_type = protein
                        organism = synthetic construct
SEQUENCE: 13
GGSSGG                                                             6

SEQ ID NO: 14           moltype = AA  length = 7
FEATURE                 Location/Qualifiers
REGION                  1..7
                        note = Synthetic
source                  1..7
                        mol_type = protein
                        organism = synthetic construct
SEQUENCE: 14
GGSSGGG                                                            7

SEQ ID NO: 15           moltype = AA  length = 8
FEATURE                 Location/Qualifiers
REGION                  1..8
                        note = Synthetic
source                  1..8
                        mol_type = protein
                        organism = synthetic construct
SEQUENCE: 15
GGGSSGGG                                                           8

SEQ ID NO: 16           moltype = AA  length = 9
FEATURE                 Location/Qualifiers
REGION                  1..9
                        note = Synthetic
source                  1..9
                        mol_type = protein
                        organism = synthetic construct
SEQUENCE: 16
GGGSGSGGG                                                          9

SEQ ID NO: 17           moltype = AA  length = 10
```

-continued

```
FEATURE                Location/Qualifiers
REGION                 1..10
                       note = Synthetic
source                 1..10
                       mol_type = protein
                       organism = synthetic construct
SEQUENCE: 17
GGGSGGSGGG                                                            10

SEQ ID NO: 18          moltype = AA  length = 21
FEATURE                Location/Qualifiers
REGION                 1..21
                       note = Synthetic
source                 1..21
                       mol_type = protein
                       organism = synthetic construct
SEQUENCE: 18
MKRVITLFAV LLMGWSVNAW S                                               21

SEQ ID NO: 19          moltype = AA  length = 20
FEATURE                Location/Qualifiers
REGION                 1..20
                       note = Synthetic
source                 1..20
                       mol_type = protein
                       organism = synthetic construct
SEQUENCE: 19
VETDTLLLWV LLLWVPGSTG                                                 20

SEQ ID NO: 20          moltype = AA  length = 279
FEATURE                Location/Qualifiers
REGION                 1..279
                       note = Synthetic
source                 1..279
                       mol_type = protein
                       organism = synthetic construct
SEQUENCE: 20
FACKTASGTA IPIGGGSANV YVNLAPCVNV GQNCVVDLST QIFCHNDYPE TITDYVTLQR  60
GSAYGGVLSS FSGTVKYSGS SYPFPTTSET PRVVYNSRTD KPWPVALYLT PVSSAGGVAI  120
KAGSLIAVLI LRQTNNYNSD DFQFVWNIYA NNDVVVPTGG CDVSARDVTV TLPDYPGSVP  180
IPLTVYCAKS QNLGYYLSGT TADAGNSIFT NTASFSPAQG VGVQLTRQGT IIPANNTVSL  240
GAVGTSAVSL GLTANYARTG GQVTAGNVQS IIGVTFVYQ                            279

SEQ ID NO: 21          moltype = AA  length = 24
FEATURE                Location/Qualifiers
REGION                 1..24
                       note = Synthetic
source                 1..24
                       mol_type = protein
                       organism = synthetic construct
SEQUENCE: 21
ADVTITVNGK VVAKGGHHHH HHHH                                            24

SEQ ID NO: 22          moltype = AA  length = 20
FEATURE                Location/Qualifiers
REGION                 1..20
                       note = Synthetic
source                 1..20
                       mol_type = protein
                       organism = synthetic construct
SEQUENCE: 22
METDTLLLWV LLLWVPGSTG                                                 20

SEQ ID NO: 23          moltype = AA  length = 279
FEATURE                Location/Qualifiers
REGION                 1..279
                       note = Synthetic
source                 1..279
                       mol_type = protein
                       organism = synthetic construct
SEQUENCE: 23
FACKTASGTA IPIGGGSANV YVNLAPVVNV GQNLVVDLST QIFCHNDYPE TITDYVTLQR  60
GSAYGGVLSS FSGTVKYSGS SYPFPTTSET PRVVYNSRTD KPWPVALYLT PVSSAGGVAI  120
KAGSLIAVLI LRQTNNYNSD DFQFVWNIYA NNDVVVPTGG CDVSARDVTV TLPDYPGSVP  180
IPLTVYCAKS QNLGYYLSGT TADAGNSIFT NTASFSPAQG VGVQLTRQGT IIPANNTVSL  240
GAVGTSAVSL GLTANYARTG GQVTAGNVQS IIGVTFVYQ                            279

SEQ ID NO: 24          moltype = AA  length = 160
FEATURE                Location/Qualifiers
```

```
REGION                1..160
                      note = Synthetic
source                1..160
                      mol_type = protein
                      organism = synthetic construct
SEQUENCE: 24
FACKTASGTA IPIGGGSANV YVNLAPVVNV GQNLVVDLST QIFCHNDYPE TITDYVTLQR  60
GSAYGGVLSS FSGTVKYSGS SYPFPTTSET PRVVYNSRTD KPWPVALYLT PVSSAGGVAI  120
KAGSLIAVLI LRQTNNYNSD DFQFVWNIYA NNDVVVPTGG                        160

SEQ ID NO: 25         moltype = AA  length = 8
FEATURE               Location/Qualifiers
REGION                1..8
                      note = Synthetic
source                1..8
                      mol_type = protein
                      organism = synthetic construct
SEQUENCE: 25
HHHHHHHH                                                           8

SEQ ID NO: 26         moltype = AA  length = 160
FEATURE               Location/Qualifiers
REGION                1..160
                      note = Synthetic
source                1..160
                      mol_type = protein
                      organism = synthetic construct
SEQUENCE: 26
FACKTASGTA IPIGGGSANV YVNLAPCVNV GQNCVVDLST QIFCHNDYPE TITDYVTLQR  60
GSAYGGVLSS FSGTVKYSGS SYPFPTTSET PRVVYNSRTD KPWPVALYLT PVSSAGGVAI  120
KAGSLIAVLI LRQTNNYNSD DFQFVWNIYA NNDVVVPTGG                        160

SEQ ID NO: 27         moltype = AA  length = 168
FEATURE               Location/Qualifiers
REGION                1..168
                      note = Synthetic
source                1..168
                      mol_type = protein
                      organism = synthetic construct
SEQUENCE: 27
FACKTANGTA IPIGGGSANV YVNLAPVVNV GQNLVVDLST QIFCHNDYPE TITDYVTLQR  60
GSAYGGVLSN FSGTVKYSGS SYPFPTTSET PRVVYNSRTD KPWPVALYLT PVSSAGGVAI  120
KAGSLIAVLI LRQTNNYNSD DFQFVWNIYA NNDVVVPTGG HHHHHHHH               168

SEQ ID NO: 28         moltype = AA  length = 279
FEATURE               Location/Qualifiers
REGION                1..279
                      note = Synthetic
source                1..279
                      mol_type = protein
                      organism = synthetic construct
SEQUENCE: 28
FACKTANGTA IPIGGGSANV YVNLAPVVNV GQNLVVDLST QIFCHNDYPE TITDYVTLQR  60
GSAYGGVLSN FSGTVKYSGS SYPFPTTSET PRVVYNSRTD KPWPVALYLT PVSSAGGVAI  120
KAGSLIAVLI LRQTNNYNSD DFQFVWNIYA NNDVVVPTGG CDVSARDVTV TLPDYPGSVP  180
IPLTVYCAKS QNLGYYLSGT TADAGNSIFT NTASFSPAQG VGVQLTRNGT IIPANNTVSL  240
GAVGTSAVSL GLTANYARTG GQVTAGNVQS IIGVTFVYQ                         279

SEQ ID NO: 29         moltype = AA  length = 279
FEATURE               Location/Qualifiers
REGION                1..279
                      note = Synthetic
source                1..279
                      mol_type = protein
                      organism = synthetic construct
SEQUENCE: 29
FACKTANGTA IPIGGGSANV YVNLAPAVNV GQNLVVDLST QIFCHNDYPE TITDYVTLQR  60
GAAYGGVLSS FSGTVKYNGS SYPFPTTSET PRVVYNSRTD KPWPVALYLT PVSSAGGVAI  120
KAGSLIAVLI LRQTNNYNSD DFQFVWNIYA NNDVVVPTGG CDVSARDVTV TLPDYPGSVP  180
IPLTVYCAKS QNLGYYLSGT TADAGNSIFT NTASFSPAQG VGVQLTRNGT IIPANNTVSL  240
GAVGTSAVSL GLTANYARTG GQVTAGNVQS IIGVTFVYQ                         279

SEQ ID NO: 30         moltype = AA  length = 325
FEATURE               Location/Qualifiers
REGION                1..325
                      note = Synthetic
source                1..325
                      mol_type = protein
                      organism = synthetic construct
```

SEQUENCE: 30
MRVENNNVSG QNHDPEQIDL IDLLVQLWRG KMTIIISVIV AIALAIGYLA VAKEKWTSTA 60
IITQPDVGQI AGYNNAMNVI YGQAAPKVSD LQETLIGRFS SAFSALAETL DNQEEPEKLT 120
IEPSVKNQQL PLTVSYVGQT AEGAQMKLAQ YIQQVDDKVN QELEKDLKDN IALGRKNLQD 180
SLRTQEVVAQ EQKDLRIRQI QEALQYANQE QVTKPQVQQT EDVTQDTLFL LGSEALESMI 240
KHEATRPLVF SSNYYQTRQN LLDIESLKVD DLDIHAYRYV MKPTLPIRRD SPKKAITLIL 300
AVLLGGMVGA GIVLGRNALR NYNAK 325

SEQ ID NO: 31 moltype = AA length = 326
FEATURE Location/Qualifiers
REGION 1..326
note = Synthetic
source 1..326
mol_type = protein
organism = synthetic construct
SEQUENCE: 31
MRVENNNVSG QNNDPEQIDL IDLLVQLWRG KMTIIISVIV AIALAIGYLA VAKEKWTSTA 60
IITQPDVGQI AGYNNAMNVI YGQAAPKVSD LQETLIGRFS SAFSALAETL DNQDEPEKLT 120
IEPSVKNQQL PLTVSYVGQT AEGAQMKLAQ YIQQVDDKVN QELEKDLKDN IALGRKNLQD 180
SLRTQEVVAQ EQKDLRIRQI QEALQYANQA QVTKPQIQQT GEDITQDTLF LLGSEALESM 240
IKHEATRPLV FSPNYYQTRQ NLLDIESLKV DDLDIHAYRY VMKPTLPIRR DSPKKAITLI 300
LAVLLGGMVG AGIVLGRNAL RNYNAK 326

SEQ ID NO: 32 moltype = AA length = 326
FEATURE Location/Qualifiers
REGION 1..326
note = Synthetic
source 1..326
mol_type = protein
organism = synthetic construct
SEQUENCE: 32
MRVENNNVSG QNHDPEQIDL IDLLVQLWRG KMTIIISVVV AIALAIGYLA VAKEKWTSTA 60
IITQPDVGQI AGYNNAMNVI YGQAAPKVSD LQETLIGRFS FAFSALAETL DNQKEPEKLT 120
IEPSVKNQQL PLTVSYVGQT AEDAQMKLAQ YIQQVDDKVN QELEKDLKDN LALGRKNLQD 180
SLRTQEVVAQ EQKDLRIRQI QEALQYANQA QVTKPQIQQT GEDITQDTLF LLGSEALESM 240
IKHEATRPLV FSPNYYQTRQ NLLDIENLKV DDLDIHAYRY VMKPTLPIRR DSPKKAITLI 300
LAVLLGGMVG AGIVLGRNAL RNYNSK 326

SEQ ID NO: 33 moltype = AA length = 326
FEATURE Location/Qualifiers
REGION 1..326
note = Synthetic
source 1..326
mol_type = protein
organism = synthetic construct
SEQUENCE: 33
MRVENNNVSG QNHDPEQIDL IDLLVQLWRG KMTIIISVIV AIALAIGYLA VAKEKWTSTA 60
IITQPDVGQI AGYNNAMNVI YGQAAPKVSD LQETLIGRFS SAFSALAETL DNQEEREKLT 120
IEPSVKNQQL PLTVSYVGQT AEGAQMKLAQ YIQQVDDKVN QELEKDLKDN IALGRKNLQD 180
SLRTQEVVAQ EQKDLRIRQI QEALQYANQA QVTKPQIQQT GEDITQDTLF LLGSEALESM 240
IKHEATRPLV FSPNYYQTRQ NLLDIESLKV DDLDIHAYRY VMKPMLPIRR DSPKKAITLI 300
LAVLLGGMVG AGIVLGRNAL RNYNAK 326

SEQ ID NO: 34 moltype = AA length = 327
FEATURE Location/Qualifiers
REGION 1..327
note = Synthetic
source 1..327
mol_type = protein
organism = synthetic construct
SEQUENCE: 34
MTVDSNTSSG RGNDPEQIDL IELLLQLWRG KMTIIVAVII AILLAVGYLM IAKEKWTSTA 60
IITQPDAAQV ATYTNALNVL YGGNAPKISE VQANFISRFS SAFSALSEVL DNQKEREKLT 120
IEQSVKGQAL PLSVSYVSTT AEGAQRRLAE YIQQVDEEVA KELEVDLKDN ITLQTKTLQE 180
SLETQEVVAQ EQKDLRIKQI EEALRYADEA KITQPQIQQT QDVTQDTMFL LGSDALKSMI 240
QNEATRPLVF SPAYYQTKQT LLDIKNLKVT ADTVHVYRYV MKPTLPVRRD SPKTAITLVL 300
AVLLGGMIGA GIVLGRNALR SYKPKAL 327

SEQ ID NO: 35 moltype = AA length = 377
FEATURE Location/Qualifiers
REGION 1..377
note = Synthetic
source 1..377
mol_type = protein
organism = synthetic construct
SEQUENCE: 35
MSSLNIKQGS DAHFPDYPLA SPSNNEIDLL NLISVLWRAK KTVMAVVFAF ACAGLLISFI 60
LPQKWTSAAV VTPPEPVQWQ ELEKSFTKLR VLDLDIKIDR TEAFNLFIKK FQSVSLLEEY 120
LRSSPYVMDQ LKEAKIDELD LHRAIVALSE KMKAVDDNAS KKKDEPSLYT SWTLSFTAPT 180

-continued

```
SEEAQTVLSG YIDYISTLVV KESLENVRNK LEIKTQFEKE KLAQDRIKTK NQLDANIQRL  240
NYSLDIANAA GIKKPVYSNG QAVKDDPDFS ISLGADGIER KLEIEKAVTD VAELNGELRN  300
RQYLVEQLTK AHVNDVNFTP FKYQLSPSLP VKKDGPGKAI IVILSALIGG MVACGGVLLR  360
YAMASRKQDA MMADHLV                                                 377

SEQ ID NO: 36          moltype = AA  length = 377
FEATURE                Location/Qualifiers
REGION                 1..377
                       note = Synthetic
source                 1..377
                       mol_type = protein
                       organism = synthetic construct
SEQUENCE: 36
MSSLNIKQGS EAHFPEYPLA SPSNNEIDLL NLIEVLWRAK KTVMAVVFAF ACAGLLISFI  60
LPQKWTSAAV VTPPEPVQWQ ELEKTFTKLR VLDLDIKIDR TEAFNLFIKK FQSVSLLEEY  120
LRSSPYVMDQ LKEAKIDPLD LHRAIVALSE KMKAVDDNAS KKKDESALYT SWTLSFTAPT  180
SEEAQKVLAG YIDYISALVV KESIENVRNK LEIKTQFEKE KLAQDRIKTK NQLDANIQRL  240
NYSLDIANAA GIKKPVYSNG QAVKDDPDFS ISLGADGIER KLEIEKAVTD VAELNGELRN  300
RQYLVEQLTK TNINDVNFTP FKYQLRPSLP VKKDGQGKAI IVILSALVGG MVACGGVLLR  360
HAMASRKQDA MMADHLV                                                 377

SEQ ID NO: 37          moltype = AA  length = 377
FEATURE                Location/Qualifiers
REGION                 1..377
                       note = Synthetic
source                 1..377
                       mol_type = protein
                       organism = synthetic construct
SEQUENCE: 37
MSSLNIKQGS DAHFPDYPLA SPSNNEIDLL NLISVLWRAK KTVMAVVFAF ACAGLLISFI  60
LPQKWTSAAV VTPPEPVQWQ ELEKSFTKLR VLDLDIKIDR TEAFNLFIKK FQSVSLLEEY  120
LRSSPYVMDQ LKEAKIDELD LHRAIVALSE KMKAVDDNAS KKKDEPSLYT SWTLSFTAPT  180
SEEAQTVLSG YIDYISTLVV KESLENVRNK LEIKTQFEKE KLAQDRIKTK NQLDANIQRL  240
NYSLDIANAA GIKKPVYSNG QAVKDDPDFS ISLGADGIER KLEIEKAVTD VAELNGELRN  300
RQYLVEQLTK AHVNDVNFTP FKYQLSPSLP VKKDGPGKAI IVILSALIGG MVACGGVLLR  360
YAMASRKQDA MMADHLV                                                 377

SEQ ID NO: 38          moltype = AA  length = 377
FEATURE                Location/Qualifiers
REGION                 1..377
                       note = Synthetic
source                 1..377
                       mol_type = protein
                       organism = synthetic construct
SEQUENCE: 38
MSSLNIKQGS DAHFPDYPLA SPSNNEIDLL NLISVLWRAK KTVMAVVFAF ACAGLLISFI  60
LPQKWTSAAV VTPPEPVQWQ ELEKTFTKLR VLDLDIKIDR TEAFNLFIKK FQSVSLLEEY  120
LRSSPYVMDQ LKEAKIDELD LHRAIVALSE KMKAVDDNAS KKKDEPSLYT SWTLSFTAPT  180
SEEAQTVLSG YIDYISALVV KESIENVRNK LEIKTQFEKE KLAQDRIKMK NQLDANIQRL  240
NYSLDIANAA GIKKPVYSNG QAVKDDPDFS ISLGADGIER KLEIEKAVTD VAELNGELRN  300
RQYLVEQLTK ANINDVNFTP FKYQLSPSLP VKKDGPGKAI IVILSALIGG MVACGSVLLR  360
YAMASRKQDA MMADHLV                                                 377

SEQ ID NO: 39          moltype = AA  length = 378
FEATURE                Location/Qualifiers
REGION                 1..378
                       note = Synthetic
source                 1..378
                       mol_type = protein
                       organism = synthetic construct
SEQUENCE: 39
MPSLNVKQEK NQSFAGYSLP PANSHEIDLF SLIEVLWQAK RRILATVFAF ACVGLLLSFL  60
LPQKWTSQAI VTPAESVQWQ GLERTLTALR VLDMEVSVDR GSVFNLFIKK FSSPSLLEEY  120
LRSSPYVMDQ LKGAQIDEQD LHRAIVLLSE KMKAVDSNVG KKNETSLFTS WTLSFTAPTR  180
EEAQKVLAGY IQYISDIVVK ETLENIRNQL EIKTRYEQEK LAMDRVRLKN QLDANIQRLH  240
YSLEIANAAG IKRPVYSNGQ AVKDDPDFSI SLGADGISRK LEIEKGVTDV AEIDGDLRNR  300
QYHVEQLAAM NVSDVKFTPF KYQLSPSLPV KKDGPGKAII IILAALIGGM MACGGVLLRH  360
AMVSRKMENA LAIDERLV                                                378

SEQ ID NO: 40          moltype = DNA  length = 22
FEATURE                Location/Qualifiers
misc_feature           1..22
                       note = Synthetic
source                 1..22
                       mol_type = other DNA
                       organism = synthetic construct
SEQUENCE: 40
gaagcaaacc gtacgcgtaa ag                                           22
```

```
SEQ ID NO: 41          moltype = DNA  length = 20
FEATURE                Location/Qualifiers
misc_feature           1..20
                       note = Synthetic
source                 1..20
                       mol_type = other DNA
                       organism = synthetic construct
SEQUENCE: 41
cgaccagctc ttacacggcg                                          20

SEQ ID NO: 42          moltype = DNA  length = 36
FEATURE                Location/Qualifiers
misc_feature           1..36
                       note = Synthetic
source                 1..36
                       mol_type = other DNA
                       organism = synthetic construct
SEQUENCE: 42
gaaataggac cactaataaa tacacaaatt aataac                        36

SEQ ID NO: 43          moltype = DNA  length = 21
FEATURE                Location/Qualifiers
misc_feature           1..21
                       note = Synthetic
source                 1..21
                       mol_type = other DNA
                       organism = synthetic construct
SEQUENCE: 43
ataattgacg atccggttgc c                                        21

SEQ ID NO: 44          moltype = DNA  length = 27
FEATURE                Location/Qualifiers
misc_feature           1..27
                       note = Synthetic
source                 1..27
                       mol_type = other DNA
                       organism = synthetic construct
SEQUENCE: 44
gctatttacg ccctgattgt cttttgt                                  27

SEQ ID NO: 45          moltype = DNA  length = 22
FEATURE                Location/Qualifiers
misc_feature           1..22
                       note = Synthetic
source                 1..22
                       mol_type = other DNA
                       organism = synthetic construct
SEQUENCE: 45
attgagaacc tgcgtaaacg gc                                       22

SEQ ID NO: 46          moltype = DNA  length = 24
FEATURE                Location/Qualifiers
misc_feature           1..24
                       note = Synthetic
source                 1..24
                       mol_type = other DNA
                       organism = synthetic construct
SEQUENCE: 46
tgaagagcgg ttcagataac ttcc                                     24

SEQ ID NO: 47          moltype = DNA  length = 21
FEATURE                Location/Qualifiers
misc_feature           1..21
                       note = Synthetic
source                 1..21
                       mol_type = other DNA
                       organism = synthetic construct
SEQUENCE: 47
cgatccggaa acctcctaca c                                        21

SEQ ID NO: 48          moltype = DNA  length = 26
FEATURE                Location/Qualifiers
misc_feature           1..26
                       note = Synthetic
source                 1..26
                       mol_type = other DNA
                       organism = synthetic construct
SEQUENCE: 48
gattattcgc gcaacgctaa acagat                                   26
```

```
SEQ ID NO: 49          moltype = DNA  length = 23
FEATURE                Location/Qualifiers
misc_feature           1..23
                       note = Synthetic
source                 1..23
                       mol_type = other DNA
                       organism = synthetic construct
SEQUENCE: 49
tgatcattga cgatccggta gcc                                   23

SEQ ID NO: 50          moltype = DNA  length = 70
FEATURE                Location/Qualifiers
misc_feature           1..70
                       note = Synthetic
source                 1..70
                       mol_type = other DNA
                       organism = synthetic construct
SEQUENCE: 50
cggtagctgt aaagccaggg gcggtagcgt ggtttaaacc caagcaacag atcggcgtcg  60
tcggtatgga                                                  70

SEQ ID NO: 51          moltype = DNA  length = 78
FEATURE                Location/Qualifiers
misc_feature           1..78
                       note = Synthetic
source                 1..78
                       mol_type = other DNA
                       organism = synthetic construct
SEQUENCE: 51
agcttccata ccgacgacgc cgatctgttg cttgggttta aaccacgcta ccgcccctgg  60
ctttacagct accgagct                                         78

SEQ ID NO: 52          moltype = DNA  length = 30
FEATURE                Location/Qualifiers
misc_feature           1..30
                       note = Synthetic
source                 1..30
                       mol_type = other DNA
                       organism = synthetic construct
SEQUENCE: 52
ggtagctgta aagccagggg cggtagcgtg                            30

SEQ ID NO: 53          moltype = DNA  length = 30
FEATURE                Location/Qualifiers
misc_feature           1..30
                       note = Synthetic
source                 1..30
                       mol_type = other DNA
                       organism = synthetic construct
SEQUENCE: 53
ccataccgac gacgccgatc tgttgcttgg                            30

SEQ ID NO: 54          moltype = AA  length = 19
FEATURE                Location/Qualifiers
REGION                 1..19
                       note = Synthetic
source                 1..19
                       mol_type = protein
                       organism = synthetic construct
SEQUENCE: 54
ETDTLLLWVL LLWVPGSTG                                        19

SEQ ID NO: 55          moltype = AA  length = 23
FEATURE                Location/Qualifiers
source                 1..23
                       mol_type = protein
                       organism = Homo sapiens
SEQUENCE: 55
MGVPRPQPWA LGLLLFLLPG SLG                                   23

SEQ ID NO: 56          moltype = AA  length = 18
FEATURE                Location/Qualifiers
source                 1..18
                       mol_type = protein
                       organism = Homo sapiens
SEQUENCE: 56
MHSSALLCCL VLLTGVRA                                         18
```

-continued

```
SEQ ID NO: 57          moltype = AA  length = 25
FEATURE                Location/Qualifiers
source                 1..25
                       mol_type = protein
                       note = [strain A2]
                       organism = Human respiratory syncytial virus A
SEQUENCE: 57
MELLILKANA ITTILTAVTF CFASG                                        25

SEQ ID NO: 58          moltype = AA  length = 15
FEATURE                Location/Qualifiers
source                 1..15
                       mol_type = protein
                       note = [strain A/Japan/305/1957 H2N2]
                       organism = Influenza A virus
SEQUENCE: 58
MAIIYLILLF TAVRG                                                   15

SEQ ID NO: 59          moltype = AA  length = 207
FEATURE                Location/Qualifiers
REGION                 1..207
                       note = Synthetic
source                 1..207
                       mol_type = protein
                       organism = synthetic construct
SEQUENCE: 59
MEGMDPLAVL AESRLLPLLT VRGGEDLAGL ATVLELMGVG ALEITLRTEK GLEALKALRK  60
SGLLLGAGTV RSPKEAEAAL EAGAAFLVSP GLLEEVAALA QARGVPYLPG VLTPTEVERA  120
LALGLSALKF FPAEPFQGVR VLRAYAEVFP EVRFLPTGGI KEEHLPHYAA LPNLLAVGGS  180
WLLQGDLAAV MKKVKAAKAL LSPQAPG                                      207

SEQ ID NO: 60          moltype = AA  length = 156
FEATURE                Location/Qualifiers
REGION                 1..156
                       note = Synthetic
source                 1..156
                       mol_type = protein
                       organism = synthetic construct
SEQUENCE: 60
MTKKVGIVDT TFARVDMAEA AIRTLKALSP NIKIIRKTVP GIKDLPVACK KLLEEEGCDI  60
VMALGMPGKA EKDKVCAHEA SLGLMLAQLM TNKHIIEVFV HEDEAKDDDE LDILALVRAI  120
EHAANVYYLL FKPEYLTRMA GKGLRQGRED AGPARE                            156

SEQ ID NO: 61          moltype = AA  length = 156
FEATURE                Location/Qualifiers
REGION                 1..156
                       note = Synthetic
source                 1..156
                       mol_type = protein
                       organism = synthetic construct
SEQUENCE: 61
MTKKVGIVDT TFARVDMASA AILTLKMESP NIKIIRKTVP GIKDLPVACK KLLEEEGCDI  60
VMALGMPGKA EKDKVCAHEA SLGLMLAQLM TNKHIIEVFV HEDEAKDDAE LKILAARRAI  120
EHALNVYYLL FKPEYLTRMA GKGLRQGFED AGPARE                            156

SEQ ID NO: 62          moltype = AA  length = 209
FEATURE                Location/Qualifiers
REGION                 1..209
                       note = Synthetic
source                 1..209
                       mol_type = protein
                       organism = synthetic construct
SEQUENCE: 62
MSTINNQLKA LKVIPVIAID NAEDIIPLGK VLAENGLPAA EITFRSSAAV KAIMLLRSAQ  60
PEMLIGAGTI LNGVQALAAK EAGATFVVSP GFNPNTVRAC QIIGIDIVPG VNNPSTVEAA  120
LEMGLTTLKF FPAEASGGIS MVKSLVGPYG DIRLMPTGGI TPSNIDNYLA IPQVLACGGT  180
WMVDKKLVTN GEWDEIARLT REIVEQVNP                                    209

SEQ ID NO: 63          moltype = AA  length = 114
FEATURE                Location/Qualifiers
REGION                 1..114
                       note = Synthetic
source                 1..114
                       mol_type = protein
                       organism = synthetic construct
SEQUENCE: 63
MPIFTLNTNI KATDVPSDFL SLTSRLVGLI LSKPGSYVAV HINTDQQLSF GGSTNPAAFG  60
TLMSIGGIEP SKNRDHSAVL FDHLNAMLGI PKNRMYIHFV NLNGDDVGWN GTTF         114
```

-continued

```
SEQ ID NO: 64          moltype = AA  length = 157
FEATURE                Location/Qualifiers
REGION                 1..157
                       note = Synthetic
source                 1..157
                       mol_type = protein
                       organism = synthetic construct
SEQUENCE: 64
MNQHSHKDYE TVRIAVVRAR WHADIVDACV EAFEIAMAAI GGDRFAVDVF DVPGAYEIPL  60
HARTLAETGR YGAVLGTAFV VNGGIYRHEF VASAVIDGMM NVQLSTGVPV LSAVLTPHRY  120
RDSAEHHRFF AAHFAVKGVE AARACIEILA AREKIAA                          157

SEQ ID NO: 65          moltype = AA  length = 205
FEATURE                Location/Qualifiers
REGION                 1..205
                       note = Synthetic
source                 1..205
                       mol_type = protein
                       organism = synthetic construct
SEQUENCE: 65
MKMEELFKKH KIVAVLRANS VEEAIEKAVA VFAGGVHLIE ITFTVPDADT VIKALSVLKE  60
KGAIIGAGTV TSVEQCRKAV ESGAEFIVSP HLDEEISQFC KEKGVFYMPG VMTPTELVKA  120
MKLGHTILKL FPGEVVGPQF VKAMKGPFPN VKFVPTGGVN LDNVCEWFKA GVLAVGVGSA  180
LVKGTPDEVR EKAKAFVEKI RGCTE                                       205

SEQ ID NO: 66          moltype = AA  length = 157
FEATURE                Location/Qualifiers
REGION                 1..157
                       note = Synthetic
source                 1..157
                       mol_type = protein
                       organism = synthetic construct
SEQUENCE: 66
MNQHSHKDYE TVRIAVVRAR WHAEIVDACV SAFEAAMADI GGDRFAVDVF DVPGAYEIPL  60
HARTLAETGR YGAVLGTAFV VNGGIYRHEF VASAVIDGMM NVQLSTGVPV LSAVLTPHRY  120
RDSDAHTLLF LALFAVKGME AARACVEILA AREKIAA                          157

SEQ ID NO: 67          moltype = AA  length = 177
FEATURE                Location/Qualifiers
REGION                 1..177
                       note = Synthetic
source                 1..177
                       mol_type = protein
                       organism = synthetic construct
SEQUENCE: 67
MFTKSGDDGN TNVINKRVGK DSPLVNFLGD LDELNSFIGF AISKIPWEDM KKDLERVQVE  60
LFEIGEDLST QSSKKKIDES YVLWLLAATA IYRIESGPVK LFVIPGGSEE ASVLHVTRSV  120
ARRVERNAVK YTKELPEINR MIIVYLNRLS SLLFAMALVA NKRRNQSEKI YEIGKSW     177

SEQ ID NO: 68          moltype = AA  length = 157
FEATURE                Location/Qualifiers
REGION                 1..157
                       note = Synthetic
source                 1..157
                       mol_type = protein
                       organism = synthetic construct
SEQUENCE: 68
MNQHSHKDYE TVRIAVVRAR WHADIVDQCV RAFEEAMADA GGDRFAVDVF DVPGAYEIPL  60
HARTLAETGR YGAVLGTAFV VNGGIYRHEF VASAVIDGMM NVQLSTGVPV LSAVLTPHRY  120
RSSREHHEFF REHFMVKGVE AAAACITILA AREKIAA                          157

SEQ ID NO: 69          moltype = AA  length = 201
FEATURE                Location/Qualifiers
REGION                 1..201
                       note = Synthetic
source                 1..201
                       mol_type = protein
                       organism = synthetic construct
SEQUENCE: 69
MGHTKGPTPQ QHDGSALRIG IVHARWNKTI IMPLLIGTIA KLLECGVKAS NIVVQSVPGS  60
WELPIAVQRL YSASQLQTPS SGPSLSAGDL LGSSTTDLTA LPTTTASSTG PFDALIAIGV  120
LIKGETMHFE YIADSVSHGL MRVQLDTGVP VIFGVLTVLT DDQAKARAGV IEGSHNHGED  180
WGLAAVEMGV RRRDWAAGKT E                                           201

SEQ ID NO: 70          moltype = AA  length = 237
FEATURE                Location/Qualifiers
REGION                 1..237
                       note = Synthetic
source                 1..237
```

```
                         mol_type = protein
                         organism = synthetic construct
SEQUENCE: 70
MYEVDHADVY DLFYLGRGKD YAAEASDIAD LVRSRTPEAS SLLDVACGTG THLEHFTKEF  60
GDTAGLELSE DMLTHARKRL PDATLHQGDM RDFQLGRKFS AVVSMFSSVG YLKTVAELGA  120
AVASFAEHLE PGGVVVVEPW WFPETFADGW VSADVVRRDG RTVARVSHSV REGNATRMEV  180
HFTVADPGKG VRHFSDVHLI TLFHQREYEA AFMAAGLRVE YLEGGPSGRG LFVGVPA     237

SEQ ID NO: 71            moltype = AA  length = 138
FEATURE                  Location/Qualifiers
REGION                   1..138
                         note = Synthetic
source                   1..138
                         mol_type = protein
                         organism = synthetic construct
SEQUENCE: 71
MGMKEKFVLI ITHGDFGKGL LSGAEVIIGK QENVHTVGLN LGDNIEKVAK EVMRIIIAKL  60
AEDKEIIIVV DLFGGSPFNI ALEMMKTFDV KVITGINMPM LVELLTSINV YDTTELLENI  120
SKIGKDGIKV IEKSSLKM                                               138

SEQ ID NO: 72            moltype = AA  length = 154
FEATURE                  Location/Qualifiers
REGION                   1..154
                         note = Synthetic
source                   1..154
                         mol_type = protein
                         organism = synthetic construct
SEQUENCE: 72
MKYDGSKLRI GILHARWNLE IIAALVAGAI KRLQEFGVKA ENIIIETVPG SFELPYGSKL  60
FVEKQKRLGK PLDAIIPIGV LIKGSTMHFE YICDSTTHQL MKLNFELGIP VIFGVLTCLT  120
DEQAEARAGL IEGKMHNHGE DWGAAAVEMA TKFN                             154

SEQ ID NO: 73            moltype = AA  length = 164
FEATURE                  Location/Qualifiers
REGION                   1..164
                         note = Synthetic
source                   1..164
                         mol_type = protein
                         organism = synthetic construct
SEQUENCE: 73
MAVKGLGEVD QKYDGSKLRI GILHARWNRK IILALVAGAV LRLLEFGVKA ENIIIETVPG  60
SFELPYGSKL FVEKQKRLGK PLDAIIPIGV LIKGSTMHFE YICDSTTHQL MKLNFELGIP  120
VIFGVLTCLT DEQAEARAGL IEGKMHNHGE DWGAAAVEMA TKFN                  164

SEQ ID NO: 74            moltype = AA  length = 175
FEATURE                  Location/Qualifiers
REGION                   1..175
                         note = Synthetic
source                   1..175
                         mol_type = protein
                         organism = synthetic construct
SEQUENCE: 74
MGANWYLDNE SSRLSFTSTK NADIAEVHRF LVLHGKVDPK GLAEVEVETE SISTGIPLRD  60
MLLRVLVFQV SKFPVAQINA QLDMRPINNL APGAQLELRL PLTVSLRGKS HSYNAELLAT  120
RLDERRFQVV TLEPLVIHAQ DFDMVRAFNA LRLVAGLSAV SLSVPVGAVL IFTAR       175

SEQ ID NO: 75            moltype = AA  length = 208
FEATURE                  Location/Qualifiers
REGION                   1..208
                         note = Synthetic
source                   1..208
                         mol_type = protein
                         organism = synthetic construct
SEQUENCE: 75
MTDYIRDGSA IKALSFAIIL AEADLRHIPQ DLQRLAVRVI HACGMVDVAN DLAFSEGAGK  60
AGRNALLAGA PILCDARMVA EGITRSRLPA DNRVIYTLSD PSVPELAKKI GNTRSAAALD  120
LWLPHIEGSI VAIGNAPTAL FRLFELLDAG APKPALIIGM PVGFVGAAES KDELAANSRG  180
VPYVIVRGRR GGSAMTAAAV NALASERE                                    208

SEQ ID NO: 76            moltype = AA  length = 128
FEATURE                  Location/Qualifiers
REGION                   1..128
                         note = Synthetic
source                   1..128
                         mol_type = protein
                         organism = synthetic construct
SEQUENCE: 76
MITVFGLKSK LAPRREKLAE VIYSSLHLGL DIPKGKHAIR FLCLEKEDFY YPFDRSDDYT  60
VIEINLMAGR SEETKMLLIF LLFIALERKL GIRAHDVEIT IKEQPAHCWG FRGRTGDSAR  120
```

```
DLDYDIYV                                                      128

SEQ ID NO: 77          moltype = AA  length = 235
FEATURE                Location/Qualifiers
REGION                 1..235
                       note = Synthetic
source                 1..235
                       mol_type = protein
                       organism = synthetic construct
SEQUENCE: 77
MGSDLQKLQR FSTCDISDGL LNVYNIPTGG YFPNLTAISP PQNSSIVGTA YTVLFAPIDD  60
PRPAVNYIDS VPPNSILVLA LEPHLQSQFH PFIKITQAMY GGLMSTRAQY LKSNGTVVFG  120
RIRDVDEHRT LNHPVFAYGV GSCAPKAVVK AVGTNVQLKI LTSDGVTQTI CPGDYIAGDN  180
NGIVRIPVQE TDISKLVTYI EKSIEVDRLV SEAIKNGLPA KAAQTARRMV LKDYI       235

SEQ ID NO: 78          moltype = AA  length = 162
FEATURE                Location/Qualifiers
REGION                 1..162
                       note = Synthetic
source                 1..162
                       mol_type = protein
                       organism = synthetic construct
SEQUENCE: 78
MSGMRVYLGA DHAGYELKQA IIAFLKMTGH EPIDCGALRY DADDDYPAFC IAAATRTVAD  60
PGSLGIVLGG SGNGEQIAAN KVPGARCALA WSVQTAALAR EHNNAQLIGI GGRMHTLEEA  120
LRIVKAFVTT PWSKAQRHQR RIDILAEYER THEAPPVPGA PA                     162

SEQ ID NO: 79          moltype = AA  length = 157
FEATURE                Location/Qualifiers
REGION                 1..157
                       note = Synthetic
source                 1..157
                       mol_type = protein
                       organism = synthetic construct
SEQUENCE: 79
MGDDARIAAI GDVDELNSQI GVLLAEPLPD DVRAALSAIQ HDLFDLGGEL CIPGHAAITE  60
DHLLRLALWL VHYNGQLPPL EEFILPGGAR GAALAHVCRT VCRRAERSIK ALGASEPLNI  120
APAAYVNLLS DLLFVLARVL NRAAGGADVL WDRTRAH                           157

SEQ ID NO: 80          moltype = AA  length = 157
FEATURE                Location/Qualifiers
REGION                 1..157
                       note = Synthetic
source                 1..157
                       mol_type = protein
                       organism = synthetic construct
SEQUENCE: 80
MILSAEQSFT LRHPHGQAAA LAFVREPAAA LAGVQRLRGL DSDGEQVWGE LLVRVPLLGE  60
VDLPFRSEIV RTPQGAELRP LTLTGERAWV AVSGQATAAE GGEMAFAFQF QAHLATPEAE  120
GEGGAAFEVM VQAAAGVTLL LVAMALPQGL AAGLPPA                           157

SEQ ID NO: 81          moltype = AA  length = 156
FEATURE                Location/Qualifiers
REGION                 1..156
                       note = Synthetic
source                 1..156
                       mol_type = protein
                       organism = synthetic construct
SEQUENCE: 81
MTKKVGIVDT TFARVDMASA AILTLKMESP NIKIIRKTVP GIKDLPVACK KLLEEEGCDI  60
VMALGMPGKK EKDKVCAHEA SLGLMLAQLM TNKHIIEVFV HEDEAKDDAE LKILAARRAI  120
EHALNVYYLL FKPEYLTRMA GKGLRQGFED AGPARE                            156

SEQ ID NO: 82          moltype = AA  length = 209
FEATURE                Location/Qualifiers
REGION                 1..209
                       note = Synthetic
source                 1..209
                       mol_type = protein
                       organism = synthetic construct
SEQUENCE: 82
MDDINNQLKR LKVIPVIAID NAEDIIPLGK VLAENGLPAA EITFRSSAAV KAIMLLRSAQ  60
PEMLIGAGTI LNGVQALAAK EAGADFVVSP GFNPNTVRAC QIIGIDIVPG VNNPSTVEQA  120
LEMGLTTLKF FPAEASGGIS MVKSLVGPYG DIRLMPTGGI TPDNIDNYLA IPQVLACGGT  180
WMVDKKLVRN GEWDEIARLT REIVEQVNP                                    209

SEQ ID NO: 83          moltype = AA  length = 114
FEATURE                Location/Qualifiers
REGION                 1..114
```

```
                        note = Synthetic
source                  1..114
                        mol_type = protein
                        organism = synthetic construct
SEQUENCE: 83
MPIFTLNTNI KADDVPSDFL SLTSRLVGLI LSKPGSYVAV HINTDQQLSF GGSTNPAAFG  60
TLMSIGGIEP DKNRDHSAVL FDHLNAMLGI PKNRMYIHFV NLNGDDVGWN GTTF        114

SEQ ID NO: 84           moltype = AA  length = 114
FEATURE                 Location/Qualifiers
REGION                  1..114
                        note = Synthetic
source                  1..114
                        mol_type = protein
                        organism = synthetic construct
SEQUENCE: 84
MPIFTLNTNI KADDVPSDFL SLTSRLVGLI LSEPGSYVAV HINTDQQLSF GGSTNPAAFG  60
TLMSIGGIEP DKNEDHSAVL FDHLNAMLGI PKNRMYIHFV DLDGDDVGWN GTTF        114

SEQ ID NO: 85           moltype = AA  length = 157
FEATURE                 Location/Qualifiers
REGION                  1..157
                        note = Synthetic
source                  1..157
                        mol_type = protein
                        organism = synthetic construct
SEQUENCE: 85
MNQHSHKDHE TVRIAVVRAR WHADIVDACV EAFEIAMAAI GGDRFAVDVF DVPGAYEIPL  60
HARTLAETGR YGAVLGTAFV VNGGIYRHEF VASAVIDGMM NVQLDTGVPV LSAVLTPHRY  120
RDSDEHHRFF AAHFAVKGVE AARACIEILN AREKIAA                           157

SEQ ID NO: 86           moltype = AA  length = 157
FEATURE                 Location/Qualifiers
REGION                  1..157
                        note = Synthetic
source                  1..157
                        mol_type = protein
                        organism = synthetic construct
SEQUENCE: 86
MNQHSHKDHE TVRIAVVRAR WHADIVDACV EAFEIAMAAI GGDRFAVDVF DVPGAYEIPL  60
HARTLAETGR YGAVLGTAFV VDGGIYDHEF VASAVIDGMM NVQLDTGVPV LSAVLTPHEY  120
EDSDEDHEFF AAHFAVKGVE AARACIEILN AREKIAA                           157

SEQ ID NO: 87           moltype = AA  length = 205
FEATURE                 Location/Qualifiers
REGION                  1..205
                        note = Synthetic
source                  1..205
                        mol_type = protein
                        organism = synthetic construct
SEQUENCE: 87
MKMEELFKKH KIVAVLRANS VEEAIEKAVA VFAGGVHLIE ITFTVPDADT VIKALSVLKE  60
KGAIIGAGTV TSVEQCRKAV ESGAEFIVSP HLDEEISQFC KEKGVFYMPG VMTPTELVKA  120
MKLGHDILKL FPGEVVGPQF VKAMKGPFPN VKFVPTGGVN LDNVCEWFKA GVLAVGVGDA  180
LVKGDPDEVR EKAKKFVEKI RGCTE                                        205

SEQ ID NO: 88           moltype = AA  length = 205
FEATURE                 Location/Qualifiers
REGION                  1..205
                        note = Synthetic
source                  1..205
                        mol_type = protein
                        organism = synthetic construct
SEQUENCE: 88
MKMEELFKKH KIVAVLRANS VEEAIEKAVA VFAGGVHLIE ITFTVPDADT VIKALSVLKE  60
KGAIIGAGTV TSVEQCRKAV ESGAEFIVSP HLDEEISQFC KEKGVFYMPG VMTPTELVKA  120
MKLGHDILKL FPGEVVGPEF VEAMKGPFPN VKFVPTGGVD LDDVCEWFDA GVLAVGVGDA  180
LVEGDPDEVR EDAKEFVEEI RGCTE                                        205

SEQ ID NO: 89           moltype = AA  length = 205
FEATURE                 Location/Qualifiers
REGION                  1..205
                        note = Synthetic
source                  1..205
                        mol_type = protein
                        organism = synthetic construct
SEQUENCE: 89
MKMEELFKKH KIVAVLRANS VEEAIEKAVA VFAGGVHLIE ITFTVPDADT VIKALSVLKE  60
KGAIIGAGTV TSVEQCRKAV ESGAEFIVSP HLDEEISQFC KEKGVFYMPG VMTPTELVKA  120
```

```
MKLGHDILKL FPGEVVGPQF VKAMKGPFPN VKFVPTGGVN LDNVCKWFKA GVLAVGVGKA  180
LVKGKPDEVR EKAKKFVKKI RGCTE                                        205

SEQ ID NO: 90          moltype = AA  length = 157
FEATURE                Location/Qualifiers
REGION                 1..157
                       note = Synthetic
source                 1..157
                       mol_type = protein
                       organism = synthetic construct
SEQUENCE: 90
MNQHSHKDHE TVRIAVVRAR WHAEIVDACV SAFEAAMRDI GGDRFAVDVF DVPGAYEIPL  60
HARTLAETGR YGAVLGTAFV VNGGIYRHEF VASAVIDGMM NVQLDTGVPV LSAVLTPHRY  120
RDSDAHTLLF LALFAVKGME AARACVEILA AREKIAA                           157

SEQ ID NO: 91          moltype = AA  length = 157
FEATURE                Location/Qualifiers
REGION                 1..157
                       note = Synthetic
source                 1..157
                       mol_type = protein
                       organism = synthetic construct
SEQUENCE: 91
MNQHSHKDHE TVRIAVVRAR WHAEIVDACV SAFEAAMRDI GGDRFAVDVF DVPGAYEIPL  60
HARTLAETGR YGAVLGTAFV VDGGIYDHEF VASAVIDGMM NVQLDTGVPV LSAVLTPHEY  120
EDSDADTLLF LALFAVKGME AARACVEILA AREKIAA                           157

SEQ ID NO: 92          moltype = AA  length = 157
FEATURE                Location/Qualifiers
REGION                 1..157
                       note = Synthetic
source                 1..157
                       mol_type = protein
                       organism = synthetic construct
SEQUENCE: 92
MNQHSHKDHE TVRIAVVRAR WHAEIVDACV SAFEAAMRDI GGDRFAVDVF DVPGAYEIPL  60
HARTLAETGR YGAVLGTAFV VNGGIYRHEF VASAVINGMM NVQLNTGVPV LSAVLTPHNY  120
DKSKAHTLLF LALFAVKGME AARACVEILA AREKIAA                           157

SEQ ID NO: 93          moltype = AA  length = 156
FEATURE                Location/Qualifiers
REGION                 1..156
                       note = Synthetic
SITE                   70
                       note = MISC_FEATURE - Xaa is A or K
source                 1..156
                       mol_type = protein
                       organism = synthetic construct
SEQUENCE: 93
MTKKVGIVDT TFARVDMASA AILTLKMESP NIKIIRKTVP GIKDLPVACK KLLEEEGCDI  60
VMALGMPGKX EKDKVCAHEA SLGLMLAQLM TNKHIIEVFV HEDEAKDDAE LKILAARRAI  120
EHALNVYYLL FKPEYLTRMA GKGLRQGFED AGPARE                            156

SEQ ID NO: 94          moltype = AA  length = 209
FEATURE                Location/Qualifiers
REGION                 1..209
                       note = Synthetic
SITE                   2
                       note = MISC_FEATURE - Xaa is S or D
SITE                   3
                       note = MISC_FEATURE - Xaa is T or D
SITE                   10
                       note = MISC_FEATURE - Xaa is A or R
SITE                   85
                       note = MISC_FEATURE - Xaa is T or D
SITE                   119
                       note = MISC_FEATURE - Xaa is A or Q
SITE                   163
                       note = MISC_FEATURE - Xaa is S or D
SITE                   189
                       note = MISC_FEATURE - Xaa is T or R
source                 1..209
                       mol_type = protein
                       organism = synthetic construct
SEQUENCE: 94
MXXINNQLKX LKVIPVIAID NAEDIIPLGK VLAENGLPAA EITFRSSAAV KAIMLLRSAQ  60
PEMLIGAGTI LNGVQALAAK EAGAXFVVSP GFNPNTVRAC QIIGIDIVPG VNNPSTVEXA  120
LEMGLTTLKF FPAEASGGIS MVKSLVGPYG DIRLMPTGGI TPXNIDNYLA IPQVLACGGT  180
WMVDKKLVXN GEWDEIARLT REIVEQVNP                                    209
```

-continued

```
SEQ ID NO: 95          moltype = AA  length = 114
FEATURE                Location/Qualifiers
REGION                 1..114
                       note = Synthetic
SITE                   13
                       note = MISC_FEATURE - Xaa is T or D
SITE                   33
                       note = MISC_FEATURE - Xaa is K or E
SITE                   71
                       note = MISC_FEATURE - Xaa is S or D
SITE                   74
                       note = MISC_FEATURE - Xaa is R or E
SITE                   101
                       note = MISC_FEATURE - Xaa is N or D
SITE                   103
                       note = MISC_FEATURE - Xaa is N or D
source                 1..114
                       mol_type = protein
                       organism = synthetic construct
SEQUENCE: 95
MPIFTLNTNI KAXDVPSDFL SLTSRLVGLI LSXPGSYVAV HINTDQQLSF GGSTNPAAFG  60
TLMSIGGIEP XKNXDHSAVL FDHLNAMLGI PKNRMYIHFV XLXGDDVGWN GTTF        114

SEQ ID NO: 96          moltype = AA  length = 157
FEATURE                Location/Qualifiers
REGION                 1..157
                       note = Synthetic
SITE                   9
                       note = MISC_FEATURE - Xaa is Y or H
SITE                   82
                       note = MISC_FEATURE - Xaa is N or D
SITE                   87
                       note = MISC_FEATURE - Xaa is R or D
SITE                   105
                       note = MISC_FEATURE - Xaa is S or D
SITE                   119
                       note = MISC_FEATURE - Xaa is R or E
SITE                   121
                       note = MISC_FEATURE - Xaa is R or E
SITE                   124
                       note = MISC_FEATURE - Xaa is A or D
SITE                   126
                       note = MISC_FEATURE - Xaa is H or D
SITE                   128
                       note = MISC_FEATURE - Xaa is R or E
SITE                   150
                       note = MISC_FEATURE - Xaa is A or N
source                 1..157
                       mol_type = protein
                       organism = synthetic construct
SEQUENCE: 96
MNQHSHKDXE TVRIAVVRAR WHADIVDACV EAFEIAMAAI GGDRFAVDVF DVPGAYEIPL  60
HARTLAETGR YGAVLGTAFV VXGGIYXHEF VASAVIDGMM NVQLXTGVPV LSAVLTPHXY  120
XDSXEXHXFF AAHFAVKGVE AARACIEILX AREKIAA                           157

SEQ ID NO: 97          moltype = AA  length = 205
FEATURE                Location/Qualifiers
REGION                 1..205
                       note = Synthetic
SITE                   126
                       note = MISC_FEATURE - Xaa is T or D
SITE                   139
                       note = MISC_FEATURE - Xaa is Q or E
SITE                   142
                       note = MISC_FEATURE - Xaa is K or E
SITE                   160
                       note = MISC_FEATURE - Xaa is N or D
SITE                   163
                       note = MISC_FEATURE - Xaa is N or D
SITE                   166
                       note = MISC_FEATURE - Xaa is E or K
SITE                   169
                       note = MISC_FEATURE - Xaa is D or K
SITE                   179
                       note = MISC_FEATURE - Xaa is S, D or K
SITE                   183
                       note = MISC_FEATURE - Xaa is K or E
SITE                   185
```

-continued

```
                     note = MISC_FEATURE - Xaa is T, D, or K
SITE                 192
                     note = MISC_FEATURE - Xaa is D or K
SITE                 195
                     note = MISC_FEATURE - Xaa is A, E, or K
SITE                 198
                     note = MISC_FEATURE - Xaa is E or K
SITE                 199
                     note = MISC_FEATURE - Xaa is E or K
source               1..205
                     mol_type = protein
                     organism = synthetic construct
SEQUENCE: 97
MKMEELFKKH KIVAVLRANS VEEAIEKAVA VFAGGVHLIE ITFTVPDADT VIKALSVLKE  60
KGAIIGAGTV TSVEQCRKAV ESGAEFIVSP HLDEEISQFC KEKGVFYMPG VMTPTELVKA  120
MKLGHXILKL FPGEVVGPXF VXAMKGPFPN VKFVPTGGVX LDXVCXWFXA GVLAVGVGXA  180
LVXGXPDEVR EXAKXFVXXI RGCTE                                        205

SEQ ID NO: 98        moltype = AA  length = 157
FEATURE              Location/Qualifiers
REGION               1..157
                     note = Synthetic
SITE                 9
                     note = MISC_FEATURE - Xaa is Y or H
SITE                 38
                     note = MISC_FEATURE - Xaa is A or R
SITE                 82
                     note = MISC_FEATURE - Xaa is N or D
SITE                 87
                     note = MISC_FEATURE - Xaa is R or D
SITE                 97
                     note = MISC_FEATURE - Xaa is N or D
SITE                 105
                     note = MISC_FEATURE - Xaa is S, N, or D
SITE                 119
                     note = MISC_FEATURE - Xaa is R, E, or N
SITE                 121
                     note = MISC_FEATURE - Xaa is R, E, or D
SITE                 122
                     note = MISC_FEATURE - Xaa is K or D
SITE                 124
                     note = MISC_FEATURE - Xaa is K or D
SITE                 126
                     note = MISC_FEATURE - Xaa is H or D
source               1..157
                     mol_type = protein
                     organism = synthetic construct
SEQUENCE: 98
MNQHSHKDXE TVRIAVVRAR WHAEIVDACV SAFEAAMXDI GGDRFAVDVF DVPGAYEIPL  60
HARTLAETGR YGAVLGTAFV VXGGIYXHEF VASAVIXGMM NVQLXTGVPV LSAVLTPHXY  120
XXSXAXTLLF LALFAVKGME AARACVEILA AREKIAA                           157

SEQ ID NO: 99        moltype = DNA  length = 142
FEATURE              Location/Qualifiers
misc_feature         1..142
                     note = Synthetic
source               1..142
                     mol_type = other DNA
                     organism = synthetic construct
SEQUENCE: 99
taatgcttaa gtcgaacaga aagtaatcgt attgtacacg gccgcataat cgaaattaat  60
acgactcact ataggggaat tgtgagcgga taacaattcc ccatcttagt atattagtta  120
agtataagaa ggagatatac tt                                           142

SEQ ID NO: 100       moltype = DNA  length = 18
FEATURE              Location/Qualifiers
misc_feature         1..18
                     note = Synthetic
source               1..18
                     mol_type = other DNA
                     organism = synthetic construct
SEQUENCE: 100
taaagaagga gatatcat                                                18

SEQ ID NO: 101       moltype = DNA  length = 17
FEATURE              Location/Qualifiers
misc_feature         1..17
                     note = Synthetic
source               1..17
```

```
                        mol_type = other DNA
                        organism = synthetic construct
SEQUENCE: 101
tgagaaggag atatcat                                                  17

SEQ ID NO: 102          moltype = AA  length = 365
FEATURE                 Location/Qualifiers
source                  1..365
                        mol_type = protein
                        organism = Homo sapiens
SEQUENCE: 102
MGVPRPQPWA LGLLLFLLPG SLGAESHLSL LYHLTAVSSP APGTPAFWVS GWLGPQQYLS  60
YNSLRGEAEP CGAWVWENQV SWYWEKETTD LRIKEKLFLE AFKALGGKGP YTLQGLLGCE  120
LGPDNTSVPT AKFALNGEEF MNFDLKQGTW GGDWPEALAI SQRWQQQDKA ANKELTFLLF  180
SCPHRLREHL ERGRGNLEWK EPPSMRLKAR PSSPGFSVLT CSAFSFYPPE LQLRFLRNGL  240
AAGTGQGDFG PNSDGSFHAS SSLTVKSGDE HHYCCIVQHA GLAQPLRVEL ESPAKSSVLV  300
VGIVIGVLLL TAAAVGGALL WRRMRSGLPA PWISLRGDDT GVLLPTPGEA QDADLKDVNV  360
IPATA                                                               365

SEQ ID NO: 103          moltype = AA  length = 62
FEATURE                 Location/Qualifiers
source                  1..62
                        mol_type = protein
                        organism = Homo sapiens
SEQUENCE: 103
MGVPRPQPWA LGLLLFLLPG SLGFACKTAN GTAIPIGGGS ANVYVNLAPV VNVGQNLVVD  60
LS                                                                  62

SEQ ID NO: 104          moltype = AA  length = 574
FEATURE                 Location/Qualifiers
source                  1..574
                        mol_type = protein
                        note = [strain A2]
                        organism = Human respiratory syncytial virus A
SEQUENCE: 104
MELLILKANA ITTILTAVTF CFASGQNITE EFYQSTCSAV SKGYLSALRT GWYTSVITIE  60
LSNIKENKCN GTDAKVKLIK QELDKYKNAV TELQLLMQST PPTNNRARRE LPRFMNYTLN  120
NAKKTNVTLS KKRKRRFLGF LLGVGSAIAS GVAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEIN LCNVDIFNPK YDCKIMTSKT DVSSSVITSL GAIVSCYGKT  420
KCTASNKNRG IIKTFSNGCD YVSNKGMDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFSN                               574

SEQ ID NO: 105          moltype = AA  length = 64
FEATURE                 Location/Qualifiers
source                  1..64
                        mol_type = protein
                        note = [strain A2]
                        organism = Human respiratory syncytial virus A
SEQUENCE: 105
MELLILKANA ITTILTAVTF CFASGFACKT ANGTAIPIGG GSANVYVNLA PVVNVGQNLV  60
VDLS                                                                64

SEQ ID NO: 106          moltype = AA  length = 178
FEATURE                 Location/Qualifiers
source                  1..178
                        mol_type = protein
                        organism = Homo sapiens
SEQUENCE: 106
MHSSALLCCL VLLTGVRASP GQGTQSENSC THFPGNLPNM LRDLRDAFSR VKTFFQMKDQ  60
LDNLLLKESL LEDFKGYLGC QALSEMIQFY LEEVMPQAEN QDPDIKAHVN SLGENLKTLR  120
LRLRRCHRFL PCENKSKAVE QVKNAFNKLQ EKGIYKAMSE FDIFINYIEA YMTMKIRN    178

SEQ ID NO: 107          moltype = AA  length = 57
FEATURE                 Location/Qualifiers
source                  1..57
                        mol_type = protein
                        organism = Homo sapiens
SEQUENCE: 107
MHSSALLCCL VLLTGVRAFA CKTANGTAIP IGGGSANVYV NLAPVVNVGQ NLVVDLS      57

SEQ ID NO: 108          moltype = AA  length = 562
FEATURE                 Location/Qualifiers
source                  1..562
                        mol_type = protein
                        note = [strain A/Japan/305/1957 H2N2]
```

-continued

```
                        organism = Influenza A virus
SEQUENCE: 108
MAIIYLILLF TAVRGDQICI GYHANNSTEK VDTNLERNVT VTHAKDILEK THNGKLCKLN  60
GIPPLELGDC SIAGWLLGNP ECDRLLSVPE WSYIMEKENP RDGLCYPGSF NDYEELKHLL  120
SSVKHFEKVK ILPKDRWTQH TTTGGSRACA VSGNPSFFRN MVWLTKEGSD YPVAKGSYNN  180
TSGEQMLIIW GVHHPIDETE QRTLYQNVGT YVSVGTSTLN KRSTPEIATR PKVNGQGGRM  240
EFSWTLLDMW DTINFESTGN LIAPEYGFKI SKRGSSGIMK TEGTLENCET KCQTPLGAIN  300
TTLPFHNVHP LTIGECPKYV KSEKLVLATG LRNVPQIESR GLFGAIAGFI EGGWQGMVDG  360
WYGYHHSNDQ GSGYAADKES TQKAFDGITN KVNSVIEKMN TQFEAVGKEF GNLERRLENL  420
NKRMEDGFLD VWTYNAELLV LMENERTLDF HDSNVKNLYD KVRMQLRDNV KELGNGCFEF  480
YHKCDDECMN SVKNGTYDYP KYEEESKLNR NEIKGVKLSS MGVYQILAIY ATVAGSLSLA  540
IMMAGISFWM CSNGSLQCRI CI                                          562

SEQ ID NO: 109          moltype = AA  length = 54
FEATURE                 Location/Qualifiers
source                  1..54
                        mol_type = protein
                        note = [strain A/Japan/305/1957 H2N2]
                        organism = Influenza A virus
SEQUENCE: 109
MAIIYLILLF TAVRGFACKT ANGTAIPIGG GSANVYVNLA PVVNVGQNLV VDLS         54
```